US007026457B2

(12) United States Patent
Maertens et al.

(10) Patent No.: US 7,026,457 B2
(45) Date of Patent: Apr. 11, 2006

(54) PURIFIED HEPATITIS C VIRUS ENVELOPE PROTEINS FOR DIAGNOSTIC AND THERAPEUTIC USE

(75) Inventors: Geert Maertens, Bruges (BE); Fons Bosman, Opwijk (BE); Guy De Martynoff, Waterloo (BE); Marie Ange Buyse, Merelbeke (BE)

(73) Assignee: Innogenetics N.V., Ghent (BE)

( * ) Notice: Subject to any disclaimer, the term of this patent is extended or adjusted under 35 U.S.C. 154(b) by 296 days.

(21) Appl. No.: 09/973,025

(22) Filed: Oct. 10, 2001

(65) Prior Publication Data

US 2002/0182706 A1 Dec. 5, 2002

Related U.S. Application Data

(60) Continuation of application No. 08/928,017, filed on Sep. 11, 1997, now abandoned, which is a division of application No. 08/612,973, filed as application No. PCT/EP95/03031 on Jul. 31, 1995, now Pat. No. 6,150,134.

(30) Foreign Application Priority Data

Jul. 29, 1994 (EP) ............................................ 94870132

(51) Int. Cl.
*C07K 16/08* (2006.01)
*C07K 16/10* (2006.01)
*A16A 39/395* (2006.01)
*G01N 33/53* (2006.01)
*G01N 33/576* (2006.01)

(52) U.S. Cl. ............................... 530/388.3; 530/388.1; 530/387.9; 424/130.1; 424/131.1; 424/134.1; 424/147.1; 424/149.1; 435/332; 435/339; 435/69.1; 435/915

(58) Field of Classification Search ............... 426/130.1, 426/131.1, 134.1, 141.1, 147.1, 149.1; 435/332, 435/339, 69.1
See application file for complete search history.

(56) References Cited

U.S. PATENT DOCUMENTS

| | | | |
|---|---|---|---|
| 5,308,750 A | * 5/1994 | Mehta et al. ............... | 435/5 |
| 5,514,539 A | 5/1996 | Bukh et al. ................. | 435/5 |
| 5,582,968 A | 12/1996 | Wang | |
| 5,610,009 A | * 3/1997 | Wantanabe et al. ........... | 435/5 |
| 5,670,152 A | 9/1997 | Weiner et al. | |
| 5,747,239 A | 5/1998 | Wang | |
| 5,830,691 A | * 11/1998 | Miyamura et al. ......... | 435/69.1 |
| 5,866,139 A | 2/1999 | Brechot et al. | |
| 5,871,962 A | * 2/1999 | Bukh et al. ................ | 435/69.1 |
| 5,919,454 A | 7/1999 | Brechot | |
| 6,074,846 A | 6/2000 | Ralston et al. | |
| 6,150,134 A | 11/2000 | Maertens et al. | |
| 6,183,949 B1 | 2/2001 | Seidel | |
| 6,245,503 B1 | 6/2001 | Maertens et al. | |

FOREIGN PATENT DOCUMENTS

| | | |
|---|---|---|
| EP | 0388232 A1 * | 9/1990 |
| EP | 0388232 | 9/1990 |
| EP | 0537626 | 4/1993 |
| EP | 0585549 | 3/1994 |
| EP | 0569537 | 6/1998 |
| EP | 1 211 315 | 6/2002 |
| GB | 2212511 A * | 7/1989 |
| WO | PCT/US91/08272 | 1/1991 |
| WO | PCT/IT92/00081 | 1/1992 |
| WO | PCT/US92/07189 | 1/1992 |
| WO | WO 92/13892 | 8/1992 |
| WO | PCT/US93/00907 | 1/1993 |
| WO | WO 93/04888 | 3/1993 |
| WO | WO 93/06247 | 4/1993 |
| WO | WO 93/18054 | 9/1993 |
| WO | WO93/18054 A2 * | 9/1993 |
| WO | WO 94/01778 | 1/1994 |

OTHER PUBLICATIONS

Petit et al. J. Biol. Chemistr. 2003, vol. 278, pp. 44385–44392.*
Matsuura et al. J. Virol. 1992, 66, No. 3, pp. 1425–1431.*
Kaito et al. J. Gene. Virol. 1994, vol. 75, pp. 1755–1760.*
Choo, et al., "Vaccination of Chimpanzees Against . . . Hepatitis C Virus", Proc. Natl. Acad. Sci., 1994, pp. 1294–1298.
Lanford, et al., "Analysis of Hepatitis C Virus . . . ", Virology 197, pp. 225–235, 1993.
Nishihara, et al., Gene 129, 1993, 207–214.
Ralson, et al., J. Virol. 67, 1993, 6753–6761.
Kohara, et al., J. Gen. Virol. 73, 1992, 2313–2318.
Choo, et al., Proc. Natl. Acad. Sci. USA 88, 1991, 2451–2455.
Farci, Science, vol. 258, 1992, 135–140.

* cited by examiner

*Primary Examiner*—James Housel
*Assistant Examiner*—Bao Qun Li
(74) *Attorney, Agent, or Firm*—Nixon & Vanderhye P.C.

(57) ABSTRACT

The present invention relates to a method for purifying recombinant HCV single or specific oligomeric envelope proteins selected from the group consisting of E1 and/or E1/E2 characterized in that upon lysing the transformed host cells to isolate the recombinantly expressed protein a disulphide bond cleavage or reduction step is carried out with a disulphide bond cleavage agent. The present invention also relates to a composition isolated by such a method. The present invention also relates to the diagnostic and therapeutic application of these compositions. Furthermore, the invention relates to the use of HCV E1 protein and peptides for prognosing and monitoring the clinical effectiveness and/or clinical outcome of HCV treatment.

18 Claims, 58 Drawing Sheets

Fig. 21A

5'   GGCATGCAAGCTTAATTAATT3'  (SEQ ID NO 1)

3'ACGTCCGTACGTTCGAATTAATTAATCGA5'  (SEQ ID NO 94)

5'CCGGGGAGGCCTGCACGTGATCGAGGGCAGACACCATCACCACCATCACTAATAGT

TAATTAACTGCA 3'  (SEQ ID NO 2)

3'CCTCCGGACGTGCACTAGCTCCCGTCTGTGGTAGTGGTGGTAGTGATTATCAATTAATTG

5'   (SEQ ID NO 95)

SEQ ID NO 3 (HCCI9A)

Figure 1:
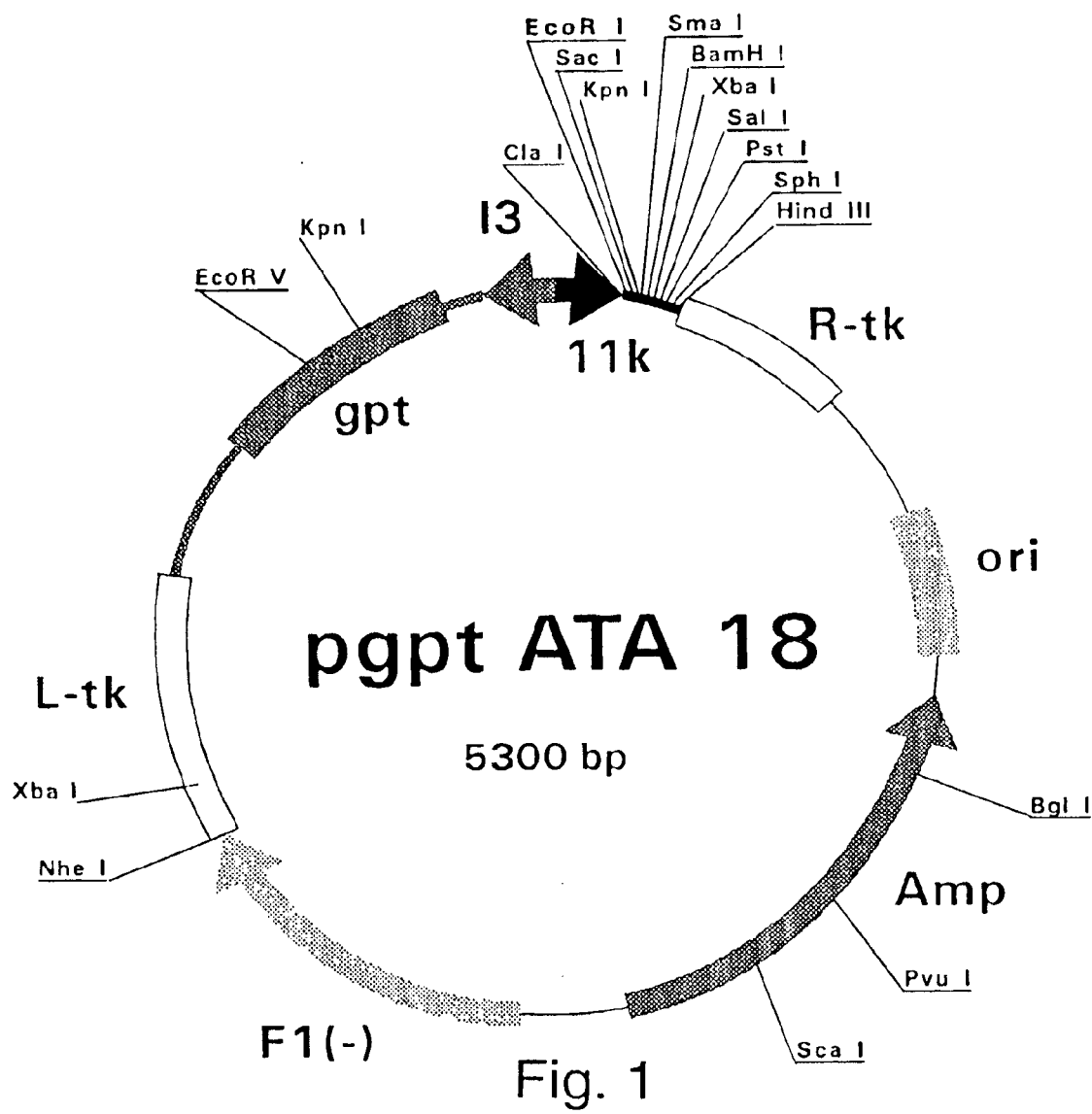

ATGCCCGGTTGCTCTTTCTCTATCTTCCTCTTGGCTTTACTGTCCTGTCTGACCATTCCA
GCTTCCGCTTATGAGGTGCGCAACGTGTCCGGGATGTACCATGTCACGAACGACTGCT
CCAACTCAAGCATTGTGTATGAGGCAGCGGACATGATCATGCACACCCCGGGTGCGT
GCCCTGCGTTCGGGAGAACAACTCTTCCCGCTGCTGGGTAGCGCTCACCCCACGCTC
GCAGCTAGGAACGCCAGCGTCCCCACCACGACAATACGACGCCACGTCGATTTGCTCG
TTGGGGCGGCTGCTCTCTGTTCCGCTATGTACGTGGGGGATCTCTGCGGATCTGTCTTC
CTCGTCTCCCAGCTGTTCACCATCTCGCCTCGCCGGCATGAGACGGTGCAGGACTGCA
ATTGCTCAATCTATCCCGGCCACATAACAGGTCACCGTATGGCTTGGGATATGATGAT
GAACTGGTCGCCTACAACGGCCCTGGTGGTATCGCAGCTGCTCCGGATCCCACAAGCT
GTCGTGGACATGGTGGCGGGGGCCCATTGGGGAGTCCTGGCGGGCCTCGCCTACTATT
CCATGGTGGGGAACTGGGCTAAGGTTTTGATTGTGATGCTACTCTTTGCTCTCTAATAG

SEQ ID NO 5 (HCCl10A)

ATGTTGGGTAAGGTCATCGATACCCTTACATGCGGCTTCGCCGACCTCGTGGGGTACA
TTCCGCTCGTCGGCGCCCCCTAGGGGGCGCTGCCAGGGCCCTGGCGCATGGCGTCCG
GGTTCTGGAGGACGGCGTGAACTATGCAACAGGGAATTTGCCCGGTTGCTCTTTCTCT
ATCTTCCTCTTGGCTTTGCTGTCCTGTCTGACCGTTCCAGCTTCCGCTTATGAAGTGCG
CAACGTGTCCGGGATGTACCATGTCACGAACGACTGCTCCAACTCAAGCATTGTGTAT
GAGGCAGCGGACATGATCATGCACACCCCGGGTGCGTGCCCTGCGTTCGGGAGAAC
AACTCTTCCCGCTGCTGGGTAGCGCTCACCCCACGCTCGCAGCTAGGAACGCCAGCG
TCCCCACCACGACAATACGACGCCACGTCGATTTGCTCGTTGGGGCGGCTGCTTTCTG

Fig. 21B

TTCCGCTATGTACGTGGGGGACCTCTGCGGATCTGTCTTCCTCGTCTCCCAGCTGTTCA
CCATCTCGCCTCGCCGGCATGAGACGGTGCAGGACTGCAATTGCTCAATCTATCCCGG
CCACATAACGGGTCACCGTATGGCTTGGGATATGATGATGAACTGGTCGCCTACAACG
GCCCTGGTGGTATCGCAGCTGCTCCGGATCCCACAAGCTGTCGTGGACATGGTGGCGG
GGGCCCATTGGGGAGTCCTGGCGGGTCTCGCCTACTATTCCATGGTGGGGAACTGGGC
TAAGGTTTTGATTGTGATGCTACTCTTTGCTCCCTAATAG

SEQ ID NO 7 (HCCI11A)

ATGTTGGGTAAGGTCATCGATACCCTTACGTGCGGCTTCGCCGACCTCATGGGGTACA
TTCCGCTCGTCGGCGCCCCCTAGGGGGTGCTGCCAGAGCCCTGGCGCATGGCGTCCG
GGTTCTGGAAGACGGCGTGAACTATGCAACAGGGAATTTGCCTGGTTGCTCTTTCTCTA
TCTTCCTCTTGGCTTTACTGTCCTGTCTGACCATTCCAGCTTCCGCTTATGAGGTGCGC
AACGTGTCCGGGATGTACCATGTCACGAACGACTGCTCCAACTCAAGCATTGTGTATG
AGGCAGCGGACATGATCATGCACACCCCGGGTGCGTGCCCTGCGTTCGGGAGAACA
ACTCTTCCCGCTGCTGGGTAGCGCTCACCCCACGCTCGCAGCTAGGAACGCCAGCGT
CCCCACTACGACAATACGACGCCACGTCGATTTGCTCGTTGGGGCGGCTGCTTTCTGTT
CCGCTATGTACGTGGGGGATCTCTGCGGATCTGTCTTCCTCGTCTCCCAGCTGTTCACC
ATCTCGCCTCGCCGGCATGAGACGGTGCAGGACTGCAATTGCTCAATCTATCCCGGCC
ACATAACAGGTCACCGTATGGCTTGGGATATGATGATGAACTGGTAATAG

SEQ ID NO 9 (HCCI12A)

ATGCCCGGTTGCTCTTTCTCTATCTTCCTCTTGGCCCTGCTGTCCTGTCTGACCATACCA
GCTTCCGCTTATGAAGTGCGCAACGTGTCCGGGGTGTACCATGTCACGAACGACTGCT
CCAACTCAAGCATAGTGTATGAGGCAGCGGACATGATCATGCACACCCCGGGTGCGT
GCCCTGCGTTCGGGAGGGCAACTCCTCCCGTTGCTGGGTGGCGCTCACTCCCACGCTC
GCGGCCAGGAACGCCAGCGTCCCCACAACGACAATACGACGCCACGTCGATTTGCTC
GTTGGGGCTGCTGCTTTCTGTTCCGCTATGTACGTGGGGGATCTCTGCGGATCTGTTTT
CCTTGTTTCCCAGCTGTTCACCTTCTCACCTCGCCGGCATCAAACAGTACAGGACTGCA
ACTGCTCAATCTATCCCGGCCATGTATCAGGTCACCGCATGGCTTGGGATATGATGAT
GAACTGGTCCTAATAG

SEQ ID NO 11 (HCCI13A)

ATGTCCGGTTGCTCTTTCTCTATCTTCCTCTTGGCCCTGCTGTCCTGTCTGACCATACCA
GCTTCCGCTTATGAAGTGCGCAACGTGTCCGGGGTGTACCATGTCACGAACGACTGCT
CCAACTCAAGCATAGTGTATGAGGCAGCGGACATGATCATGCACACCCCGGGTGCGT

Fig. 21C

GCCCTGCGTTCGGGAGGGCAACTCCTCCCGTTGCTGGGTGGCGCTCACTCCCACGCTC
GCGGCCAGGAACGCCAGCGTCCCCACAACGACAATACGACGCCACGTCGATTTGCTC
GTTGGGGCTGCTGCTTTCTGTTCCGCTATGTACGTGGGGGATCTCTGCGGATCTGTTTT
CCTTGTTTCCCAGCTGTTCACCTTCTCACCTCGCCGGCATCAAACAGTACAGGACTGCA
ACTGCTCAATCTATCCCGGCCATGTATCAGGTCACCGCATGGCTTGGGATATGATGAT
GAACTGGTAATAG

SEQ ID NO 13 (HCCl17A)
ATGCTGGGTAAGGCCATCGATACCCTTACGTGCGGCTTCGCCGACCTCGTGGGGTACA
TTCCGCTCGTCGGCGCCCCCTAGGGGGCGCTGCCAGGGCCCTGGCGCATGGCGTCCG
GGTTCTGGAAGACGGCGTGAACTATGCAACAGGGAATTTGCCTGGTTGCTCTTTCTCTA
TCTTCCTCTTGGCTTTACTGTCCTGTCTAACCATTCCAGCTTCCGCTTACGAGGTGCGC
AACGTGTCCGGGATGTACCATGTCACGAACGACTGCTCCAACTCAAGCATTGTGTATG
AGGCAGCGGACATGATCATGCACACCCCGGGTGCGTGCCCTGCGTTCGGGAGAACA
ACTCTTCCCGCTGCTGGGTAGCGCTCACCCCCACGCTCGCGGCTAGGAACGCCAGCAT
CCCCACTACAACAATACGACGCCACGTCGATTTGCTCGTTGGGGCGGCTGCTTTCTGTT
CCGCTATGTACGTGGGGGATCTCTGCGGATCTGTCTTCCTCGTCTCCCAGCTGTTCACC
ATCTCGCCTCGCCGGCATGAGACGGTGCAGGACTGCAATTGCTCAATCTATCCCGGCC
ACATAACGGGTCACCGTATGGCTTGGGATATGATGATGAACTGGTACTAATAG

SEQ ID NO 15 (HCPr51)
ATGCCCGGTTGCTCTTTCTCTATCTT

SEQ ID NO 16 (HCPr52)
ATGTTGGGTAAGGTCATCGATACCCT

SEQ ID NO 17 (HCPr53)
CTATTAGGACCAGTTCATCATCATATCCCA

SEQ ID NO 18 (HCPr54)
CTATTACCAGTTCATCATCATATCCCA

SEQ ID NO 19 (HCPr107)
ATACGACGCCACGTCGATTCCCAGCTGTTCACCATC

Fig. 21D

SEQ ID NO 20 (HCPr108)
GATGGTGAACAGCTGGGAATCGACGTGGCGTCGTAT

SEQ ID NO 21 (HCCl37)
ATGTTGGGTAAGGTCATCGATACCCTTACATGCGGCTTCGCCGACCTCGTGGGGTACA
TTCCGCTCGTCGGCGCCCCCTAGGGGGCGCTGCCAGGGCCCTGGCGCATGGCGTCCG
GGTTCTGGAGGACGGCGTGAACTATGCAACAGGGAATTTGCCCGGTTGCTCTTTCTCT
ATCTTCCTCTTGGCTTTGCTGTCCTGTCTGACCGTTCCAGCTTCCGCTTATGAAGTGCG
CAACGTGTCCGGGATGTACCATGTCACGAACGACTGCTCCAACTCAAGCATTGTGTAT
GAGGCAGCGGACATGATCATGCACACCCCGGGTGCGTGCCCTGCGTTCGGGAGAAC
AACTCTTCCCGCTGCTGGGTAGCGCTCACCCCACGCTCGCAGCTAGGAACGCCAGCG
TCCCCACCACGACAATACGACGCCACGTCGATTCCCAGCTGTTCACCATCTCGCCTCG
CCGGCATGAGACGGTGCAGGACTGCAATTGCTCAATCTATCCCGGCCACATAACGGGT
CACCGTATGGCTTGGGATATGATGATGAACTGGTCGCCTACAACGGCCCTGGTGGTAT
CGCAGCTGCTCCGGATCCCACAAGCTGTCGTGGACATGGTGGCGGGGGCCCATTGGGG
AGTCCTGGCGGGTCTCGCCTACTATTCCATGGTGGGGAACTGGGCTAAGGTTTTGATTG
TGATGCTACTCTTTGCTCCCTAATAG

SEQ ID NO 23 (HCCl38)
ATGTTGGGTAAGGTCATCGATACCCTTACATGCGGCTTCGCCGACCTCGTGGGGTACA
TTCCGCTCGTCGGCGCCCCCTAGGGGGCGCTGCCAGGGCCCTGGCGCATGGCGTCCG
GGTTCTGGAGGACGGCGTGAACTATGCAACAGGGAATTTGCCCGGTTGCTCTTTCTCT
ATCTTCCTCTTGGCTTTGCTGTCCTGTCTGACCGTTCCAGCTTCCGCTTATGAAGTGCG
CAACGTGTCCGGGATGTACCATGTCACGAACGACTGCTCCAACTCAAGCATTGTGTAT
GAGGCAGCGGACATGATCATGCACACCCCGGGTGCGTGCCCTGCGTTCGGGAGAAC
AACTCTTCCCGCTGCTGGGTAGCGCTCACCCCACGCTCGCAGCTAGGAACGCCAGCG
TCCCCACCACGACAATACGACGCCACGTCGATTCCCAGCTGTTCACCATCTCGCCTCG
CCGGCATGAGACGGTGCAGGACTGCAATTGCTCAATCTATCCCGGCCACATAACGGGT
CACCGTATGGCTTGGGATATGATGATGAACTGGTAA
TAG

SEQ ID NO 25 (HCCl39)
ATGTTGGGTAAGGTCATCGATACCCTTACATGCGGCTTCGCCGACCTCGTGGGGTACA
TTCCGCTCGTCGGCGCCCCCTAGGGGGCGCTGCCAGGGCCCTGGCGCATGGCGTCCG
GGTTCTGGAGGACGGCGTGAACTATGCAACAGGGAATTTGCCCGGTTGCTCTTTCTCT

Fig. 21E

ATCTTCCTCTTGGCTTTGCTGTCCTGTCTGACCGTTCCAGCTTCCGCTTATGAAGTGCG
CAACGTGTCCGGGATGTACCATGTCACGAACGACTGCTCCAACTCAAGCATTGTGTAT
GAGGCAGCGGACATGATCATGCACACCCCGGGTGCGTGCCCTGCGTTCGGGAGAAC
AACTCTTCCCGCTGCTGGGTAGCGCTCACCCCACGCTCGCAGCTAGGAACGCCAGCG
TCCCCACCACGACAATACGACGCCACGTCGATTCCCAGCTGTTCACCATCTCGCCTCG
CCGGCATGAGACGGTGCAGGACTGCAATTGCTCAATCTATCCCGGCCACATAACGGGT
CACCGTATGGCTTGGGATATGATGATGAACTGGTCGCCTACAACGGCCCTGGTGGTAT
CGCAGCTGCTCCGGATCCTCTAATAG

SEQ ID NO 27 (HCCl40)
ATGTTGGGTAAGGTCATCGATACCCTTACATGCGGCTTCGCCGACCTCGTGGGGTACA
TTCCGCTCGTCGGCGCCCCCCTAGGGGGCGCTGCCAGGGCCCTGGCGCATGGCGTCCG
GGTTCTGGAGGACGGCGTGAACTATGCAACAGGGAATTTGCCCGGTTGCTCTTTCTCT
ATCTTCCTCTTGGCTTTGCTGTCCTGTCTGACCGTTCCAGCTTCCGCTTATGAAGTGCG
CAACGTGTCCGGGATGTACCATGTCACGAACGACTGCTCCAACTCAAGCATTGTGTAT
GAGGCAGCGGACATGATCATGCACACCCCGGGTGCGTGCCCTGCGTTCGGGAGAAC
AACTCTTCCCGCTGCTGGGTAGCGCTCACCCCACGCTCGCAGCTAGGAACGCCAGCG
TCCCCACCACGACAATACGACGCCACGTCGATTCCCAGCTGTTCACCATCTCGCCTCG
CCGGCATGAGACGGTGCAGGACTGCAATTGCTCAATCTATCCCGGCCACATAACGGGT
CACCGTATGGCTTGGGATATGATGATGAACTGGTCGCCTACAACGGCCCTGGTGGTAT
CGCAGCTGCTCCGGATCGTGATCGAGGGCAGACACCATCACCACCATCACTAATAG

SEQ ID NO 29 (HCCl62)
ATGGGTAAGGTCATCGATACCCTTACGTGCGGATTCGCCGATCTCATGGGGTACATCC
CGCTCGTCGGCGCTCCCGTAGGAGGCGTCGCAAGAGCCCTTGCGCATGGCGTGAGGGC
CCTTGAAGACGGGATAAATTTCGCAACAGGGAATTTGCCCGGTTGCTCCTTTTCTATTT
TCCTTCTCGCTCTGTTCTCTTGCTTAATTCATCCAGCAGCTAGTCTAGAGTGGCGGAAT
ACGTCTGGCCTCTATGTCCTTACCAACGACTGTTCCAATAGCAGTATTGTGTACGAGGC
CGATGACGTTATTCTGCACACACCCGGCTGCATACCTTGTGTCCAGGACGGCAATACA
TCCACGTGCTGGACCCCAGTGACACCTACAGTGGCAGTCAAGTACGTCGGAGCAACCA
CCGCTTCGATACGCAGTCATGTGGACCTATTAGTGGGCGCGGCCACGATGTGCTCTGC
GCTCTACGTGGGTGACATGTGTGGGGCTGTCTTCCTCGTGGGACAAGCCTTCACGTTCA
GACCTCGTCGCCATCAAACGGTCCAGACCTGTAACTGCTCGCTGTACCCAGGCCATCT
TTCAGGACATCGAATGGCTTGGGATATGATGATGAACTGGTAATAG

Fig. 21F

SEQ ID NO 31 (HCCl63)

ATGGGTAAGGTCATCGATACCCTAACGTGCGGATTCGCCGATCTCATGGGGTATATCC
CGCTCGTAGGCGGCCCCATTGGGGGCGTCGCAAGGGCTCTCGCACACGGTGTGAGGGT
CCTTGAGGACGGGGTAAACTATGCAACAGGGAATTTACCCGGTTGCTCTTTCTCTATCT
TTATTCTTGCTCTTCTCTCGTGTCTGACCGTTCCGGCCTCTGCAGTTCCCTACCGAAATG
CCTCTGGGATTTATCATGTTACCAATGATTGCCCAAACTCTTCCATAGTCTATGAGGCA
GATAACCTGATCCTACACGCACCTGGTTGCGTGCCTTGTGTCATGACAGGTAATGTGA
GTAGATGCTGGGTCCAAATTACCCCTACACTGTCAGCCCCGAGCCTCGGAGCAGTCAC
GGCTCCTCTTCGGAGAGCCGTTGACTACCTAGCGGGAGGGGCTGCCCTCTGCTCCGCG
TTATACGTAGGAGACGCGTGTGGGGCACTATTCTTGGTAGGCCAAATGTTCACCTATA
GGCCTCGCCAGCACGCTACGGTGCAGAACTGCAACTGTTCCATTTACAGTGGCCATGT
TACCGGCCACCGGATGGCATGGGATATGATGATGAACTGGTAATAG

SEQ ID NO 33 (HCPr109)

TGGGATATGATGATGAACTGGTC

SEQ ID NO 34 (HCPr72)

CTATTATGGTGGTAAKGCCARCARGAGCAGGAG

SEQ ID NO 35 (HCCL22A)

TGGGATATGATGATGAACTGGTCGCCTACAACGGCCCTGGTGGTATCGCAGCTGCTCC
GGATCCCACAAGCTGTCGTGGACATGGTGGCGGGGGCCCATTGGGGAGTCCTGGCGG
GCCTCGCCTACTATTCCATGGTGGGGAACTGGGCTAAGGTTTTGGTTGTGATGCTACTC
TTTGCCGGCGTCGACGGGCATACCCGCGTGTCAGGAGGGGCAGCAGCCTCCGATACCA
GGGGCCTTGTGTCCCTCTTTAGCCCCGGGTCGGCTCAGAAAATCCAGCTCGTAAACAC
CAACGGCAGTTGGCACATCAACAGGACTGCCCTGAACTGCAACGACTCCCTCCAAAC
AGGGTTCTTTGCCGCACTATTCTACAAACACAAATTCAACTCGTCTGGATGCCCAGAG
CGCTTGGCCAGCTGTCGCTCCATCGACAAGTTCGCTCAGGGGTGGGGTCCCCTCACTT
ACACTGAGCCTAACAGCTCGGACCAGAGGCCCTACTGCTGGCACTACGCGCCTCGACC
GTGTGGTATTGTACCCGCGTCTCAGGTGTGCGGTCCAGTGTATTGCTTCACCCCGAGCC
CTGTTGTGGTGGGGACGACCGATCGGTTTGGTGTCCCCACGTATAACTGGGGGGCGAA
CGACTCGGATGTGCTGATTCTCAACAACACGCGGCCGCCGCGAGGCAACTGGTTCGGC
TGTACATGGATGAATGGCACTGGGTTCACCAAGACGTGTGGGGGCCCCCGTGCAACA
TCGGGGGGGCCGGCAACAACACCTTGACCTGCCCCACTGACTGTTTTCGGAAGCACCC
CGAGGCCACCTACGCCAGATGCGGTTCTGGGCCCTGGCTGACACCTAGGTGTATGGTT

Fig. 21G

CATTACCCATATAGGCTCTGGCACTACCCTGCACTGTCAACTTCACCATCTTCAAGGT
TAGGATGTACGTGGGGGGCGTGGAGCACAGGTTCGAAGCCGCATGCAATTGGACTCG
AGGAGAGCGTTGTGACTTGGAGGACAGGGATAGATCAGAGCTTAGCCCGCTGCTGCTG
TCTACAACAGAGTGGCAGATACTGCCCTGTTCCTTCACCACCCTGCCGGCCCTATCCA
CCGGCCTGATCCACCTCCATCAGAACATCGTGGACGTGCAATACCTGTACGGTGTAGG
GTCGGCGGTTGTCTCCCTTGTCATCAAATGGGAGTATGTCCTGTTGCTCTTCCTTCTCCT
GGCAGACGCGCATCTGCGCCTGCTTATGGATGATGCTGCTGATAGCTCAAGCTGAG
GCCGCCTTAGAGAACCTGGTGGTCCTCAATGCGGCGGCCGTGGCCGGGGCGCATGGC
ACTCTTTCCTTCCTTGTGTTCTTCTGTGCTGCCTGGTACATCAAGGGCAGGCTGGTCCC
TGGTGCGGCATACGCCTTCTATGGCGTGTGGCCGCTGCTCCTGCTTCTGCTGGCCTTAC
CACCACGAGCTTATGCCTAGTAA

SEQ ID NO 37 (HCCI41)
GATCCCACAAGCTGTCGTGGACATGGTGGCGGGGGCCCATTGGGGAGTCCTGGCGGG
CCTCGCCTACTATTCCATGGTGGGGAACTGGGCTAAGGTTTTGGTTGTGATGCTACTCT
TTGCCGGCGTCGACGGGCATACCCGCGTGTCAGGAGGGGCAGCAGCCTCCGATACCA
GGGGCCTTGTGTCCCTCTTTAGCCCCGGGTCGGCTCAGAAAATCCAGCTCGTAAACAC
CAACGGCAGTTGGCACATCAACAGGACTGCCCTGAACTGCAACGACTCCCTCCAAAC
AGGGTTCTTTGCCGCACTATTCTACAAACACAAATTCAACTCGTCTGGATGCCCAGAG
CGCTTGGCCAGCTGTCGCTCCATCGACAAGTTCGCTCAGGGGTGGGGTCCCCTCACTT
ACACTGAGCCTAACAGCTCGGACCAGAGGCCCTACTGCTGGCACTACGCGCCTCGACC
GTGTGGTATTGTACCCGCGTCTCAGGTGTGCGGTCCAGTGTATTGCTTCACCCCGAGCC
CTGTTGTGGTGGGGACGACCGATCGGTTTGGTGTCCCCACGTATAACTGGGGGGCGAA
CGACTCGGATGTGCTGATTCTCAACAACACGCGGCCGCCGCGAGGCAACTGGTTCGGC
TGTACATGGATGAATGGCACTGGGTTCACCAAGACGTGTGGGGGCCCCCGTGCAACA
TCGGGGGGGCCGGCAACAACACCTTGACCTGCCCCACTGACTGTTTTCGGAAGCACCC
CGAGGCCACCTACGCCAGATGCGGTTCTGGGCCCTGGCTGACACCTAGGTGTATGGTT
CATTACCCATATAGGCTCTGGCACTACCCTGCACTGTCAACTTCACCATCTTCAAGGT
TAGGATGTACGTGGGGGGCGTGGAGCACAGGTTCGAAGCCGCATGCAATTGGACTCG
AGGAGAGCGTTGTGACTTGGAGGACAGGGATAGATCAGAGCTTAGCCCGCTGCTGCTG
TCTACAACAGAGTGGCAGAGTGGCAGAGCTTAATTAATTAG

SEQ ID NO 39 (HCCI42)
GATCCCACAAGCTGTCGTGGACATGGTGGCGGGGGCCCATTGGGGAGTCCTGGCGGG
CCTCGCCTACTATTCCATGGTGGGGAACTGGGCTAAGGTTTTGGTTGTGATGCTACTCT

Fig. 21H

```
TTGCCGGCGTCGACGGGCATACCCGCGTGTCAGGAGGGGCAGCAGCCTCCGATACCA
GGGGCCTTGTGTCCCTCTTTAGCCCCGGGTCGGCTCAGAAAATCCAGCTCGTAAACAC
CAACGGCAGTTGGCACATCAACAGGACTGCCCTGAACTGCAACGACTCCCTCCAAAC
AGGGTTCTTTGCCGCACTATTCTACAAACACAAATTCAACTCGTCTGGATGCCCAGAG
CGCTTGGCCAGCTGTCGCTCCATCGACAAGTTCGCTCAGGGGTGGGGTCCCCTCACTT
ACACTGAGCCTAACAGCTCGGACCAGAGGCCCTACTGCTGGCACTACGCGCCTCGACC
GTGTGGTATTGTACCCGCGTCTCAGGTGTGCGGTCCAGTGTATTGCTTCACCCCGAGCC
CTGTTGTGGTGGGGACGACCGATCGGTTTGGTGTCCCCACGTATAACTGGGGGGCGAA
CGACTCGGATGTGCTGATTCTCAACAACACGCGGCCGCCGCGAGGCAACTGGTTCGGC
TGTACATGGATGAATGGCACTGGGTTCACCAAGACGTGTGGGGGCCCCCGTGCAACA
TCGGGGGGGCCGGCAACAACACCTTGACCTGCCCCACTGACTGTTTTCGGAAGCACCC
CGAGGCCACCTACGCCAGATGCGGTTCTGGGCCTGGCTGACACCTAGGTGTATGGTT
CATTACCCATATAGGCTCTGGCACTACCCCTGCACTGTCAACTTCACCATCTTCAAGGT
TAGGATGTACGTGGGGGGCGTGGAGCACAGGTTCGAAGCCGCATGCAATTGGACTCG
AGGAGAGCGTTGTGACTTGGAGGACAGGGATAGATCAGAGCTTAGCCCGCTGCTGCTG
TCTACAACAGGTGATCGAGGGCAGACACCATCACCACCATCACTAATAG
```

SEQ ID NO 41 (HCCI43)

```
ATGGTGGGGAACTGGGCTAAGGTTTTGGTTGTGATGCTACTCTTTGCCGGCGTCGACG
GGCATACCCGCGTGTCAGGAGGGGCAGCAGCCTCCGATACCAGGGGCCTTGTGTCCCT
CTTTAGCCCCGGGTCGGCTCAGAAAATCCAGCTCGTAAACACCAACGGCAGTTGGCAC
ATCAACAGGACTGCCCTGAACTGCAACGACTCCCTCCAAACAGGGTTCTTTGCCGCAC
TATTCTACAAACACAAATTCAACTCGTCTGGATGCCCAGAGCGCTTGGCCAGCTGTCG
CTCCATCGACAAGTTCGCTCAGGGGTGGGGTCCCCTCACTTACACTGAGCCTAACAGC
TCGGACCAGAGGCCCTACTGCTGGCACTACGCGCCTCGACCGTGTGGTATTGTACCCG
CGTCTCAGGTGTGCGGTCCAGTGTATTGCTTCACCCCGAGCCCTGTTGTGGTGGGGAC
GACCGATCGGTTTGGTGTCCCCACGTATAACTGGGGGGCGAACGACTCGGATGTGCTG
ATTCTCAACAACACGCGGCCGCCGCGAGGCAACTGGTTCGGCTGTACATGGATGAATG
GCACTGGGTTCACCAAGACGTGTGGGGGCCCCCGTGCAACATCGGGGGGGCCGGCA
ACAACACCTTGACCTGCCCCACTGACTGTTTTCGGAAGCACCCCGAGGCCACCTACGC
CAGATGCGGTTCTGGGCCTGGCTGACACCTAGGTGTATGGTTCATTACCCATATAGG
CTCTGGCACTACCCCTGCACTGTCAACTTCACCATCTTCAAGGTTAGGATGTACGTGGG
GGGCGTGGAGCACAGGTTCGAAGCCGCATGCAATTGGACTCGAGGAGAGCGTTGTGA
CTTGGAGGACAGGGATAGATCAGAGCTTAGCCCGCTGCTGCTGTCTACAACAGAGTGG
CAGAGCTTAATTAATTAG
```

Fig. 21I

SEQ ID NO 43 (HCCI44)

ATGGTGGGGAACTGGGCTAAGGTTTTGGTTGTGATGCTACTCTTTGCCGGCGTCGACG
GGCATACCCGCGTGTCAGGAGGGGCAGCAGCCTCCGATACCAGGGGCCTTGTGTCCCT
CTTTAGCCCCGGGTCGGCTCAGAAAATCCAGCTCGTAAACACCAACGGCAGTTGGCAC
ATCAACAGGACTGCCCTGAACTGCAACGACTCCTCCAAACAGGGTTCTTTGCCGCAC
TATTCTACAAACACAAATTCAACTCGTCTGGATGCCCAGAGCGCTTGGCCAGCTGTCG
CTCCATCGACAAGTTCGCTCAGGGGTGGGGTCCCTCACTTACACTGAGCCTAACAGC
TCGGACCAGAGGCCCTACTGCTGGCACTACGCGCCTCGACCGTGTGGTATTGTACCCG
CGTCTCAGGTGTGCGGTCCAGTGTATTGCTTCACCCCGAGCCCTGTTGTGGTGGGGAC
GACCGATCGGTTTGGTGTCCCCACGTATAACTGGGGGCGAACGACTCGGATGTGCTG
ATTCTCAACAACACGCGGCCGCCGCGAGGCAACTGGTTCGGCTGTACATGGATGAATG
GCACTGGGTTCACCAAGACGTGTGGGGGCCCCCGTGCAACATCGGGGGGGCCGGCA
ACAACACCTTGACCTGCCCCACTGACTGTTTTCGGAAGCACCCCGAGGCCACCTACGC
CAGATGCGGTTCTGGGCCTGGCTGACACCTAGGTGTATGGTTCATTACCCATATAGG
CTCTGGCACTACCCCTGCACTGTCAACTTCACCATCTTCAAGGTTAGGATGTACGTGGG
GGGCGTGGAGCACAGGTTCGAAGCCGCATGCAATTGGACTCGAGGAGAGCGTTGTGA
CTTGGAGGACAGGGATAGATCAGAGCTTAGCCCGCTGCTGCTGTCTACAACAGGTGAT
CGAGGGCAGACACCATCACCACCATCACTAATAG

SEQ ID NO 45 (HCCL64)

ATGGTGGCGGGGGCCCATTGGGGAGTCCTGGCGGGCCTCGCCTACTATTCCATGGTGG
GGAACTGGGCTAAGGTTTTGGTTGTGATGCTACTCTTTGCCGGCGTCGACGGGCATAC
CCGCGTGTCAGGAGGGGCAGCAGCCTCCGATACCAGGGGCCTTGTGTCCCTCTTTAGC
CCCGGGTCGGCTCAGAAAATCCAGCTCGTAAACACCAACGGCAGTTGGCACATCAAC
AGGACTGCCCTGAACTGCAACGACTCCTCCAAACAGGGTTCTTTGCCGCACTATTCT
ACAAACACAAATTCAACTCGTCTGGATGCCCAGAGCGCTTGGCCAGCTGTCGCTCCAT
CGACAAGTTCGCTCAGGGGTGGGGTCCCTCACTTACACTGAGCCTAACAGCTCGGAC
CAGAGGCCCTACTGCTGGCACTACGCGCCTCGACCGTGTGGTATTGTACCCGCGTCTC
AGGTGTGCGGTCCAGTGTATTGCTTCACCCCGAGCCCTGTTGTGGTGGGGACGACCGA
TCGGTTTGGTGTCCCCACGTATAACTGGGGGCGAACGACTCGGATGTGCTGATTCTC
AACAACACGCGGCCGCCGCGAGGCAACTGGTTCGGCTGTACATGGATGAATGGCACT
GGGTTCACCAAGACGTGTGGGGGCCCCCGTGCAACATCGGGGGGGCCGGCAACAAC
ACCTTGACCTGCCCCACTGACTGTTTTCGGAAGCACCCCGAGGCCACCTACGCCAGAT
GCGGTTCTGGGCCTGGCTGACACCTAGGTGTATGGTTCATTACCCATATAGGCTCTGG
CACTACCCCTGCACTGTCAACTTCACCATCTTCAAGGTTAGGATGTACGTGGGGGGCG

Fig. 21J

TGGAGCACAGGTTCGAAGCCGCATGCAATTGGACTCGAGGAGAGCGTTGTGACTTGGA
GGACAGGGATAGATCAGAGCTTAGCCCGCTGCTGCTGTCTACAACAGAGTGGCAGATA
CTGCCCTGTTCCTTCACCACCCTGCCGGCCCTATCCACCGGCCTGATCCACCTCCATCA
GAACATCGTGGACGTGCAATACCTGTACGGTGTAGGGTCGGCGGTTGTCTCCCTTGTC
ATCAAATGGGAGTATGTCCTGTTGCTCTTCCTTCTCCTGGCAGACGCGCGCATCTGCGC
CTGCTTATGGATGATGCTGCTGATAGCTCAAGCTGAGGCCGCCTTAGAGAACCTGGTG
GTCCTCAATGCGGCGGCCGTGGCCGGGGCGCATGGCACTCTTTCCTTCCTTGTGTTCTT
CTGTGCTGCCTGGTACATCAAGGGCAGGCTGGTCCTGGTGCGGCATACGCCTTCTAT
GGCGTGTGGCCGCTGCTCCTGCTTCTGCTGGCCTTACCACCACGAGCTTATGCCTAGTAA

SEQ ID NO 47 (HCCI65)

AATTTGGGTAAGGTCATCGATACCCTTACATGCGGCTTCGCCGACCTCGTGGGGTACA
TTCCGCTCGTCGGCGCCCCCTAGGGGGCGCTGCCAGGGCCCTGGCGCATGGCGTCCG
GGTTCTGGAGGACGGCGTGAACTATGCAACAGGGAATTTGCCCGGTTGCTCTTTCTCT
ATCTTCCTCTTGGCTTTGCTGTCCTGTCTGACCGTTCCAGCTTCCGCTTATGAAGTGCG
CAACGTGTCCGGGATGTACCATGTCACGAACGACTGCTCCAACTCAAGCATTGTGTAT
GAGGCAGCGGACATGATCATGCACACCCCGGGTGCGTGCCCTGCGTTCGGGAGAAC
AACTCTTCCCGCTGCTGGGTAGCGCTCACCCCCACGCTCGCAGCTAGGAACGCCAGCG
TCCCCACCACGACAATACGACGCCACGTCGATTGCTCGTTGGGGCGGCTGCTTTCTG
TTCCGCTATGTACGTGGGGGACCTCTGCGGATCTGTCTTCCTCGTCTCCCAGCTGTTCA
CCATCTCGCCTCGCCGGCATGAGACGGTGCAGGACTGCAATTGCTCAATCTATCCCGG
CCACATAACGGGTCACCGTATGGCTTGGGATATGATGATGAACTGGTCGCCTACAACG
GCCCTGGTGGTATCGCAGCTGCTCCGGATCCCACAAGCTGTCGTGGACATGGTGGCGG
GGGCCCATTGGGGAGTCCTGGCGGGCCTCGCCTACTATTCCATGGTGGGGAACTGGGC
TAAGGTTTTGGTTGTGATGCTACTCTTTGCCGGCGTCGACGGGCATACCCGCGTGTCAG
GAGGGGCAGCAGCCTCCGATACCAGGGGCCTTGTGTCCCTCTTTAGCCCCGGGTCGGC
TCAGAAAATCCAGCTCGTAAACACCAACGGCAGTTGGCACATCAACAGGACTGCCCT
GAACTGCAACGACTCCCTCCAAACAGGGTTCTTTGCCGCACTATTCTACAAACACAAA
TTCAACTCGTCTGGATGCCCAGAGCGCTTGGCCAGCTGTCGCTCCATCGACAAGTTCG
CTCAGGGGTGGGGTCCCCTCACTTACACTGAGCCTAACAGCTCGGACCAGAGGCCCTA
CTGCTGGCACTACGCGCCTCGACCGTGTGGTATTGTACCCGCGTCTCAGGTGTGCGGT
CCAGTGTATTGCTTCACCCCGAGCCCTGTTGTGGTGGGGACGACCGATCGGTTTGGTGT
CCCCACGTATAACTGGGGGGCGAACGACTCGGATGTGCTGATTCTCAACAACACGCGG
CCGCCGCGAGGCAACTGGTTCGGCTGTACATGGATGAATGGCACTGGGTTCACCAAGA
CGTGTGGGGGCCCCCGTGCAACATCGGGGGGGCCGGCAACAACACCTTGACCTGCC

Fig. 21K

CCACTGACTGTTTTCGGAAGCACCCCGAGGCCACCTACGCCAGATGCGGTTCTGGGCC
CTGGCTGACACCTAGGTGTATGGTTCATTACCCATATAGGCTCTGGCACTACCCCTGCA
CTGTCAACTTCACCATCTTCAAGGTTAGGATGTACGTGGGGGGCGTGGAGCACAGGTT
CGAAGCCGCATGCAATTGGACTCGAGGAGAGCGTTGTGACTTGGAGGACAGGGATAG
ATCAGAGCTTAGCCCGCTGCTGCTGTCTACAACAGAGTGGCAGATACTGCCCTGTTCC
TTCACCACCCTGCCGGCCCTATCCACCGGCCTGATCCACCTCCATCAGAACATCGTGG
ACGTGCAATACCTGTACGGTGTAGGGTCGGCGGTTGTCTCCCTTGTCATCAAATGGGA
GTATGTCCTGTTGCTCTTCCTTCTCCTGGCAGACGCGCGCATCTGCGCCTGCTTATGGA
TGATGCTGCTGATAGCTCAAGCTGAGGCCGCCTTAGAGAACCTGGTGGTCCTCAATGC
GGCGGCCGTGGCCGGGGCGCATGGCACTCTTTCCTTCCTTGTGTTCTTCTGTGCTGCCT
GGTACATCAAGGGCAGGCTGGTCCCTGGTGCGGCATACGCCTTCTATGGCGTGTGGCC
GCTGCTCCTGCTTCTGCTGGCCTTACCACCACGAGCTTATGCCTAGTAAGCTT

SEQ ID NO 49 (HCC166)

ATGAGCACGAATCCTAAACCTCAAAGAAAAACCAAACGTAACACCAACCGCCGCCCA
CAGGACGTCAAGTTCCCGGGCGGTGGTCAGATCGTTGGTGGAGTTTACCTGTTGCCGC
GCAGGGGCCCCAGGTTGGGTGTGCGCGCGACTAGGAAGACTTCCGAGCGGTCGCAAC
CTCGTGGGAGGCGACAACCTATCCCCAAGGCTCGCCGACCCGAGGGTAGGGCCTGGG
CTCAGCCCGGGTACCCTTGGCCCCTCTATGGCAATGAGGGCATGGGGTGGGCAGGATG
GCTCCTGTCACCCCGCGGCTCTCGGCCTAGTTGGGGCCCTACAGACCCCCGGCGTAGG
TCGCGTAATTTGGGTAAGGTCATCGATACCCTTACATGCGGCTTCGCCGACCTCGTGG
GGTACATTCCGCTCGTCGGCGCCCCCTAGGGGGCGCTGCCAGGGCCCTGGCGCATGG
CGTCCGGGTTCTGGAGGACGGCGTGAACTATGCAACAGGGAATTTGCCCGGTTGCTCT
TTCTCTATCTTCCTCTTGGCTTTGCTGTCCTGTCTGACCGTTCCAGCTTCCGCTTATGAA
GTGCGCAACGTGTCCGGGATGTACCATGTCACGAACGACTGCTCCAACTCAAGCATTG
TGTATGAGGCAGCGGACATGATCATGCACACCCCGGGTGCGTGCCCTGCGTTCGGGA
GAACAACTCTTCCCGCTGCTGGGTAGCGCTCACCCCACGCTCGCAGCTAGGAACGCC
AGCGTCCCACCACGACAATACGACGCCACGTCGATTTGCTCGTTGGGGCGGCTGCTT
TCTGTTCCGCTATGTACGTGGGGGACCTCTGCGGATCTGTCTTCCTCGTCTCCCAGCTG
TTCACCATCTCGCCTCGCCGGCATGAGACGGTGCAGGACTGCAATTGCTCAATCTATC
CCGGCCACATAACGGGTCACCGTATGGCTTGGGATATGATGATGAACTGGTCGCCTAC
AACGGCCCTGGTGGTATCGCAGCTGCTCCGGATCCCACAAGCTGTCGTGGACATGGTG
GCGGGGGCCCATTGGGGAGTCCTGGCGGGCCTCGCCTACTATTCCATGGTGGGGAACT
GGGCTAAGGTTTTGGTTGTGATGCTACTCTTTGCCGGCGTCGACGGGCATACCCGCGT
GTCAGGAGGGGCAGCAGCCTCCGATACCAGGGGCCTTGTGTCCCTCTTTAGCCCCGGG

Fig. 21L

```
TCGGCTCAGAAAATCCAGCTCGTAAACACCAACGGCAGTTGGCACATCAACAGGACT
GCCCTGAACTGCAACGACTCCCTCCAAACAGGGTTCTTTGCCGCACTATTCTACAAAC
ACAAATTCAACTCGTCTGGATGCCCAGAGCGCTTGGCCAGCTGTCGCTCCATCGACAA
GTTCGCTCAGGGGTGGGGTCCCCTCACTTACACTGAGCCTAACAGCTCGGACCAGAGG
CCCTACTGCTGGCACTACGCGCCTCGACCGTGTGGTATTGTACCCGCGTCTCAGGTGT
GCGGTCCAGTGTATTGCTTCACCCCGAGCCTGTTGTGGTGGGACGACCGATCGGTT
TGGTGTCCCCACGTATAACTGGGGGCGAACGACTCGGATGTGCTGATTCTCAACAAC
ACGCGGCCGCCGCGAGGCAACTGGTTCGGCTGTACATGGATGAATGGCACTGGGTTCA
CCAAGACGTGTGGGGGCCCCCGTGCAACATCGGGGGGGCCGGCAACAACACCTTGA
CCTGCCCCACTGACTGTTTTCGGAAGCACCCGAGGCCACCTACGCCAGATGCGGTTC
TGGGCCCTGGCTGACACCTAGGTGTATGGTTCATTACCCATATAGGCTCTGGCACTAC
CCCTGCACTGTCAACTTCACCATCTTCAAGGTTAGGATGTACGTGGGGGGCGTGGAGC
ACAGGTTCGAAGCCGCATGCAATTGGACTCGAGGAGAGCGTTGTGACTTGGAGGACA
GGGATAGATCAGAGCTTAGCCCGCTGCTGCTGTCTACAACAGAGTGGCAGATACTGCC
CTGTTCCTTCACCACCCTGCCGGCCCTATCCACCGGCCTGATCCACCTCCATCAGAAC
ATCGTGGACGTGCAATACCTGTACGGTGTAGGGTCGGCGGTTGTCTCCCTTGTCATCA
AATGGGAGTATGTCCTGTTGCTCTTCCTTCTCCTGGCAGACGCGCGCATCTGCGCCTGC
TTATGGATGATGCTGCTGATAGCTCAAGCTGAGGCCGCCTTAGAGAACCTGGTGGTCC
TCAATGCGGCGGCCGTGGCCGGGGCGCATGGCACTCTTTCCTTCCTTGTGTTCTTCTGT
GCTGCCTGGTACATCAAGGGCAGGCTGGTCCCTGGTGCGGCATACGCCTTCTATGGCG
TGTGGCCGCTGCTCCTGCTTCTGCTGGCCTTACCACCACGAGCTTATGCCTAGTAA
```

Fig. 22

OD measured at 450 nm
construct

| Fraction | volume | dilution | 39<br>Type<br>1b | 40<br>Type<br>1b | 62<br>Type<br>3a | 63<br>Type<br>5a |
|---|---|---|---|---|---|---|
| START | 23 ml | 1/20 | 2.517 | 1.954 | 1.426 | 1.142 |
| FLOW THROUGH | 23 ml | 1/20 | 0.087 | 0.085 | 0.176 | 0.120 |
| 1 | 0.4 ml | 1/200 | 0.102 | 0.051 | 0.048 | 0.050 |
| 2 | | | 0.396 | 0.550 | 0.090 | 0.067 |
| 3 | | | 2.627 | 2.603 | 2.481 | 2.372 |
| 4 | | | 3 | 2.967 | 3 | 2.694 |
| 5 | | | 3 | 2.810 | 2.640 | 2.154 |
| 6 | | | 2.694 | 2.499 | 1.359 | 1.561 |
| 7 | | | 2.408 | 2.481 | 0.347 | 1.390 |
| 8 | | | 2.176 | 1.970 | 1.624 | 0.865 |
| 9 | | | 1.461 | 1.422 | 0.887 | 0.604 |
| 10 | | | 1.286 | 0.926 | 0.543 | 0.519 |
| 11 | | | 0.981 | 0.781 | 0.294 | 0.294 |
| 12 | | | 0.812 | 0.650 | 0.249 | 0.199 |
| 13 | | | 0.373 | 0.432 | 0.239 | 0.209 |
| 14 | | | 0.653 | 0.371 | 0.145 | 0.184 |
| 15 | | | 0.441 | 0.348 | 0.151 | 0.151 |
| 16 | | | 0.321 | 0.374 | 0.098 | 0.106 |
| 17 | | | 0.525 | 0.186 | 0.099 | 0.108 |
| 18 | | | 0.351 | 0.171 | 0.083 | 0.090 |
| 19 | | | 0.192 | 0.164 | 0.084 | 0.087 |

Fig. 24

|  |  |  | OD measured at 450 nm construct | | | |
|---|---|---|---|---|---|---|
| Fraction | volume | dilution | 39 Type 1b | 40 Type 1b | 62 Type 3a | 63 Type 5a |
| 20 | 250 µl | 1/200 | 0.072 | 0.130 | 0.096 | 0.051 |
| 21 |  |  | 0.109 | 0.293 | 0.084 | 0.052 |
| 22 |  |  | 0.279 | 0.249 | 0.172 | 0.052 |
| 23 |  |  | 0.093 | 0.151 | 0.297 | 0.054 |
| 24 |  |  | 0.080 | 0.266 | 0.438 | 0.056 |
| 25 |  |  | 0.251 | 0.100 | 0.457 | 0.048 |
| 26 |  |  | 3 | 1.649 | 0.722 | 0.066 |
| 27 |  |  | 3 | 3 | 2.528 | 0.889 |
| 28 |  |  | 3 | 3 | 3 | 2.345 |
| 29 |  |  | 3 | 3 | 2.849 | 2.580 |
| 30 |  |  | 2.227 | 1.921 | 1.424 | 1.333 |
| 31 |  |  | 0.263 | 0.415 | 0.356 | 0.162 |
| 32 |  |  | 0.071 | 0.172 | 0.154 | 0.064 |
| 33 |  |  | 0.103 | 0.054 | 0.096 | 0.057 |
| 34 |  |  | 0.045 | 0.045 | 0.044 | 0.051 |
| 35 |  |  | 0.043 | 0.047 | 0.045 | 0.046 |
| 36 |  |  | 0.045 | 0.045 | 0.049 | 0.040 |
| 37 |  |  | 0.045 | 0.047 | 0.046 | 0.048 |
| 38 |  |  | 0.046 | 0.048 | 0.047 | 0.057 |
| 39 |  |  | 0.045 | 0.048 | 0.050 | 0.057 |
| 40 |  |  | 0.046 | 0.049 | 0.048 | 0.049 |

Lane 1: Crude Lysate
Lane 2: Flow through Lentil Chromatography
Lane 3: Wash with EMPIGEN Lentil Chromatography
Lane 4: Eluate Lentil Chromatography
Lane 5: Flow through during concentration lentil eluate
Lane 6: Pool of E1 after Size Exclusion Chromatography

SILVER STAIN OF PURIFIED E2

1. 30 mM IMIDAZOLE WASH Ni-IMAC
2. 0.5 ug E2

| No. | Ret. (ml) | Peak start (ml) | Peak end (ml) | Dur (ml) | Area (ml*mAU) | Height (mAU) |
|---|---|---|---|---|---|---|
| 1 | -0.45 | -0.46 | -0.43 | 0.04 | 0.0976 | 4.579 |
| 2 | 1.55 | 0.75 | 3.26 | 2.51 | 796.4167 | 889.377 |
| 3 | 3.27 | 3.26 | 3.31 | 0.05 | 0.0067 | 0.224 |
| 4 | 3.33 | 3.32 | 3.33 | 0.02 | 0.0002 | 0.018 |

Total number of detected peaks = 4
Total Area above baseline = 0.796522 ml*AU
Total area in evaluated peaks = 0.796521 ml*AU
Ratio peak area / total area = 0.999999
Total peak duration = 2.613583 ml

Figure 7:
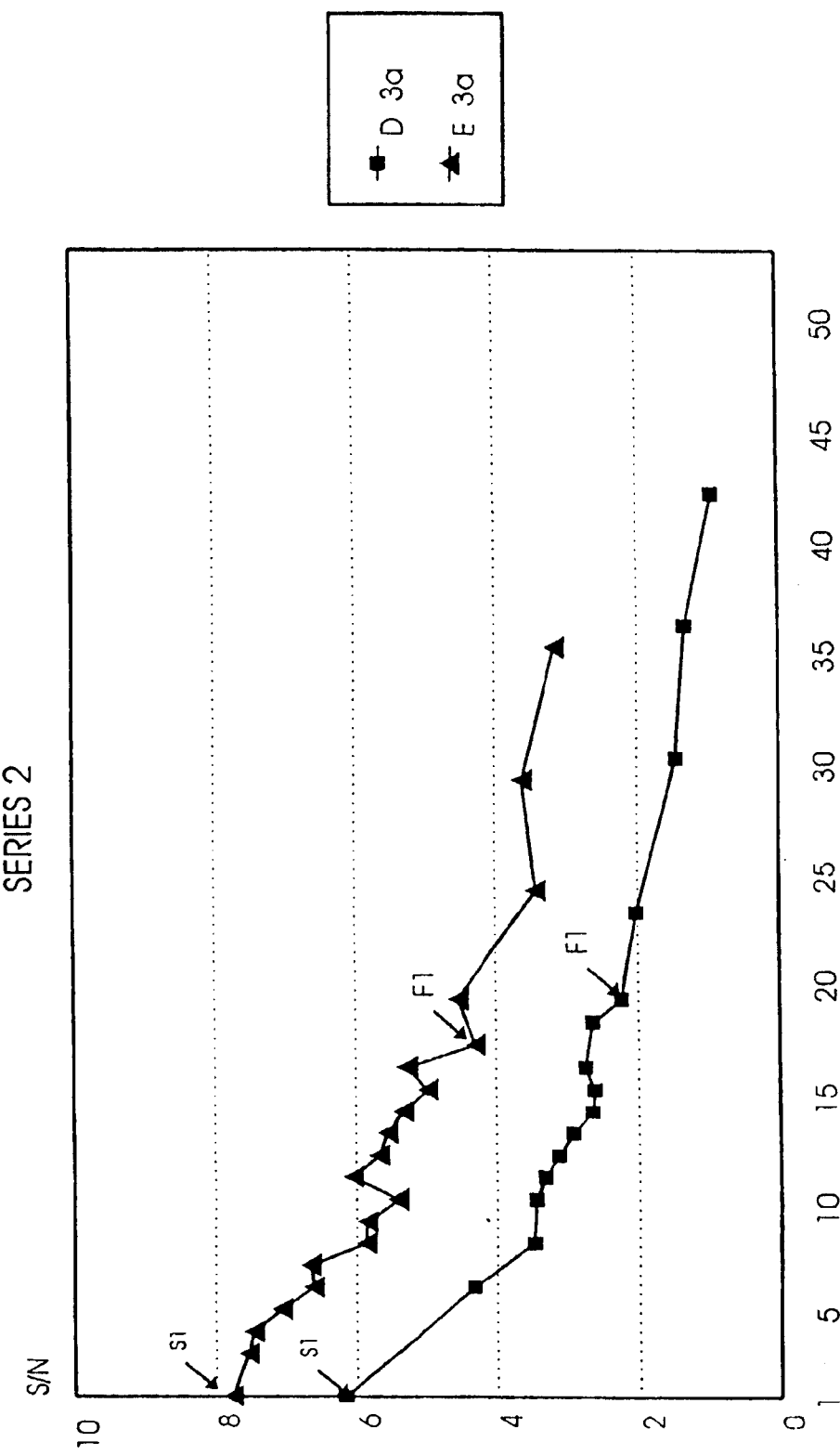
Figure 8:
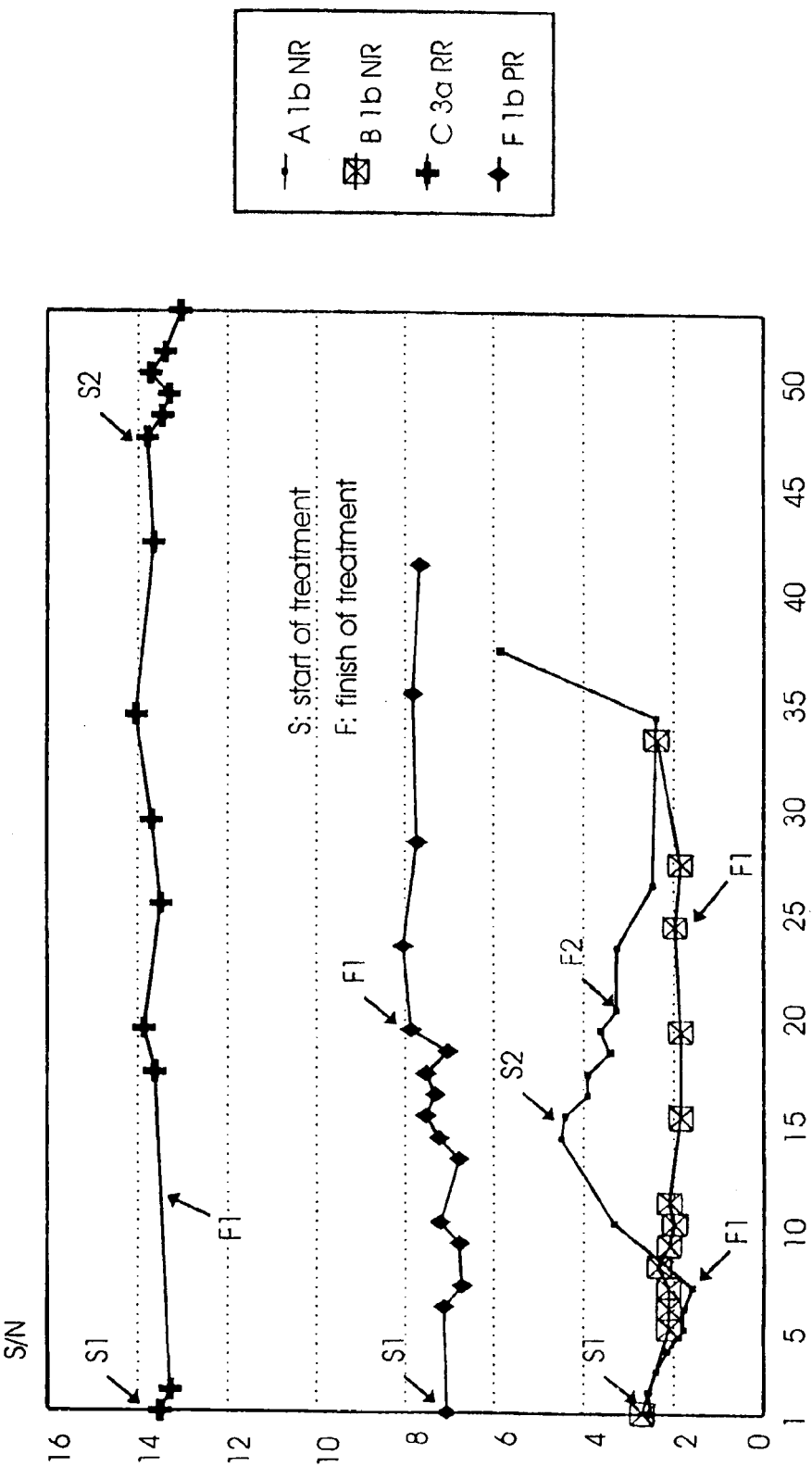
Figures 1, 35A:
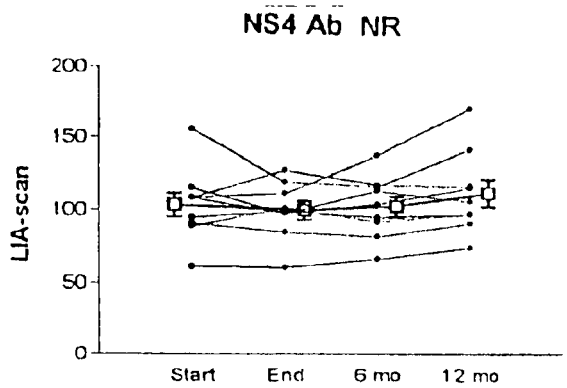
Figures 2, 35A:
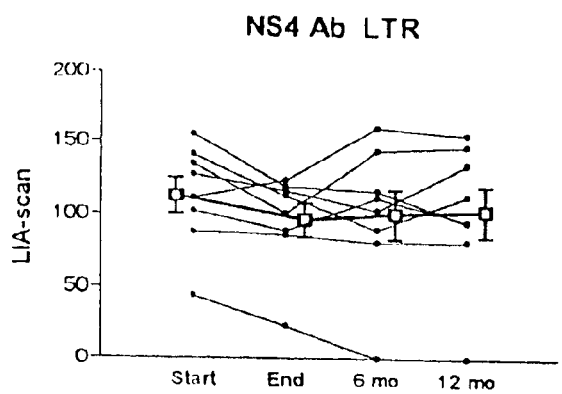
Figures 3, 35A:
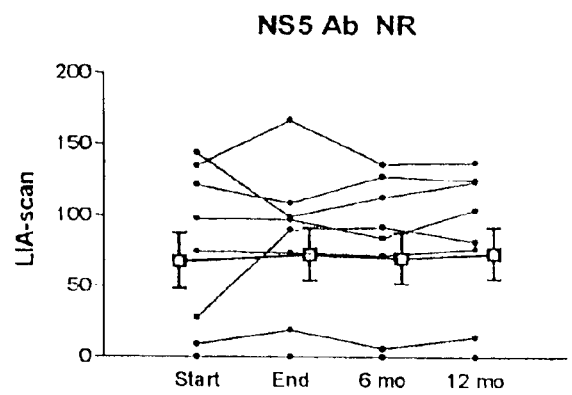
Figures 4, 35A:
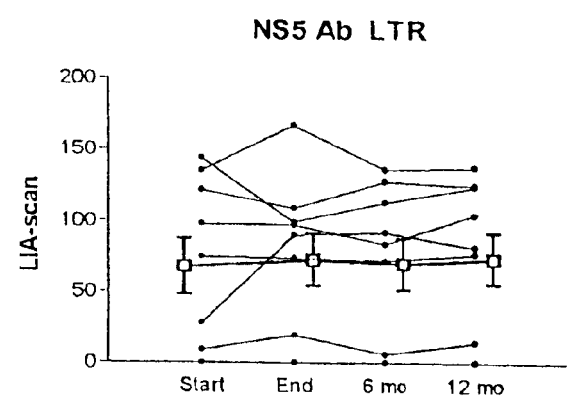
Figures 5, 35A:
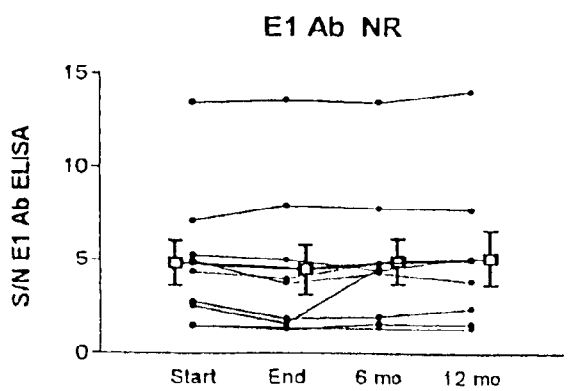
Figures 6, 35A:
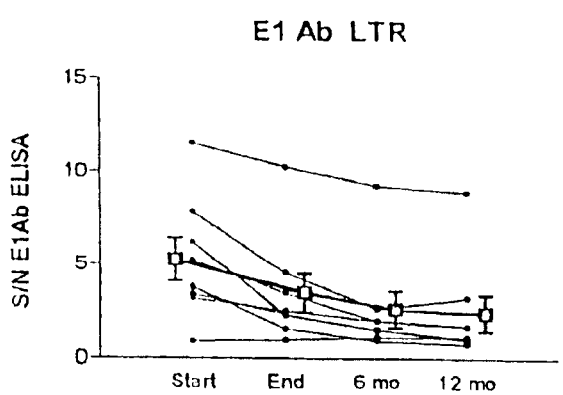

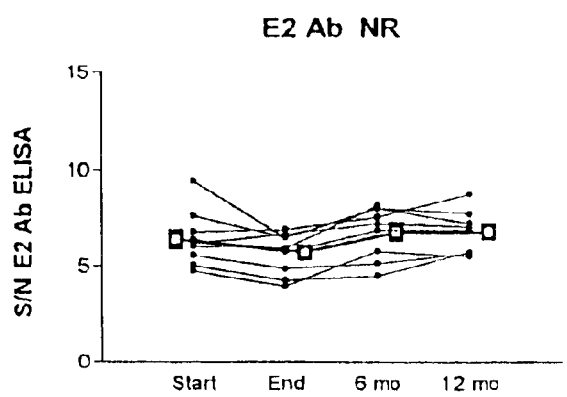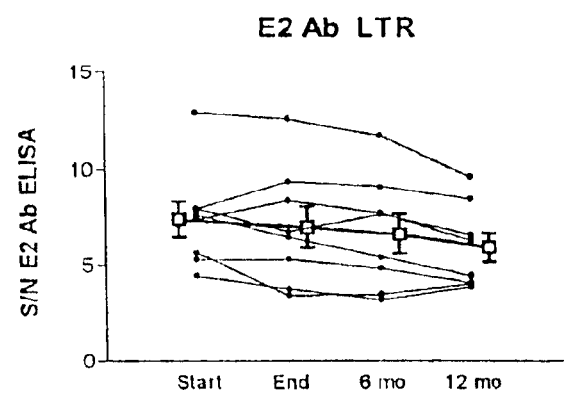
Fig. 35A-7　　　　　Fig. 35A-8

Figures 1, 35B:
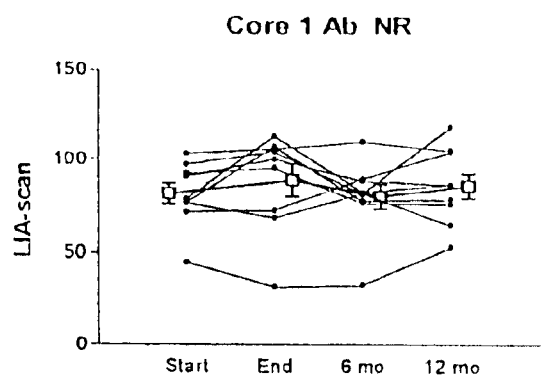
Figures 2, 35B:
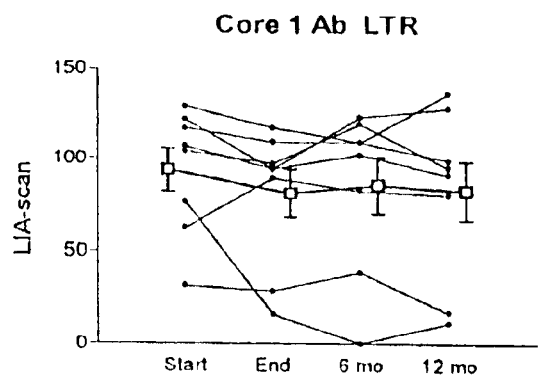
Figures 3, 35B:
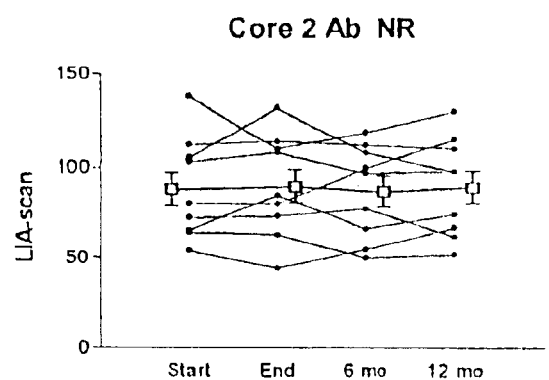
Figures 4, 35B:
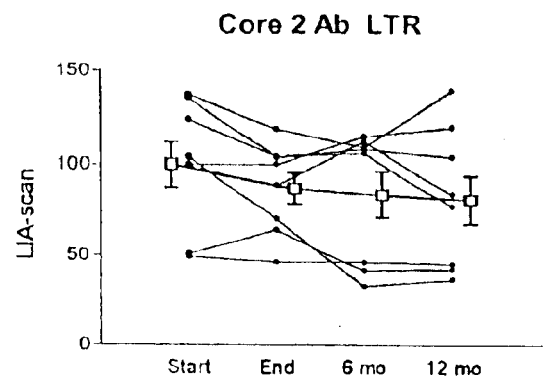
Figures 5, 35B:
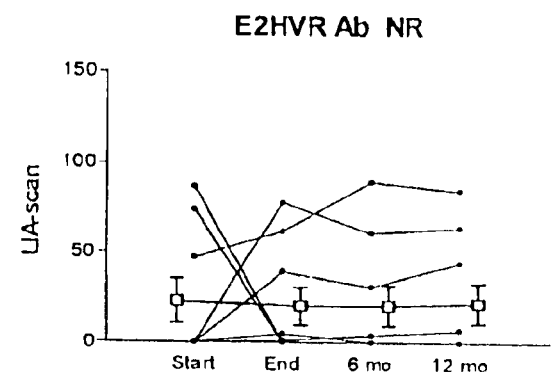
Figures 6, 35B:
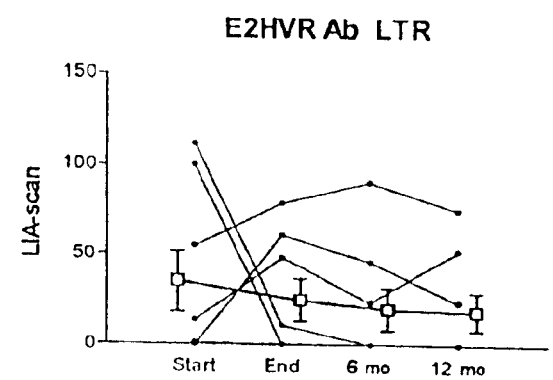

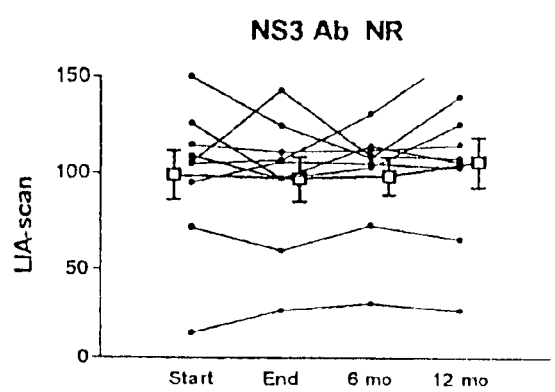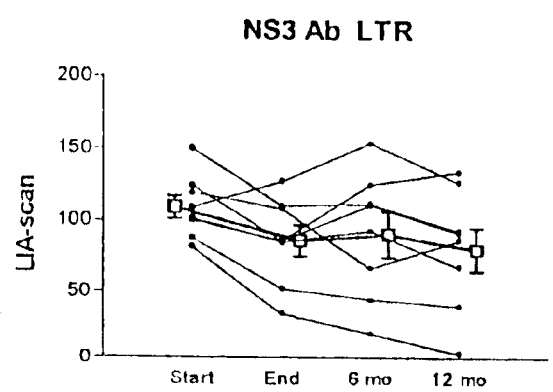
Fig. 35B-7   Fig. 35B-8

E1 Ab

E2 Ab

Long Term Responders

Type 3a

Non Responders

Type 1b

Relative Map Positions of anti-E2 monoclonal antibodies

Figure 39:
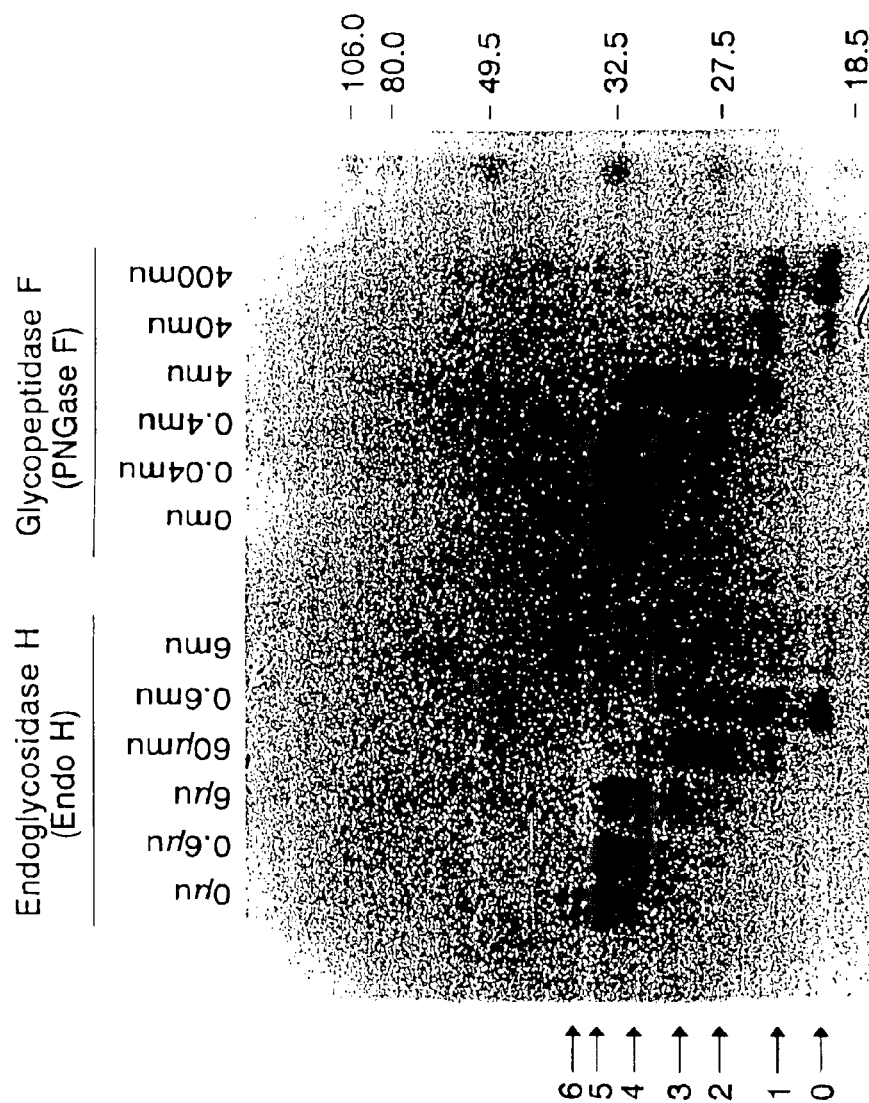

Fig.39 PARTIAL DEGLYCOSYLATION OF HCV E1 ENVELOPE PROTEIN

Fig. 41 *In Vitro* Mutagenesis of HCV E1 glycoprotein

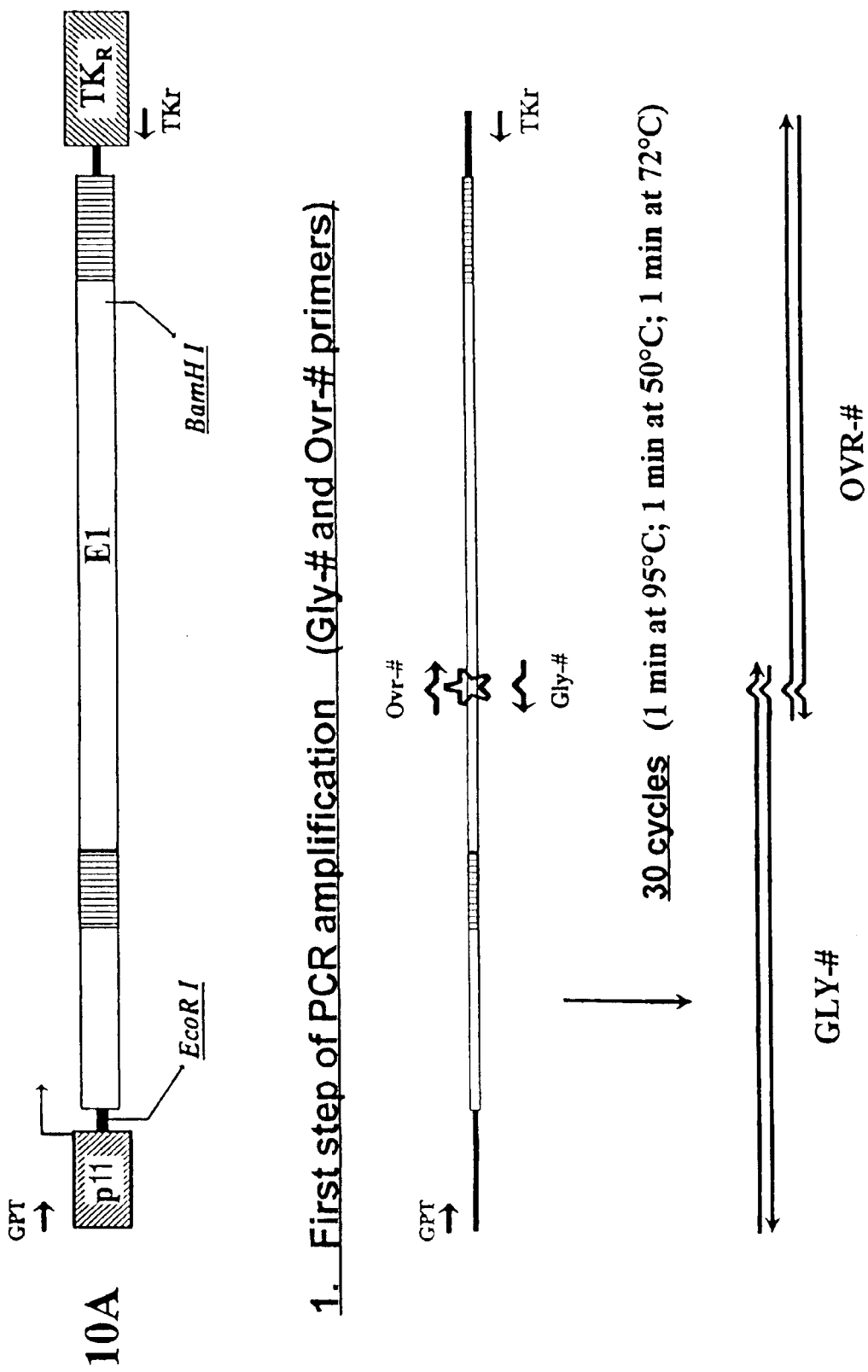
Fig. 42A *In Vitro* Mutagenesis of HCV E1 glycoprotein

Fig. 43 *In Vitro* Mutagenesis of HCV E1 glycoprotein

PURIFIED HEPATITIS C VIRUS ENVELOPE PROTEINS FOR DIAGNOSTIC AND THERAPEUTIC USE

The present application is continuation of U.S. application Ser. No. 08/928,017, filed Sep. 11, 1997 (now abandoned), which is a divisional of U.S. application Ser. No. 08/612,973, filed Mar. 11, 1996 (now U.S. Pat. No. 6,150,134, issued Nov. 21, 2000), which is a 371 U.S. National Phase of PCT/EP95/03031,filed Jul. 31, 1995, which designated the U.S., the entire contents of each of which are hereby incorporated by reference.

FIELD OF THE INVENTION

The present invention relates to the general fields of recombinant protein expression, purification of recombinant proteins, synthetic peptides, diagnosis of HCV infection, prophylactic treatment against HCV infection and to the prognosis/monitoring of the clinical efficiency of treatment of an individual with chronic hepatitis, or the prognosis/monitoring of natural disease.

More particularly, the present invention relates to purification methods for hepatitis C virus envelope proteins, the use in diagnosis, prophylaxis or therapy of HCV envelope proteins purified according to the methods described in the present invention, the use of single or specific oligomeric E1 and/or E2 and/or E1/E2 envelope proteins in assays for monitoring disease, and/or diagnosis of disease, and/or treatment of disease. The invention also relates to epitopes of the E1 and/or E2 envelope proteins and monoclonal antibodies thereto, as well their use in diagnosis, prophylaxis or treatment.

BACKGROUND OF THE INVENTION

The E2 protein purified from cell lysates according to the methods described in the present invention reacts with approximately 95% of patient sera. This reactivity is similar to the reactivity obtained with E2 secreted from CHO cells (Spaete et al., 1992). However, the intracellularly expressed form of E2 may more closely resemble the native viral envelope protein because it contains high mannose carbohydrate motifs, whereas the E2 protein secreted from CHO cells is further modified with galactose and sialic acid sugar moieties. When the aminoterminal half of E2 is expressed in the baculovirus system, only about 13 to 21% of sera from several patient groups can be detected (Inoue et al., 1992). After expression of E2 from *E. coli*, the reactivity of HCV sera was even lower and ranged from 14 (Yokosuka et al., 1992) to 17% (Mita et al., 1992).

About 75% of HCV sera (and 95% of chronic patients) are anti-E1 positive using the purified, vaccinia-expressed recombinant E1 protein of the present invention, in sharp contrast with the results of Kohara et al. (1992) and Hsu et al. (1993). Kohara et al. used a vaccinia-virus expressed E1 protein and detected anti-E1 antibodies in 7 to 23% of patients, while Hsu et al. only detected 14/50 (28%) sera using baculovirus-expressed E1.

These results show that not only a good expression system but also a good purification protocol are required to reach a high reactivity of the envelope proteins with human patient sera. This can be obtained using the proper expression system and/or purification protocols of the present invention which guarantee the conservation of the natural folding of the protein and the purification protocols of the present invention which guarantee the elimination of contaminating proteins and which preserve the conformation, and thus the reactivity of the HCV envelope proteins. The amounts of purified HCV envelope protein needed for diagnostic screening assays are in the range of grams per year. For vaccine purposes, even higher amounts of envelope protein would be needed. Therefore, the vaccinia virus system may be used for selecting the best expression constructs and for limited upscaling, and large-scale expression and purification of single or specific oligomeric envelope proteins containing high-mannose carbohydrates may be achieved when expressed from several yeast strains. In the case of hepatitis B for example, manufacturing of HBsAg from mammalian cells was much more costly compared with yeast-derived hepatitis B vaccines.

AIMS OF THE INVENTION

It is an aim of the present invention to provide a new purification method for recombinantly expressed E1 and/or E2 and/or E1/E2 proteins such that said recombinant proteins are directly usable for diagnostic and vaccine purposes as single or specific oligomeric recombinant proteins free from contaminants instead of aggregates.

It is another aim of the present invention to provide compositions comprising purified (single or specific oligomeric) recombinant E1 and/or E2 and/or E1/E2 glycoproteins comprising conformational epitopes from the E1 and/or E2 domains of HCV.

It is yet another aim of the present invention to provide novel recombinant vector constructs for recombinantly expressing E1 and/or E2 and/or E1/E2 proteins, as well as host cells transformed with said vector constructs.

It is also an aim of the present invention to provide a method for producing and purifying recombinant HCV E1 and/or E2 and/or E1/E2 proteins.

It is also an aim of the present invention to provide diagnostic and immunogenic uses of the recombinant HCV E1 and/or E2 and/or E1/E2 proteins of the present invention, as well as to provide kits for diagnostic use, vaccines or therapeutics comprising any of the recombinant HCV E1 and/or E2 and/or E1/E2 proteins of the present invention.

It is further an aim of the present invention to provide for a new use of E1, E2, and/or E1/E2 proteins, or suitable parts thereof, for monitoring/prognosing the response to treatment of patients (e.g. with interferon) suffering from HCV infection.

It is also an aim of the present invention to provide for the use of the recombinant E1, E2, and/or E1/E2 proteins of the present invention in HCV screening and confirmatory antibody tests.

It is also an aim of the present invention to provide E1 and/or 2 peptides which can be used for diagnosis of HCV infection and for raising antibodies. Such peptides may also be used to isolate human monoclonal antibodies.

It is also an aim of the present invention to provide monoclonal antibodies, more particularly human monoclonal antibodies or mouse monoclonal antibodies which are humanized, which react specifically with E1 and/or E2 epitopes, either comprised in peptides or conformational epitopes comprised in recombinant proteins.

It is also an aim of the present invention to provide possible uses of anti-E1 or anti-E2 monoclonal antibodies for HCV antigen detection or for therapy of chronic HCV infection.

It is also an aim of the present invention to provide kits for monitoring/prognosing the response to treatment (e.g. with interferon) of patients suffering from HCV infection or monitoring/prognosing the outcome of the disease.

All the aims of the present invention are considered to have been met by the embodiments as set out below.

DEFINITIONS

The following definitions serve to illustrate the different terms and expressions used in the present invention.

The term 'hepatitis C virus single envelope protein' refers to a polypeptide or an analogue thereof (e.g. mimotopes) comprising an amino acid sequence (and/or amino acid analogues) defining at least one HCV epitope of either the E1 or the E2 region. These single envelope proteins in the broad sense of the word may be both monomeric or homooligomeric forms of recombinantly expressed envelope proteins. Typically, the sequences defining the epitope correspond to the amino acid sequence of either the E1 or the E2 region of HCV (either identically or via substitution of analogues of the native amino acid residue that do not destroy the epitope). In general, the epitope-defining sequence will be 3 or more amino acids in length, more typically, 5 or more amino acids in length, more typically 8 or more amino acids in length, and even more typically 10 or more amino acids in length. With respect to conformational epitopes, the length of the epitope-defining sequence can be subject to wide variations, since it is believed that these epitopes are formed by the three-dimensional shape of the antigen (e.g. folding). Thus, the amino acids defining the epitope can be relatively few in number, but widely dispersed along the length of the molecule being brought into the correct epitope conformation via folding. The portions of the antigen between the residues defining the epitope may not be critical to the conformational structure of the epitope. For example, deletion or substitution of these intervening sequences may not affect the conformational epitope provided sequences critical to epitope conformation are maintained (e.g. cysteines involved in disulfide bonding, glycosylation sites, etc.). A conformational epitope may also be formed by 2 or more essential regions of subunits of a homooligomer or heterooligomer.

The HCV antigens of the present invention comprise conformational epitopes from the E1 and/or E2 (envelope) domains of HCV. The E1 domain, which is believed to correspond to the viral envelope protein, is currently estimated to span amino acids 192–383 of the HCV polyprotein (Hijikata et al., 1991). Upon expression in a mammalian system (glycosylated), it is believed to have an approximate molecular weight of 35 kDa as determined via SOS-PAGE. The E2 protein, previously called NS1, is believed to span amino acids 384–809 or 384–746 (Grakoui et al., 1993) of the HCV polyprotein and to also be an envelope protein. Upon expression in a vaccinia system (glycosylated), it is believed to have an apparent gel molecular weight of about 72 kDa. It is understood that these protein endpoints are approximations (e.g. the carboxy terminal end of E2 could lie somewhere in the 730–820 amino acid region, e.g. ending at amino acid 730, 735, 740, 742, 744, 745, preferably 746, 747, 748, 750, 760, 770, 780, 790, 800, 809, 810, 820). The E2 protein may also be expressed together with the E1, P7 (aa 747–809), NS2 (aa 810–1026), NS4A (aa 1658–1711) or NS4B (aa 1712–1972). Expression together with these other HCV proteins may be important for obtaining the correct protein folding.

It is also understood that the isolates used in the examples section of the present invention were not intended to limit the scope of the invention and that any HCV isolate from type 1, 2, 3, 4, 5, 6, 7, 8, 9, 10 or any other new genotype of HCV is a suitable source of E1 and/or E2 sequence for the practice of the present invention.

The E1 and E2 antigens used in the present invention may be full-length viral proteins, substantially full-length versions thereof, or functional fragments thereof (e.g. fragments which are not missing sequence essential to the formation or retention of an epitope). Furthermore, the HCV antigens of the present invention can also include other sequences that do not block or prevent the formation of the conformational epitope of interest. The presence or absence of a conformational epitope can be readily determined though screening the antigen of interest with an antibody (polyclonal serum or monoclonal to the conformational epitope) and comparing its reactivity to that of a denatured version of the antigen which retains only linear epitopes (if any). In such screening using polyclonal antibodies, it may be advantageous to adsorb the polyclonal serum first with the denatured antigen and see if it retains antibodies to the antigen of interest.

The HCV antigens of the present invention can be made by any recombinant method that provides the epitope of intrest. For example, recombinant intracellular expression in mammalian or insect cells is a preferred method to provide glycosylated E1 and/or E2 antigens in 'native' conformation as is the case for the natural HCV antigens. Yeast cells and mutant yeast strains (e.g. mnn 9 mutant (Kniskern et al., 1994) or glycosylation mutants derived by means of vanadate resistance selection (Ballou et al., 1991)) may be ideally suited for production of secreted high-mannose-type sugars; whereas proteins secreted from mammalian cells may contain modifications including galactose or sialic acids which may be undesirable for certain diagnostic or vaccine applications. However, it may also be possible and sufficient for certain applications, as it is known for proteins, to express the antigen in other recombinant hosts (such as *E. coli*) and renature the protein after recovery.

The term 'fusion polypeptide' intends a polypeptide in which the HCV antigen(s) are part of a single continuous chain of amino acids, which chain does not occur in nature. The HCV antigens may be connected directly to each other by peptide bonds or be separated by intervening amino acid sequences. The fusion polypeptides may also contain amino acid sequences exogenous to HCV.

The term 'solid phase' intends a solid body to which the individual HCV antigens or the fusion polypeptide comprised of HCV antigens are bound covalently or by noncovalent means such as hydrophobic adsorption.

The term 'biological sample' intends a fluid or tissue of a mammalian individual (e.g. an anthropoid, a human) that commonly contains antibodies produced by the individual, more particularly antibodies against HCV. The fluid or tissue may also contain HCV antigen. Such components are known in the art and include, without limitation, blood, plasma, serum, urine, spinal fluid, lymph fluid, secretions of the respiratory, intestinal or genitourinary tracts, tears, saliva, milk, white blood cells and myelomas. Body components include biological liquids. The term 'biological liquid' refers to a fluid obtained from an organism. Some biological fluids are used as a source of other products, such as clotting factors (e.g. Factor VIII; C), serum albumin, growth hormone and the like. In such cases, it is important that the source of biological fluid be free of contamination by virus such as HCV.

The term 'immunologically reactive' means that the antigen in question will react specifically with anti-HCV antibodies present in a body component from an HCV infected individual.

The term 'immune complex' intends the combination formed when an antibody binds to an epitope on an antigen.

'E1' as used herein refers to a protein or polypeptide expressed within the first 400 amino acids of an HCV polyprotein, sometimes referred to as the E, ENV or S protein. In its natural form it is a 35 kDa glycoprotein which is found in strong association with membranes. In most natural HCV strains, the E1 protein is encoded in the viral polyprotein following the C (core) protein. The E1 protein extends from approximately amino acid (aa) 192 to about aa 383 of the full-length polyprotein.

The term 'E1' as used herein also includes analogs and truncated forms that are immunologically cross-reactive with natural E1, and includes E1 proteins of genotypes 1, 2, 3, 4, 5, 6, 7, 8, 9, 10, or any other newly identified HCV type or subtype.

'E2' as used herein refers to a protein or polypeptide expressed within the first 900 amino acids of an HCV polyprotein, sometimes referred to as the NS1 protein. In its natural form it is a 72 kDa glycoprotein that is found in strong association with membranes. In most natural HCV strains, the E2 protein is encoded in the viral polyprotein following the E1 protein. The E2 protein extends from approximately amino acid position 384 to amino acid position 746, another form of E2 extends to amino acid position 809. The term 'E2' as used herein also includes analogs and truncated forms that are immunologically cross-reactive with natural E2. For example, insertions of multiple codons between codon 383 and 384, as well as deletions of amino acids 384–387 have been reported by Kato et al. (1992).

'E1/E2' as used herein refers to an oligomeric form of envelope proteins containing at least one E1 component and at least one E2 component.

The term 'specific oligomeric' E1 and/or E2 and/or E1/E2 envelope proteins refers to all possible oligomeric forms of recombinantly expressed E1 and/or E2 envelope proteins which are not aggregates. E1 and/or E2 specific oligomeric envelope proteins are also referred to as homo-oligomeric E1 or E2 envelope proteins (see below).

The term 'single or specific oligomeric' E1 and/or E2 and/or E1/E2 envelope proteins refers to single monomeric E1 or E2 proteins (single in the strict sense of the word) as well as specific oligomeric E1 and/or E2 and/or E1/E2 recombinantly expressed proteins. These single or specific oligomeric envelope proteins according to the present invention can be further defined by the following formula $(E1)_x (E2)_y$, wherein x can be a number between 0 and 100, and y can be a number between o and 100, provided that x and y are not both 0. With x=1 and y=0 said envelope proteins include monomeric E1.

The term 'homo-oligomer' as used herein refers to a complex of E1 and/or E2 containing more than one E1 or E2 monomer, e.g. E1/E1 dimers, E1/E1/E1 trimers or E1/E1/E1/E1 tetramers and E2/E2 dimers, E2/E2/E2 trimers or E2/E2/E2/E2 tetramers, E1 pentamers and hexamers, E2 pentamers and hexamers or any higher-order homo-oligomers of E1 or E2 are all 'homo-oligomers' within the scope of this definition. The oligomers may contain one, two, or several different monomers of E1 or E2 obtained from different types or subtypes of hepatitis C virus including for example those described in an international application published under WO 94/25601 and European application No. 94870166.9 both by the present applicants. Such mixed oligomers are still homo-oligomers within the scope of this invention, and may allow more universal diagnosis, prophylaxis or treatment of HCV.

The term 'purified' as applied to proteins herein refers to a composition wherein the desired protein comprises at least 35% of the total protein component in the composition. The desired protein preferably comprises at least 40%, more preferably at least about 50%, more preferably at least about 60%, still more preferably at least about 70%, even more preferably at least about 80%, even more preferably at least about 90%, and most preferably at least about 95% of the total protein component. The composition may contain other compounds such as carbohydrates, salts, lipids, solvents, and the like, without affecting the determination of the percentage purity as used herein. An 'isolated' HCV protein intends an HCV protein composition that is at least 35% pure.

The term 'essentially purified proteins' refers to proteins purified such that they can be used for in vitro diagnostic methods and as a therapeutic compound. These proteins are substantially free from cellular proteins, vector-derived proteins or other HCV viral components. Usually these proteins are purified to homogeneity (at least 80% pure, preferably, 90%, more preferably 95%, more preferably 97%, more preferably 98%, more preferably 99%, even more preferably 99.5%, and most preferably the contaminating proteins should be undetectable by conventional methods like SDS-PAGE and silver staining.

The term 'recombinantly expressed' used within the context of the present invention refers to the fact that the proteins of the present invention are produced by recombinant expression methods be it in prokaryotes, or lower or higher eukaryotes as discussed in detail below.

The term 'lower eukaryote' refers to host cells such as yeast, fungi and the like. Lower eukaryotes are generally (but not necessarily) unicellular. Preferred lower eukaryotes are yeasts, particularly species within *Saccharomyces, Schizosaccharomyces, Kluveromyces, Pichia* (e.g. *Pichia pastoris*), *Hansenula* (e.g. *Hansenula polymorpha*), *Yarowia, Schwaniomyces, Schizosaccharomyces, Zyqsaccharomyces* and the like. *Saccharomyces cerevisiae, S. carlsbergensis* and *K. lactis* are the most commonly used yeast hosts, and are convenient fungal hosts.

The term 'prokaryotes' refers to hosts such as *E. coli, Lactobacillus, Lactococcus, Salmonella, Streptococcus, Bacillus subtilis* or *Streptomyces*. Also these hosts are contemplated within the present invention.

The term 'higher eukaryote' refers to host cells derived from higher animals, such as mammals, reptiles, insects, and the like. Presently preferred higher eukaryote host cells are derived from Chinese hamster (e.g. CHO), monkey (e.g. COS and Vero cells), baby hamster kidney (BHK), pig kidney (PK15), rabbit kidney 13 cells (RK 13), the human osteosarcoma cell line 143 B, the human cell line HeLa and human hepatoma cell lines like Hep G2, and insect cell lines (e.g. *Spodoptera frugiperda*). The host cells may be provided in suspension or flask cultures, tissue cultures, organ cultures and the like.

Alternatively the host cells may also be transgenic animals.

The term 'polypeptide' refers to a polymer of amino acids and does not refer to a specific length of the product; thus, peptides, oligopeptides, and proteins are included within the definition of polypeptide. This term also does not refer to or exclude post-expression modifications of the polypeptide, for example, glycosylations, acetylations, phosphorylations and the like. Included within the definition are, for example, polypeptides containing one or more analogues of an amino acid (including, for example, unnatural amino acids, PNA, etc.), polypeptides with substituted linkages, as well as other modifications known in the art, both naturally occurring and non-naturally occurring.

The term 'recombinant polynucleotide or nucleic acid' intends a polynucleotide or nucleic acid of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature.

The term 'recombinant host cells', 'host cells', 'cells', 'cell lines', 'cell cultures', and other such terms denoting microorganisms or higher eukaryotic cell lines cultured as unicellular entities refer to cells which can be or have been, used as recipients for a recombinant vector or other transfer polynucleotide, and include the progeny of the original cell which has been transfected. It is understood that the progeny of a single parental cell may not necessarily be completely identical in morphology or in genomic or total DNA complement as the original parent, due to natural, accidental, or deliberate mutation.

The term 'replicon' is any genetic element, e.g., a plasmid, a chromosome, a virus, a cosmid, etc., that behaves as an autonomous unit of polynucleotide replication within a cell; i.e., capable of replication under its own control.

The term 'vector' is a replicon further comprising sequences providing replication and/or expression of a desired open reading frame.

The term 'control sequence' refers to polynucleotide sequences which are necessary to effect the expression of coding sequences to which they are ligated. The nature of such control sequences differs depending upon the host organism; in prokaryotes, such control sequences generally include promoter, ribosomal binding site, and terminators; in eukaryotes, generally, such control sequences include promoters, terminators and, in some instances, enhancers. The term 'control sequences' is intended to include, at a minimum, all components whose presence is necessary for expression, and may also include additional components whose presence is advantageous, for example, leader sequences which govern secretion.

The term 'promoter' is a nucleotide sequence which is comprised of consensus sequences which allow the binding of RNA polymerase to the DNA template in a manner such that mRNA production initiates at the normal transcription initiation site for the adjacent structural gene.

The expression 'operably linked' refers to a juxtaposition wherein the components so described are in a relationship permitting them to function in their intended manner. A control sequence 'operably linked' to a coding sequence is ligated in such a way that expression of the ceding sequence is achieved under conditions compatible with the control sequences.

An 'open reading frame' (ORF) is a region of a polynucleotide sequence which encodes a polypeptide and does not contain stop codons; this region may represent a portion of a coding sequence or a total coding sequence.

A 'coding sequence' is a polynucleotide sequence which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include but is not limited to mRNA, DNA (including cDNA), and recombinant polynucleotide sequences.

As used herein, 'epitope' or 'antigenic determinant' means an amino acid sequence that is immunoreactive. Generally an epitope consists of at least 3 to 4 amino acids, and more usually, consists of at least 5 or 6 amino acids, sometimes the epitope consists of about 7 to 8, or even about 10 amino acids. As used herein, an epitope of a designated polypeptide denotes epitopes with the same amino acid sequence as the epitope in the designated polypeptide, and immunologic equivalents thereof. Such equivalents also include strain, subtype (=genotype), or type(group)-specific variants, e.g. of the currently known sequences or strains belonging to genotypes 1a, 1b, 1c, 1d, 1e, 1f, 2a, 2b, 2c, 2d, 2e, 2f, 2g, 2h, 2i, 3a, 3b, 3c, 3d, 3e, 3f, 3g, 4a, 4b, 4c, 4d, 4e, 4f, 4g, 4h, 4i, 4j, 4k, 4l, 5a, 5b, 6a, 6b, 6c, 7a, 7b, 7c, 8a, 9b, 9a, 9b, 10a, or any other newly defined HCV (sub)type. It is to be understood that the amino acids constituting the epitope need not be part of a linear sequence, but may be interspersed by any number of amino acids, thus forming a conformational epitope.

The term 'immunogenic' refers to the ability of a substance to cause a humoral and/or cellular response, whether alone or when linked to a carrier, in the presence or absence of an adjuvant. 'Neutralization' refers to an immune response that blocks the infectivity, either partially or fully, of an infectious agent. A 'vaccine' is an immunogenic composition capable of eliciting protection against HCV, whether partial or complete. A vaccine may also be useful for treatment of an individual, in which case it is called a therapeutic vaccine.

The term 'therapeutic' refers to a composition capable of treating HCV infection.

The term 'effective amount' refers to an amount of epitope-bearing polypeptide sufficient to induce an immunogenic response in the individual to which it is administered, or to otherwise detectably immunoreact in its intended system (e.g., immunoassay). Preferably, the effective amount is sufficient to effect treatment, as defined above. The exact amount necessary will vary according to the application. For vaccine applications or for the generation of polyclonal antiserum/antibodies, for example, the effective amount may vary depending on the species, age, and general condition of the individual, the severity of the condition being treated, the particular polypeptide selected and its mode of administration, etc. It is also believed that effective amounts will be found within a relatively large, non-critical range. An appropriate effective amount can be readily determined using only routine experimentation. Preferred ranges of E1 and/or E2 and/or E1/E2 single or specific oligomeric envelope proteins for prophylaxis of HCV disease are 0.01 to 100 µg/dose, preferably 0.1 to 50 µg/dose. Several doses may be needed per individual in order to achieve a sufficient immune response and subsequent protection against HCV disease.

DETAILED DESCRIPTION OF THE INVENTION

More particularly, the present invention contemplates a method for isolating or purifying recombinant HCV single or specific oligomeric envelope protein selected from the group consisting of E1 and/or E2 and/or E1/E2, characterized in that upon lysing the transformed host cells to isolate the recombinantly expressed protein a disulphide bond cleavage or reduction step is carried out with a disculphide bond cleaving agent.

The essence of these 'single or specific oligomeric' envelope proteins of the invention is that they are free from contaminating proteins and that they are not disulphide bond linked with contaminants.

The proteins according to the present invention are recombinantly expressed in lower or higher eukaryotic cells or in prokaryotes. The recombinant proteins of the present invention are preferably glycosylated and may contain high-mannose-type, hybrid, or complex glycosylations. Preferentially said proteins are expressed from mammalian cell lines as discussed in detail in the Examples section, or in yeast such as in mutant yeast strains also as detailed in the Examples section.

The proteins according to the present invention may be secreted or expressed within components of the cell, such as the ER or the Golgi Apparatus. Preferably, however, the proteins of the present invention bear high-mannose-type glycosylations and are retained in the ER or Golgi Apparatus of mammalian cells or are retained in or secreted from yeast cells, preferably secreted from yeast mutant strains such as the mnn9 mutant (Kniskern et al., 1994), or from mutants that have been selected by means of vanadate resistence (Ballou et al., 1991).

Upon expression of HCV envelope proteins, the present inventors could show that some of the free thiol groups of cysteines not involved in intra- or inter-molecular disulphide bridges, react with cysteines of host or expression-system-derived (e.g. vaccinia) proteins or of other HCV envelope proteins (single or oligomeric), and form aspecific intermolecular bridges. This results in the formation of 'aggregates' of HCV envelope proteins together with contaminating proteins. It was also shown in WO 92/08734 that 'aggregates' were obtained after purification, but it was not described which protein interactions were involved. In patent application WO 92/08734, recombinant E1/E2 protein expressed with the vaccinia virus system were partially purified as aggregates and only found to be 70% pure, rendering the purified aggregates not useful for diagnostic, prophylactic or therapeutic purposes.

Therefore, a major aim of the present invention resides in the separation of single or specific-oligomeric HCV envelope proteins from contaminating proteins, and to use the purified proteins (>95% pure) for diagnostic, prophylactic and therapeutic purposes. To those purposes, the present inventors have been able to provide evidence that aggregated protein complexes ('aggregates') are formed on the basis of disulphide bridges and non-covalent protein-protein interactions. The present invention thus provides a means for selectively cleaving the disulphide bonds under specific conditions and for separating the cleaved proteins from contaminating proteins which greatly interfere with diagnostic, prophylactic and therapeutic applications. The free thiol groups may be blocked (reversibly or irreversibly) in order to prevent the reformation of disulphide bridges, or may be left to oxidize and oligomerize with other envelope proteins (see definition homo-oligomer). It is to be understood that such protein oligomers are essentially different from the 'aggregates' described in WO 92/08734 and WO 94/01778, since the level of contaminating proteins is undetectable.

Said disulphide bond cleavage may also be achieved by:
(1) performic acid oxidation by means of cysteic acid in which case the cysteine residues are modified into cysteic acid (Moore et al., 1963).
(2) Sulfitolysis (R—S—S—R→2 R—SO$^-_3$) for example by means of sulphite (SO$^{2-}_3$) together with a proper oxidant such as Cu$^{2-}$ in which case the cysteine is modified into S-sulpho-cysteine (Bailey and Cole, 1959).
(3) Reduction by means of mercaptans, such as dithiotreitol (DDT), β-mercapto-ethanol, cysteine, glutathione Red, ε-mercapto-ethylamine, or thioglycollic acid, of which DTT and β-mercapto-ethanol are commonly used (Cleland, 1964), is the preferred method of this invention because the method can be performed in a water environment and because the cysteine remains unmodified.
(4) Reduction by means of a phosphine (e.g. Bu$_3$P) (Ruegg and Rudinger, 1977).

All these compounds are thus to be regarded as agents or means for cleaving disulphide bonds according to the present invention.

Said disulphide bond cleavage (or reducing) step of the present invention is preferably a partial disulphide bond cleavage (reducing) step (carried out under partial cleavage or reducing conditions).

A preferred disulphide bond cleavage or reducing agent according to the present invention is dithiothreitol (DTT). Partial reduction is obtained by using a low concentration of said reducing agent, i.e. for DTT for example in the concentration range of about 0.1 to about 50 mM, preferably about 0.1 to about 20 mM, preferably about 0.5 to about 10 mM, preferably more than 1 mM, more than 2 mM or more than mM, more preferably about 1.5 mM, about 2.0 mM, about 2.5 mM, about 5 mM or about 7.5 mM.

Said disulphide bond cleavage step may also be carried out in the presence of a suitable detergent (as an example of a means for cleaving disulphide bonds or in combination with a cleaving agent) able to dissociate the expressed proteins, such as DecylPEG, EMPIGEN-BB, NP-40, sodium cholate, Triton X-100.

Said reduction or cleavage step (preferably a partial reduction or cleavage step) is carried out preferably in in the presence of (with) a detergent. A preferred detergent according to the present invention is Empigen-BB. The amount of detergent used is preferably in the range of 1 to 10%, preferably more than 3%, more preferably about 3.5% of a detergent such as Empigen-BB.

A particularly preferred method for obtaining disulphide bond cleavage employs a combination of a classical disulphide bond cleavage agent as derailed above and a detergent (also as detailed above). As contemplated in the Examples section, the particular combination of a low concentration of DTT (1.5 to 7.5 mM) and about 3.5% of Empigen-BB is proven to be a particularly preferred combination of reducing agent and detergent for the purification of recombinantly expressed E1 and E2 proteins. Upon gelfiltration chromatography, said partial reduction is shown to result in the production of possibly dimeric E1 protein and separation of this E1 protein from contaminating proteins that cause false reactivity upon use in immunoassays.

It is, however, to be understood that also any other combination of any reducing agent known in the art with any detergent or other means known in the art to make the cysteines better accessible is also within the scope of the present invention, insofar as said combination reaches the same goal of disulphide bridge cleavage as the preferred combination examplified in the present invention.

Apart from reducing the disulphide bonds, a disulphide bond cleaving means according to the present invention may also include any disulphide bridge exchanging agents (competitive agent being either organic or proteinaeous, see for instance Creighton, 1988) known in the art which allows the following type of reaction to occur:

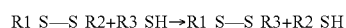

R1, R2: compounds of protein aggregates
R3 SH: competitive agent (organic, proteinaeous)

The term 'disulphide bridge exchanging agent' is to be interpretated as including disulphide bond reforming as well as disulphide bond blocking agents.

The present invention also relates to methods for purifying or isolating HCV single or specific oligomeric envelope proteins as set out above further including the use of any SH group blocking or binding reagent known in the art such as chosen from the following list:

Glutathion 5.5'-dithiobis-(2-nitrobenzoic acid) or bis-(3-carboxy-4-nitrophenyl)-disulphide (DTNB or Ellman's reagent) (Elmann, 1959)

N-ethylmaleimide (NEM; Benesch et al., 1956)

N-(4-dimethylamino-3,5-dinitrophenyl) maleimide or Tuppy's maleimide which provides a color to the protein P-chloromercuribenzoate (Grassetti et al., 1969)

4-vinylpyridine (Friedman and Krull, 1969) can be liberated after reaction by acid hydrolysis acrylonitrile, can be liberated after reaction by acid hydrolysis (Weil and Seibles, 1961)

NEM-biotin (e.g. obtained from Sigma B1267)

2,2'-dithiopyridine (Grassetti and Murray, 1967)

4,4'-dithiopyridine (Grassetti and Murray, 1967)

6,6'-dithiodinicontinic acid (DTDNA; Brown and Cunnigham, 1970)

2,2'-dithiobis-(5'-nitropyridine) (DTNP; U.S. Pat. No. 3,597,160) or other dithiobis (heterocyclic derivative) compounds (Grassetti and Murray, 1969)

A survey of the publications cited shows that often different reagents for sulphydryl groups will react with varying numbers of thiol groups of the same protein or enzyme molecule. One may conclude that this variation in reactivity of the thiol groups is due to the steric environment of these groups, such as the shape of the molecule and the surrounding groups of atoms and their charges, as well as to the size, shape and charge of the reagent molecule, or ion. Frequently the presence of adequate concentrations of denaturants such as sodium dodecylsulfate, urea or guanidine hydrochoride will cause sufficient unfolding of the protein molecule to permit equal access to all of the reagents for thiol groups. By varying the concentration of denaturant, the degree of unfolding can be controlled and in this way thiol groups with different degrees of reactivity may be revealed. Although up to date most of the work reported has been done with p-chloromercuribenzoate, N-ethylmaleimide and DTNB, it is likely that the other more recently developed reagents may prove equally useful. Because of their varying structures, it seems likely, in fact, that they may respond differently to changes in the steric environment of the thiol groups.

Alternatively, conditions such as low pH (preferably lower than pH 6) for preventing free SH groups from oxidizing and thus preventing the formation of large intermolecular aggregates upon recombinant expression and purification of E1 and E2 (envelope) proteins are also within the scope of the present invention.

A preferred SH group blocking reagent according to the present invention is N-ethylmaleimide (NEM). Said SH group blocking reagent may be administrated during lysis of the recombinant host cells and after the above-mentioned partial reduction process or after any other process for cleaving disulphide bridges. Said SH group blocking reagent may also be modified with any group capable of providing a detectable label and/or any group aiding in the immobilization of said recombinant protein to a solid substrate, e.g. biotinylated NEM.

Methods for cleaving cysteine bridges and blocking free cysteines have also been described in Darbre (1987), Means and Feeney (1971), and by Wong (1993).

A method to purify single or specific oligomeric recombinant E1 and/or E2 and/or E1/E2 proteins according to the present invention as defined above is further characterized as comprising the following steps:

lysing recombinant E1 and/or E2 and/or E1/E2 expressing host cells, preferably in the presence of an SH group blocking agent, such as N-ethylmaleimide (NEM), and possibly a suitable detergent, preferably Empigen-BB, recovering said HCV envelope protein by affinity purification for instance by means lectin-chromatography, such as lentil-lectin chromatography, or immunoaffinity chromatography using anti-E1 and/or anti-E2 specific monoclonal antibodies, followed by, reduction or cleavage of disulphide bonds with a disulphide bond cleaving agent, such as DTT, preferably also in the presence of an SH group blocking agent, such as NEM or Biotin-NEM, and, recovering the reduced HCV E1 and/or E2 and/or E1/E2 envelope proteins for instance by gelfiltration (size exclusion chromatography or molecular sieving) and possibly also by an additional $Ni^{2+}$-IMAC chromatography and desalting step.

It is to be understood that the above-mentioned recovery steps may also be carried out using any other suitable technique known by the person skilled in the art.

Preferred lectin-chromatography systems include *Galanthus nivalis* agglutinin (GNA)-chromatography, or *Lens culinaris* agglutinin (LCA) (lentil) lectin chromatography as illustrated in the Examples section. Other useful lectins include those recognizing high-mannose type sugars, such as *Narcissus pseudonarcissus* agglutinin (NPA), *Pisum sativum* agglutinin (PSA), or *Allium ursinum* agglutinin (AUA).

Preferably said method is usable to purify single or specific oligomeric HCV envelope protein produced intracellularly as detailed above.

For secreted E1 or E2 or E1/E2 oligomers, lectins binding complex sugars such as *Ricinus communis* agglutinin I (RCA I), are preferred lectins.

The present invention more particularly contemplates essentially purified recombinant HCV single or specific oligomeric envelope proteins, selected from the group consisting of E1 and/or E2 and/or E1/E2, characterized as being isolated or purified by a method as defined above.

The present invention more particularly relates to the purification or isolation of recombinant envelope proteins which are expressed from recombinant mammalian cells such as vaccinia.

The present invention also relates to the purification or isolation of recombinant envelope proteins which are expressed from recombinant yeast cells.

The present invention equally relates to the purification or isolation of recombinant envelope proteins which are expressed from recombinant bacterial (prokaryotic) cells.

The present invention also contemplates a recombinant vector comprising a vector sequence, an appropriate prokaryotic, eukaryotic or viral or synthetic promoter sequence followed by a nucleotide sequence allowing the expression of the single or specific oligomeric E1 and/or E2 and/or E1/E2 of the invention.

Particularly, the present invention contemplates a recombinant vector comprising a vector sequence, an appropriate prokaryotic, eukaryotic or viral or synthetic promoter sequence followed by a nucleotide sequence allowing the expression of the single E1or E1 of the invention.

Particularly, the present invention contemplates a recombinant vector comprising a vector sequence, an appropriate prokaryotic, eukaryotic or viral or synthetic promoter sequence followed by a nucleotide sequence allowing the expression of the single E1 or E2 of the invention.

The segment of the HCV cDNA encoding the desired E1 and/or E2 sequence inserted into the vector sequence may be attached to a signal sequence. Said signal sequence may be that from a non-HCV source, e.g. the IgG or tissue plasminogen activator (tpa) leader sequence for expression in mammalian cells, or the α-mating factor sequence for expression into yeast cells, but particularly preferred constructs according to the present invention contain signal sequences appearing in the HCV genome before the respective start points of the E1 and E2 proteins. The segment of the HCV cDNA encoding the desired E1 and/or E2 sequence inserted into the vector may also include deletions e.g. of the hydrophobic domain(s) as illustrated in the examples section, or of the E2 hypervariable region I.

More particularly, the recombinant vectors according to the present invention encompass a nucleic acid having an HCV cDNA segment encoding the polyprotein starting in the region between amino acid positions 1 and 192 and ending in the region between positions 250 and 400 of the HCV polyprotein, more preferably ending in the region between positions 250 and 341, even more preferably ending in the region between positions 290 and 341 for expression of the HCV single E1 protein. Most preferably, the present recombinant vector encompasses a recombinant nucleic acid having a HCV cDNA segment encoding part of the HCV polyprotein starting in the region between positions 117 and 192, and ending at any position in the region between positions 263 and 326, for expression of HCV single E1 protein. Also within the scope of the present invention are forms that have the first hydrophobic domain deleted (positions 264 to 293 plus or minus 8 amino acids), or forms to which a 5'-terminal ATG codon and a 3'-terminal stop codon has been added, or forms which have a factor Xa cleavage site and/or 3 to 10, preferably 6 Histidine codons have been added.

More particularly, the recombinant vectors according to the present invention encompass a nucleic acid having an HCV cDNA segment encoding the polyprotein starting in the region between amino acid positions 290 and 406 and ending in the region between positions 600 and 820 of the HCV polyprotein, more preferably starting in the region between positions 322 and 406, even more preferably staring in the region between positions 347 and 406, even still more preferably starting in the region between positions 364 and 406 for expression of the HCV single E2 protein. Most preferably, the present recombinant vector encompasses a recombinant nucleic acid having a HCV cDNA segment encoding the polyprotein starting in the region between positions 290 and 406, and ending at any position of positions 623, 650, 661, 673, 710, 715, 720, 746 or 809, for expression of HCV single E2 protein. Also within the scope of the present invention are forms to which a 5'-terminal ATG codon and a 3'-terminal stop codon has been added, or forms which have a factor Xa cleavage site and/or 3 to 10, preferably 6 Histidine codons have been added.

A variety of vectors may be used to obtain recombinant expression of HCV single or specific oligomeric envelope proteins of the present invention. Lower eukaryotes such as yeasts and glycosylation mutant strains are typically transformed with plasmids, or are transformed with a recombinant virus. The vectors may replicate within the host independently, or may integrate into the host cell genome.

Higher eukaryotes may be transformed with vectors, or may be infected with a recombinant virus, for example a recombinant vaccinia virus. Techniques and vectors for the insertion of foreign DNA into vaccinia virus are well known in the art, and utilize, for example homologous recombination. A wide variety of viral promoter sequences, possibly terminator sequences and poly(A)-addition sequences, possibly enhancer sequences and possibly amplification sequences, all required for the mammalian expression, are available in the art. Vaccinia is particularly preferred since vaccinia halts the expression of host cell proteins. Vaccinia is also very much preferred since it allows the expression of E1 and E2 proteins of HCV in cells or individuals which are immunized with the live recombinant vaccinia virus. For vaccination of humans the avipox and Ankara Modified Virus (AMV) are particularly useful vectors.

Also known are insect expression transfer vectors derived from baculovirus *Autographa californica* nuclear polyhedrosis virus (AcNPV), which is a helper-independent viral expression vector. Expression vectors derived from this system usually use the strong viral polyhedrin gene promoter to drive the expression of heterologous genes. Different vectors as well as methods for the introduction of heterologous DNA into the desired site of baculovirus are available to the man skilled in the art for baculovirus expression. Also different signals for posttranslational modification recognized by insect cells are known in the art.

Also included within the scope of the present invention is a method for producing purified recombinant single or specific oligomeric HCV E1 or E2 or E1/E2 proteins, wherein the cysteine residues involved in aggregates formation are replaced at the level of the nucleic acid sequence by other residues such that aggregate formation is prevented. The recombinant proteins expressed by recombinant vectors caarrying such a mutated E1 and/or E2 protein encoding nucleic acid are also within the scope of the present invention.

The present invention also relates to recombinant E1 and/or E2 and/or E1/E2 proteins characterized in that at least one of their glycosylation sites has been removed and are consequently termed glycosylation mutants. As explained in the Examples section, different glycosylation mutants may be desired to diagnose (screening, confirmation, prognosis. etc.) and prevent HCV disease according to the patient in question. An E2 protein glycosylation mutant lacking the GLY4 has for instance been found to improve the reactivity of certain sera in diagnosis. These glycosylation mutants are preferably purified according to the method disclosed in the present invention. Also contemplated within the present invention are recombinant vectors carrying the nucleic acid insert encoding such a E1 and/or E2 and/or E1/E2 glycosylation mutant as well as host cells tranformed with such a recombinant vector.

The present invention also relates to recombinant vectors including a polynucleotide which also forms part of the present invention. The present invention relates more particularly to the recombinant nucleic acids as represented in SEQ ID NO 3, 5, 7, 9, 11, 13, 21, 23, 25, 27, 29, 31, 35, 37, 39, 41, 43, 45, 47 and 49, or parts thereof.

The present invention also contemplates host cells transformed with a recombinant vector as defined above, wherein said vector comprises a nucleotide sequence encoding HCV E1 and/or E2 and/or E1/E2 protein as defined above in addition to a regulatory sequence operably linked to said HCV E1 and/or E2 and/or E1/E2 sequence and capable of regulating the expression of said HCV E1 and/or E2 and/or E1/E2 protein.

Eukaryotic hosts include lower and higher eukaryotic hosts as described in the definitions section. Lower eukaryotic hosts include yeast cells well known in the art. Higher eukaryotic hosts mainly include mammalian cell lines known in the art and include many immortalized cell lines available from the ATCC, inluding HeLa cells, Chinese hamster ovary (CHO) cells, Baby hamster kidney (BHK) cells, PK15, RK13 and a number of other cell lines.

The present invention relates particularly to a recombinant E1 and/or E2 and/or E1/E2 protein expressed by a host cell as defined above containing a recombinany vector as defined above. These recombinant proteins are particularly purified according to the method of the present invention.

A preferred method for isolating or purifying HCV envelope proteins as defined above is further characterized as comprising at least the following steps:

- growing a host cell as defined above transformed with a recombinant vector according to the present invention or with a known recombinant vector expressing E1 and/or E2 and/or E1/E2 HCV envelope proteins in a suitable culture medium,
- causing expression of said vector sequence as defined above under suitable conditions, and,
- lysing said transformed host cells, preferably in the presence of a SH group blocking agent, such as N-ethylmaleimide (NEM), and possibly a suitable detergent, preferably Empigen-BB,
- recovering said HCV envelope protein by affinity purification such as by means of lectin-chromatography or immunoaffinity chromatography using anti-E1 and/or anti-E2 specific monoclonal antibodies, with said lectin being preferably lentil-lectin or GNA, followed by,
- incubation of the eluate of the previous step with a disulphide bond cleavage means, such as DTT, preferably followed by incubation with an SH group blocking agent, such as NEM or Biotin-NEM, and,
- isolating the HCV single or specific oligomeric E1 and/or E2 and/or E1/E2 proteins such as by means of gelfiltration and possibly also by a subsequent $Ni^{2+}$-IMAC chromatography followed by a desalting step.

As a result of the above-mentioned proces, E1 and/or E2 and/or E1/E2 proteins may be produced in a form which elute differently from the large aggregates containing vector-derived components and/or cell components in the void volume of the gelfiltration column or the IMAC collumn as illustrated in the Examples section. The disulphide bridge cleavage step advantageously also eliminates the false reactivity due to the presence of host and/or expression-system-derived proteins. The presence of NEM and a suitable detergent during lysis of the cells may already partly or even completely prevent the aggregation between the HCV envelope proteins and contaminants.

$Ni^{2+}$-IMAC chromatography followed by a desalting step is preferably used for contructs bearing a $(His)_6$ as described by Janknecht et al., 1991, and Hochuli et al., 1988.

The present invention also relates to a method for producing monoclonal antibodies in small animals such as mice or rats, as well as a method for screening and isolating human B-cells that recognize anti-HCV antibodies, using the HCV single or specific oligomeric envelope proteins of the present invention.

The present invention further relates to a composition comprising at least one of the following E1 peptides as listed in Table 3:

- E1-31 (SEQ ID NO 56) spanning amino acids 181 to 200 of the Core/E1 V1 region,
- E1-33 (SEQ ID NO 57) spanning amino acids 193 to 212 of the E1 region,
- E1-35 (SEQ ID NO 58) spanning amino acids 205 to 224 of the E1 V2 region (epitope B),
- E1-35A (SEQ ID NO 59) spanning amino acids 208 to 227 of the E1 V2 region (epitope B),
- 1bE1 (SEQ ID NO 53) spanning amino acids 192 to 228 of E1 regions (V1, C1, and V2 regions (containing epitope B)),
- E1-51 (SEQ ID NO 66) spanning amino acids 301 to 320 of the E1 region,
- E1-53 (SEQ ID NO 67) spanning amino acids 313 to 332 of the E1 C4 region (epitope A),
- E1-55 (SEQ ID NO 68) spanning amino acids 325 to 344 of the E1 region.

Figure 19:
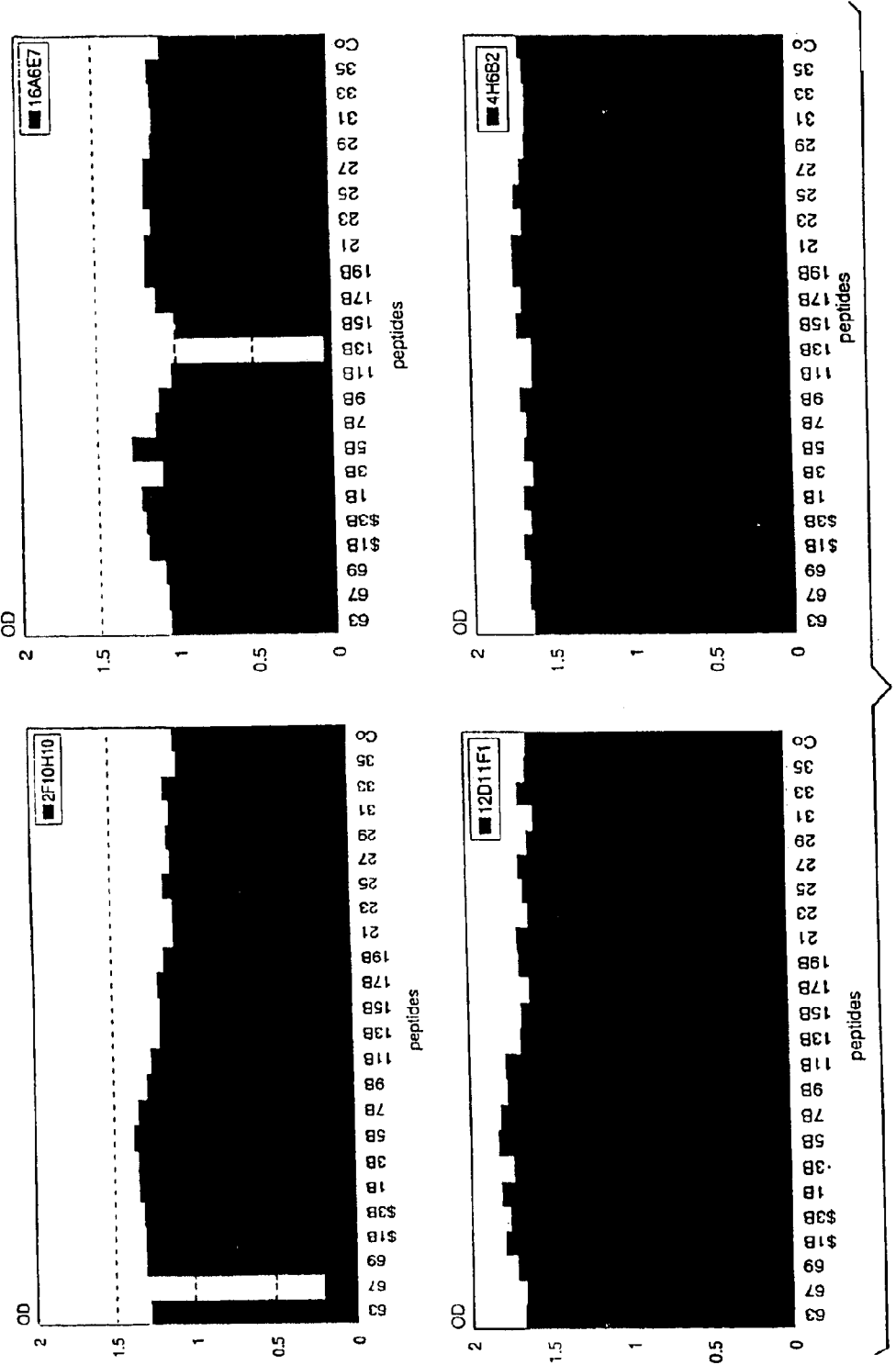

The present invention also relates to a composition comprising at least one of the following E2 peptides as listed in Table 3:

- Env 67 or E2-67 (SEQ ID NO 72) spanning amino acid positions 397 to 416 of the E2 region (epitope A, recognized by monoclonal antibody 2F10H10, see FIG. 19),
- Env 69 or E2-69 (SEQ ID NO 73) spanning amino acid positions 409 to 428 of the E2 region (epitope A),
- Env 23 or E2-23 (SEQ ID NO 86) spanning positions 583 to 602 of the E2 region (epitope E),
- Env 25 or E2-25 (SEQ ID NO 87) spanning positions 595 to 614 of the E2 region (epitope E),
- Env 27 or E2-27 (SEQ ID NO 88) spanning positions 607 to 626 of the E2 region (epitope E),
- Env 17B or E2-17B (SEQ ID NO 83) spanning positions 547 to 566 of the E2 region (epitope D),
- Env 13B or E2-13B (SEQ ID NO 82) spanning positions 523 to 542 of the E2 region (epitope C; recognized by monoclonal antibody 16A6E7, see FIG. 19).

The present invention also relates to a composition comprising at least one of the following E2 conformational epitopes:

- epitope F recognized by monoclonal antibodies 15C8C1, 12D11F1 and 8G10D1H9,
- epitope G recognized by monoclonal antibody 9G3E6,
- epitope H (or C) recognized by monoclonal antibody 10D3C4 and 4H6B2, or,
- epitope I recognized by monoclonal antibody 17F2C2.

The present invention also relates to an E1 or E2 specific antibody raised upon immunization with a peptide or protein composition, with said antibody being specifically reactive with any of the polypeptides or peptides as defined above, and with said antibody being preferably a monoclonal antibody.

The present invention also relates to an E1 or E2 specific antibody screened from a variable chain library in plasmids or phages or from a population of human B-cells by means of a process known in the art, with said antibody being reactive with any of the polypeptides or peptides as defined above, and with said antibody being preferably a monoclonal antibody.

The E1 or E2 specific monoclonal antibodies of the invention can be produced by any hybridoma liable to be formed according to classical methods from splenic cells of an animal, particularly from a mouse or rat, immunized against the HCV polypeptides or peptides according to the invention, as defined above on the one hand, and of cells of a myeloma cell line on the other hand, and to be selected by the ability of the hybridoma to produce the monoclonal antibodies recognizing the polypeptides which has been initially used for the immunization of the animals.

The antibodies involved in the invention can be labelled by an appropriate label of the enzymatic, fluorescent, or radioactive type.

The monoclonal antibodies according to this preferred embodiment of the invention may be humanized versions of mouse monoclonal antibodies made by means of recombinant DNA technology, departing from parts of mouse and/or human genomic DNA sequences coding for H and L chains from cDNA or genomic clones coding for H and L chains.

Alternatively the monoclonal antibodies according to this preferred embodiment of the invention may be human monoclonal antibodies. These antibodies according to the present embodiment of the invention can also be derived from human peripheral blood lymphocytes of patients infected with HCV, or vaccinated against HCV. Such human monoclonal antibodies are prepared, for instance, by means of human peripheral blood lymphocytes (PBL) repopulation of severe combined immune deficiency (SCID) mice (for recent review, see Duchosal et al., 1992).

The invention also relates to the use of the proteins or peptides of the invention, for the selection of recombinant antibodies by the process of repertoire cloning (Persson et al., 1991).

Antibodies directed to peptides or single or specific oligomeric envelope proteins derived from a certain genotype may be used as a medicament, more particularly for incorporation into an immunoassay for the detection of HCV genotypes (for detecting the presence of HCV E1 or E2 antigen), for prognosing/monitoring of HCV disease, or as therapeutic agents.

Alternatively, the present invention also relates to the use of any of the above-specified E1 or E2 specific monoclonal antibodies for the preparation of an immunoassay kit for detecting the presence of E1 or E2 antigen in a biological sample, for the preparation of a kit for prognosing/monitoring of HCV disease or for the preparation of a HCV medicament.

The present invention also relates to the a method for in vitro diagnosis or detection of HCV antigen present in a biological sample, comprising at least the following steps:
(i) contacting said biological sample with any of the E1 and/or E2 specific monoclonal antibodies as defined above, preferably in an immobilized form under appropriate conditions which allow the formation of an immune complex,
(ii) removing unbound components,
(iii) incubating the immune complexes formed with heterologous antibodies, which specifically bind to the antibodies present in the sample to be analyzed, with said heterologous antibodies having conjugated to a detectable label under appropriate conditions,
(iv) detecting the presence of said immune complexes visually or mechanically (e.g. by means of densitometry, fluorimetry, colorimetry).

The present invention also relates to a kit for in vitro diagnosis of HCV antigen present in a biological sample, comprising:
at least one monoclonal antibody as defined above, with said antibody being preferentially immobilized on a solid substrate,
a buffer or components necessary for producing the buffer enabling binding reaction between these antibodies and the HCV antigens present in the biological sample,
a means for detecting the immune complexes formed in the preceding binding reaction,
possibly also including an automated scanning and interpretation device for inferring the HCV antigens present in the sample from the observed binding pattern.

The present invention also relates to a composition comprising E1 and/or E2 and/or E1, E2 recombinant HCV proteins purified according to the method of the present invention or a composition comprising at least one peptides as specified above for use as a medicament.

The present invention more particularly relates to a composition comprising at least one of the above-specified envelope peptides or a recombinant envelope protein composition as defined above, for use as a vaccine for immunizing a mammal, preferably humans, against HCV, comprising administering a sufficient amount of the composition possibly accompanied by pharmaceutically acceptable adjuvant(s), to produce an immune response.

More particularly, the present invention relates to the use of any of the compositions as described here above for the preparation of a vaccine as described above.

Also, the present invention relates to a vaccine composition for immunizing a mammal, preferably humans, against HCV, comprising HCV single or specific oligomeric proteins or peptides derived from the E1 and/or the E2 region as described above.

Immunogenic compositions can be prepared according to methods known in the art. The present compositions comprise an immunogenic amount of a recombinant E1 and/or E2 and/or E1/E2 single or specific oligomeric proteins as defined above or E1 or E2 peptides as defined above, usually combined with a pharmaceutically acceptable carrier, preferably further comprising an adjuvant.

The single or specific oligomeric envelope proteins of the present invention, either E1 and/or E2 and/or E1/E2, are expected to provide a particularly useful vaccine antigen, since the formation of antibodies to either E1 or E2 may be more desirable than to the other envelope protein, and since the E2 protein is cross-reactive between HCV types and the E1 protein is type-specific. Cocktails including type 1 E2 protein and E1 proteins derived from several genotypes may be particularly advantageous. Cocktails containing a molar excess of E1 versus E2 or E2 versus E1 may also be particularly useful. Immunogenic compositions may be administered to animals to induce production of antibodies, either to provide a source of antibodies or to induce protective immunity in the animal.

Pharmaceutically acceptable carriers include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers; and inactive virus particles. Such carriers are well known to those of ordinary skill in the art.

Preferred adjuvants to enhance effectiveness of the composition include, but are not limited to: aluminim hydroxide (alum), N-acetyl-muramyl-L-threonyl-D-isoglutamine (thr-MDP) as found in U.S. Pat. No. 4,606,918, N-acetyl-normuramyl-L-alanyl-D-isoglutamine (nor-MOP), N-acetylmuramyl-L-alanyl-D-isoglutaminyl-L-alanine-2-(1'-2'-dipalmitoyl-sn-glycero-3-hydroxyphosphoryloxy)-ethylamine (MTP-PE) and RIBI, which contains three components extracted from bacteria, monophosphoryl lipid A. trehalose dimycolate, and cell wall skeleton (MPL+TDM+CWS) in a 2% squalene, Tween 80 emulsion. Any of the 3 components MPL, TDM or CWS may also be used alone or combined 2 by 2. Additionally, adjuvants such as Stimulon (Cambridge Bioscience, Worcester, Mass.) or SAP-1 (Syntax) may be used. Further, Complete Freund's Adjuvant (CFA) and Incomplete Freund's Adjuvant (IFA) may be used for non-human applications and research purposes.

The immunogenic compositions typically will contain pharmaceutically acceptable vehicles, such as water, saline, glycerol, ethanol, etc. Additionally, auxiliary substances, such as wetting or emulsifying agents, pH buffering substances, preservatives, and the like, may be included in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect. The E1 and E2 proteins may also be incorporated into Immune Stimulating Complexes together with saponins, for example Quil A (ISCOMS).

Immunogenic compositions used as vaccines comprise a 'sufficient amount' or 'an immunologically effective amount' of the envelope proteins of the present invention, as well as any other of the above mentioned components, as needed. 'Immunologically effective amount', means that the administration of that amount to an individual, either in a single dose or as part of a series, is effective for treatment, as defined above. This amount varies depending upon the health and physical condition of the individual to be treated, the taxonomic group of individual to be treated (e.g. non-human primate, primate, etc.), the capacity of the individual's immune system to synthesize antibodies, the degree of protection desired, the formulation of the vaccine, the treating doctor's assessment of the medical situation, the strain of infecting HCV, and other relevant factors. It is expected that the amount will fall in a relatively broad range that can be determined through routine trials. Usually, the amount will vary from 0.01 to 1000 μg/dose, more particularly from 0.1 to 100 μg/dose.

The single or specific oligomeric envelope proteins may also serve as vaccine carriers to present homologous (e.g. T cell epitopes or 8 cell epitopes from the core, NS2, NS3, NS4 or NS5 regions) or heterologous (non-HCV) haptens, in the same manner as Hepatitis B surface antigen (see European Patent Application 174,444). In this use, envelope proteins provide an immunogenic carrier capable of stimulating an immune response to haptens or antigens conjugated to the aggregate. The antigen may be conjugated either by conventional chemical methods, or may be cloned into the gene encoding E1 and/or E2 at a location corresponding to a hydrophilic region of the protein. Such hydrophylic regions include the V1 region (encompassing amino acid positions 191 to 202), the V2 region (encompassing amino acid positions 213 to 223), the V3 region (encompassing amino acid positions 230 to 242), the V4 region (encompassing amino acid positions 230 to 242), the V4 region (encompassing amino acid positions 294 to 303) and the V6 region (encompassing amino acid positions 329 to 336). Another useful location for insertion of haptens is the hydrophobic region (encompassing approximately amino acid positions 264 to 293). It is shown in the present invention that this region can be deleted without affecting the reactivity of the deleted E1 protein with antisera. Therefore, haptens may be inserted at the site of the deletion.

The immunogenic compositions are conventionally administered parenterally, typically by injection, for example, subcutaneously or intramuscularly. Additional formulations suitable for other methods of administration include oral formulations and suppositories. Dosage treatment may be a single dose schedule or a multiple dose schedule. The vaccine may be administered in conjunction with other immunoregulatory agents.

The present invention also relates to a composition comprising peptides or polypeptides as described above, for in vitro detection of HCV antibodies present in a biological sample.

The present invention also relates to the use of a composition as described above for the preparation of an immunoassay kit for detecting HCV antibodies present in a biological sample.

The present invention also relates to a method for in vitro diagnosis of HCV antibodies present in a biological sample, comprising at least the following steps:

(i) contacting said biological sample with a composition comprising any of the envelope peptide or proteins as defined above, preferably in an immobilized form under appropriate conditions which allow the formation of an immune complex, wherein said peptide or protein can be a biotinylated peptide or protein which is covalently bound to a solid substrate by means of streptavidin or avidin complexes, (ii) removing unbound components, (iii) incubating the immune complexes formed with heterologous antibodies, with said heterologous antibodies having conjugated to a detectable label under appropriate conditions, (iv) detecting the presence of said immune complexes visually or mechanically (e.g. by means of densitometry, fluorimetry, colorimetry).

Alternatively, the present invention also relates to competition immunoassay formats in which recombinantly produced purified single or specific oligomeric protein E1 and/or E2 and/or E1/E2 proteins as disclosed above are used in combination with E1 and/or E2 peptides in order to compete for HCV antibodies present in a biological sample.

The present invention also relates to a kit for determining the presence of HCV antibodies, in a biological sample, comprising:

at least one peptide or protein composition as defined above, possibly in combination with other polypeptides or peptides from HCV or other types of HCV, with said peptides or proteins being preferentially immobilized on a solid substrate, more preferably on different microwells of the same ELISA plate, and even more preferentially on one and the same membrane strip, a buffer or components necessary for producing the buffer enabling binding reaction between these polypeptides or peptides and the antibodies against HCV present in the biological sample, means for detecting the immune complexes formed in the preceding binding reaction, possibly also including an automated scanning and interpretation device for inferring the HCV genotypes present in the sample from the observed binding pattern.

The immunoassay methods according to the present invention utilize single or specific oligomeric antigens from the E1 and/or E2 domains that maintain linear (in case of peptides) and conformational epitopes (single or specific oligomeric proteins) recognized by antibodies in the sera from individuals infected with HCV. It is within the scope of the invention to use for instance single or specific oligomeric antigens, dimeric antigens, as well as combinations of single or specific oligomeric antigens. The HCV E1 and E2 antigens of the present invention may be employed in virtually any assay format that employs a known antigen to detect antibodies. Of course, a format that denatures the HCV conformational epitope should be avoided or adapted. A common feature of all of these assays is that the antigen is contacted with the body component suspected of containing HCV antibodies under conditions that permit the antigen to bind to any such antibody present in the component. Such conditions will typically be physiologic temperature, pH and ionic strenght using an excess of antigen. The incubation of the antigen with the specimen is followed by detection of immune complexes comprised of the antigen.

Design of the immunoassays is subject to a great deal of variation, and many formats are known in the art. Protocols may, for example, use solid supports, or immunoprecipitation. Most assays involve the use of labeled antibody or polypeptide; the labels may be, for example, enzymatic, fluorescent, chemiluminescent, radioactive, or dye molecules. Assays which amplify the signals from the immune complex are also known; examples of which are assays which utilize biotin and avidin or streptavidin, and enzyme-labeled and mediated immunoassays, such as ELISA assays.

The immunoassay may be, without limitation, in a heterogeneous or in a homogeneous format, and of a standard or competitive type. In a heterogeneous format, the polypeptide is typically bound to a solid matrix or support to facilitate separation of the sample from the polypeptide after incubation. Examples of solid supports that can be used are nitrocellulose (e.g., in membrane or microtiter well form), polyvinyl chloride (e.g., in sheets or microtiter wells), polystyrene latex (e.g., in beads or microtiter plates, polyvinylidene fluoride (known as Immunolon™), diazotized paper, nylon membranes, activated beads, and Protein A beads. For example, Dynatech Immunolon™ 1 or Immunlon™ 2 microtiter plates or 0.25 inch polystyrene beads (Precision Plastic Ball) can be used in the heterogeneous format. The solid support containing the antigenic polypeptides is typically washed after separating it from the test sample, and prior to detection of bound antibodies. Both standard and competitive formats are know in the art.

In a homogeneous format, the test sample is incubated with the combination of antigens in solution. For example, it may be under conditions that will precipitate any antigen-antibody complexes which are formed. Both standard and competitive formats for these assays are known in the art.

In a standard format, the amount of HCV antibodies in the antibody-antigen complexes is directly monitored. This may be accomplished by determining whether labeled anti-xenogeneic (e.g. anti-human) antibodies which recognize an epitope on anti-HCV antibodies will bind due to complex formation. In a competitive format, the amount of HCV antibodies in the sample is deduced by monitoring the competitive effect on the binding of a known amount of labeled antibody (or other competing ligand) in the complex.

Complexes formed comprising anti-HCV antibody (or in the case of competitive assays, the amount of competing antibody) are detected by any of a number of known techniques, depending on the format. For example, unlabeled HCV antibodies in the complex may be detected using a conjugate of anti-xenogeneic lg complexed with a label (e.g. an enzyme label).

In an immunoprecipitation or agglutination assay format the reaction between the HCV antigens and the antibody forms a network that precipitates from the solution or suspension and forms a visible layer or film of precipitate. If no anti-HCV antibody is present in the test specimen, no visible precipitate is formed.

There currently exist three specific types of particle agglutination (PA) assays. These assays are used for the detection of antibodies to various antigens when coated to a support. One type of this assay is the hemagglutination assay using red blood cells (RBCs) that are sensitized by passively adsorbing antigen (or antibody) to the RBC. The addition of specific antigen antibodies present in the body component, if any, causes the RBCs coated with the purified antigen to agglutinate.

To eliminate potential non-specific reactions in the hemagglutination assay, two artificial carriers may be used instead of RBC in the PA. The most common of these are latex particles. However, gelatin particles may also be used. The assays utilizing either of these carriers are based on passive agglutination of the particles coated with purified antigens.

The HCV single or specififc oligomeric E1 and/or E2 and/or E1/E2 antigens of the present invention comprised of conformational epitopes will typically be packaged in the form of a kit for use in these immunoassays. The kit will normally contain in separate containers the native HCV antigen, control antibody formulations (positive and/or negative), labeled antibody when the assay format requires the same and signal generating reagents (e.g. enzyme substrate) if the label does not generate a signal directly. The native HCV antigen may be already bound to a solid matrix or separate with reagents for binding it to the matrix. Instructions (e.g. written, tape, CD-ROM, etc.) for carrying out the assay usually will be included in the kit.

Immunoassays that utilize the native HCV antigen are useful in screening blood for the preparation of a supply from which potentially infective HCV is lacking. The method for the preparation of the blood supply comprises the following steps. Reacting a body component, preferably blood or a blood component, from the individual donating blood with HCV E1 and/or E2 proteins of the present invention to allow an immunological reaction between HCV antibodies, if any, and the HCV antigen. Detecting whether anti-HCV antibody-HCV antigen complexes are formed as a result of the reacting. Blood contributed to the blood supply is from donors that do not exhibit antibodies to the native HCV antigens, E1 or E2.

In cases of a positive reactivity to the HCV antigen, it is preferable to repeat the immunoassay to lessen the possibility of false positives. For example, in the large scale screening of blood for the production of blood products (e.g. blood transfusion, plasma, Factor VIII, immunoglobulin, etc.) 'screening' tests are typically formatted to increase sensitivity (to insure no contaminated blood passes) at the expense of specificity; i.e. the false-positive rate is increased. Thus, it is typical to only defer for further testing those donors who are 'repeatedly reactive'; i.e. positive in two or more runs of the immunoassay on the donated sample. However, for confirmation of HCV-positivity, the 'confirmation' tests are typically formatted to increase specificity (to insure that no false-positive samples are confirmed) at the expense of sensitivity. Therefore the purification method described in the present invention for E1 and E2 will be very advantageous for including single or specific oligomeric envelope proteins into HCV diagnostic assays.

The solid phase selected can include polymeric or glass beads, nitrocellulose, microparticles, microwells of a reaction tray, test tubes and magnetic beads. The signal generating compound can include an enzyme, a luminescent compound, a chromogen, a radioactive element and a chemiluminescent compound. Examples of enzymes include alkaline phosphatase, horseradish peroxidase and beta-galactosidase. Examples of enhancer compounds include biotin, anti-biotin and avidin. Examples of enhancer compounds binding members include biotin, anti-biotin and avidin, in order to block the effects of rheumatoid factor-like substances, the test sample is subjected to conditions sufficient to block the effect of rheumatoid factor-like substances. These conditions comprise contacting the test sample with a quantity of anti-human IgG to form a mixture, and incubating the mixture for a time and under conditions sufficient to form a reaction mixture product substantially free of rheumatoid factor-like substance.

The present invention further contemplates the use of E1 proteins, or parts thereof, more particularly HCV single or specific oligomeric E1 proteins as defined above, for in vitro monitoring HCV disease or prognosing the response to treatment (for instance with Interferon) of patients suffering from HCV infection comprising:

incubating a biological sample from a patient with hepatitis C infection with an E1 protein or a suitable part thereof under conditions allowing the formation of an immunological complex, removing unbound components, calculating the anti-E1 titers present in said sample (for example at the start of and/or during the course of (interferon) therapy), monitoring the natural course of HCV disease, or prognosing the response to treatment of said patient on the basis of the amount anti-E1 titers found in said sample at the start of treatment and/or during the course of treatment.

Patients who show a decrease of 2, 3, 4, 5, 7, 10, 15, or preferably more than 20 times of the initial anti-E1 titers could be concluded to be long-term, sustained responders to HCV therapy, more particularly to interferon therapy. It is illustrated in the Examples section, that an anti-E1 assay may be very useful for prognosing long-term response to IFN treatment, or to treatment of Hepatitis C virus disease in general.

More particularly the following E1 peptides as listed in Table 3 were found to be useful for in vitro monitoring HCV disease or prognosing the response to interferon treatment of patients suffering from HCV infection:

Et-31 (SEQ ID NO 56) spanning amino acids 181 to 200 of the Core/E1 V1 region,

E1-33 (SEQ ID NO 57) spanning amino acids 193 to 212 of the E1 region.

E1-35 (SEQ ID NO 58) spanning amino acids 205 to 224 of the E1 V2 region (epitope B), E1-35A (SEQ ID NO 59) spanning amino acids 208 to 227 of the E1 V2 region (epitope B), 1bE1 (SEQ ID NO 53) spanning amino acids 192 to 223 of E1 regions (V1, C1, and V2 regions (containing epitope B)), E1-51 (SEQ ID NO 66) spanning amino acids 301 to 320 of the E1 region, E1-53 (SEQ ID NO 67) spanning amino acids 313 to 332 of the E1 C4 region (epitope A), E1-55 (SEQ ID NO 68) spanning amino acids 325 to 344 of the E1 region.

It is to be understood that smaller fragments of the above-mentioned peptides also fall within the scope of the present invention. Said smaller fragments can be easily prepared by chemical synthesis and can be tested for their ability to be used in an assay as detailed above and in the Examples section.

The present invention also relates to a kit for monitoring HCV disease or prognosing the response to treatment (for instance to interferon) of patients suffering from HCV infection comprising:

at least one E1 protein or E1 peptide, more particularly an E1 protein or E1 peptide as defined above, a buffer or components necessary for producing the buffer enabling the binding reaction between these proteins or peptides and the anti-E1 antibodies present in a biological sample, means for detecting the immune complexes formed in the preceding binding reaction, possibly also an automated scanning and interpretation device for inferring a decrease of anti-E1 titers during the progression of treatment.

It is to be understood that also E2 protein and peptides according to the present invention can be used to a certain degree to monitor/prognose HCV treatment as indicated above for the E1 proteins or peptides because also the anti-E2 levels decrease in comparison to antibodies to the other HCV antigens. It is to be understood, however, that it might be possible to determine certain epitopes in the E2 region which would also be suited for use in an test for monitoring/prognosing HCV disease.

The present invention also relates to a serotyping assay for detecting one or more serological types of HCV present in a biological sample, more particularly for detecting antibodies of the different types of HCV to be detected combined in one assay format, comprising at least the following steps:

(i) contacting the biological sample to be analyzed for the presence of HCV antibodies of one or more serological types, with at least one of the E1 and/or E2 and/or E1/E2 protein compositions or at least one of the E1 or E2 peptide compositions as defined above, preferantially in an immobilized form under appropriate conditions which allow the formation of an immune complex, (ii) removing unbound components, (iii) incubating the immune complexes formed with heterologous antibodies, with said heterologous antibodies being conjugated to a detectable label under appropriate conditions, (iv) detecting the presence of said immune complexes visually or mechanically (e.g. by means of densitometry, fluorimetry, colorimetry) and inferring the presence of one or more HCV serological types present from the observed binding pattern.

It is to be understood that the compositions of proteins or peptides used in this method are recombinantly expressed type-specific envelope proteins or type-specific peptides.

The present invention further relates to a kit for serotyping one or more serological types of HCV present in a biological sample, more particularly for detecting the antibodies to these serological types of HCV comprising:

at least one E1 and/or E2 and/or E1/E2 protein or E1 or E2 peptide, as defined above, a buffer or components necessary for producing the buffer enabling the binding reaction between these proteins or peptides and the anti-E1 antibodies present in a biological sample, means for detecting the immune complexes formed in the preceding binding reaction, possibly also an automated scanning and interpretation device for detecting the presence of one or more serological types present from the observed binding pattern.

The present invention also relates to the use of a peptide or protein composition as defined above, for immobilization on a solid substrate and incorporation into a reversed phase hybridization assay, preferably for immobilization as parallel lines onto a solid support such as a membrane strip, for determining the presence or the genotype of HCV according to a method as defined above. Combination with other type-specific antigens from other HCV polyprotein regions also lies within the scope of the present invention.

FIGURE AND TABLE LEGENDS

FIG. 1: Restriction map of plasmid pgpt ATA 18

Figure 2:
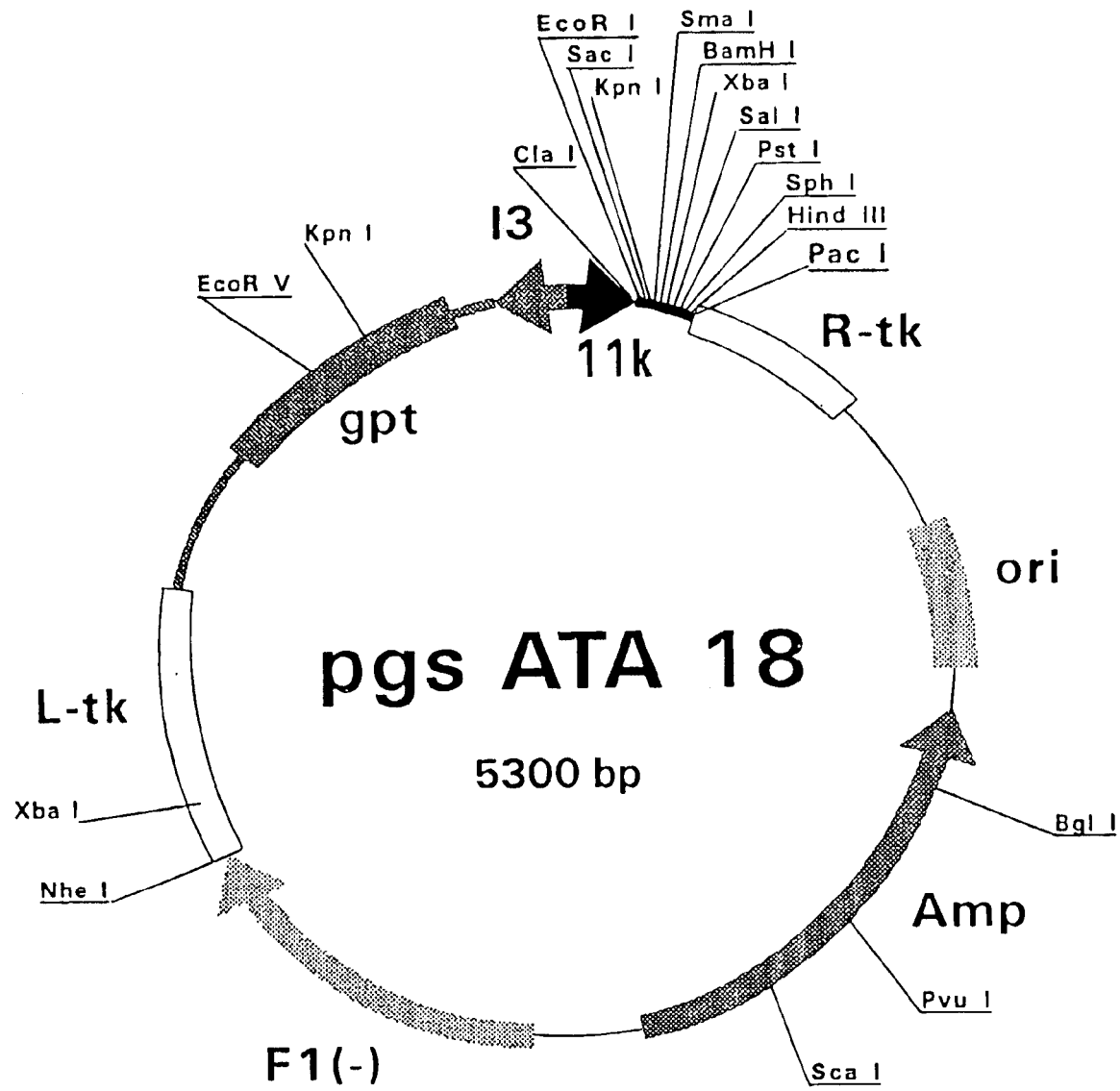

FIG. 2: Restriction map of plasmid pgs ATA 18

Figure 3:
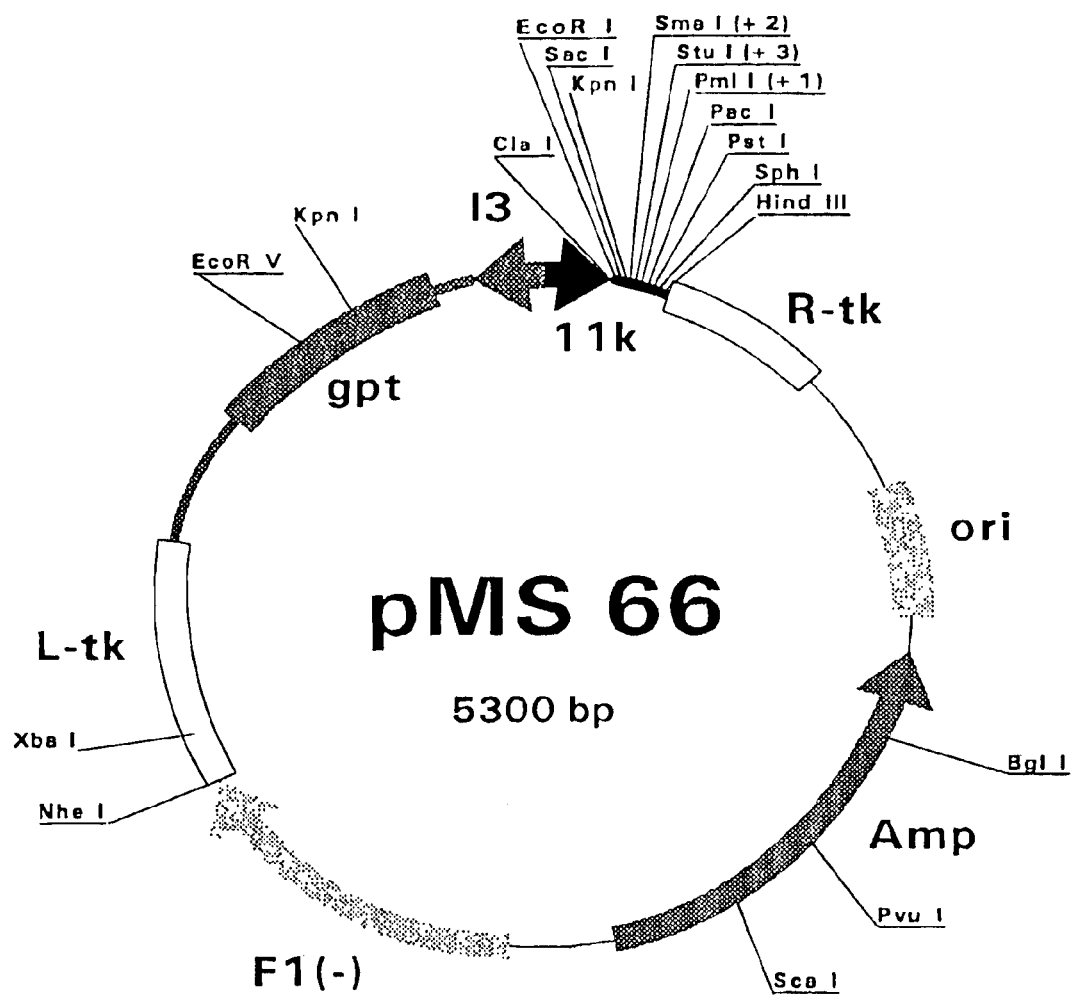

FIG. 3: Restriction map of plasmid pMS 66

Figure 4:
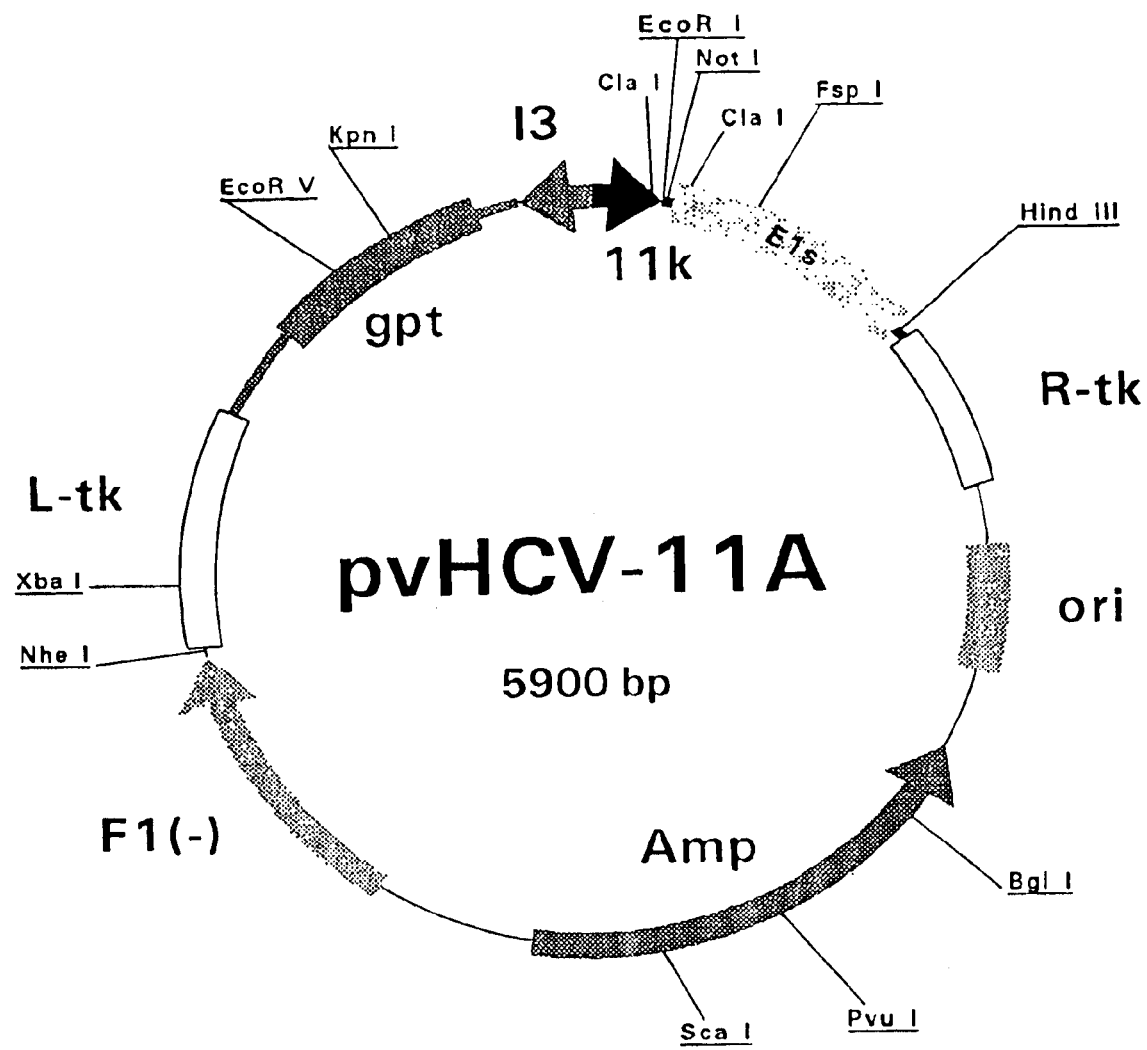

FIG. 4: Restriction map of plasmid pv HCV-11A

Figure 5:
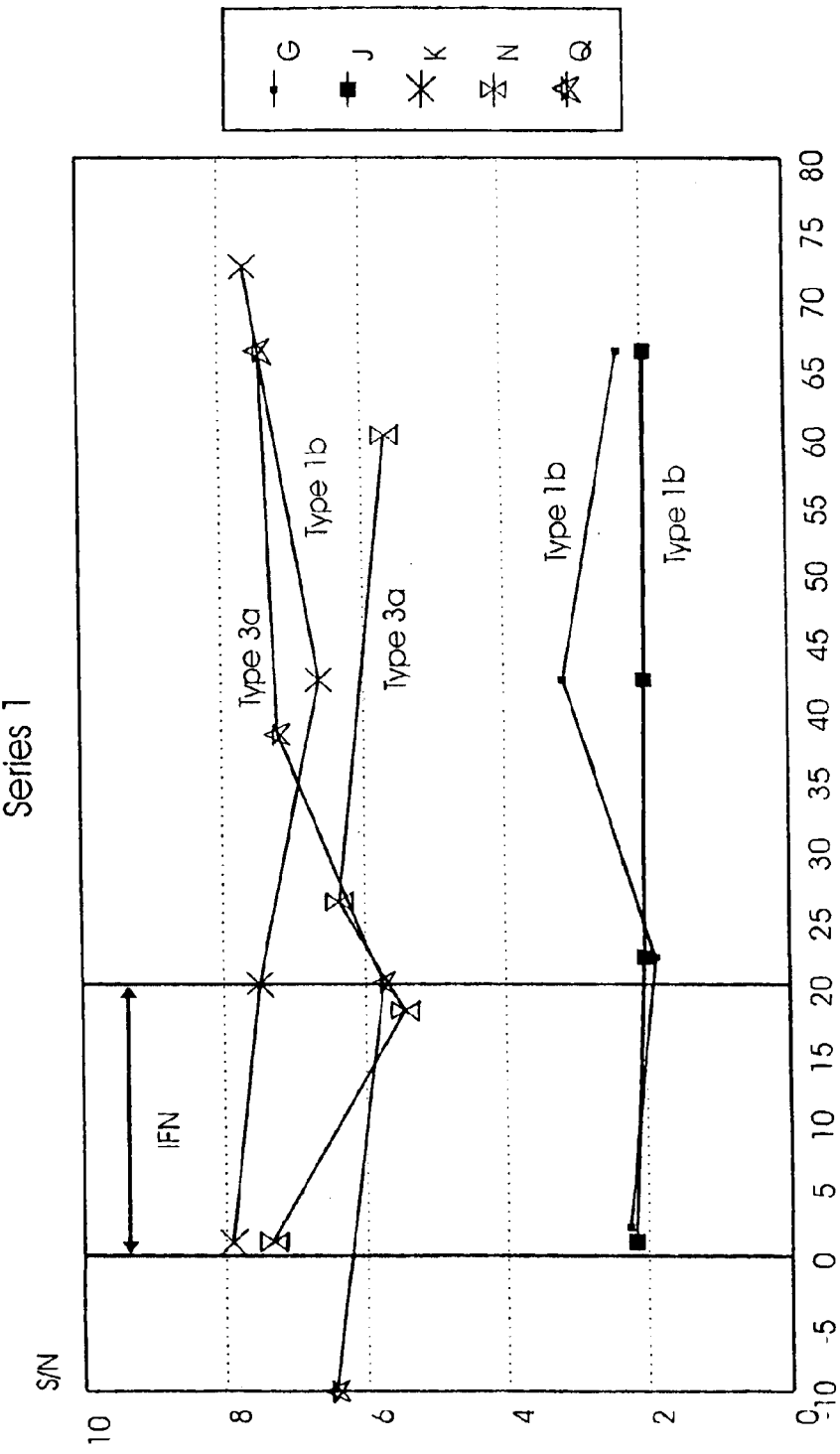

FIG. 5: Anti-E1 levels in non-responders to IFN treatment

Figure 6:
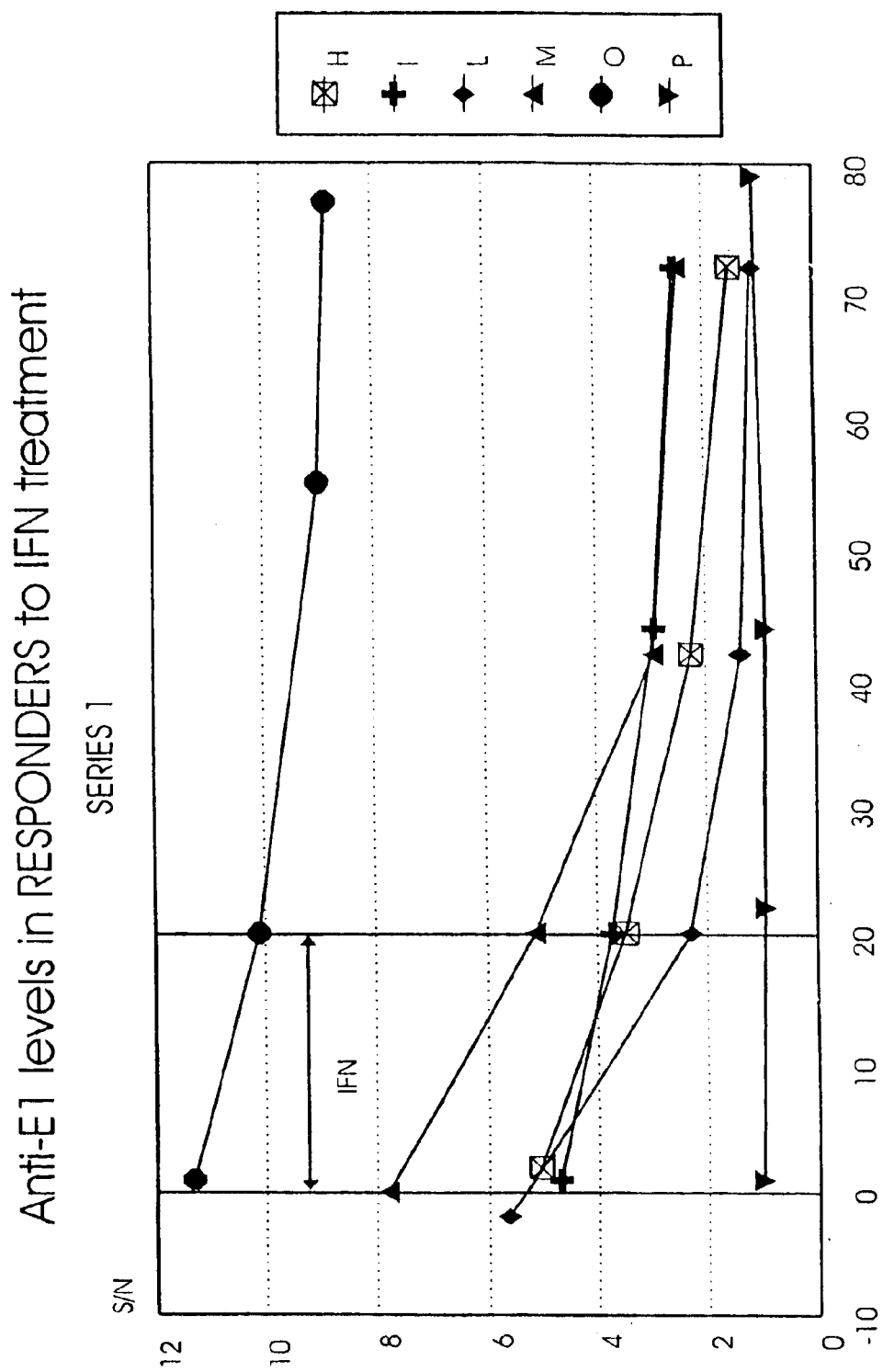

FIG. 6: Anti-E1 levels in responders to IFN treatment

FIG. 7: Anti-E1 levels in patients with complete response to IFN treatment

FIG. 8: Anti-E1 levels in incomplete responders to IFN treatment

Figure 9:
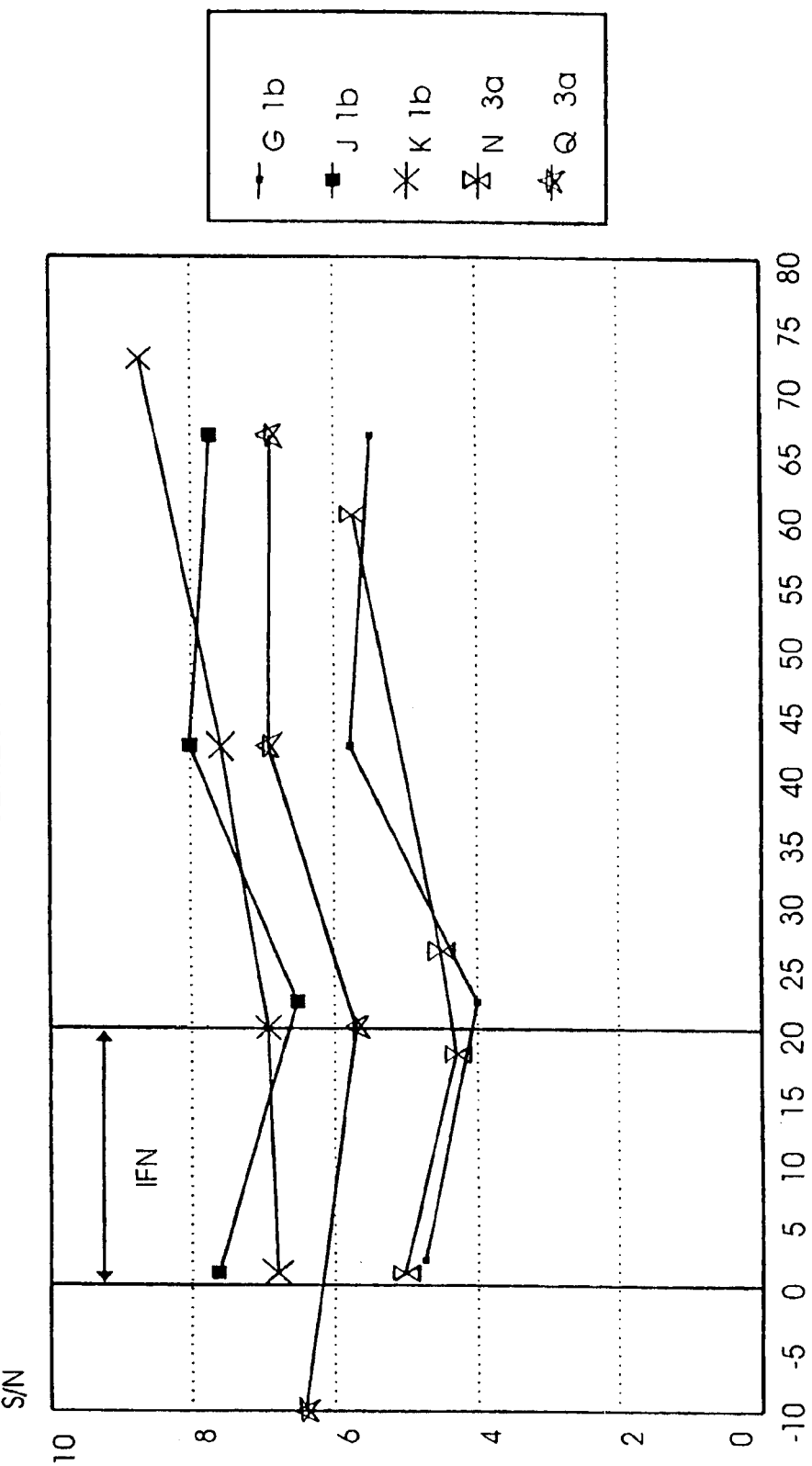

FIG. 9: Anti-E2 levels in non-responders to IFN treatment

Figure 10:
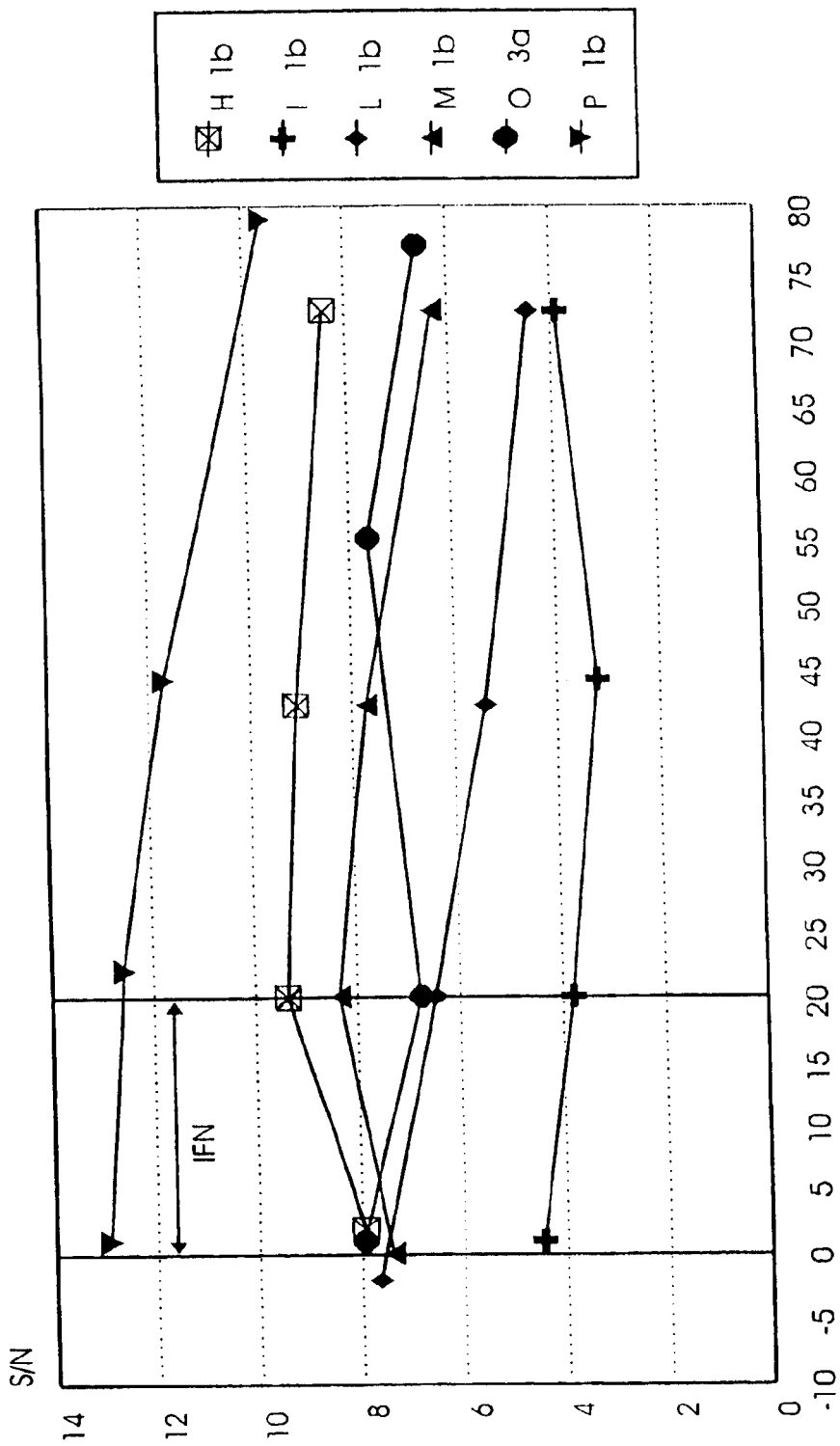

FIG. 10: Anti-E2 levels in responders to IFN treatment

Figure 11:
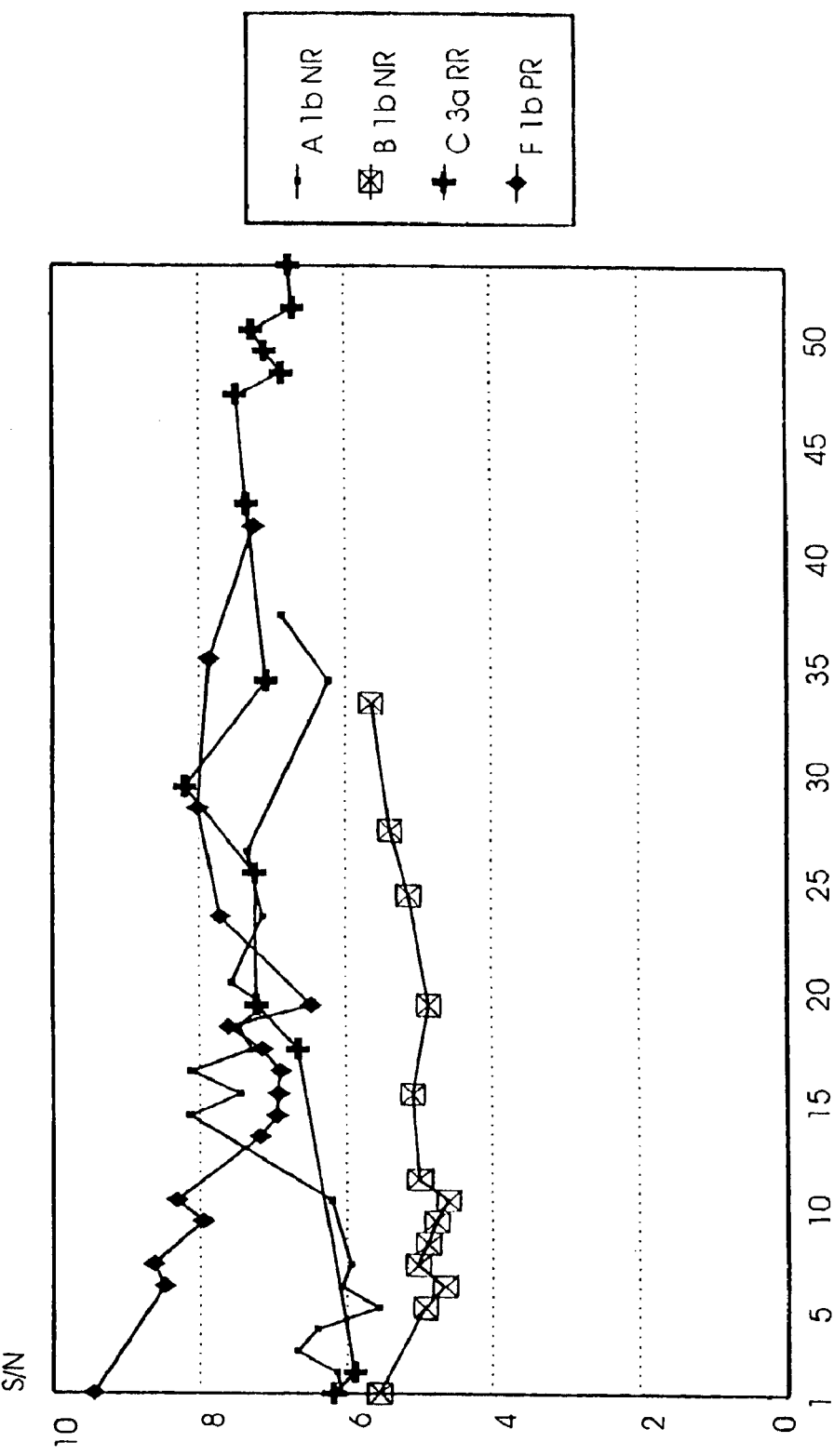

FIG. 11: Anti-E2 levels in incomplete responders to IFN treatment

Figure 12:
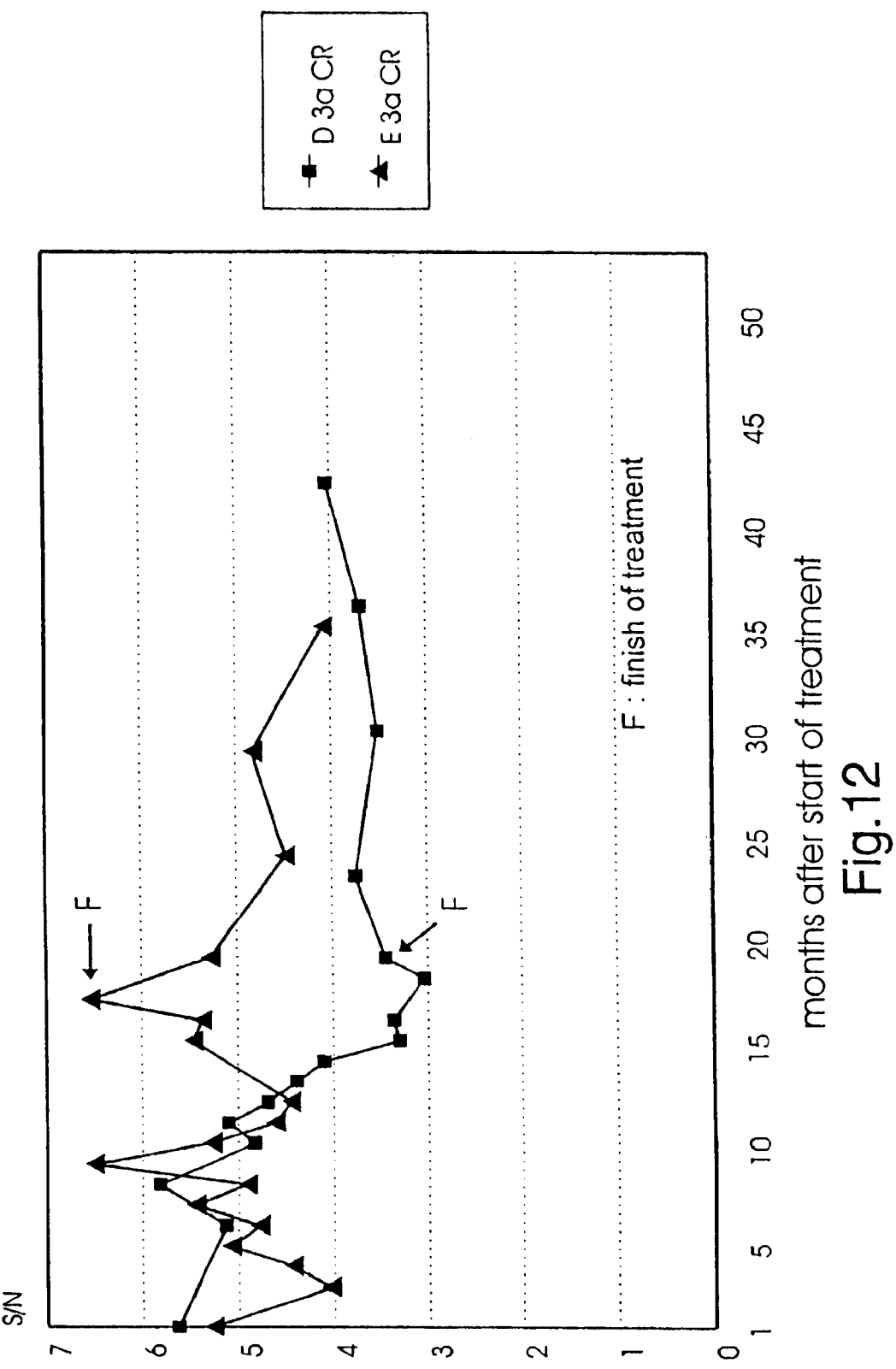

FIG. 12: Anti-E2 levels in complete responders to IFN treatment

Figure 13:
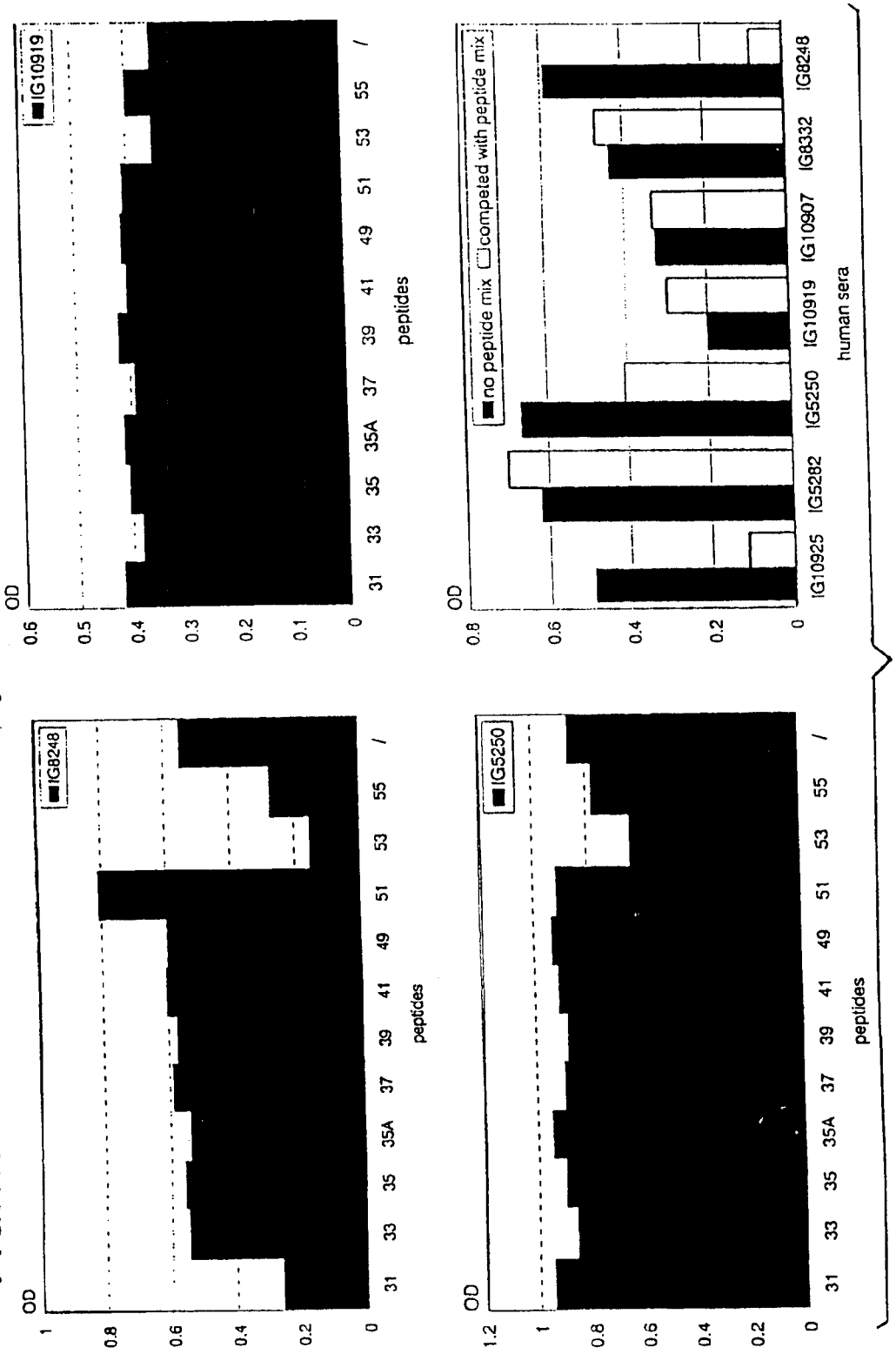

FIG. 13: Human anti-E1 reactivity competed with peptides

Figure 14:
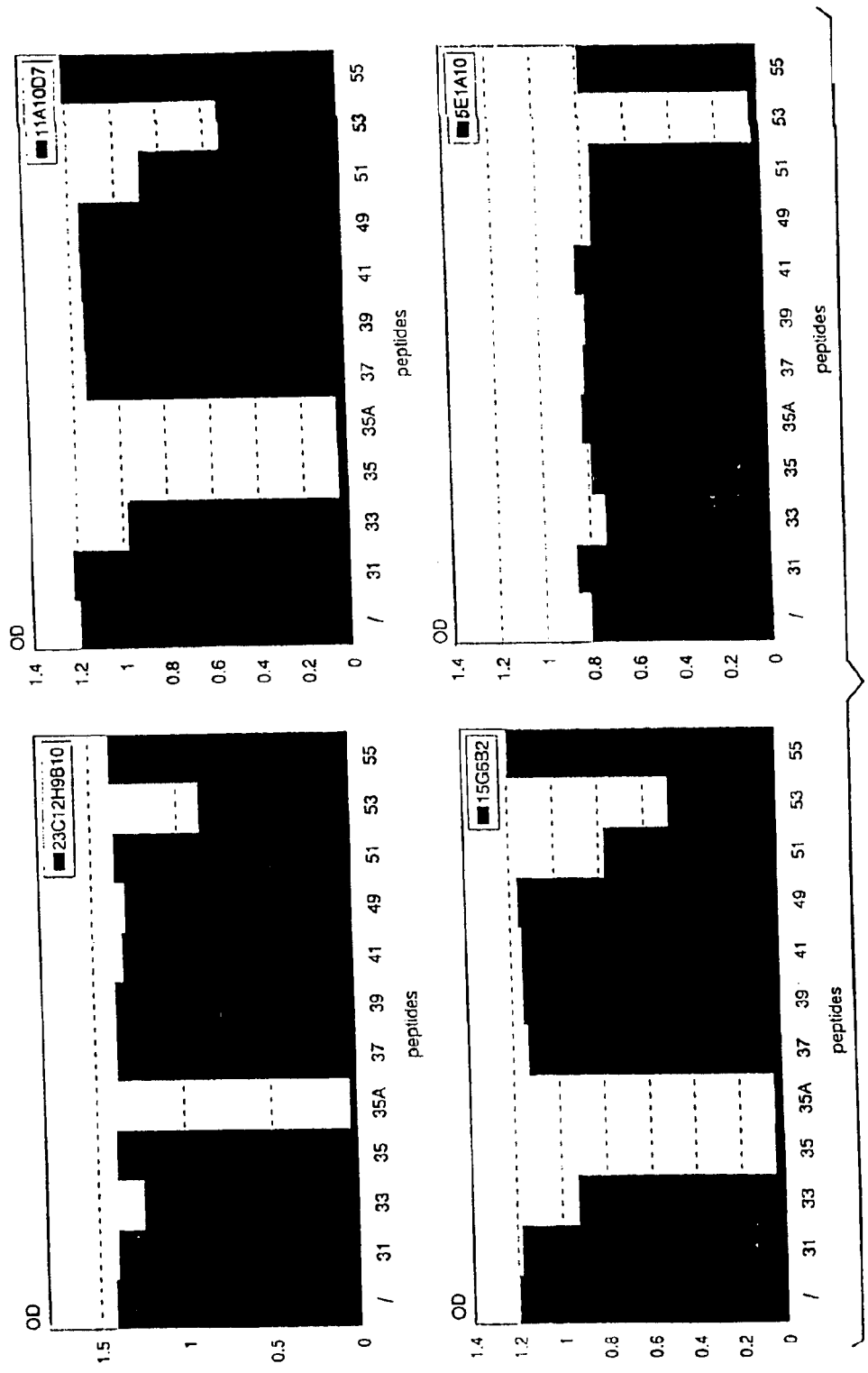
Figure 15:
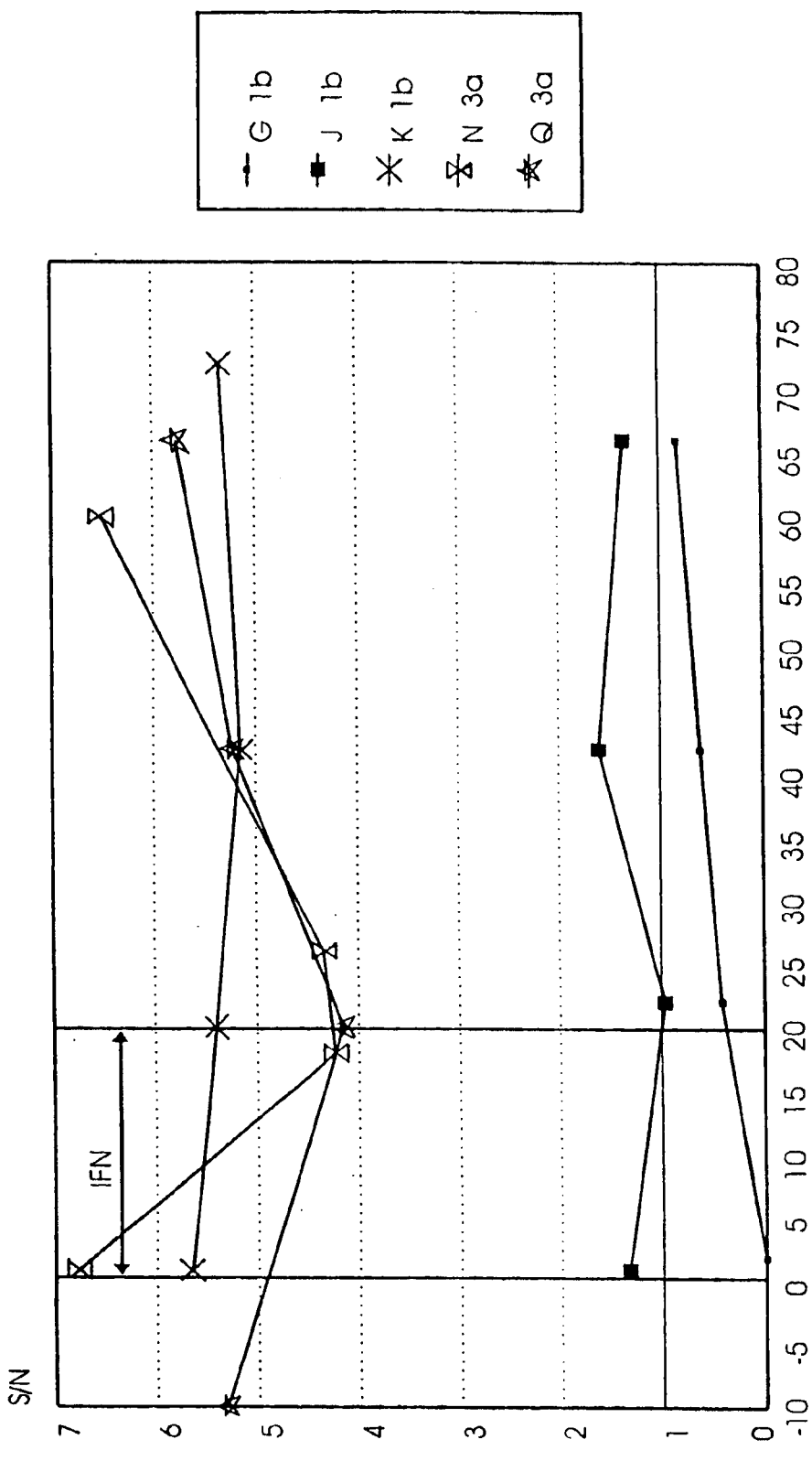
Figure 16:
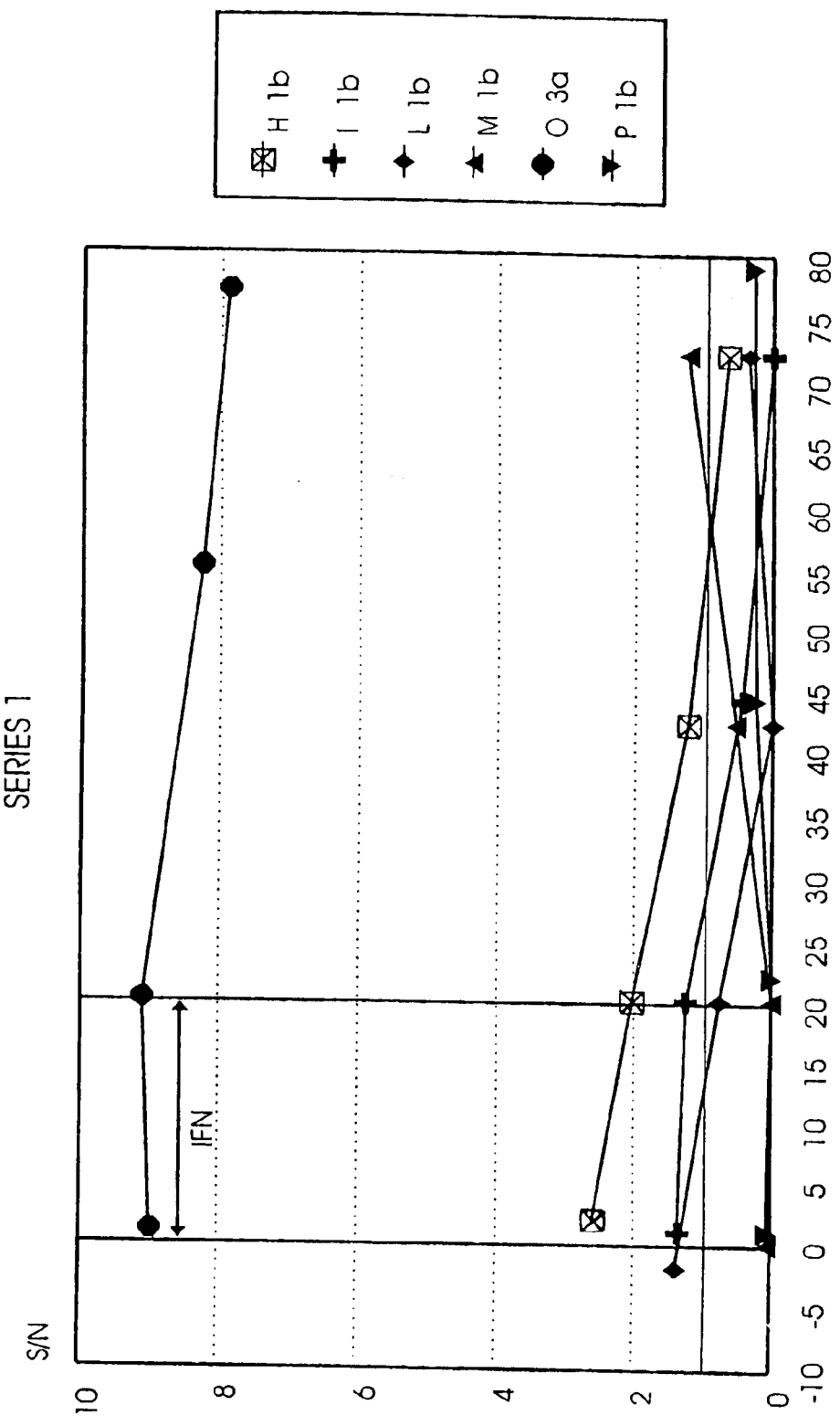
Figure 17:
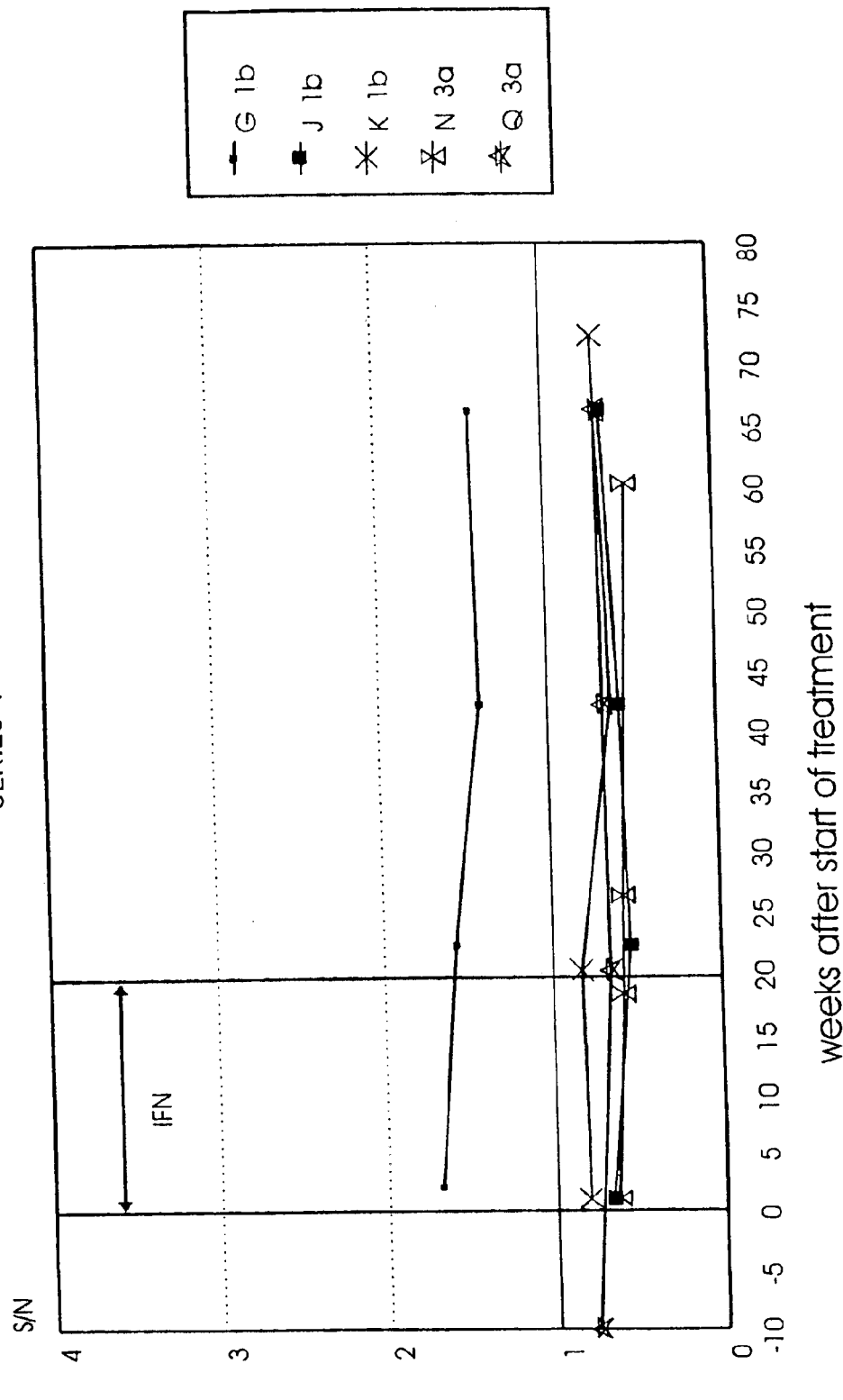
Figure 18:
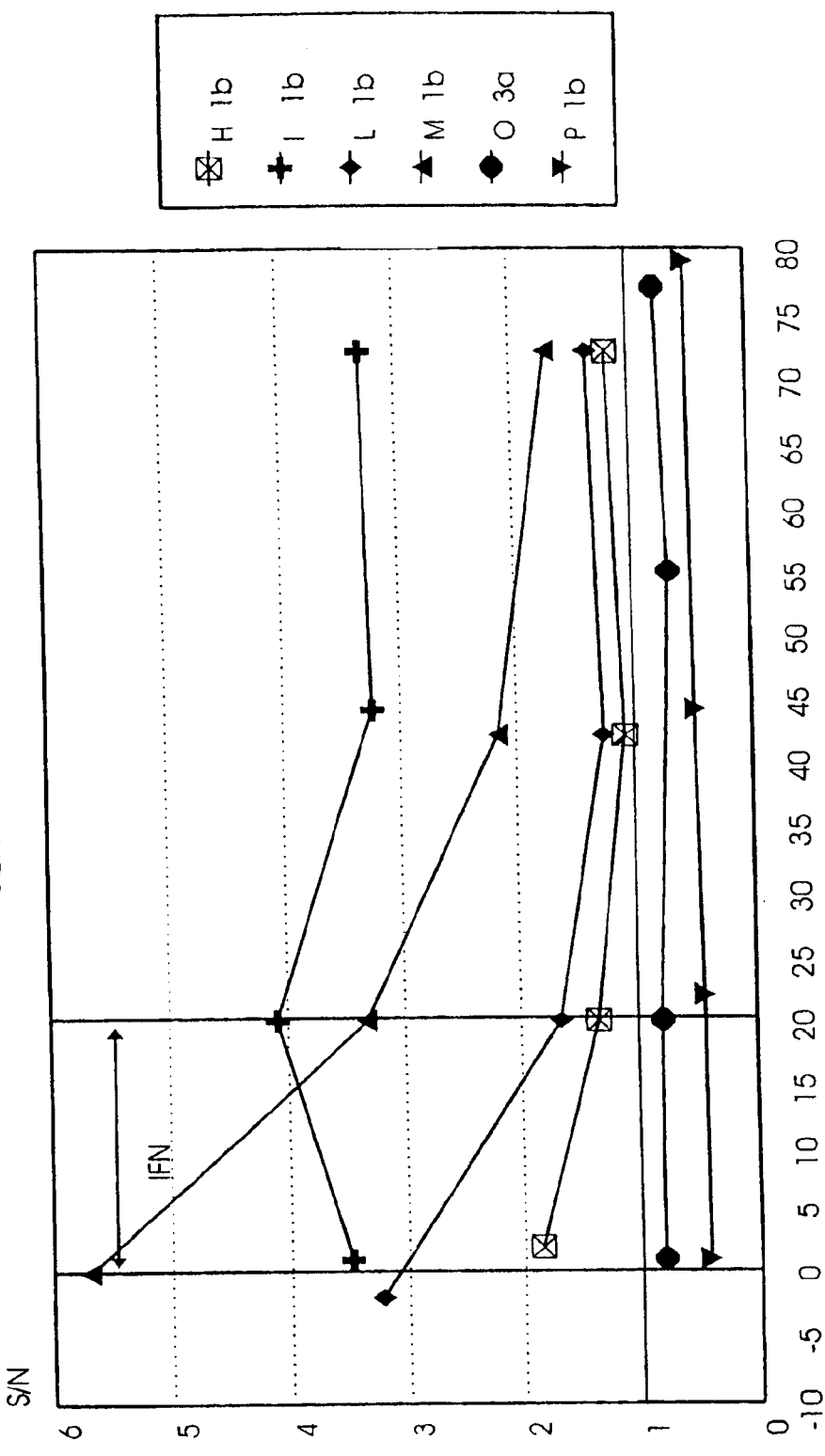

FIG. 14: Competition of reactivity of anti-E1 monoclonal antibodies with peptides FIG. 15: Anti-E1 (epitope 1) levels in non-responders to IFN treatment FIG. 16: Anti-E1 (epitope 1) levels in responders to IFN treatment FIG. 17: Anti-E1 (epitope 2) levels in non-responders to IFN treatment FIG. 18: Anti-E1 (epitope 2) levels in responders to IFN treatment FIG. 19: Competition of reactivity of anti-E2 monoclonal antibodies with peptides FIG. 20: Human anti-E2 reactivity competed with peptides FIG. 21: FIGS. 21A–L provide nucleic acid sequences of the present invention. The nucleic acid sequences encoding an E1 or E2 protein according to the present invention may be translated (SEQ ID NO 3 to 13, 21–31, 35 and 41–49 are translated in a reading frame starting from residue number 1, SEQ ID NO 37–39 are translated in a reading frame starting from residue number 2), into the amino acid sequences of the respective E1 or E2 proteins as shown in the sequence listing.

FIG. 22: ELISA results obtained from lentil lectin chromatography eluate fractions of 4 different E1 purifications of cell lysates infected with vvHCV39 (type 1b), vvHCV40 (type 1b), vvHCV62:(type 3a) and vvHCV63 (type 5a)

Figure 23:
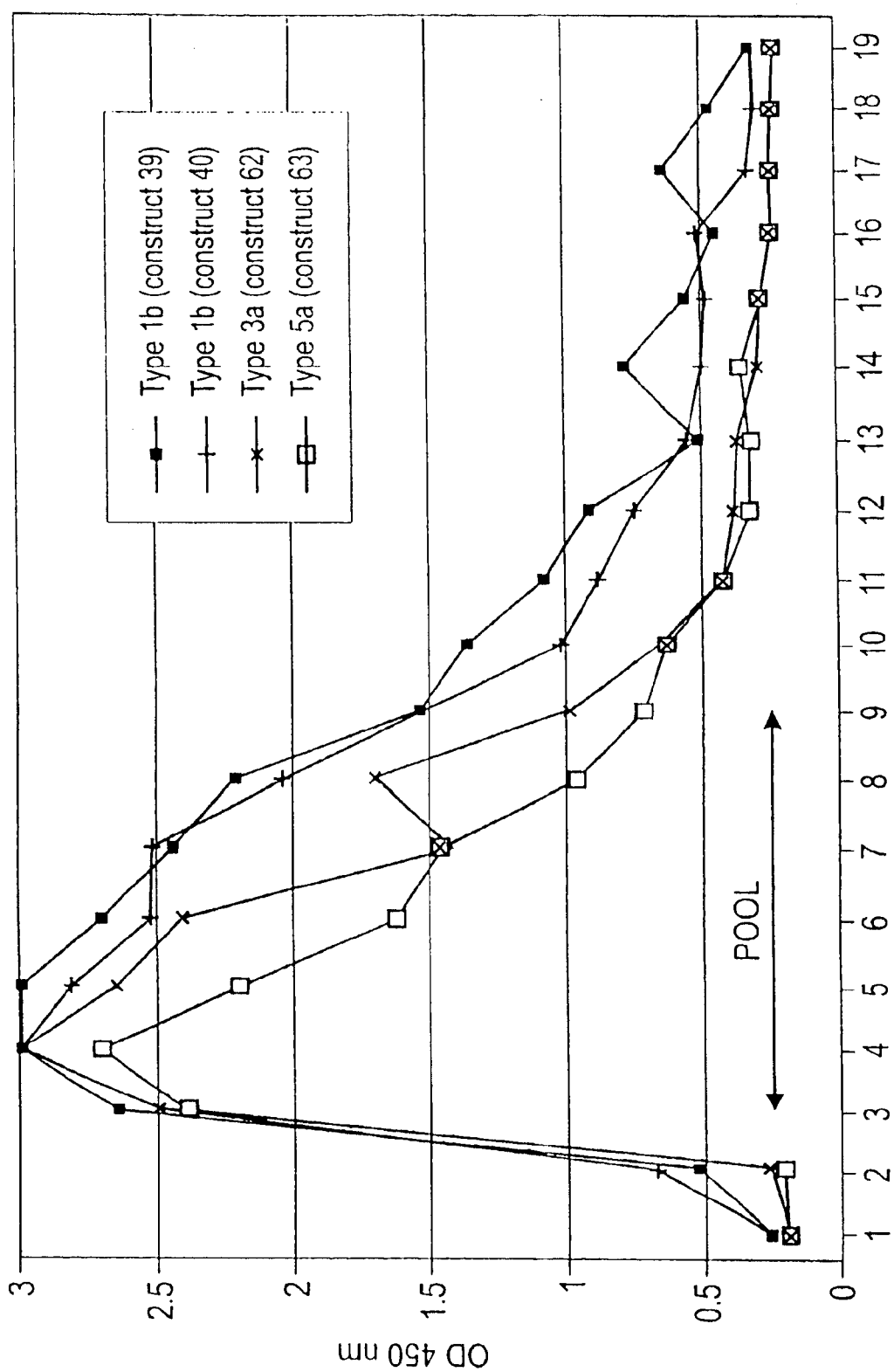

FIG. 23: Elution profiles obtained from the lentil lectin chromatography of the 4 different E1 constructs on the basis of the values as shown in FIG. 22.

FIG. 24: ELISA results obtained from fractions obtained after gelfiltration chromatography of 4 different E1 purifications of cell lysates infected with vvHCV39 (type 1b). vvHCV40 (type 1b), vvHCV62 (type 3a), and vvHCV63 (type 5a).

FIG. 25: Profiles obtained from purifications of E1 proteins of type 1b (1), type 3a (2), and type 5a (3) (from RK13 cells infected with vvHCV39, vvHCV62, and vvHCV63, respectively; purified on lentil lectin and reduced as in example 5.2–5.3) and a standard (4). The peaks indicated with ‘1’, ‘2’, and ‘3’, represent pure E1 protein peaks (see FIG. 24. E1 reactivity mainly in fractions 26 to 30).

FIG. 26: Silver staining of an SDS-PAGE as described in example 4 of a raw lysate of E1 vvHCV40 (type 1b) (lane 1), pool 1 of the gelfiltration of vvHCV40 representing fractions 10 to 17 as shown in FIG. 25 (lane 2), pool 2 of the gelfiltration of vvHCV40 representing fractions 13 to 25 as shown in FIG. 25 (lane 3), and E1 pool (fractions 26 to 30) (lane 4).

FIG. 27: Streptavidine-alkaline phosphatase blot of the fractions of the gelfiltration of E1 constructs 39 (type 1b) and 62 (type 3a). The proteins were labelled with NEM-biotin. Lane 1: start gelfiltration construct 39, lane 2: fraction 26 construct 39, lane 3: fraction 27 construct 39, lane 4: fraction 28 construct 39, lane 5: fraction 29 construct 39, lane 6: fraction 30 construct 39, lane 7 fraction 31 construct 39, lane 8: molecular weight marker, lane 9: start gelfiltration construct 62, lane 10: fraction 26 construct 62, lane 11: fraction 27 construct 62, lane 12: fraction 28 construct 62, lane 13: fraction 29 construct 62, lane 14: fraction 30 construct 62, lane 15: fraction 31 construct 62.

FIG. 28: Siver staining of an SDS-PAGE gel of the gelfiltration fractions of vvHCV-39 (E1s, type 1b) and vvHCV-62 (E1s, type 3a) run under identical conditions as FIG. 26. Lane 1: start gelfiltration construct 39, lane 2: fraction 26 construct 39, lane 3: fraction 27 construct 39, lane 4: fraction 28 construct 39, lane 5: fraction 29 construct 39, lane 6: fraction 30 construct 39, lane 7 fraction 31 construct 39, lane 8: molecular weight marker, lane 9: start gelfiltration construct 62, lane 10: fraction 26 construct 62, lane 11: fraction 27 construct 62, lane 12: fraction 28 construct 62, lane 13: fraction 29 construct 62, lane 14: fraction 30 construct 62, lane 15: fraction 31 construct 62.

FIG. 29: Western Blot analysis with anti-E1 mouse monoclonal antibody 5E1A10 giving a complete overview of the purification procedure. Lane 1: crude lysate, Lane 2: flow through of lentil chromagtography. Lane 3: wash with Empigen BE after lentil chromatography, Lane 4: Eluate of lentil chromatography, Lane 5: Flow through during concentration of the lentil eluate, Lane 6: Pool of E1 after Size Exclusion Chromatography (gelfiltration).

FIG. 30: $OD_{280}$ profile (continuous line) of the lentil lectin chromatography of E2 protein from RK13 cells infected with vvHCV44. The doted line represents the E2 reactivity as detected by ELISA (as in example 6).

FIG. 31A: $OD_{280}$ profile (continuous line) of the lentil-lectin gelfiltration chromatography E2 protein pool from RK13 cells infected with vvHCV44 in which the E2 pool is applied immediately on the gelfiltration column (non-reduced conditions). The dotted line represents the E2 reactivity as detected by ELISA (as in example 6).

FIG. 31B: $OD_{280}$ profile (continuous line) of the lentil-lectin gelfiltration chromatography E2 protein pool from RK13 cells infected with vvHCV44 in which the E2 pool was reduced and blocked according to Example 5.3 (reduced conditions). The dotted line represents the E2 reactivity as detected by ELISA (as in example 6).

FIG. 32: $Ni^{2+}$-IMAC chromatography and ELISA reactivity of the E2 protein as expressed from vvHCV44 after gelfiltration under reducing conditions as shown in FIG. 31B.

FIG. 33: Silver staining of an SOS-PAGE of 0.5 μg of purified E2 protein recovered by a 200 mM imidazole elution step (lane 2) and a 30 mM imidazole wash (lane 1) of the $Ni^{2+}$-IMAC chromatography as shown in FIG. 32.

FIG. 34: OD profiles of a desalting step of the purified E2 protein recovered by 200 mM imidazole as shown in FIG. 33, intended to remove imidazole.

FIGS. 35A-1 to 35A-8: Antibody levels to the different HCV antigens (Core 1, Core 2, E2HCVR, NS3) for NR and LTR followed during treatment and over a period of 6 to 12 months after treatment determined by means of the LIAscan method. The average values are indicated by the curves with the open squares.

FIGS. 35B-1 to 35B-8: Antibody levels to the different HCV antigens (NS4, NS5, E1 and E2) for NR and LTR followed during treatment and over a period of 6 to 12 months after treatment determined by means of the L1Ascan method. The average values are indicated by the curve with the open squares.

Figure 36A:
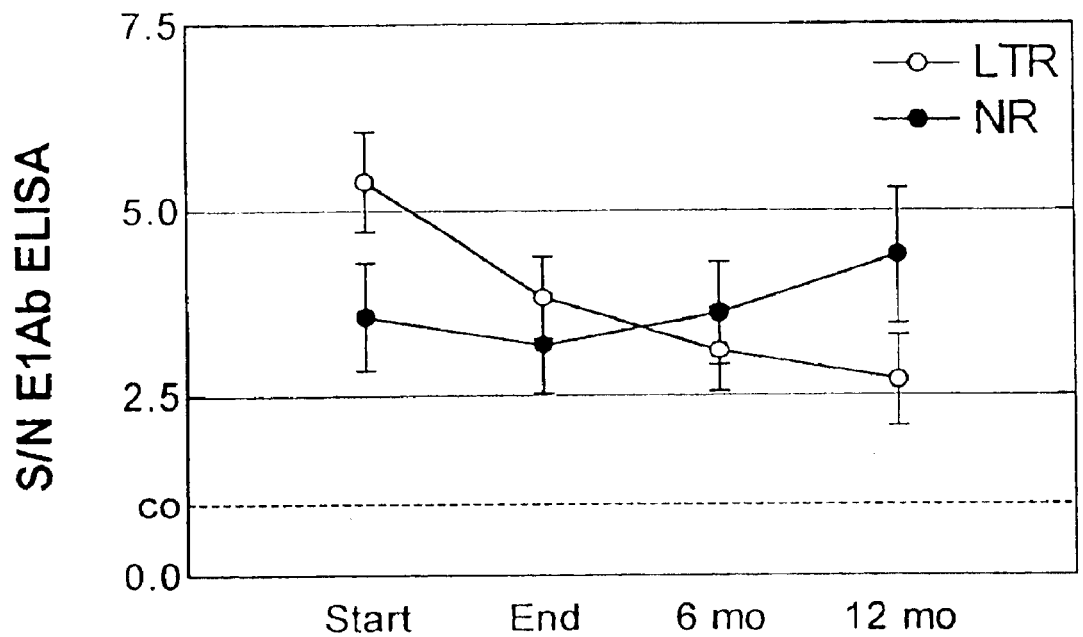
Figure 36B:
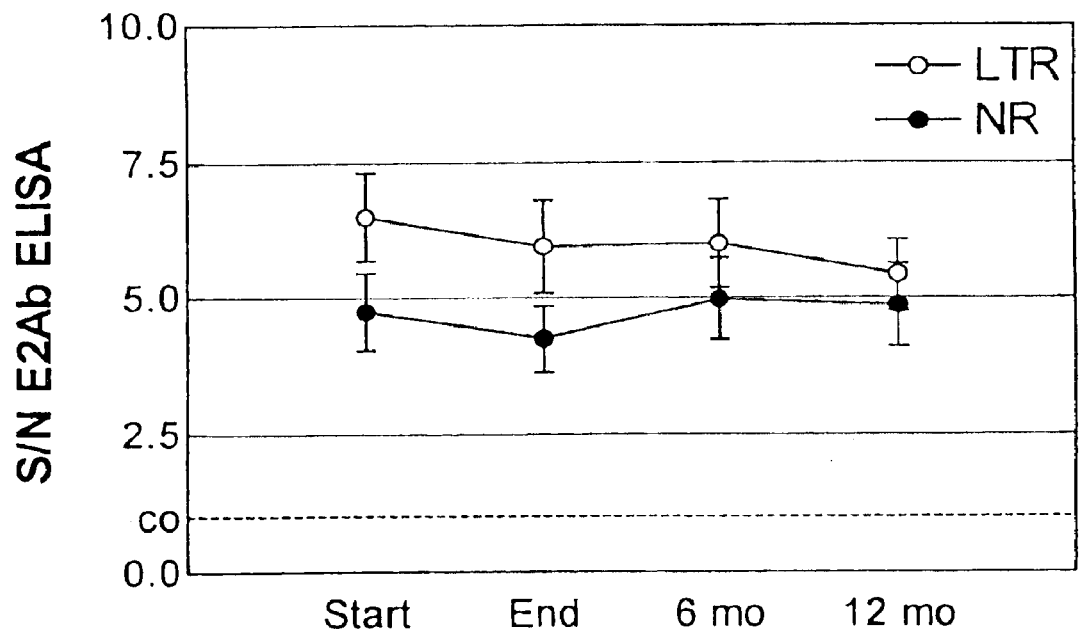
Figure 37B:
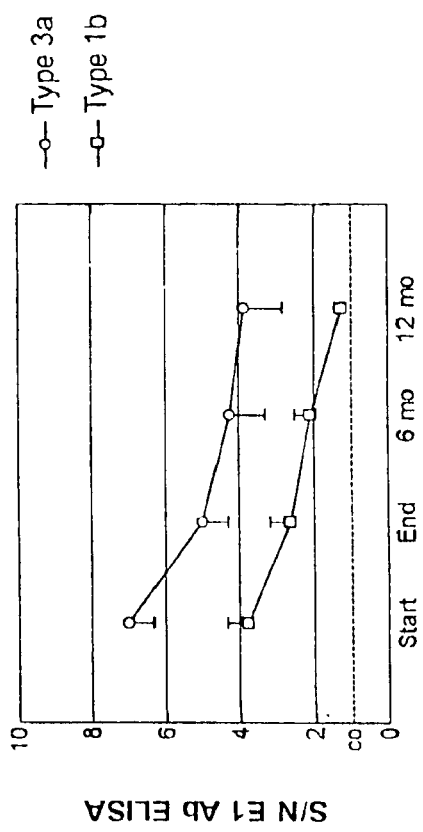
Figure 37D:
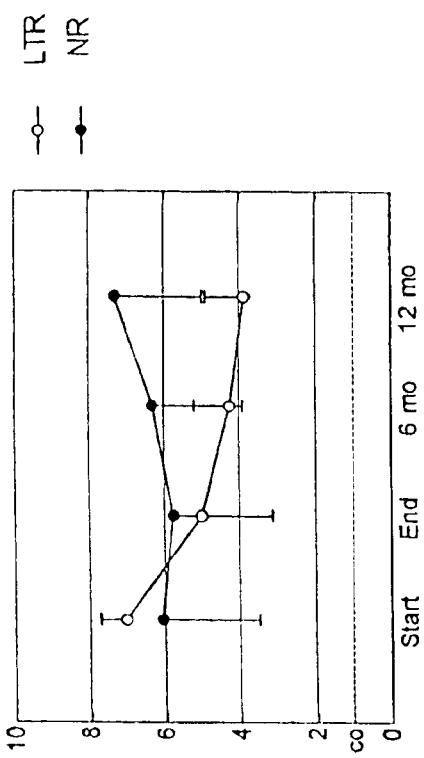
Figure 37A:
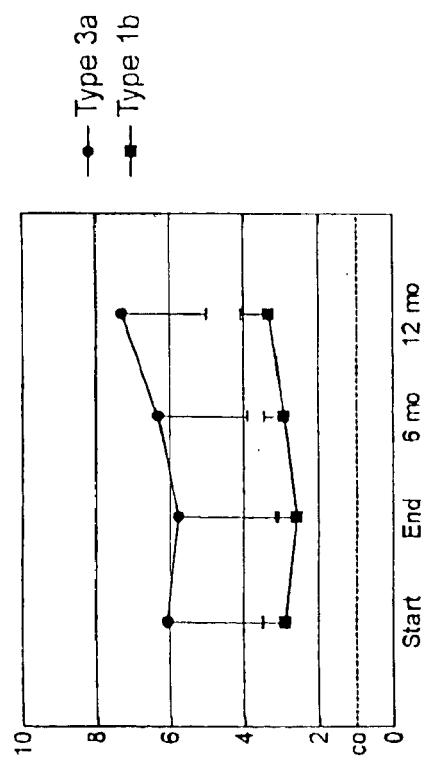
Figure 37C:
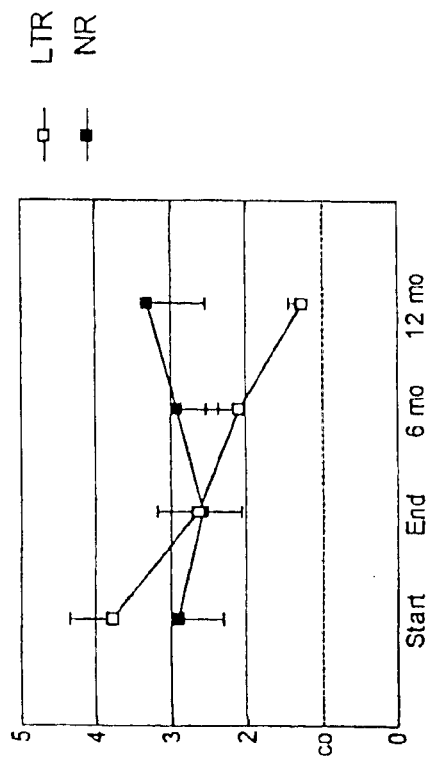

FIGS. 36A and 36B: Average E1 antibody (E1Ab) and E2 antibody (E2Ab) levels in the LTR and NR groups.

FIGS. 37A–D: Averages E1 antibody (E1Ab) levels for non-responders (NR) and long term responders (LTR) for type 1b and type 3a.

Figure 38:
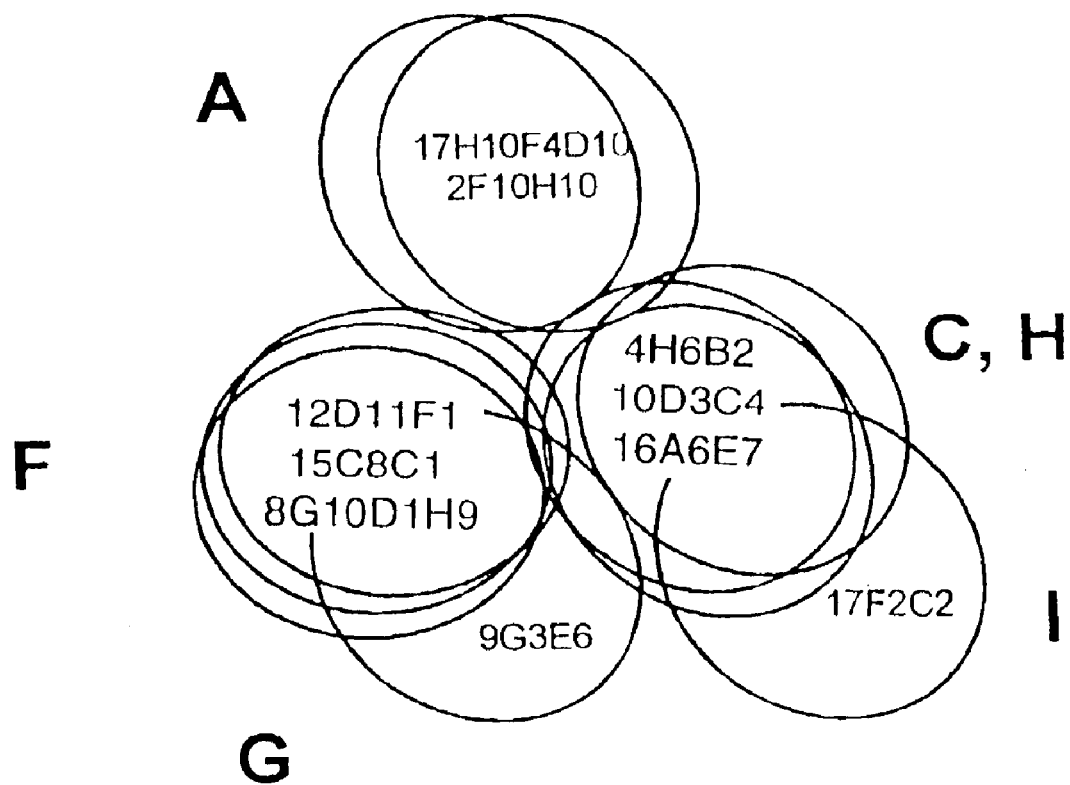

FIG. 38: Relative map positions of the anti-E2 monoclonal antibodies.

FIG. 39: Partial deglycosylation of HCV E1 envelope protein. The lysate of vvHCV10A-infected RK13 cells were incubated with different concentrations of glycosidases according to the manufacturer's instructions. Right panel: Glycopeptidase P (PNGase F). Left panel: Endoglycosidase H (Endo H).

Figure 40:
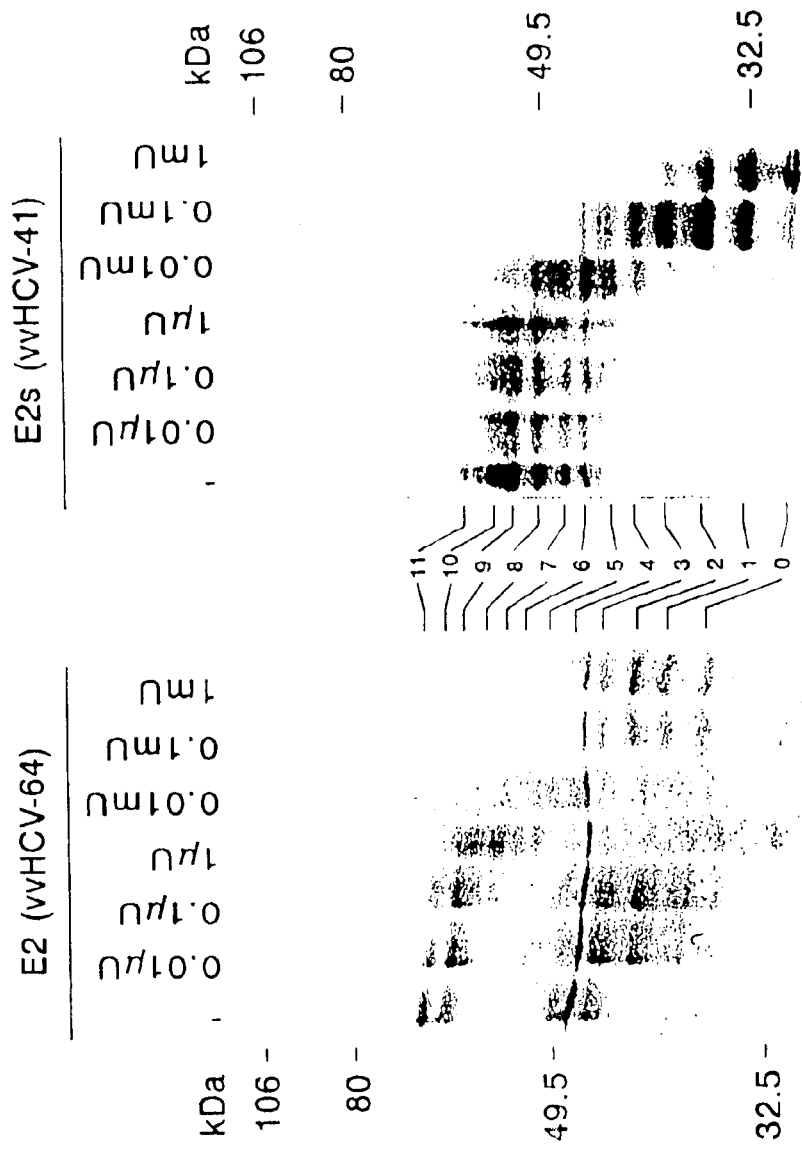

FIG. 40: Partial deglycosylation of HCV E2 envelope proteins. The lysate of vvHCV64-infected (E2) and vvHCV41-infected (E2s) RK13 cells were incubated with different concentrations of Glycopeptidase F (PNGase F) according to the manufacturer's instructions.

FIG. 41: In vitro mutagenesis of HCV E1 glycoproteins. Map of the mutated sequences and the creation of new restriction sites.

FIG. 42A: In vitro mutagenesis of HCV E1 glycoprotein (part 1). First step of PCR amplification.

Figure 42B:
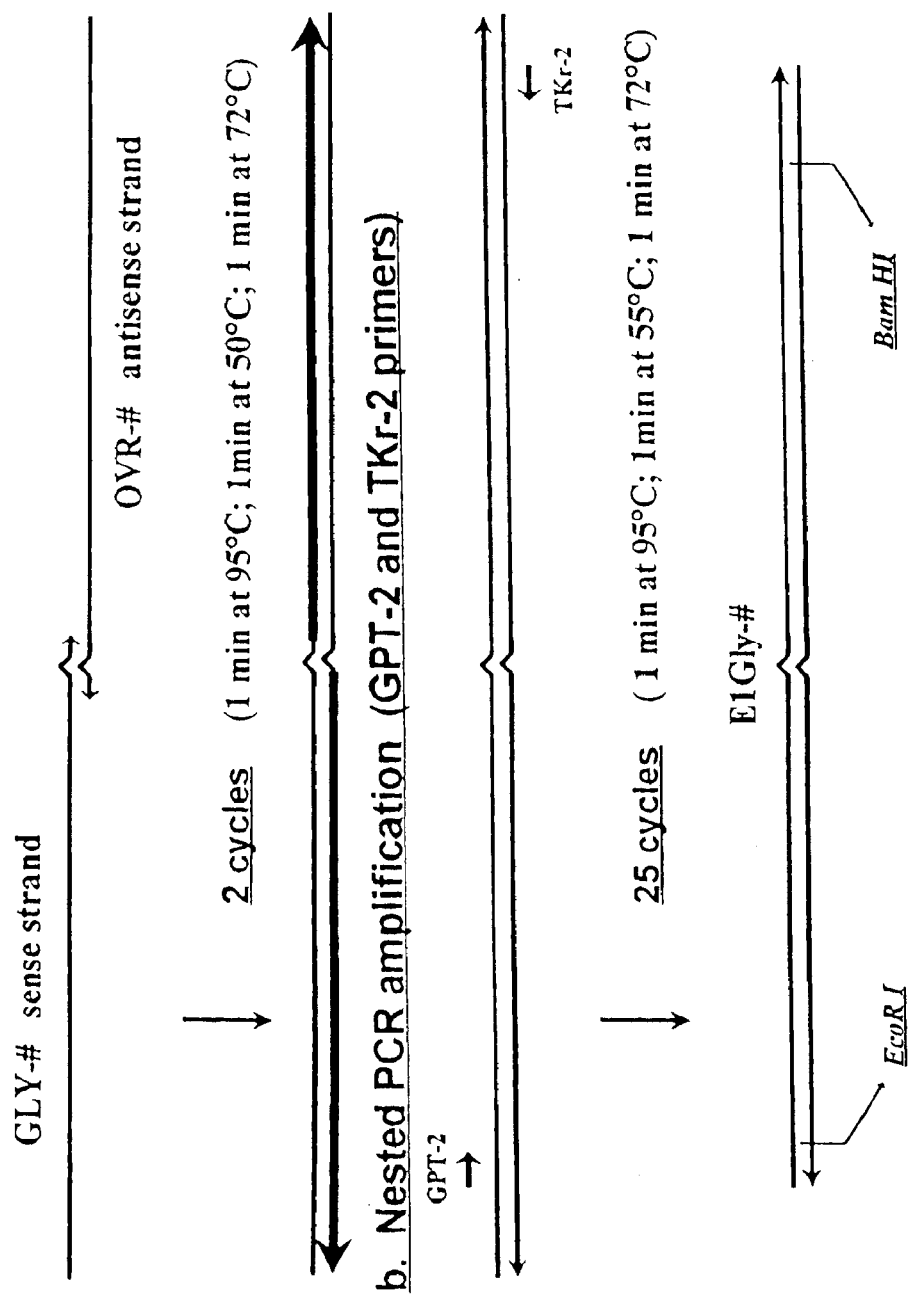

FIG. 42B: In vitro mutagensis of HCV E1 glycoprotein (part 2). Overlap extension and nested PCR.

FIG. 43: In vitro mutagenesis of HCV E1 glycoproteins. Map of the PCR mutated fragments (GLY-# and OVR-#) synthesized during the first step of amplification.

Figure 44A:
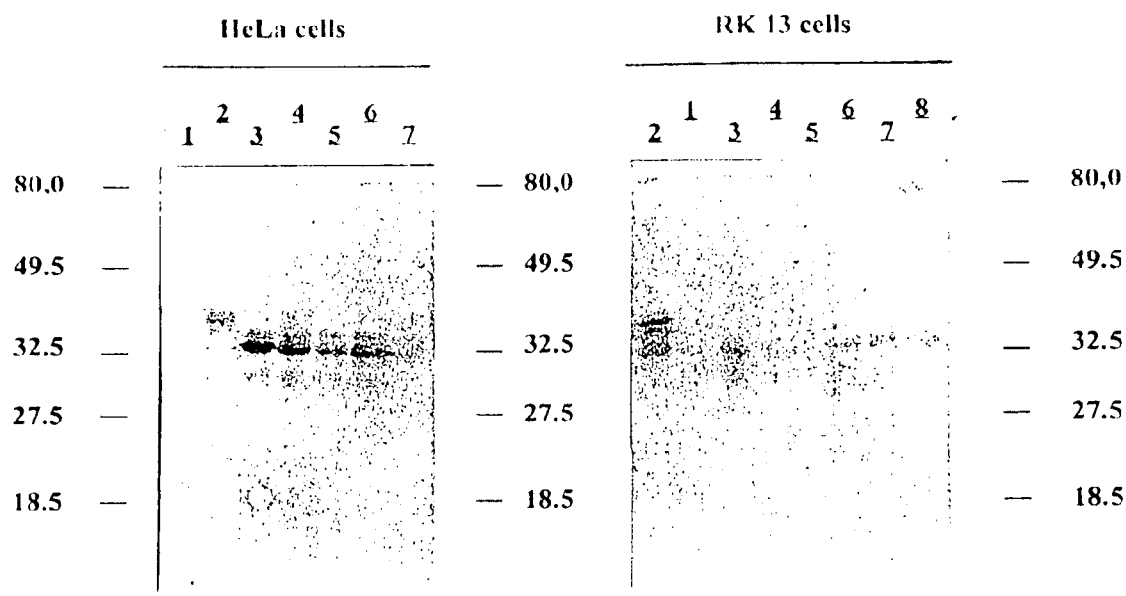

FIG. 44A: Analysis of E1 glycoprotein mutants by Western blot expressed in HeLa (left) and RK13 (right) cells. Lane 1: wild type VV (vaccinia virus). Lane 2: original E1 protein (vvHCV-10A), Lane 3: E1 mutant Gly-1 (vvHCV-81). Lane 4: E1 mutant Gly-2 (vvHCV-82), Lane 5: E1 mutant Gly-3 (vvHCV-83), Lane 6: E1 mutant Gly-4 (vvHCV-84), Lane 7: E1 mutant Gly-5 (vvHCV-85), Lane 8: E1 mutant Gly-6 (vvHCV-86).

Figure 44B:
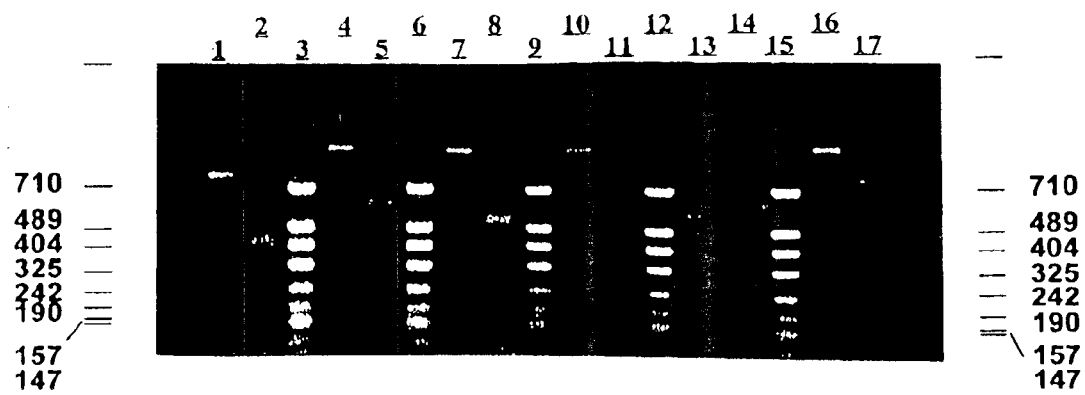

FIG. 44B: Analysis of E1 glycosylation mutant vaccinia viruses by PCR amplification/restriction. Lane 1: E1 (vvHCV-10A), BspE 1. Lane 2: E1.GLY-1 (vvHCV-81), BspE I, Lane 4: E1 (vvHCV-10A), Sac I, Lane: 5: E1.GLY-2 (vvHCV-82), Sac I, Lane 7: E1 (vvHCV-10A). Sac I, Lane 8: E1.GLY-3 (vvHCV-83), Sac I, Lane 10: E1 (vvHCV-10A), Stu I, Lane 11: E1.GLY-4 (vvHCV-84), Stu I, Lane 13: E1 (vvHCV-10A), Sma I, Lane 14: E1.GLY-5 (vvHCV-85), Sma I, Lane 16: E1 (vvHCV-10A), Stu I, Lane 17: E1.GLY-6 (vvHCV-86), Stu I, Lane 3–6–9–12–15: Low Molecular Weight Marker, pBluescript SK+, Msp I.

Figure 45:
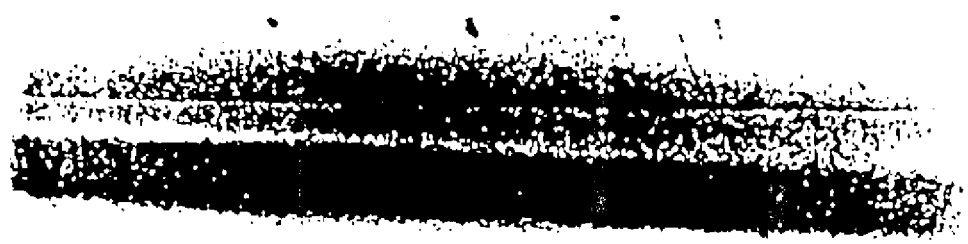

FIG. 45: SOS polyacrylamide gel electrophoresis of recombinant E2 expressed in *S. cerevisiae*. Innoculates were grown in leucine selective medium for 72 hrs. and diluted 1/15 in complete medium. After 10 days of culture at 28° C., medium samples were taken. The equivalent of 200 µl of culture supernatant concentrated by speedvac was loaded on the gel. Two independent transformants were analysed.

Figure 46:

FIG. 46: SDS polyacrylamide gel electrophoresis of recombinant E2 expressed in a glycosylation deficient *S. cerevisiae* mutant. Innoculae were grown in leucine selective medium for 72 hrs. and diluted 1/15 in complete medium. After 10 days of culture at 28° C., medium samples were taken. The equivalent of 350 µl of culture supernatant, concentrated by ion exchange chromatography, was loaded on the gel.

Table 1: Features of the respective clones and primers used for amplification for constructing the different forms of the E1 protein as despected in Example 1.

Table 2: Summary of Anti-E1 tests

Table 3: Synthetic peptides for competition studies

Table 4: Changes of envelope antibody levels over time.

Table 5: Difference between LTR and NR

Table 6: Competition experiments between murine E2 monoclonal antibodies

Table 7: Primers for construction of E1 glycosylation mutants

Table 8: Analysis of E1 glycosylation mutants by ELISA

EXAMPLE 1

Cloning and Expression of the Hepatitis C Virus E1 Protein

1. Construction of Vaccinia Virus Recombination Vectors

The pgptATA18 vaccinia recombination plasmid is a modified version of pATA18 (Stunnenberg et al, 1988) with an additional insertion containing the *E. coli* xanthine guanine phosphoribosyl transferase gene under the control of the vaccinia virus 13 intermediate promoter (FIG. 1). The plasmid pgsATA18 was constructed by inserting an oligonucleotide linker with SEQ ID NO 1/94, containing stop codons in the three reading frames, into the Pst I and HindIII-cut pATA18 vector. This created an extra Pac I restriction site (FIG. 2). The original HindIII site was not restored.

```
Oligonucleotide linker with SEQ ID NO 1/94:
    G GCATGC AAGCTT AATTAATT           3'

ACGTC CGTACG TTCGAA TTAATTAA TCGA      5'

PstI  SphI   HindIII  PacI(HindIII)
```

In order to facilitate rapid and efficient purification by means of Ni$^{2-}$ chelation of engineered histidine stretches fused to the recombinant proteins, the vaccinia recombination vector pMS66 was designed to express secreted proteins with an additional carboxy-terminal histidine tag. An oligonucleotide linker with SEQ ID NO 2/95, containing unique sites for 3 restriction enzymes generating blunt ends (Sma I, Stu I and PmI I/Bbr PI) was synthesized in such a way that the carboxy-terminal end of any cDNA could be inserted in frame with a sequence encoding the protease factor Xa cleavage site followed by a nucleotide sequence encoding 6 histidines and 2 stop codons (a new Pac I restriction site was also created downstream the 3'end). This oligonucleotide with SEQ ID NO 2/95 was introduced between the Xma I and Pst I sites of pgptATA18 (FIG. 3).

```
Oligonucleotide linker with SEQ ID NO 2/95:
'5' CCGGG GAGGCCTGCACGTGATCGAGGGCAGACACCATCACCACCATCACTAATAGTTAATTAA CTGCAT3
```

```
-continued
3'    C  CTCCGGACGTGCACTAGCTCCCGTCTGTGGTAGTGGTGGTAGTGATTATCAATTAATT G
         ‾‾‾‾                                                  ‾‾‾‾‾
         XmaI                                                  PstI
```

EXAMPLE 2
Construction of HCV Recombinant Plasmids
2.1. Constructs Encoding Different Forms of the E1 Protein Polymerase Chain Reaction (PCR) products were derived from the serum samples by RNA preparation and subsequent reverse-transcription and PCR as described previously (Stuyver et al., 1993b). Table 1 shows the features of the respective clones and the primers used for amplification. The PCR fragments were cloned into the Sma I-cut pSP72 (Promega) plasmids. The following clones were selected for insertion into vaccinia recombination vectors: HCCI9A (SEQ ID NO 3), HCCI10A (SEQ ID NO 5), HCCI11A (SEQ ID NO 7). HCCI12A (SEQ ID NO 9), HCCI13A (SEQ ID NO 11), and HCCI17A (SEQ ID NO 13) as depicted in FIG. 21. cDNA fragments containing the E1-coding regions were cleaved by EcoRI and HindIII restriction from the respective pSP72 plasmids and inserted into the EcoRI/HindIII-cut pgptATA-18 vaccinia recombination vector (described in example 1), downstream of the 11K vaccinia virus late promoter. The respective plasmids were designated pvHCV-9A, pvHCV-10A, pvHCV-11A, pvHCV-12A, pvHCV-13A and pvHCV-17A, of which pvHCV-11A is shown in FIG. 4.

2.2. Hydrophobic Region E1 Deletion Mutants

Clone HCCI37, containing a deletion of codons Asp264 to Val287 (nucleotides 790 to 861, region encoding hydrophobic domain I) was generated as follows: 2 PCR fragments were generated from clone HCCI10A with primer sets HCPr52 (SEQ ID NO 16)/HCPr107 (SEQ ID NO 19) and HCPr108 (SEQ ID NO 20)/HCPR54 (SEQ ID NO 18). These primers are shown in FIG. 21. The two PCR fragments were purified from agarose gel after electrophoresis and 1 ng of each fragment was used together as template for PCR by means of primers HCPrS52 (SEQ ID NO 16) and HCPr54 (SEQ ID NO 18). The resulting fragment was cloned into the Sma I-cut pSP72 vector and clones containing the deletion were readily identified because of the deletion of 24 codons (72 base pairs). Plasmid pSP72HCCI37 containing clone HCCI37 (SEQ ID 15) was selected. A recombinant vaccinia plasmid containing a full-length E1 cDNA lacking hydrophobic domain I was constructed by inserting the HCV sequence surrounding the deletion (fragment cleaved by Xma I and BamH I from the vector pSP72-HCCI37) into the Xma I-Bam H I sites of the vaccinia plasmid pvHCV-10A. The resulting plasmid was named pvHCV-37. After confirmatory sequencing, the amino-terminal region containing the internal deletion was isolated from this vector pvHCV-37 (cleavage by EcoRI and BstE II) and reinserted into the Eco RI and Bst EII-cut pvHCV-11A plasmid. This construct was expected to express an E1 protein with both hydrophobic domains deleted and was named pvHCV-38. The E1-coding region of clone HCCI38 is represented by SEQ ID NO 23.

As the hydrophilic region at the E1 carboxyterminus (theoretically extending to around amino acids 337–340) was not completely included in construct pvHCV-38, a larger E1 region lacking hydrophobic domain I was isolated from the pvHCV-37 plasmid by EcoRI/Bam HI cleavage and cloned into an EcoRI/BamHI-cut pgsATA-18 vector. The resulting plasmid was named pvHCV-39 and contained clone HCCI39 (SEQ ID NO 25). The same fragment was cleaved from the pvHCV-37 vector by BamH I (of which the sticky ends were filled with Klenow DNA Polymerase I (Boehringer)) and subsequently by EcoR I (5' cohesive end). This sequence was inserted into the EcoRI and Bbr PI-cut vector pMS-66. This resulted in clone HCCI40 (SEQ ID NO 27) in plasmid pvHCV-40, containing a 6 histidine tail at its carboxy-terminal end.

2.3. E1 of other Genotypes

Clone HCCI62 (SEQ ID NO 29) was derived from a type 3a-infected patient with chronic hepatitis C (serum BR36, clone BR36-9-13, SEQ ID NO 19 in WO 94/25601, and see also Stuyver et al. 1993a) and HCCI63 (SEQ ID NO 31) was derived from a type 5a-infected child with post-transfusion hepatitis (serum BE95, clone PC4-1, SEQ ID NO 45 in WO 94/25601).

2.4. E2 Constructs

The HCV E2 PCR fragment 22 was obtained from serum BE11 (genotype 1b) by means of primers HCPr109 (SEQ ID NO 33) and HCPr72 (SEQ ID NO 34) using techniques of RNA preparation, reverse-transcription and PCR, as described in Stuyver et al., 1993b, and the fragment was cloned into the Sma I-cut pSP72 vector. Clone HCCI22A (SEQ ID NO 35) was cut with NcoI/AlwNI or by BamHI/AlwNI and the sticky ends of the fragments were blunted (Ncol and BamHI sites with Klenow DNA Polymerase I (Boehringer), and AlwNI with T4 DNA polymerase (Boehringer)). The BamHI/AlwNI cDNA fragment was then inserted into the vaccinia pgsATA-18 vector that had been linearized by EcoR I and Hind III cleavage and of which the cohesive ends had been filled with Klenow DNA Polymerase (Boehringer). The resulting plasmid was named pvHCV-41 and encoded the E2 region from amino acids Met347 to Gln673, including 37 amino acids (from Met347 to Gly383) of the E1 protein that can serve as signal sequence. The same HCV cDNA was inserted into the EcoR I and Bbr PI-cut vector pMS66, that had subsequently been blunt ended with Klenow DNA Polymerase. The resulting plasmid was named pvHCV-42 and also encoded amino acids 347 to 683. The NcoI/AlwNI fragment was inserted in a similar way into the same sites of pgsATA-18 (pvHCV-43) or pMS-66 vaccinia vectors (pvHCV-14). pvHCV-43 and pvHCV-44 encoded amino acids 364 to 673 of the HCV polyprotein, of which amino acids 364 to 383 were derived from the natural carboxyterminal region of the E1 protein encoding the signal sequence for E2, and amino acids 384 to 673 of the mature E2 protein.

2.5. Generation of Recombinant HCV-Vaccinia Viruses

Rabbit kidney RK13 cells (ATCC CCL 37), human osteosarcoma 143B thymidine kinase deficient (TK⁻) (ATCC CRL 8303), HeLa (ATCC CCL 2). and Hep G2 (ATCC HB 8065) cell lines were obtained from the American Type Culture Collection (ATCC, Rockville, Md., USA). The cells were grown in Dulbecco's modified Eagle medium (DMEM) supplemented with 10% foetal calf serum, and with Earle's salts (EMEM) for RK13 and 143 B (TK−), and with glucose (4 g/l) for Hep G2. The vaccinia virus WR strain (Western Reserve, ATTC VR119) was routinely propagated in either 143B or RK13 cells, as described previously (Panicali & Paoletti, 1982; Piccini et al., 1987; Mackett et al., 1982, 1984, and 1986). A confluent monolayer of 1438 cells was infected with wild type vaccinia virus at a multiplicity of infection (m.o.i.) of 0.1 (=0.1 plaque forming unit (PFU) per cell). Two hours later, the vaccinia recombination plasmid was transfected into the infected cells in the form of a calcium phosphate coprecipitate containing 500 ng of the plasmid DNA to allow homologous recombination (Graham & van der Eb, 1973; Mackett et al., 1985). Recombinant viruses expressing the *Escherichia coli* xanthine-guanine phosphoribosyl transferase (gpt) protein were selected on rabbit kidney RK13 cells incubated in selection medium (EMEM containing 25 µg/ml mycophenolic acid (MPA), 250 µg/ml xanthine, and 15 µg/ml hypoxanthine; Falkner and Moss. 1988; Janknecht et al. 1991). Single recombinant viruses were purified on fresh monolayers of RK13 cells under a 0.9% agarose overlay in selection medium. Thymidine kinase deficient (TK⁻) recombinant viruses were selected and then plaque purified on fresh monolayers of human 143B calls (TK−) in the presence of 25 µg/ml 5-bromo-2'-deoxyuridine. Stocks of purified recombinant HCV-vaccinia viruses were prepared by infecting either human 143 B or rabbit RK13 cells at an m.o.i. of 0.05 (Mackett et al, 1988). The insertion of the HCV cDNA fragment in the recombinant vaccinia viruses was confirmed on an aliquot (50 µl) of the cell lysate after the MPA selection by means of PCR with the primers used to clone the respective HCV fragments (see Table 1). The recombinant vaccinia-HCV viruses were named according to the vaccinia recombination plasmid number, e.g. the recombinant vaccinia virus vvHCV-10A was derived from recombining the wild type WR strain with the pvHCV-10A plasmid.

EXAMPLE 3

Infection of Cells with Recombinant Vaccinia Viruses

A confluent monolayer of RK13 cells was infected at a m.o.i. of 3 with the recombinant HCV-vaccinia viruses as described in example 2. For infection, the cell monolayer was washed twice with phosphate-buffered saline pH 7.4 (PSS) and the recombinant vaccinia virus stock was diluted in MEM medium. Two hundred µl of the virus solution was added per $10^5$ cells such that the m.o.i. was 3, and incubated for 45 min at 24° C. The virus solution was aspirated and 2 ml of complete growth medium (see example 2) was added per $10^5$ cells. The cells were incubated for 24 hr at 37° C. during which expression of the HCV proteins took place.

EXAMPLE 4

Analysis of Recombinant Proteins by Means of Western Blotting

The infected cells were washed two times with PBS, directly lysed with lysis buffer (50 mM Tris.HCl pH 7.5, 150 mM NaCl, 1% Triton X-100, 5 mM MgCl$_2$, 1 µg/ml aprotinin (Sigma, Bornem, Belgium)) or detached from the flasks by incubation in 50 mM Tris.HCL pH 7.51/10 mM EDTA/150 mM NaCl for 5 min, and collected by centrifugation (5 min at 1000 g). The cell pellet was then resuspended in 200 µl lysis buffer (50 mM Tris.HCL pH 8.0, 2 mM EDTA, 150 mM NaCl, 5 mM MgCl$_2$ aprotinin, 1% Triton X-100) per $10^5$ cells. The cell lysates were cleared for 5 min at 14,000 rpm in an Eppendorf centrifuge to remove the insoluble debris. Proteins of 20 µl lysate were separated by means of sodium dodecyl sulphate-polyacrylamide gel electrophoresis (SDS-PAGE). The proteins were then electro-transferred from the gel to a nitrocellulose street (Amersham) using a Hoefer HSI transfer unit cooled to 4° C. for 2 hr at 100 V constant voltage, in transfer buffer (25 mM Tris.HCl pH 8.0, 192 mM glycine, 20% (v/v) methanol). Nitrocellulose filters were blocked with Blotto (5% (w/v) fat-free instant milk powder in PBS; Johnson et al., 1981) and incubated with primary antibodies diluted in Blotto/0.1% Tween 20. Usually, a human negative control serum or serum of a patient infected with HCV were 200 times diluted and preincubated for 1 hour at room temperature with 200 times diluted wild type vaccinia virus-infected cell lysate in order to decrease the non-specific binding. After washing with Blotto/0.1% Tween 20, the nitrocellulose filters were incubated with alkaline phosphatase substrate solution diluted in Blotto/0.1% Tween 20. After washing with 0.1% Tween 20 in PBS, the filters were incubated with alkaline phosphatase substrate solution (100 mM Tris.HCl pH 9.5, 100 mM NaCl, 5 mM MgCl$_2$, 0.38 µg/ml nitroblue tetrazolium, 0.165 µg/ml 5-bromo-4-chloro-3-indolylphosphate). All steps, except the electrotransfer, were performed at room temperature.

EXAMPLE 5

Purification of Recombinant E1 or E2 Protein 5.1. Lysis

Infected RK13 cells (carrying E1 or E2 constructs) were washed 2 times with phosphate-buffered saline (PBS) and detached from the culture recipients by incubation in PBS containing 10 mM EDTA. The detached cells were washed twice with PBS and 1 ml of lysis buffer (50 mM Tris.HCl pH 7.5, 150 mM NaCl, 1% Triton X-100, 5 mM MgCl$_2$, 1 µg/ml aprotinin (Sigma, Bornem, Belgium) containing 2 mM biotinylated N-ethylmaleimide (biotin-NEM) (Sigma) was added per $10^5$ cells at 4° C. This lysate was homogenized with a type B douncer and left at room temperature for 0.5 hours. Another 5 volumes of lysis buffer containing 10 mM N-ethylmaleimide (NEM, Aldrich, Bornem, Belgium) was added to the primary lysate and the mixture was left at room temperature for 15 min. Insoluble cell debris was cleared from the solution by centrifugation in a Beckman JA-14 rotor at 14,000 rpm (30100 g at $r_{max}$) for 1 hour at 4° C.

5.2. Lectin Chromatography

The cleared cell lysate was loaded at a rate of 1 ml/min on a 0.8 by 10 cm Lentil-lectin Sepharose 4B column (Pharmacia) that had been equilibrated with 5 column volumes of lysis buffer at a rate of 1 ml/min. The lentil-lectin column was washed with 5 to 10 column volumes of buffer 1 (0.1M potassium phosphate pH 7.3, 500 mM KCl, 5% glycerol, 1 mM 6-NH$_2$-hexanoic acid, 1 mM MgCl$_2$, and 1% DecylPEG (KWANT, Bedum, The Netherlands). In some experiments, the column was subsequently washed with 10 column volumes of buffer 1 containing 0.5% Empigen-BB (Calbiochem, San Diego, Calif., USA) instead of 1% DecylPEG. The bound material was eluted by applying elution buffer (10 mM potassium phosphate pH 7.3, 5% glycerol, 1 mM hexanoic acid, 1 mM MgCl$_2$, 0.5% Empigen-BB, and 0.5 M α-methyl-mannopyranoside). The eluted material was fractionated and fractions were screened for the presence of E1 or E2 protein by means of ELISA as described in example 6. FIG. 22 shows ELISA results obtained from lentil lectin eluate fractions of 4 different E1 purifications of cell lysates infected with vvHCV39 (type 1b), vvHCV40 (type 1b), vvHCV62 (type 3a), and vvHCV63 (type 5a). FIG. 23 shows the profiles obtained from the values shown in FIG. 22. These results show that the lectin affinity column can be employed for envelope proteins of the different types of HCV.

5.3. Concentration and Partial Reduction

The E1- or E2-positive fractions were pooled and concentrated on a Centricon 30 kDa (Amicon) by centrifugation for 3 hours at 5,000 rpm in a Beckman JA-20 rotor at 4° C. In some experiments the E1- or E2-positive fractions were pooled and concentrated by nitrogen evaporation. An equivalent of 3.10⁸ cells was concentrated to approximately 200 μl. For partial reduction, 30% Empigen-BB (Calbiochem, San Diego, Calif., USA) was added to this 200 μl to a final concentration of 3.5%, and 1M DTT in $H_2O$ was subsequently added to a final concentration of 1.5 to 7.5 mM and incubated for 30 min at 37° C. NEM (1M in dimethylsulphoxide) was subsequently added to a final concentration of 50 mM and left to react for another 30 min at 37° C. to block the free sulphydryl groups.

5.4. Gel Filtration Chromatography

A Superdex-200 HR 10/20 column (Pharmacia) was equilibrated with 3 column volumes PBS/3% Empigen-BB. The reduced mixture was injected in a 500 μl sample loop of the Smart System (Pharmacia) and PBS/3% Empigen-BB buffer was added for gelfiltration. Fractions of 250 μl were collected from $V_0$ to $V_1$. The fractions were screened for the presence of E1 or E2 protein as described in example 6.

Figure 25:
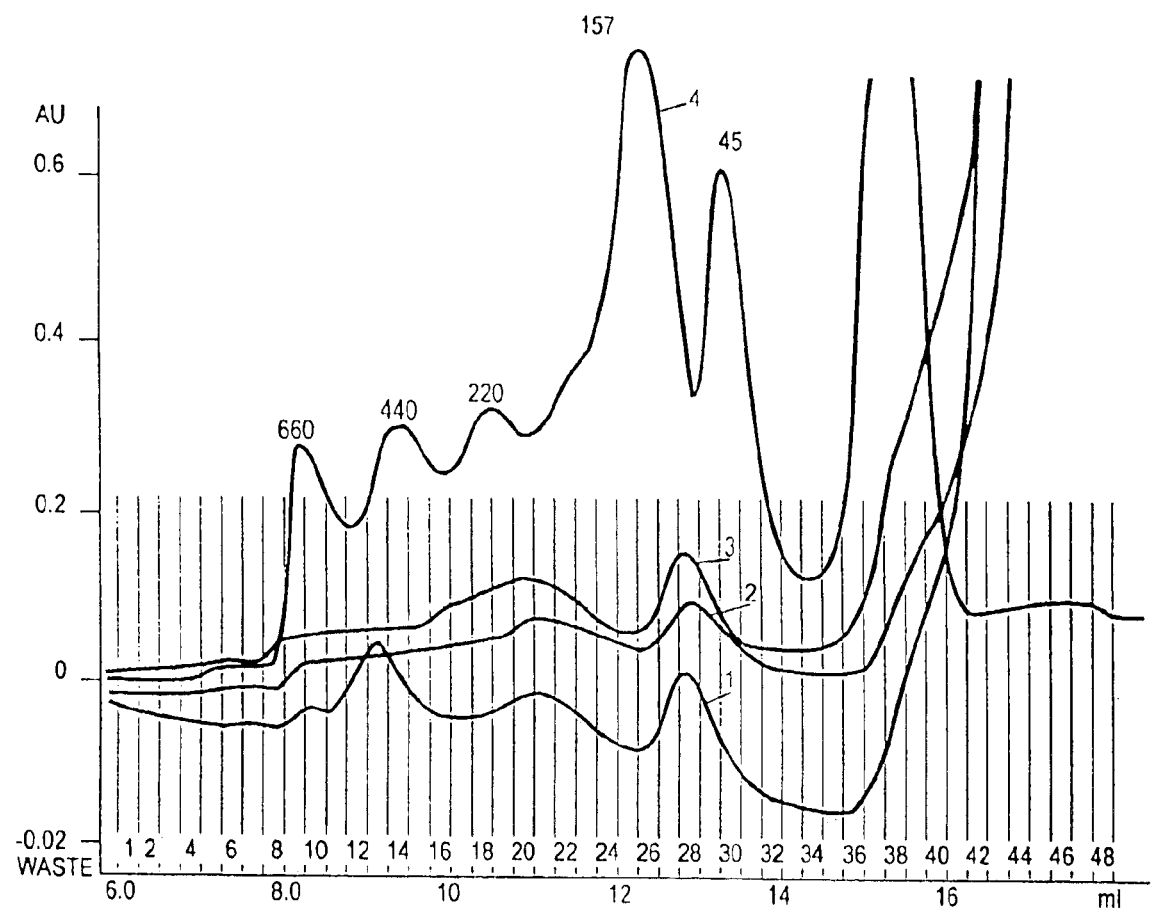
Figure 26:
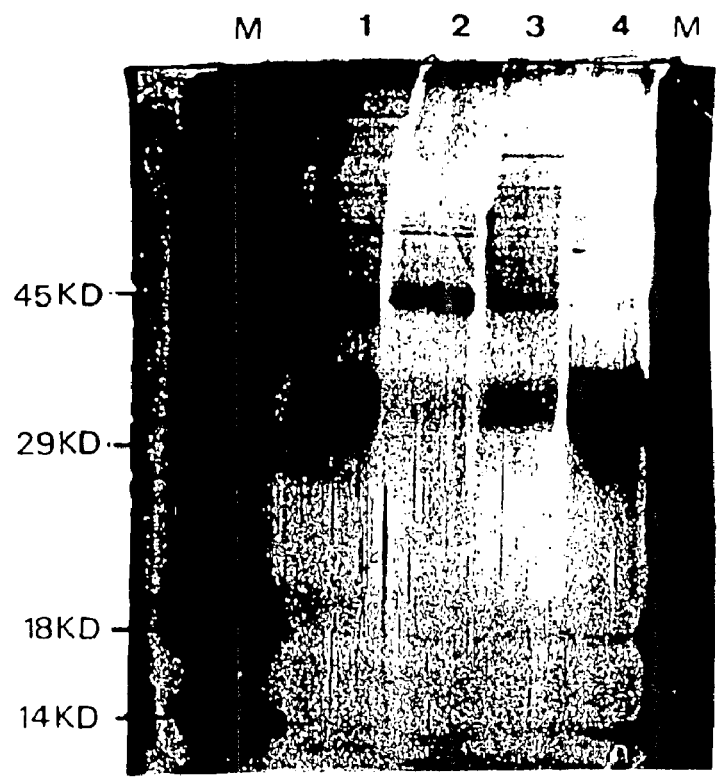
Figure 27:
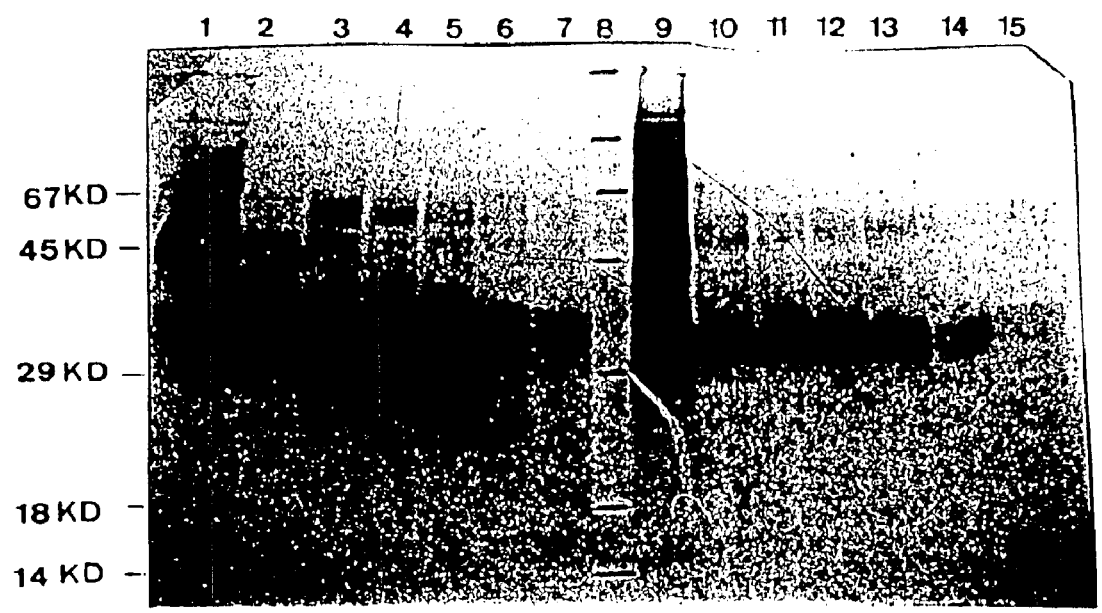
Figure 28:
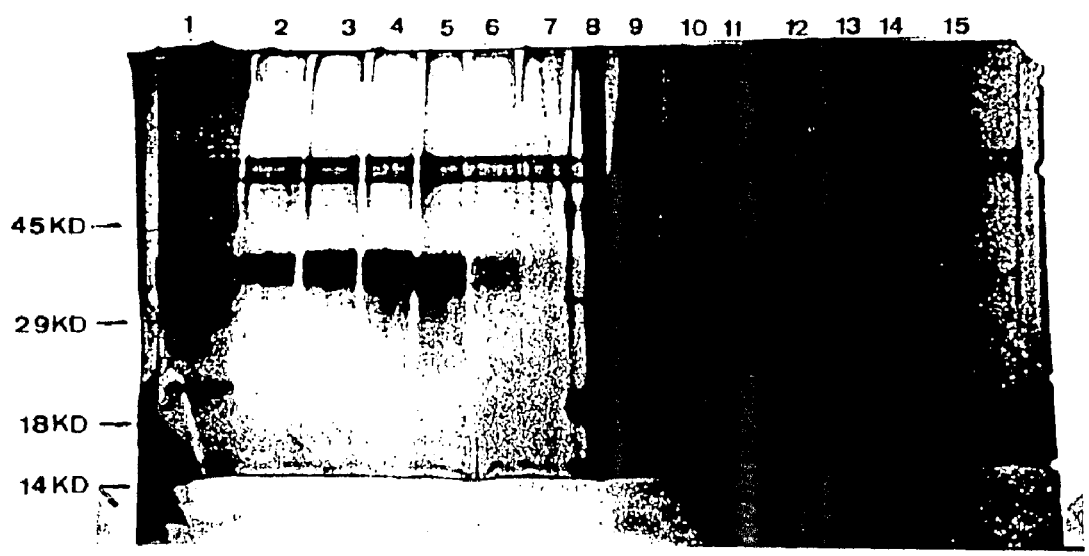
Figure 29:
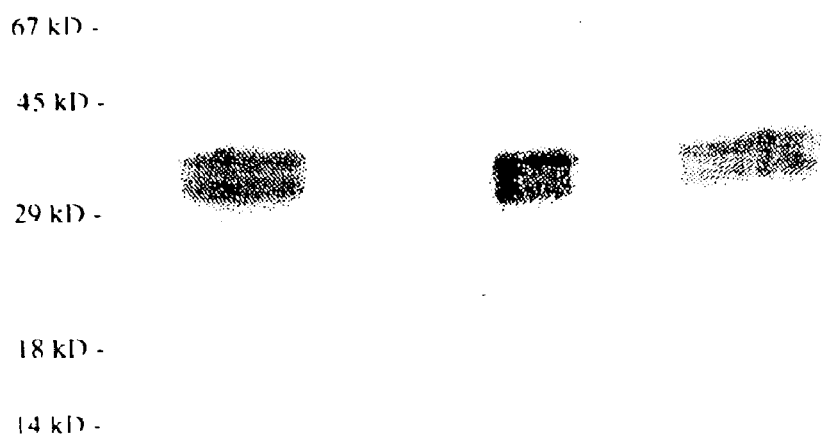
Figure 30:
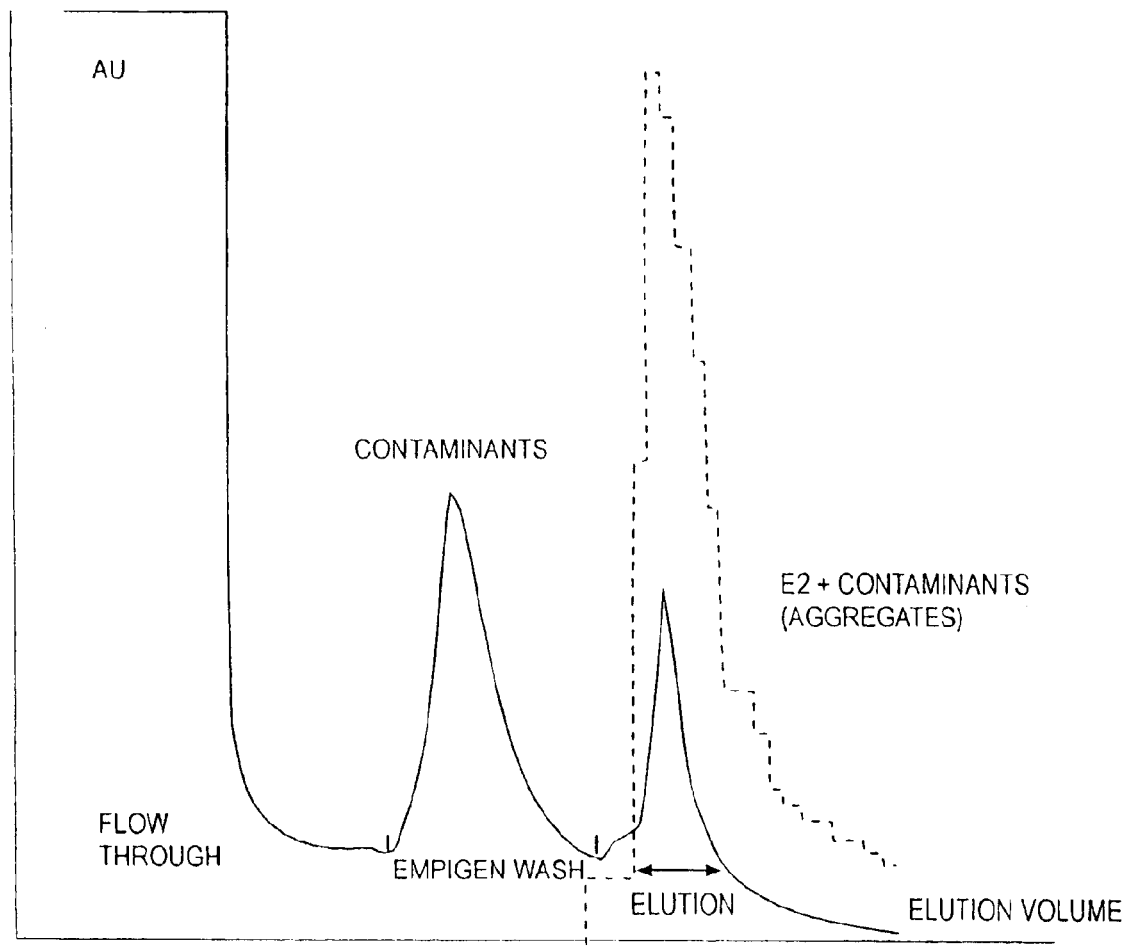
Figure 31A:
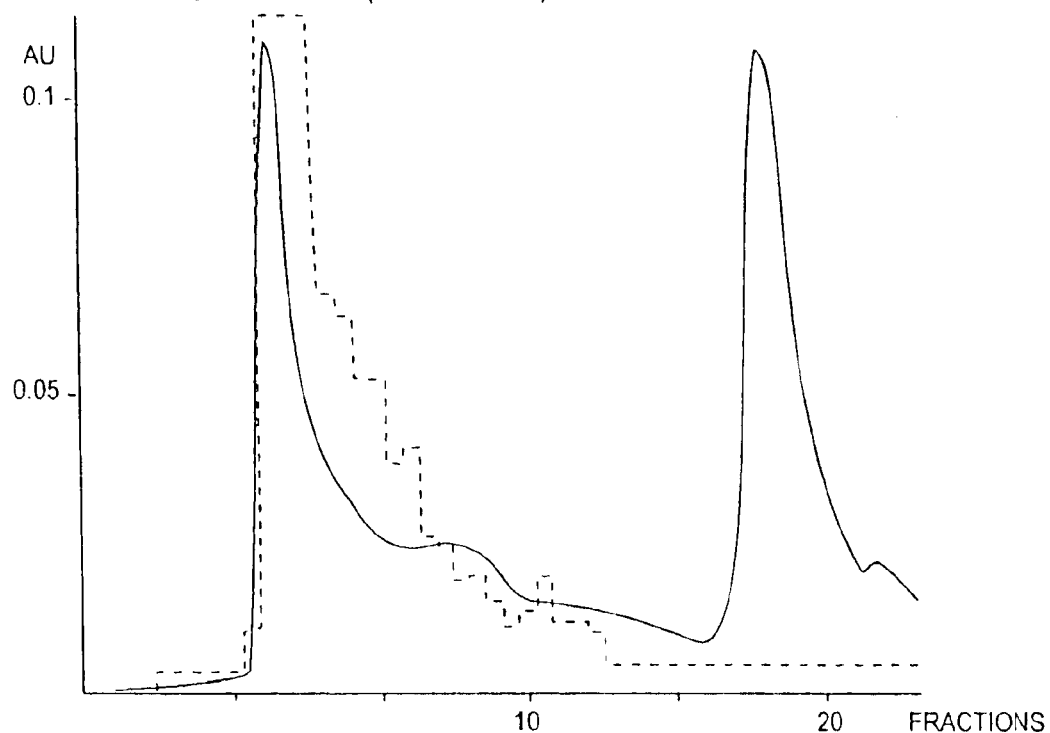
Figure 31B:
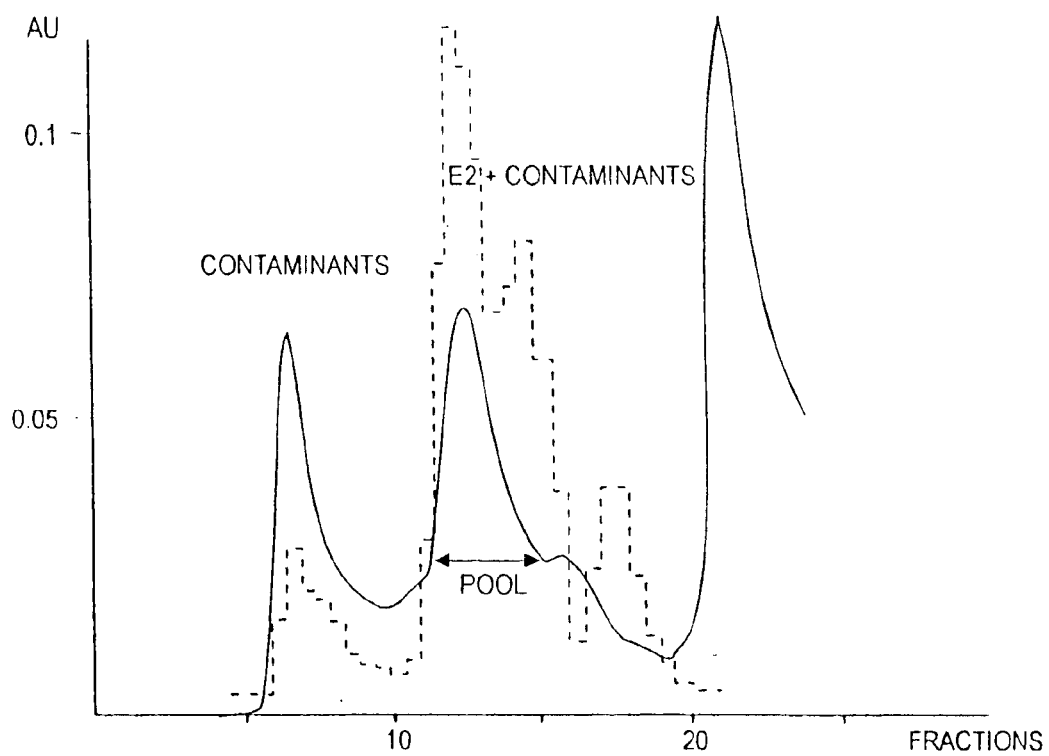
Figure 32:
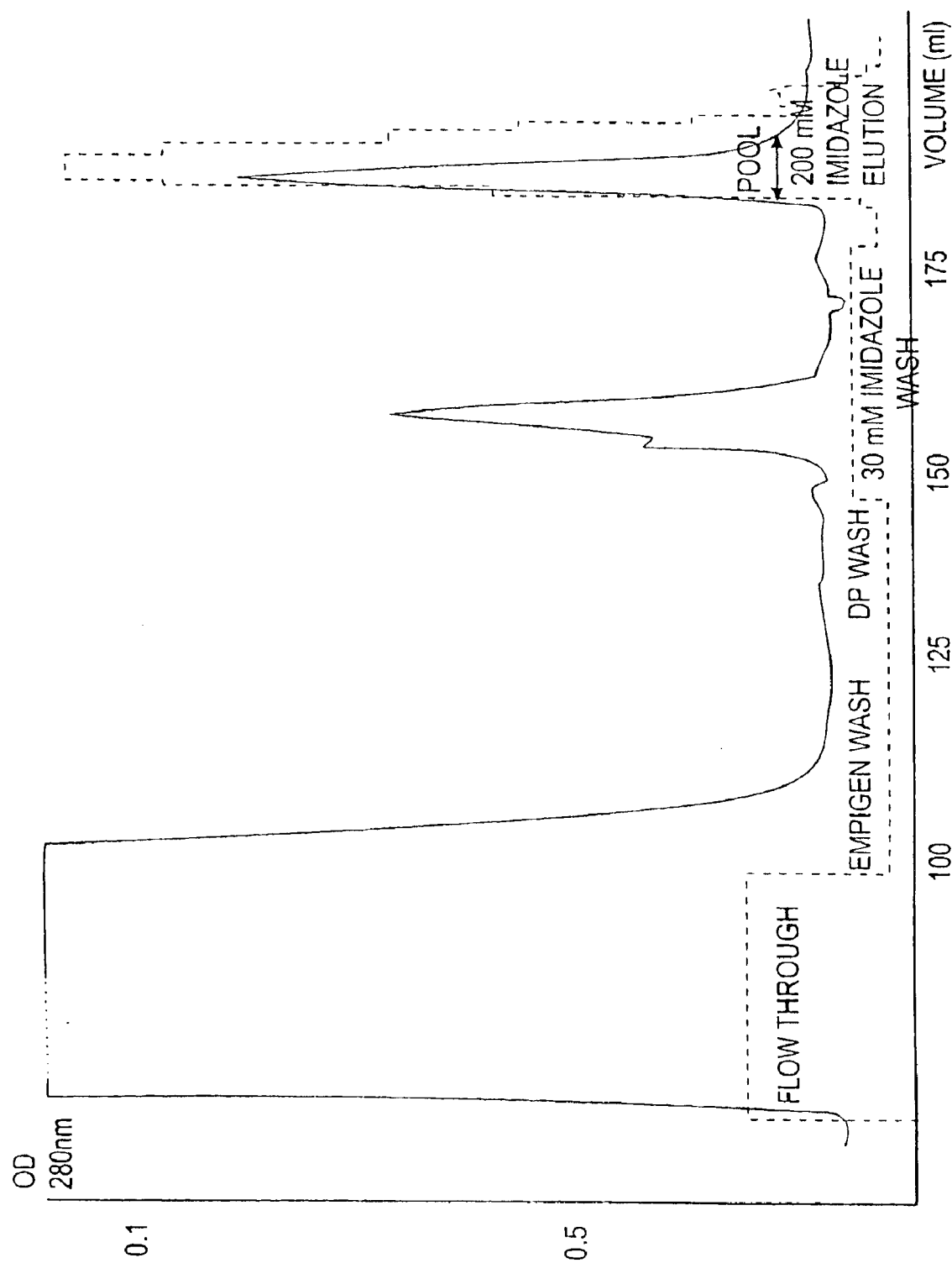
Figure 33:
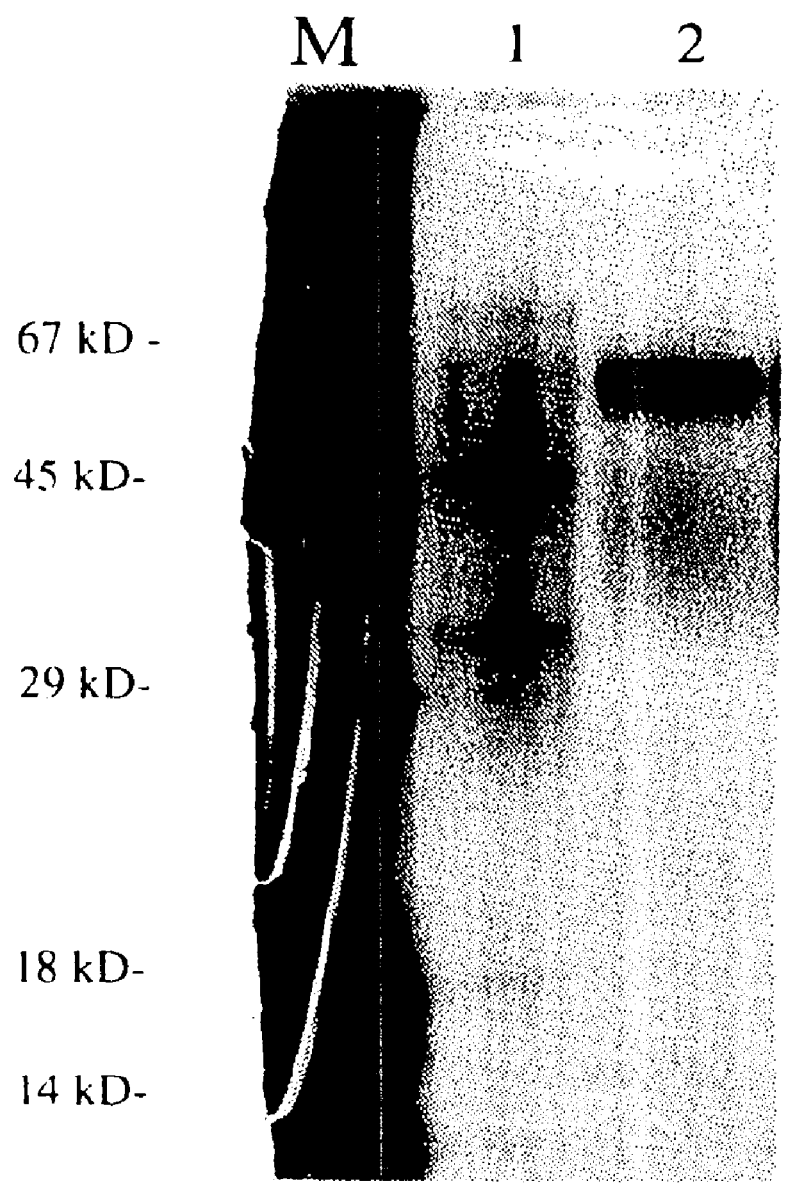
Figure 34:
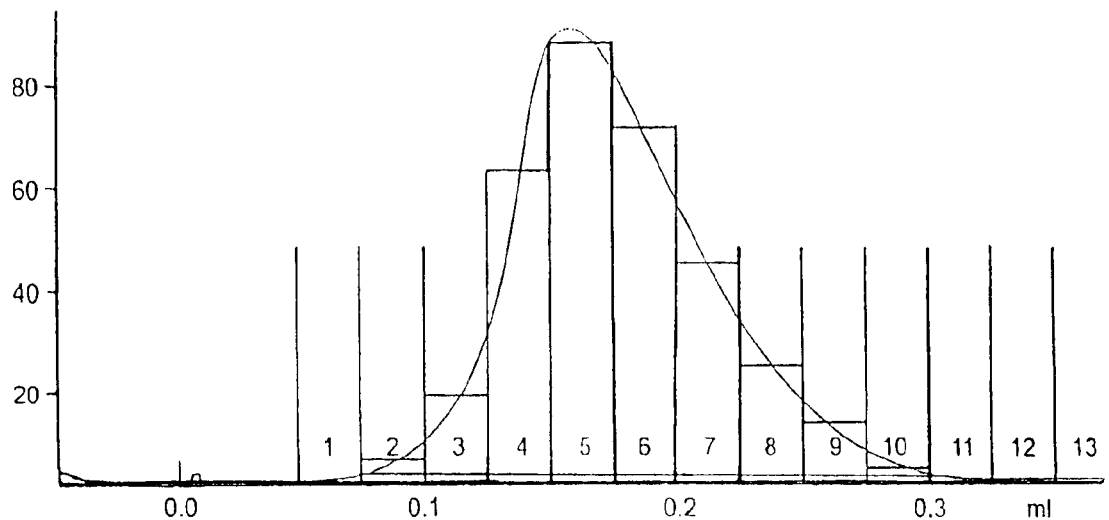

FIG. 24 shows ELISA results obtained from fractions obtained after gelfiltration chromatography of 4 different E1 purifications of cell lysates infected with vvHCV39 (type 1b), vvHCV40 (type 1b), vvHCV62 (type 3a), and vvHCV63 (type 5a). FIG. 25 shows the profiles obtained from purifications of E1 proteins of types 1b, 3a, and 5a (from RK13 cells infected with vvHCV39, vvHCV62, and vvHCV63, respectively; purified on lentil lectin and reduced as in the previous examples). The peaks indicated with '1', '2', and '3', represent pure E1 protein peaks (E1 reactivity mainly in fractions 26 to 30). These peaks show very similar molecular weights of approximately 70 kDa, corresponding to dimeric E1 protein. Other peaks in the three profiles represent vaccinia virus and/or cellular proteins which could be separated from E1 only because of the reduction step as outlined in example 5.3, and because of the subsequent gelfiltration step in the presence of the proper detergent. As shown in FIG. 26 pool 1 (representing fractions 10 to 17) and pool 2 (representing fractions 18 to 25) contain contaminating proteins not present in the E1 pool (fractions 26 to 30). The E1 peak fractions were ran on SDS/PAGE and blotted as described in example 4. Proteins labelled with NEM-biotin were detected by streptavidin-alkaline phosphatase as shown in FIG. 27. It can be readily observed that, amongst others, the 29 kDa and 45 kDa contaminating proteins present before the gelfiltration chromatography (lane 1) are only present at very low levels in the fractions 26 to 30. The band at approximately 65 kDa represents the E1 dimeric form that could not be entirely disrupted into the monomeric E1 form. Similar results were obtained for the type 3a E1 protein (lanes 10 to 15), which shows a faster mobility on SDS/PAGE because of the presence of only 5 carbohydrates instead of 6. FIG. 23 shows a silver stain of an SOS/PAGE gel run in identical conditions as in FIG. 26. A complete overview of the purification procedure is given in FIG. 29.

The presence of purified E1 protein was further confirmed by means of western blotting as described in example 4. The dimeric E1 protein appeared to be non-aggregated and free of contaminants. The subtype 1b E1 protein purified from vvHCV40-infected cells according to the above scheme was aminoterminally sequenced on an 477 Perkins-Elmer sequencer and appeared to contain a tyrosine as first residue. This confirmed that the E1 protein had been cleaved by the signal peptidase at the correct position (between A191 and Y192) from its signal sequence. This confirms the finding of Hijikata et al. (1991) that the aminoterminus of the mature E1 protein starts at amino acid position 192.

5.5. Purification of the E2 Protein

The E2 protein (amino acids 384 to 673) was purified from RK13 calls infected with vvHCV44 as indicated in Examples 5.1 to 5.4. FIG. 30 shows the $OD_{280}$ profile (continuous line) of the lentil lectin chromatography. The dotted line represents the E2 reactivity as detected by ELISA (see example 6). FIG. 31 shows the same profiles obtained from gelfiltration chromatography of the lentil-lectin E2 pool (see FIG. 30), part of which was reduced and blocked according to the methods as set out in example 5.3., and part of which was immediately applied to the column. Both parts of the E2 pool were run on separate gelfiltration columns. It could be demonstrated that E2 forms covalently-linked aggregates with contaminating proteins if no reduction has been performed. After reduction and blocking, the majority of contaminating proteins segregated into the $V_0$ fraction. Other contaminating proteins copurified with the E2 protein, were not covalently linked to the E2 protein any more because these contaminants could be removed in a subsequent step. FIG. 32 shows an additional $Ni^{2+}$-IMAC purification step carried out for the E2 protein purification. This affinity purification step employs the 6 histidine residues added to the E2 protein as expressed from vvHCV44. Contaminating proteins either run through the column or can be removed by a 30 mM imidazole wash. FIG. 33 shows a silver-stained SOS/PAGE of 0.5 µg of purified E2 protein and a 30 mM imidazole wash. The pure E2 protein could be easily recovered by a 200 mM imidazole elution step. FIG. 34 shows an additional desalting step intended to remove imidazole and to be able to switch to the desired buffer, e.g. PBS, carbonate buffer, saline.

Starting from about 50,000 $cm^2$ of RK13 cells infected with vvHCV11A (or vvHCV40) for the production of E1 or vvHCV41, vvHCV42, vvHCV43, or vvHCV44 for production of E2 protein, the procedures described in examples 5.1 to 5.5 allow the purification of approximately 1.3 mg of E1 protein and 0.6 mg of E2 protein.

It should also be remarked that secreted E2 protein (constituting approximately 30–40%, 60–70% being in the intracellular form) is characterized by aggregate formation (contrary to expectations). The same problem is thus posed to purify secreted E2. The secreted E2 can be purified as disclosed above.

EXAMPLE 6

ELISA for the Detection of Anti-E1 or Anti-E2 Antibodies or for the Detection of E1 or E2 Proteins Maxisorb microwell plates (Nunc. Roskilde, Denmark) were coated with 1 volume (e.g. 50 µl or 100 µl or 200 µl) per well of a 5 µg/ml solution of Streptavidin (Boehringer Mannheim) in PES for 16 hours at 4° C. or for 1 hour at 37° C. Alternatively, the wells were coated with 1 volume of 5 µg/ml of *Galanthus nivalis* agglutinin (GNA) in 50 mM sodium carbonate buffer pH 9.6 for 16 hours at 4° C. or for 1 hour at 37° C. In the case of coating with GNA, the plates were washed 2 times with 400 µl of Washing Solution of the Innotest HCV Ab III kit (Innogenetics, Zwijndrecht, Belgium). Unbound coating surfaces were blocked with 1.5 to 2 volumes of blocking solution (0.1% casein and 0.1% $NaN_3$ in PBS) for 1 hour at 37° C. or for 16 hours at 4° C. Blocking solution was aspirated. Purified E1 or E2 was diluted to 100–1000 ng/ml (concentration measured at A=280 nm) or column fractions to be screened for E1 or E2 (see example 5), or E1 or E2 in non-purified cell lysates (example 5.1.) were diluted 20 times in blocking solution, and 1 volume of the E1 or E2 solution was added to each well and incubated for 1 hour at 37° C. on the Streptavidin- or GNA-coated plates. The microwells were washed 3 times with 1 volume of Washing Solution of the Innotest, HCV Ab III kit (Innogenetics, Zwijndrecht, Belgium). Serum samples were diluted 20 times or monoclonal anti-E1 or anti-E2 antibodies were diluted to a concentration of 20 ng/ml in Sample Diluent of the Innotest HCV Ab III kit and 1 volume of the solution was left to react with the E1 or E2 protein for 1 hour at 37° C. The microwells were washed 5 times with 400 µl of Washing Solution of the Innotest HCV Ab III kit (Innogenetics, Zwijndrecht, Belgium). The bound antibodies were detected by incubating each well for 1 hour at 37° C. with a goat anti-human or anti-mouse IgG, peroxidase-conjugated secondary antibody (DAKO, Glostrup, Denmark) diluted 1/80,000 in 1 volume of Conjugate Diluent of the Innotest HCV Ab III kit (Innogenetics, Zwijndrecht, Belgium). and color development was obtained by addition of substrate of the Innotest HCV Ab III kit (Innogenetics, Zwijndrecht, Belgium) diluted 100 times in 1 volume of Substrate Solution of the Innotest HCV Ab III kit (Innogenetics, Zwijndrecht, Belgium) for 30 min at 24° C. after washing of the plates 3 times with 400 µl of Washing Solution of the Innotest HCV Ab III kit (Innogenetics, Zwijndrecht, Belgium).

EXAMPLE 7

Follow up of Patient Groups with Different Clinical Profiles 7.1. Monitoring of Anti-E1 and Anti-E2 Antibodies The current hepatitis C virus (HCV) diagnostic assays have been developed for screening and confirmation of the presence of HCV antibodies. Such assays do not seem to provide information useful for monitoring of treatment or for prognosis of the outcome of disease. However, as is the case for hepatitis B, detection and quantification of anti-envelope antibodies may prove more useful in a clinical setting. To investigate the possibility of the use of anti-E1 antibody titer and anti-E2 antibody titer as prognostic markers for outcome of hepatitis C disease, a series of IFN-α treated patients with long-term sustained response (defined as patients with normal transaminase levels and negative HCV-RNA test (PCR in the 5' non-coding region) in the blood for a period of at least 1 year after treatment) was compared with patients showing no response or showing biochemical response with relapse at the end of treatment.

A group of 8 IFN-α treated patients with long-term sustained response (LTR, follow up 1 to 3.5 years, 3 type 3a and 5 type 1b) was compared with 9 patients showing non-complete responses to treatment (NR, follow up 1 to 4 years, 6 type 1b and 3 type 3a). Type 1b (vvHCV-39, see example 2.5.) and 3a E1 (vvHCV-62, see example 2.5.) proteins were expressed by the vaccinia virus system (see examples 3 and 4) and purified to homogeneity (example 5). The samples derived from patients infected with a type 1b hepatitis C virus were tested for reactivity with purified type 1b E1 protein, while samples of a type 3a infection were tested for reactivity of anti-type 3a E1 antibodies in an ELISA as desribed in example 6. The genotypes of hepatitis C viruses infecting the different patients were determined by means of the Inno-LiPA genotyping assay (Innogenetics, Zwijndrecht, Belgium). FIG. 5 shows the anti-E1 signal-to-noise ratios of these patients followed during the course of interferon treatment and during the follow-up period after treatment. LTR cases consistently showed rapidly declining anti-E1 levels (with complete negativation in 3 cases), while anti-E1 levels of NR cases remained approximately constant. Some of the obtained anti-E1 data are shown in Table 2 as average S/N ratios±SD (mean anti-E1 titer). The anti-E1 titer could be deduced from the signal to noise ratio as show in FIGS. 5, 6, 7, and 8.

Already at the end of treatment, marked differences could be observed between the 2 groups. Anti-E1 antibody titers had decreased 6.9 times in LTR but only 1.5 times in NR. At the end of follow up, the anti-E1 titers had declined by a factor of 22.5 in the patients with sustained response and even slightly increased in NR. Therefore, based on these data, decrease of anti-E1 antibody levels during monitoring of IFN-α therapy correlates with long-term, sustained response to treatment. The anti-E1 assay may be very useful for prognosis of long-term response to IFN treatment, or to treatment of the hepatitis C disease in general.

This finding was not expected. On the contrary, the inventors had expected the anti-E1 antibody levels to increase during the course of IFN treatment in patients with long term response. As is the case for hepatitis B, the virus is cleared as a consequence of the seroconversion for anti-HBsAg antibodies. Also in many other virus infections, the virus is eliminated when anti-envelope antibodies are raised. However, in the experiments of the present invention, anti-E1 antibodies clearly decreased in patients with a long-term response to treatment, while the antibody-level remained approximately at the same level in non-responding patients. Although the outcome of these experiments was not expected, this non-obvious finding may be very important and useful for clinical diagnosis of HCV infections. As shown in FIGS. 9, 10, 11, and 12, anti-E2 levels behaved very differently in the same patients studied and no obvious decline in titers was observed as for anti-E1 antibodies. FIG. 35 gives a complete overview of the pilot study.

As can be deduced from Table 2, the anti-E1 titers were on average at least 2 times higher at the start of treatment in long term responders compared with incomplete responders to treatment. Therefore, measuring the titer of anti-E1 antibodies at the start of treatment, or monitoring the patient during the course of infection and measuring the anti-E1 titer, may become a useful marker for clinical diagnosis of hepatitis C. Furthermore, the use of more defined regions of the E1 or E2 proteins may become desirable, as shown in example 7.3.

7.2. Analysis of E1 and E2 Antibodies in a Larger Patient Cohort

The pilot study lead the inventors to conclude that, in case infection was completely cleared, antibodies to the HCV envelope proteins changed more rapidly than antibodies to the more conventionally studied HCV antigens, with E1 antibodies changing most vigorously. We therefore included more type 1b and 3a-infected LTR and further supplemented the cohort with a matched series of NR, such that both groups included 14 patients each. Some partial responders (PR) and responders with relapse (RR) were also analyzed.

FIG. 36 depicts average E1 antibody (E1Ab) and E2 antibody (E2Ab) levels in the LTR and NR groups and Tables 4 and 5 show the statistical analyses. In this larger cohort, higher E1 antibody levels before IFN-α therapy were associated with LTR (P<0.03). Since much higher E1 antibody levels were observed in type 3a-infected patients compared with type 1b-infected patients (FIG. 37), the genotype was taken into account (Table 4). Within the type 1b-infected group, LTR also had higher E1 antibody levels than NR at the initiation of treatment [P<0.05]; the limited number of type 3a-infected NR did not allow statistical analysis.

Of antibody levels monitored in LTR during the 1.5-year follow up period, only E1 antibodies cleared rapidly compared with levels measured at initiation of treatment [P=0.0058, end of therapy; P=0.004.7 and P=0.0051 at 6 and 12 months after therapy, respectively]. This clearance remained significant within type 1- or type 3-infected LTR (average P values <0.05). These data confirmed the initial finding that E1Ab levels decrease rapidly in the early phase of resolvement. This feature seems to be independent of viral genotype. In NR, PR, or RR, no changes in any of the antibodies measured were observed throughout the follow up period. In patients who responded favourably to treatment with normalization of ALT levels and HCV-RNA negative during treatment, there was a marked difference between sustained responders (LTR) and responders with a relapse (RR). In contrast to LTR, RR did not show any decreasing E1 antibody levels, indicating the presence of occult HCV infection that could neither be demonstrated by PCR or other classical techniques for detection of HCV-RNA, nor by raised ALT levels. The minute quantities of viral RNA, still present in the RR group during treatment, seemed to be capable of anti-E1 B cell stimulation. Anti-E1 monitoring may therefore not only be able to discriminate LTR from NR, but also from RR.

7.3. Monitoring of Antibodies of Defined Regions of the E1 Protein

Although the molecular biological approach of identifying HCV antigens resulted in unprecedented breakthrough in the development of viral diagnostics, the method of immune screening of λgt11 libraries predominantly yielded linear epitopes dispersed throughout the core and non-structural regions, and analysis of the envelope regions had to await cloning and expression of the E1/E2 region in mammalian cells. This approach sharply contrasts with many other viral infections of which epitopes to the envelope regions had already been mapped long before the deciphering of the genomic structure. Such epitopes and corresponding antibodies often had neutralizing activity useful for vaccine development and/or allowed the development of diagnostic assays with clinical or prognostic significance (e.g. antibodies to hepatitis surface antigen). As no HCV vaccines or tests allowing clinical diagnosis and prognosis of hepatitis C disease are available today, the characterization of viral envelope regions exposed to immune surveillance may significantly contribute to new directions in HCV diagnosis and prophylaxis.

Several 20-mer peptides (Table 3) that overlapped each other by 8 amino acids, were synthesized according to a previously described method (EP-A-0 489 968) based on the HC-J1 sequence (Okamoto et al., 1990). None of these, except peptide env35 (also referred to as E1-35), was able to detect antibodies in sera of approximately 200 HCV cases. Only 2 sera reacted slightly with the env35 peptide. However, by means of the anti-E1 ELISA as described in example 6, it was possible to discover additional epitopes as follows: The anti-E1 ELISA as described in example 6 was modified by mixing 50 µg/ml of E1 peptide with the 1/20 diluted human serum in sample diluent. FIG. 13 shows the results of reactivity of human sera to the recombinant E1 (expressed from vvHCV-40) protein, in the presence of single or of a mixture of E1 peptides. While only 2% of the sera could be detected by means of E1 peptides coated on strips in a Line Immunoassay format, over half of the sera contained anti-E1 antibodies which could be competed by means of the same peptides, when tested on the recombinant E1 protein. Some of the murine monoclonal antibodies obtained from Balb/C mice after injection with purified E1 protein were subsequently competed for reactivity to E1 with the single peptides (FIG. 14). Clearly, the region of env53 contained the predominant epitope, as the addition of env53 could substantially compete reactivity of several sera with E1, and antibodies to the env31 region were also detected. This finding was surprising, since the env53 and env31 peptides had not shown any reactivity when coated directly to the solid phase.

Therefore peptides were synthesized using technology described by applicant previously (in WO 93/18054). The following peptides were synthesized:

peptide env35A-biotin

NH$_2$-SNSSEAADMIMHTPGCV-GKbiotin (SEQ ID NO 51)

spanning amino acids 208 to 227 of the HCV polyprotein in the E1 region
peptide biotin-env53 ('epitope A')

H$_2$N-YEVRNVSGIYHVTNDCSNSSIVYEAADMIMHTPGCGK-biotin (SEQ ID NO 53)

spanning amino acids to 313 of 332 of the HCV polyprotein in the E1 region
peptide 1bE1 ('epitope B')

biotin-GG-ITGHRMAWDMMMNWSPTTAL-COOH (SEQ ID NO 52)

spanning amino acids 192 to 228 of the HCV polyprotein in the E1 region and compared with the reactivities of peptides E1a-BB (biotin-GG-TPTPTVATRDGKLPATQLRRHIDLL, SEQ ID NO 54) and E1 b-BB (biotin-GG-TPTLAARDASVPTTTIRRHVDLL, SEQ ID NO 55) which are derived from the same region of sequences of genotype 1a and 1b respectively and which have been described at the IXth international virology meeting in Glasgow, 1993 ('epitope C'). Reactivity of a panel of HCV sera was tested an epitopes A, B and C and epitope B was also compared with env35A (of 47 HCV-positive sera, 8 were positive on epitope B and none reacted with env35A). Reactivity towards epitopes A, B, and C was tested directly to the biotinylated peptides (50 µg/ml) bound to streptavidin-coated plates as described in example 6. Clearly, epitopes A and B were most reactive while epitopes C and env35A-biotin were much less reactive. The same series of patients that had been monitored for their reactivity towards the complete E1 protein (example 7.1.) was tested for reactivity towards epitopes A, B, and C. Little reactivity was seen to epitope C, while as shown in FIGS. 15, 16, 17, and 18, epitopes A and B reacted with the majority of sera. However, antibodies to the most reactive epitope (epitope A) did not seem to predict remission of disease, while the anti-1bE1 antibodies (epitope B) were present almost exclusively in long term responders at the start of IFN treatment. Therefore, anti-1bE1 (epitope B) antibodies and anti-env53 (epitope A) antibodies could be shown to be useful markers for prognosis of hepatitis C disease. The env53 epitope may be advantageously used for the detection of cross-reactive antibodies (antibodies that cross-react between major genotypes) and antibodies to the env53 region may be very useful for universal E1 antigen detection in serum or liver tissue. Monoclonal antibodies that recognized the env53 region were reacted with a random epitope library. In 4 clones that reacted upon immunoscreening with the monoclonal antibody 5E1A10, the sequence -GWD- was present. Because of its analogy with the universal HCV sequence present in all HCV variants in the env53 region, the sequence AWD is thought to contain the essential sequence of the env53 cross-reactive murine epitope. The env31 clearly also contains a variable region which may contain an epitope in the amino terminal sequence -YCVRNSTCL- (SEQ ID NO 93) and may be useful for diagnosis. Env31 or E1-31 as shown in Table 3, is a par; of the peptide 1bE1. Peptides E1-33 and E1-51 also reacted to some extent with the murine antibodies, and peptide E1-55 (containing the variable region 6 (V6); spanning amino acid positions 329–330) also reacted with some of the patient sera.

Anti-E2 antibodies clearly followed a different pattern than the anti-E1 antibodies, especially in patients with a long-term response to treatment. Therefore, it is clear that the decrease in anti-envelope antibodies could not be measured as efficiently with an assay employing a recombinant E1/E2 protein as with a single anti-E1 or anti-E2 protein. The anti-E2 response would clearly blur the anti-E1 response in an assay measuring both kinds of antibodies at the same time. Therefore, the ability to test anti-envelope antibodies to the single E1 and E2 proteins, was shown to be useful.

7.4. Mapping of Anti-E2 Antibodies

Figure 20:
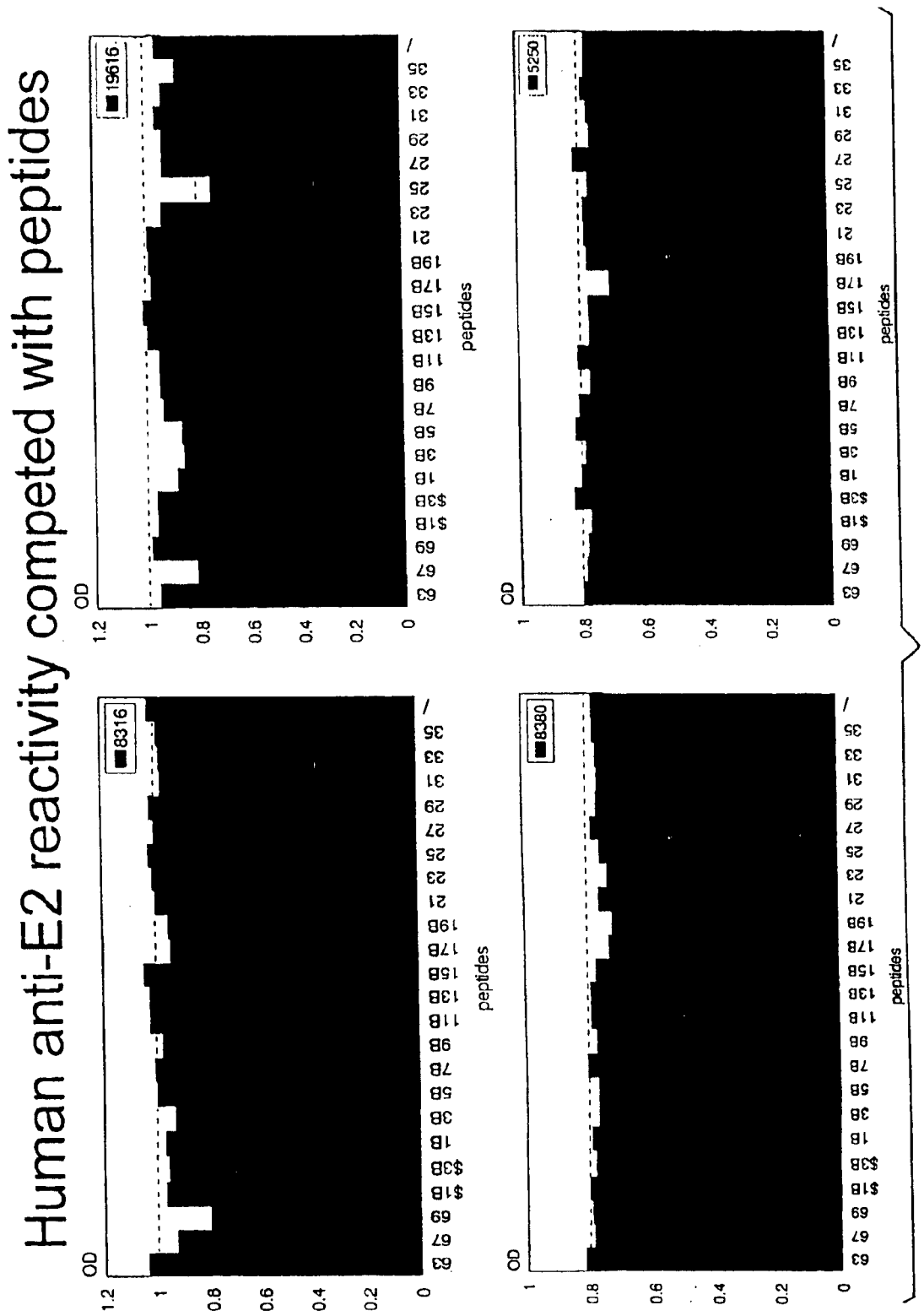

Of the 24 anti-E2 Mabs only three could be competed for reactivity to recombinant E2 by peptides, two of which reacted with the HVRI region (peptides E2-67 and E2-69, designated as epitope A) and one which recognized an epitope competed by peptide E2-13B (epitope C). The majority of murine antibodies recognized conformational anti-E2 epitopes (FIG. 19). A human response to HVRI (epitope A), and to a lesser extent HVRII (epitope B) and a third linear epitope region (competed by peptides E2-23, E2-25 or E2-27, designated epitope E) and a fourth linear epitope region (competed by peptide E2-17B, epitope D) could also frequently be observed, but the majority of sera reacted with conformational epitopes (FIG. 20). These conformational epitopes could be grouped according to their relative positions as follows: the IgG antibodies in the supernatant of hybridomas 15C8C1, 12D11F1, 9G3E6, 8G10D1H9, 10D3C4, 4H6B2, 17F2C2, 5H6A7, 15B7A2 recognizing conformational epitopes were purified by means of protein A affinity chromatography and 1 mg/ml of the resulting IgG's were biotinylated in berate buffer in the presence of biotin. Biotinylated antibodies were separated from free biotin by means of gelfiltration chromatography. Pooled biotinylated antibody fractions were diluted 100 to 10,000 times. E2 protein bound to the solid phase was detected by the biotinylated IgG in the presence of 100 times the amount of non-biotinylated competing antibody and subsequently detected by alkaline phosphatase labeled streptavidin.

Percentages of competition are given in Table 6. Based on these results, 4 conformational anti-E2 epitope regions (epitopes F, G, H and I) could be delineated (FIG. 38). Alternatively, these Mabs may recognize mutant linear epitopes not represented by the peptides used in this study. Mabs 4H6B2 and 10D3C4 competed reactivity of 16A6E7, but unlike 16A6E7, they did not recognize peptide E2-13B. These Mabs may recognize variants of the same linear epitope (epitope C) or recognize a conformational epitope which is sterically hindered or changes conformation after binding of 16A6E7 to the E2-13B region (epitope H).

Monoclonal antibody identified as 17H10F4D10 has been deposited under the conditions of the Budapest Treaty on Dec. 3, 1998 with the ECACC (European Collection of Cell Cultures), Center for Applied Microbiology and Research, Salisbury, Wiltshire SP40JG, UK (Telephone: +44 1980 612512, Fax: +44 1980 611315) and assigned Accession No. 98031215.

Monoclonal antibodies identified as 16A6E7 and 12D11F1 have been deposited under the conditions of the Budapest Treaty on Sep. 10, 2003 with DSMZ (Deutsche Sammiung von Mikroorganismen und Zeilkulturen GmbH), Mascheroder Weg 1b, D-38124 Braunschweig, DE, and have been assigned accession numbers DSM ACC 2616 and DSM ACC 2615, respectively.

EXAMPLE 8

E1 Glycosylation Mutants 8.1. Introduction

The E1 protein encoded by vvHCV10A, and the E2 protein encoded by vvHCV41 to 44 expressed from mammalian cells contain 6 and 11 carbohydrate moieties, respectively. This could be shown by incubating the lysate of vvHCV10A-infected or vvHCV44-infected RK13 cells with decreasing concentrations of glycosidases (PNGase F or Endoglycosidase H, (Boehringer Mannhein Biochemica) according to the manufacturer's instructions), such that the proteins in the lysate (including E1) are partially deglycosylated (FIGS. 39 and 40, respectively).

Mutants devoid of some of their glycosylation sites could allow the selection of envelope proteins with improved immunological reactivity. For HIV for example, gp120 proteins lacking certain selected sugar-addition motifs, have been found to be particularly useful for diagnostic or vaccine purpose. The addition of a new oligosaccharide side chain in the hemagglutinin protein of an escape mutant of the A/Hong Kong/3/68 (H3N2) influenza virus prevents reactivity with a neutralizing monoclonal antibody (Skehel et al, 1984). When novel glycosylation sites were introduced into the influenza hemaglutinin protein by site-specific mutagenesis, dramatic antigenic changes were observed, suggesting that the carbohydrates serve as a modulator of antigenicity (Gallagher et al., 1988). In another analysis, the 8 carbohydrate-addition motifs of the surface protein gp70 of the Friend Murine Leukemia Virus were deleted. Although seven of the mutations did not affect virus infectivity, mutation of the fourth glycosylation signal with respect to the amino terminus resulted in a non-infectious phenotype (Kayman et al., 1991). Furthermore, it is known in the art that addition of N-linked carbohydrate chains is important for stabilization of folding intermediates and thus for efficient folding, prevention of malfolding and degradation in the endoplasmic reticulum, oligomerization, biological activity, and transport of glycoproteins (see reviews by Rose et al., 1988; Doms et al., 1993; Helenius, 1994).

After alignment of the different envelope protein sequences of HCV genotypes, it may be inferred that not all 6 glycosylation sites on the HCV subtype 1b E1 protein are required for proper folding and reactivity, since some are absent in certain (sub)types. The fourth carbohydrate motif (on Asn251), present In types 1b, 6a, 7, 8, and 9, is absent in all other types know today. This sugar-addition motif may be mutated to yield a type 1b E1 protein with improved reactivity. Also the type 2b sequences show an extra glycosylation site in the V5 region (on Asn299). The isolate S83, belonging to genotype 2c, even lacks the first carbohydrate motif in the V1 region (on Asn), while it is present on all other isolates (Stuyver et al., 1994) However, even among the completely conserved sugar-addition motifs, the presence of the carbohydrate may not be required for folding, but may have a role in evasion of immune surveillance. Therefore, identification of the carbohydrate addition motifs which are not required for proper folding (and reactivity) is not obvious, and each mutant has to be analyzed and tested for reactivity. Mutagenesis of a glycosylation motif (NXS or NXT sequences) can be achieved by either mutating the codons for N, S, or T, in such a way that these codons encode amino acids different from N in the case of N, and/or amino acids different from S or T in the case of S and in the case of T. Alternatively, the X position may be mutated into P;

since it is known that NPS or NPT are not frequently modified with carbohydrates. After establishing which carbohydrate-addition motifs are required for folding and/or reactivity and which are not, combinations of such mutations may be made.

8.2. Mutagenesis of the E1 Protein

All mutations were performed on the E1 sequence of clone HCCl10A (SEQ ID NO. 5). The first round of PCR was performed using sense primer 'GPT' (see Table 7) targetting the GPT sequence located upstream of the vaccinia 11K late promoter, and an antisense primer (designated GLY#, with # representing the number of the glycosylation site, see FIG. 41) containing the desired base chance to obtain the mutagenesis. The six GLY# primers (each specific for a given glycosylation site) were designed such that:

Modification of the codon encoding for the N-glycosylated Asn (AAC or AAT) to a Gln codon (CAA or CAG). Glutamine was chosen because it is very similar to asparagine (both amino acids are neutral and contain non-polar residues, glutamine has a longer side chain (one more —$CH_2$— groups.

The introduction of silent mutations in one or several of the codons downstream of the glycosylation site, in order to create a new unique or rare (e.g. a second SmaI site for E1Gly5) restriction enzyme site. Without modifying the amino acid sequence, this mutation will provide a way to distinguish the mutated sequences from the original E1 sequence (pvHCV-10A) or from each other (FIG. 41). This additional restriction site may also be useful for the construction of new hybrid (double, triple, etc.) glycosylation mutants.

18 nucleotides extend 5' of the first mismatched nucleotide and 12 to 16 nucleotides extend to the 3' end. Table 7 depicts the sequences of the six GLY# primers overlapping the sequence of N-linked glycosylation sites.

For site-directed mutagenesis, the 'mispriming' or 'overlap extension' (Horton, 1993) was used. The concept is illustrated in FIGS. 42 and 43. First, two separate fragments were amplified from the target gene for each mutated site. The PCR product obtained from the 5' end (product GLY#) was amplified with the 5' sense GPT primer (see Table 7) and with the respective 3' antisense GLY# primers. The second fragment (product OVR#) was amplified with the 3' antisense $TK_R$ primer and the respective 5' sense primers (OVR# primers, see Table 7, FIG. 43).

The OVR# primers target part of the GLY# primer sequence. Therefore, the two groups of PCR products share an overlap region of identical sequence. When these intermediate products are mixed (GLY-1 with OVR-1, GLY-2 with OVR-2. etc.), melted at high temperature, and reannealed, the top sense strand of product GLY# can anneal to the antisense strand of product OVR# (and vice versa) in such a way that the two strands act as primers for one another (see FIG. 42.B.). Extension of the annealed overlap by Taq polymerase during two PCR cycles created the full-length mutant molecule E1 Gly#, which carries the mutation destroying the glycosylation site number #. Sufficient quantities of the E1GLY# products for cloning were generated in a third PCR by means of a common set of two internal nested primers. These two new primers are respectively overlapping the 3' end of the vaccinia 11K promoter (sense GFP-2 primer) and the 5' end of the vaccinia thymidine kinase locus (antisense $TK_R$-2 primer, see Table 7). All PCR conditions were performed as described in Stuyver et al. (1993).

Each of these PCR products was cloned by EcoRI/BamHI cleavage into the EcoRI/BamHI-cut vaccinia vector containing the original E1 sequence (pvHCV-10A).

The selected clones were analyzed for length of insert by EcoRI/BamHI cleavage and for the presence of each new restriction site. The sequences overlapping the mutated sites were confirmed by double-stranded sequencing.

8.3. Analysis of E1 Glycosylation Mutants

Starting from the 6 plasmids containing the mutant E1 sequences as described in example 8.2, recombinant vaccinia viruses were generated by recombination with wt vaccinia virus as described in example 2.5. Briefly, 175 $cm^2$-flasks of subconfluent RK13 cells were infected with the 6 recombinant vaccinia viruses carrying the mutant E1 sequences, as well as with the vvHCV-10A (carrying the non-mutated E1 sequence) and wt vaccinia viruses. Cells were lysed after 24 hours of infection and analyzed on western blot as described in example 4 (see FIG. 44A). All mutants showed a faster mobility (corresponding to a smaller molecular weight of approximately 2 to 3 kDa) on SDS-PAGE than the original E1 protein; confirming that one carbohydrate moiety was not added. Recombinant viruses were also analyzed by PCR and restriction enzyme analysis to confirm the identity of the different mutants. FIG. 44B shows that all mutants (as shown in FIG. 41) contained the expected additional restriction sites. Another part of the cell lysate was used to test the reactivity of the different mutant by ELISA. The lysates were diluted 20 times and added to microwell plates coated with the lectin GNA as described in example 6. Captured (mutant) E1 glycoproteins were left to react with 20-times diluted sera of 24 HCV-infected patients as described in example 6. Signal to noise (S/N) values (OD of GLY#/OD of wt) for the six mutants and E1 are shown in Table 8. The table also shows the ratios between S/N values of GLY# and E1 proteins. It should be understood that the approach to use cell lysates of the different mutants for comparison of reactivity with patient sera may result in observations that are the consequence of different expression levels rather then reactivity levels. Such difficulties can be overcome by purification of the different mutants as described in example 5, and by testing identical quantities of all the different E1 proteins. However, the results shown in table 5 already indicate that removal of the 1st (GLY1), 3rd (GLY3), and 6th (GLY6) glycosylation motifs reduces reactivity of some sera, while removal of the 2nd and 5th site does not. Removal of GLY4 seems to improve the reactivity of certain sera. These data indicate that different patients react differently to the glycosylation mutants of the present invention. Thus, such mutant E1 proteins may be useful for the diagnosis (screening, confirmation, prognosis, etc.) and prevention of HCV disease.

EXAMPLE 9

Expression of HCV E2 Protein in Glycosylation-Deficient Yeasts

The E2 sequence corresponding to clone HCCL41 was provided with the α-mating factor pre/pro signal sequence, inserted in a yeast expression vector and *S. cerevisiae* cells transformed with this construct secreted E2 protein into the growth medium. It was observed that most glycosylation sites were modified with high-mannose type glycosylations upon expression of such a construct in *S. cerevisiae* strains (FIG. 45). This resulted in a too high level of heterogeneity and in shielding of reactivity, which is not desirable for either vaccine or diagnostic purposes. To overcome this problem, *S. cerevisiae* mutants with modified glycosylation pathways were generated by means of selection of vanadate-resistant clones. Such clones were analyzed for modified glycosylation pathways by analysis of the molecular weight and heterogeneity of the glycoprotein invertase. This allowed us to identify different glycosylation deficient *S. cerevisiae* mutants. The E2 protein was subsequently expressed in some of the selected mutants and left to react with a monoclonal antibody as described in example 7, on western blot as described in example 4 (FIG. 46).

EXAMPLE 10

General Utility

The present results show that not only a good expression system but also a good purification protocol are required to reach a high reactivity of the HCV envelope proteins with human patient sera. This can be obtained using the proper HCV envelope protein expression system and/or purification protocols of the present invention which guarantee the conservation of the natural folding of the protein and the purification protocols of the present invention which guarantee the elimination of contaminating proteins and which preserve the conformation, and thus the reactivity of the HCV envelope proteins. The amounts of purified HCV envelope protein needed for diagnostic screening assays are in the range of grams per year. For vaccine purposes, even higher amounts of envelope protein would be needed. Therefore, the vaccinia virus system may be used for selecting the best expression constructs and for limited upscaling, and large-scale expression and purification of single or specific oligomeric envelope proteins containing high-mannose carbohydrates may be achieved when expressed from several yeast strains. In the case of hepatitis B for example, manufacturing of HBsAg from mammalian cells was much more costly compared with yeast-derived hepatitis B vaccines.

The purification method disclosed in the present invention may also be used for 'viral envelope proteins' in general. Examples are those derived from Flaviviruses, the newly discovered GB-A, GB-B and GB-C Hepatitis viruses, Pestiviruses (such as Bovine viral Diarrhoea Virus (BVDV), Hog Cholera Virus (HCV), Border Disease Virus (BDV)), but also less related virusses such as Hepatitis B Virus (mainly for the purification of HBsAg).

The envelope protein purification method of the present invention may be used for intra—as well as extracellularly expressed proteins in lower or higher eukaryotic cells or in prokaryotes as set out in the detailed description section.

TABLE 1

Recombinant vaccinia plasmids and viruses

| Plasmid name | Name | cDNA subclone construction | Length (nt/aa) | Vector used for insertion |
|---|---|---|---|---|
| pvHCV-13A | E1s | EcoR I - Hind III | 472/157 | pgptATA-18 |
| pvHCV-12A | E1s | EcoR I - Hind III | 472/158 | pgptATA-18 |
| pvHCV-9A | E1 | EcoR I - Hind III | 631/211 | pgptATA-18 |
| pvHCV-11A | E1s | EcoR I - Hind III | 625/207 | pgptATA-18 |
| pvHCV-17A | E1s | EcoR I - Hind III | 625/208 | pgptATA-18 |
| pvHCV-10A | E1 | EcoR I - Hind III | 783/262 | pgptATA-18 |
| pvHCV-18A | COREs | Acc I (Kl) - EcoR I (Kl) | 403/130 | pgptATA-18 |
| pvHCV-34 | CORE | Acc I (Kl) - Fsp I | 595/197 | pgptATA-18 |
| pvHCV-33 | CORE-E1 | Acc I (Kl) | 1150/380 | pgptATA-18 |
| pvHCV-35 | CORE-E1b.his | EcoR I - BamH I (Kl) | 1032/352 | pMS-66 |
| pvHCV-36 | CORE-E1n.his | EcoR I - Nco I (Kl) | 1106/376 | pMS-66 |
| pvHCV-37 | E1 Δ | Xma I - BamH I | 711/239 | pvHCV-10A |
| pvHCV-38 | E1 Δs | EcoR I - BstE II | 553/183 | pvHCV-11A |
| pvHCV-39 | E1 Δb | EcoR I - BamH I | 960/313 | pgsATA-18 |
| pvHCV-40 | E1 Δb.his | EcoR I - BamH I (Kl) | 960/323 | pMS-66 |
| pvHCV-41 | E2bs | BamH I (Kl) - AlwN I (T4) | 1005/331 | pgsATA-18 |
| pvHCV-42 | E2bs.his | BamH I (Kl) - AlwN I (T4) | 1005/341 | pMS-66 |
| pvHCV-43 | E2ns | Nco I (Kl) - AlwN I (T4) | 932/314 | pgsATA-18 |
| pvHCV-44 | E2ns.his | Nco I (Kl) - AlwN I (T4) | 932/321 | pMS-66 |
| pvHCV-62 | E1s (type 3a) | EcoR I - Hind III | 625/207 | pgsATA-18 |
| pvHCV-63 | E1s (type 5) | EcoR I - Hind III | 625/207 | pgsATA-18 |
| pvHCV-64 | E2 | BamH I - Hind III | 1410/463 | pgsATA-18 |
| pvHCV-65 | E1-E2 | BamH I - Hind III | 2072/691 | pvHCV-10A |
| pvHCV-66 | CORE-E1-E2 | BamH I - Hind III | 2427/809 | pvHCV-33 |

| Plasmid Name | Name | HCV cDNA subclone Construction | Length (nt/aa) | Vector used for insertion |
|---|---|---|---|---|
| pvHCV-81 | E1*-GLY 1 | EcoR I - BamH I | 783/262 | pvHCV-10A |
| pvHCV-82 | E1*-GLY 2 | EcoR I - BamH I | 783/262 | pvHCV-10A |
| pvHCV-83 | E1*-GLY 3 | EcoR I - BamH I | 783/262 | pvHCV-10A |
| pvHCV-84 | E1*-GLY 4 | EcoR I - BamH I | 783/262 | pvHCV-10A |
| pvHCV-85 | E1*-GLY 5 | EcoR I - BamH I | 783/262 | pvHCV-10A |
| pvHCV-86 | E1*-GLY 6 | EcoR I - BamH I | 783/262 | pvHCV-10A | nt: nucleotide aa: aminoacid Kl: Klenow DNA Pol filling T4: T4 DNA Pol filling
Position: aminoacid position in the HCV polyprotein sequence

TABLE 2

Summary of anti-E1 tests

S/N ± SD (mean anti-E1 titer)

| | Start of treatment | End of treatment | Follow-up |
|---|---|---|---|
| LTR | 6.94 ± 2.29 (1:3946) | 4.48 ± 2.69 (1:568) | 2.99 ± 2.69 (1:175) |
| NR | 5.77 ± 3.77 (1:1607) | 5.29 ± 3.99 (1:1060) | 6.08 ± 3.73 (1:1978) |

LTR: Long-term, sustained response for more than 1 year
NR: No response, response with relapse, or partial response

TABLE 3

Synthetic peptides for competition studies

| PROTEIN | PEPTIDE | AMINO ACID SEQUENCE | POSITION | SEQ ID NO |
|---|---|---|---|---|
| E1 | E1-31 | LLSCLTVPASAYQVRNSTGL | 181–200 | 56 |
|  | E1-33 | QVRNSTGLYHVTNDCPNSSI | 193–212 | 57 |
|  | E1-35 | NDCPNSSIVYEAHDAILHTP | 205–224 | 58 |
|  | E1-35A | SNSSIVYEAADMIMHTPGCV | 208–227 | 59 |
|  | E1-37 | HDAILHTPGCVPCVREGNVS | 217–236 | 60 |
|  | E1-39 | CVREGNVSRCWVAMTPTVAT | 229–248 | 61 |
|  | E1-41 | AMTPTVATRDGKLPATQLRR | 241–260 | 62 |
|  | E1-43 | LPATQLRRHIDLLVGSATLC | 253–272 | 63 |
|  | E1-45 | LVGSATLCSALYVGDLCGSV | 265–284 | 64 |
|  | E1-49 | QLFTFSPRRHWTTQGCNCSI | 289–308 | 65 |
|  | E1-51 | TQGCNCSIYPGHITGHRMAW | 301–320 | 66 |
|  | E1-53 | ITGHRMAWDMMMNWSPTAAL | 313–332 | 67 |
|  | E1-55 | NWSPTAALVMAQLLRIPQAI | 325–344 | 68 |
|  | E1-57 | LLRIPQAILDMIAGAHWGVL | 337–356 | 69 |
|  | E1-59 | AGAHWGVLAGIAYFSMVGNM | 349–368 | 70 |
|  | E1-63 | VVLLLFAGVDAETIVSGGQA | 373–392 | 71 |
| E2 | E2-67 | SGLVSLFTPGAKQNIQLINT | 397–416 | 72 |
|  | E2-69 | QNIQLINTNGSWHINSTALN | 409–428 | 73 |
|  | E2-$3B | LNCNESLNTGWWLAGLIYQHK | 427–446 | 74 |
|  | E2-$1B | AGLIYQHKFNSSGCPERLAS | 439–458 | 75 |
|  | E2-1B | GCPERLASCRPLTDFDQGWG | 451–470 | 76 |
|  | E2-3B | TDFDQGWGPISYANGSGPDQ | 463–482 | 77 |
|  | E2-5B | ANGSGPDQRPYCWHYPPKPC | 475–494 | 78 |
|  | E2-7B | WHYPPKPCGIVPAKSVCGPV | 487–506 | 79 |
|  | E2-9B | AKSVCGPVYCFTPSPVVVGT | 499–518 | 80 |
|  | E2-11B | PSPVVVGTTDRSGAPTYSWG | 511–530 | 81 |
|  | E2-13B | GAPTYSWGENDTDVFVLNNT | 523–542 | 82 |
|  | E2-17B | GNWFGCTWMNSTGFTKVCGA | 547–566 | 83 |
|  | E2-19B | GFTKVCGAPPVCIGGAGNNT | 559–578 | 84 |
|  | E2-21 | IGGAGNNTLHCPTDCFRKHP | 571–590 | 85 |
|  | E2-23 | TDCFRKHPDATYSRCGSGPW | 583–602 | 86 |
|  | E2-25 | SRCGSGPWITPRCLVDYPYR | 595–614 | 87 |
|  | E2-27 | CLVDYPYRLWHYPCTINYTI | 607–626 | 88 |
|  | E2-29 | PCTINYTIFKIRMYVGGVEH | 619–638 | 89 |
|  | E2-31 | MYVGGVEHRLEAACNWTPGE | 631–650 | 90 |
|  | E2-33 | ACNWTPGERCDLEDRDRSEL | 643–662 | 91 |
|  | E2-35 | EDRDRSELSPLLLTTTQWQV | 655–674 | 92 |

TABLE 4

Change of Envelope Antibody levels over time (complete study, 28 patients)

| Wilcoxon Signed Rank test (P values) | E1 Ab NR All | E1Ab NR type 1b | E1Ab NR type 3a | E1Ab LTR All | E1Ab LTR type 1b | E1Ab LTR type 3a | E2Ab NR All | E1Ab LTR All |
|---|---|---|---|---|---|---|---|---|
| End of therapy* | 0.1167 | 0.2604 | 0.285 | 0.0058** | 0.043** | 0.0499** | 0.0186** | 0.0640 |
| 6 months follow up* | 0.86 | 0.7213 | 0.5930 | 0.0047** | 0.043** | 0.063 | 0.04326 | 0.0464** |
| 12 months follow up* | 0.7989 | 0.3105 | 1 | 0.0051** | 0.0679 | 0.0277** | 0.0869 | 0.0058** |

*Data were compared with values obtained at Initiation of therapy
**P values <0.05

TABLE 5

Difference between LTR and NR (complete study)

| Mann-Withney U test (P values) | E1Ab S/N All | E1Ab titers All | E1Ab S/N type 1b | E1Ab S/N type 3a | E2Ab S/N All |
|---|---|---|---|---|---|
| Initiation of therapy | 0.0257* |  | 0.05* | 0.68 | 0.1078 |
| End of therapy | 0.1742 |  |  |  | 0.1295 |
| 6 months follow up | 1 |  | 0.6099 | 0.425 | 0.3081 |
| 12 months follow up | 0.67 |  | 0.23 | 0.4386 | 0.6629 |

*P values <0.05

TABLE 6

Competition experiments between murine E2 monoclonal antibodies

Decrease (%) of anti-E2 reactivity of biotinylated anti-E2 mabs

| Competitor | 17H10F4D10 | 2F10H10 | 16A6E7 | 10D3C4 | 4H6B2 | 17C2F2 | 9G3E6 | 12D11F1 | 15C8C1 | 8G10D1H9 |
|---|---|---|---|---|---|---|---|---|---|---|
| 17H10F4D10 | — | 62 | 10 | ND | 11 | ND | 5 | 6 | 30 | ND |
| 2F10H10 | 90 | — | 1 | ND | 30 | ND | 0 | 4 | 12 | ND |
| 16A6E7 | ND | ND | — | ND | ND | ND | ND | ND | ND | ND |
| 10D3C4 | 11 | 50 | 92 | — | 94 | 26 | 28 | 43 | 53 | 30 |
| 4H6B2 | ND | ND | 82 | ND | — | ND | ND | ND | ND | ND |
| 17C2F2 | 2 | ND | 76 | ND | 56 | — | 11 | 10 | 0 | 0 |
| 9G3E6 | ND | ND | 68 | ND | 11 | ND | — | 60 | 76 | ND |
| 12D11F1 | ND | ND | 26 | ND | 13 | ND | ND | — | 88 | ND |
| 15C8C1 | ND | ND | 18 | ND | 10 | ND | ND | ND | — | ND |
| 8G10D1H9 | 2 | 2 | 11 | ND | 15 | ND | 67 | 082 | 81 | — |
| Competitor controls | | | | | | | | | | |
| 5B7A2 | 0 | 0 | 9 | 15 | 10 | 9 | 0 | 0 | 0 | 5 |
| H6A7 | 0 | 2 | 0 | 12 | 8 | 0 | 0 | 4 | 0 | 0 |
| 3C12H9 | ND | ND | 2 | 12 | ND | 4 | ND | ND | ND | 2 |

ND, not done

TABLE 7

Primers

| | | |
|---|---|---|
| SEQ ID NO. 96 | GPT | 5'-GTTTAACCACTGCATGATG-3' |
| SEQ ID NO. 97 | TK$_n$ | 5'-GTCCCATCGAGTGCGGCTAC-3' |
| SEQ ID NO. 98 | GLY1 | 5'-CGTGACATGGTACATTCCGGACACTTGGCGCACTTCATAAGCGGA-3' |
| SEQ ID NO. 99 | GLY2 | 5'-TGCCTCATACACAATGGAGCTCTGGGACGAGTCGTTCGTGAC-3' |
| SEQ ID NO. 100 | GLY3 | 5'-TACCCAGCAGCGGGAGCTCTGTTGCTCCCGAACGCAGGGCAC-3' |
| SEQ ID NO. 101 | GLY4 | 5'-TGTCGTGGTGGGGACGGAGGCCTGCCTAGCTGCGAGCGTGGG-3' |
| SEQ ID NO. 102 | GLY5 | 5'-CGTTATGTGGCCCGGGTAGATTGAGCACTGGCAGTCCTGCACCGTCTC-3' |
| SEQ ID NO. 103 | GLY6 | 5'-CAGGGCCGTTGTAGGCCTCCACTGCATCATCATATCCCAAGC-3' |
| SEQ ID NO. 104 | OVR1 | 5'-CCGGAATGTACCATGTCACGAACGAC-3' |
| SEQ ID NO. 105 | OVR2 | 5'-GCTCCATTGTGTATGAGGCAGCGG-3' |
| SEQ ID NO. 106 | OVR3 | 5'-GAGCTCCCGCTGCTGGGTAGCGC-3' |
| SEQ ID NO, 107 | OVR4 | 5'-CCTCCGTCCCCACCACGACAATACG-3' |
| SEQ ID NO. 108 | OVR5 | 5'-CTACCCGGGCCACATAACGGGTCACCG-3' |
| SEQ ID NO. 109 | OVR6 | 5'-GGAGGCCTACAACGGCCCTGGTGG-3' |
| SEQ ID NO. 110 | GPT-2 | 5'-TTCTATCGATTAAATAGAATTC -3' |
| SEQ ID NO. 111 | TK$_n$-2 | 5'-GCCATACGCTCACAGCCGATCCC-3' | nucleotides underlined represent additional restriction site
nucleotides in bold represent mutations with respect to the original HCCI10A sequence

TABLE 8

Analysis of E1 glycosylation mutants by ELISA

SERUM

| | 1 | 2 | 3 | 4 | 5 | 6 | 7 | 8 | 9 | 10 | 11 |
|---|---|---|---|---|---|---|---|---|---|---|---|
| SNGiLY1 | 1.802462 | 2.120971 | 1.403871 | 1.205597 | 2.120191 | 2.866913 | 1.950345 | 1.866183 | 1.730193 | 2.468162 | 1.220654 |
| SNGiLY2 | 2.400795 | 1.76818 | 2.325495 | 2.639308 | 2.459019 | 5.043993 | 2.146302 | 1.595477 | 1.688973 | 2.482212 | 1.467582 |
| SNGiLY3 | 1.642718 | 1.715477 | 2.261646 | 2.354748 | 1.591818 | 4.833742 | 1.96692 | 1.482099 | 1.602222 | 2.191558 | 1.464216 |

TABLE 8-continued

Analysis of E1 glycosylation mutants by ELISA

| | | | | | | | | | | | |
|---|---|---|---|---|---|---|---|---|---|---|---|
| SNGiLY4 | 2.578154 | 3.824038 | 3.874605 | 1.499387 | 3.15 | 4.71302 | 4.198751 | 3.959542 | 3.710507 | 5.170841 | 4.250784 |
| SNGiLY5 | 2.482051 | 1.793761 | 2.409344 | 2.627358 | 1.715311 | 4.964765 | 2.13912 | 1.576336 | 1.708937 | 3.021807 | 1.562092 |
| SNGiLY6 | 2.031487 | 1.495737 | 2.131613 | 2.527925 | 2.494833 | 4.784027 | 2.02069 | 1.496489 | 1.704976 | 2.677757 | 1.529608 |
| SNE1 | 2.828205 | 2.227036 | 2.512792 | 2.790881 | 3.131579 | 4.869128 | 2.287753 | 1.954198 | 1.805556 | 2.616822 | 1.55719 |

| | 12 | 13 | 14 | 15 | 16 | 17 | 18 | 19 | 20 | 21 | 22 |
|---|---|---|---|---|---|---|---|---|---|---|---|
| SNGiLY1 | 1.629403 | 5.685561 | 3.233604 | 3.763498 | 1.985105 | 2.317721 | 6.675179 | 1.93476 | 2.47171 | 4.378633 | 1.188740 |
| SNGiLY2 | 2.070524 | 7.556682 | 2.567613 | 3.621928 | 3.055649 | 2.933792 | 7.65433 | 2.127712 | 2.921288 | 4.680101 | 1.150781 |
| SNGiLY3 | 1.721164 | 7.930538 | 2.763055 | 3.016099 | 2.945628 | 2.515305 | 5.775357 | 1.980185 | 2.557384 | 4.268633 | 0.97767 |
| SNGiLY4 | 3.955153 | 8.176816 | 6.561122 | 5.707668 | 5.684498 | 5.604813 | 6.4125 | 3.813321 | 3.002535 | 4.293038 | 2.393011 |
| SNGiLY5 | 2.07278 | 8.883408 | 2.940334 | 3.125561 | 3.338912 | 2.654224 | 5.424107 | 2.442804 | 3.126761 | 4.64557 | 1.153656 |
| SNGiLY6 | 1.744221 | 8.005561 | 2.499952 | 2.621704 | 2.572385 | 2.363301 | 5.194107 | 1.506716 | 2.665433 | 2.781063 | 1.280743 |
| SNE1 | 2.593886 | 8.825112 | 3.183771 | 3.067265 | 3.280335 | 2.980354 | 7.191964 | 2.771218 | 3.678068 | 5.35443 | 1.167286 |

| | 23 | 24 | Sum S/N | Average S/N |
|---|---|---|---|---|
| SNGiLY1 | 2.158889 | 1.706992 | 59.88534 | 2.495223 |
| SNGiLY2 | 1.661914 | 1.632785 | 69.65243 | 2.902185 |
| SNGiLY3 | 1.336775 | 1.20376 | 62.09872 | 2.587447 |
| SNGiLY4 | 3.68213 | 2.481585 | 102.6978 | 4.279076 |
| SNGiLY5 | 1.817901 | 1.638211 | 69.26511 | 2.886046 |
| SNGiLY6 | 1.475062 | 1.716423 | 61.32181 | 2.555075 |
| SNE1 | 2.083333 | 1.78252 | 76.54068 | 3.189195 |

SERUM

| | 1 | 2 | 3 | 4 | 5 | 6 | 7 | 8 | 9 | 10 | 11 |
|---|---|---|---|---|---|---|---|---|---|---|---|
| GLY1/E1 | 0.637316 | 0.952374 | 0.55869 | 0.431977 | 0.677036 | 0.588794 | 0.852516 | 0.954961 | 0.958261 | 0.94319 | 0.783882 |
| GLY2/E1 | 0.848876 | 0.793961 | 0.925463 | 0.94569 | 0.785233 | 1.035913 | 0.93817 | 0.816436 | 0.935431 | 0.94856 | 0.942455 |
| GLY3/E1 | 0.580834 | 0.770296 | 0.900053 | 0.84373 | 0.508312 | 0.992733 | 0.859761 | 0.758418 | 0.887385 | 0.837488 | 0.940294 |
| GLY4/E1 | 0.911587 | 1.717097 | 1.541952 | 0.537245 | 1.005882 | 0.967939 | 1.835317 | 2.026172 | 2.05505 | 1.976 | 2.72978 |
| GLY5/E1 | 0.877607 | 0.805447 | 0.958831 | 0.941408 | 0.547746 | 1.019642 | 0.935031 | 0.806641 | 0.946488 | 1.154762 | 1.003148 |
| GLY6/E1 | 0.718296 | 0.671626 | 0.848305 | 0.90578 | 0.796669 | 0.982522 | 0.883264 | 0.765781 | 0.944294 | 1.023286 | 0.982288 |

| | 12 | 13 | 14 | 15 | 16 | 17 | 18 | 19 | 20 | 21 | 22 |
|---|---|---|---|---|---|---|---|---|---|---|---|
| GLY1/E1 | 0.628171 | 0.644248 | 1.015652 | 1.226988 | 0.605153 | 0.777666 | 0.928144 | 0.698162 | 0.672013 | 0.817759 | 1.018386 |
| GLY2/E1 | 0.798232 | 0.85627 | 0.806469 | 1.180833 | 0.931505 | 0.984377 | 1.064289 | 0.76779 | 0.794245 | 0.874061 | 0.98586 |
| GLY3/E1 | 0.663547 | 0.898633 | 0.867856 | 0.983319 | 0.897966 | 0.843962 | 0.803029 | 0.714554 | 0.695306 | 0.797215 | 0.837558 |
| GLY4/E1 | 1.524798 | 0.92654 | 2.060802 | 1.860833 | 1.732902 | 1.880587 | 0.89162 | 1.376045 | 0.816335 | 0.801773 | 2.050064 |
| GLY5/E1 | 0.799102 | 1.006606 | 0.923538 | 1.019006 | 1.017857 | 0.890574 | 0.75419 | 0.881491 | 0.850109 | 0.867612 | 0.988323 |
| GLY6/E1 | 0.672435 | 0.907134 | 0.785217 | 0.854737 | 0.784184 | 0.79296 | 0.72221 | 0.543702 | 0.724683 | 0.519395 | 1.097197 |

| | 23 | 24 | Sum E1/GLY# | Average E1/GLY# |
|---|---|---|---|---|
| GLY1/E1 | 1.036267 | 0.957628 | 19.36524 | 0.806885 |
| GLY2/E1 | 0.797719 | 0.915998 | 21.67384 | 0.903077 |
| GLY3/E1 | 0.641652 | 0.675314 | 19.19921 | 0.799967 |
| GLY4/E1 | 1.767422 | 1.392178 | 36.38592 | 1.51608 |
| GLY5/E1 | 0.872593 | 0.919042 | 21.78679 | 0.907783 |
| GLY6/E1 | 0.70803 | 0.962919 | 19.59691 | 0.816538 |

REFERENCES

Bailey, J. and Cole, R. (1959) J. Biol. Chem. 234, 1733–1739.
Ballou, L., Hitzeman, R., Lewis, M. & Ballou, C. (1991) PNAS 88, 3209–3212.
Benesch, R., Benesch, R. E., Gutcho, M. & Lanfer, L. (1956) Science 123, 981.
Cavins, J. & Friedman. (1970) Anal. Biochem. 35, 489.
Cleland, W. (1964) Biochemistry 3, 480
Creighton, E. (1988) Biossays 8, 57
Darbre, A., John Wiley & Sons Ltd. (1987) Practical Protein Chemistry—A Handbook.
Darbre, A., John Wiley & Sons Ltd. (1987) Practical Proteinchemistry p. 69–79.
Doms et al, (1993), Virology 193, 545–562.
Ellman, G. (1959) Arch. Biochem. Biohys. 82, 70.
Falkner, F. & Moss, B. (1988) J. Virol. 62, 1849–1854.
Friedman, M. & Krull, (1969) Biochem. Biophys. Res. Commun. 37, 630.
Gallagher J. (1988) J. Cell Biol. 107, 2059–2073.
Glazer, A., Delange, R., Sigman, D. (1975) North Holland publishing company.
Elsevier, Biomedical. Part: Modification of protein (p. 116).
Graham, F. & van der Eb, A. (1973) Virology 52, 456–467.
Grakoui et al. (1993) Journal of Virology 67:1385–1395.
Grassetti, D. & Murray. J. (1969) Analyt. Chim. Acta. 46, 139.
Grassetti, D. & Murray, J. (1967) Arch. Biochem Biophys. 119, 41.
Helenius, Mol. Biol. Cell (1994), 5: 253–265.
Hijikata, M., Kato, N., Ootsuyama, Y., Nakagawa, M. & Shimotohno, K. (1991) Proc. Natl. Acad. Sci. U.S.A. 88(13):5537–51.

Hochuli, E., Bannwarth, W., Döbeli, H., Gentz, R., Stüber, D. (1988) Biochemistry 88, 8976.

Hsu. H., Donets, M., Greenberg, H. & Feinstone. S. (1993) Hepatology 17:763–771.

Inoue. Y., Suzuki, R., Matsuura, Y., Harada, S., Chiba. J., Watanabe. Y., Saito, I. & Miyamura, T. (1992) J. Gen. Virol. 73:2151–2154.

Janknecht, R., de Martynoff, G. et al., (1991) Proc. Natl. Acad. Sci. USA 88, 8972–8976.

Kayman (1991) J. Virology 65, 5323–5332.

Kato, N., Oostuyama, Y., Tanaka, T., Nakagawa, M., Muraiso, K., Ohkoshi. S., Hijikata, M., Shimitohno, K. (1992) Virus Res. 22:107–123.

Kniskern, P., Hagopian, A., Burke, P., Schultz, L., Montgomery, D., Hurni, W., Yu Ip, C., Schulman, C., Maigetter, R., Wampler, D., Kubek, D., Sitrin, R., West, D., Ellis, R., Miller, W. (1994) Vaccine 12:1021–1025.

Kohara, M., Tsukiyama-Kohara, K., Maki, N., Asano, K., Yoshizawa, K., Miki. K., Tanaka, S., Hattori, N., Matsuura, Y., Saito, I., Miyamura, T. & Nomoto, A. (1992) J. Gen. Virol. 73:2313–2318.

Mackett, M., Smith, G. & Moss, B. (1985) In: 'DNA cloning: a practical approach' (Ed. Glover, D.) IRL Press, Oxford.

Mackett, M., & Smith, G. (1986) J. Gen. Virol. 67, 2067–2082.

Mackett, M., Smith, G. & Moss, B. (1984) J. Virol. 49, 857–861.

Mackett, M., Smith, G. & Moss, B. (1984) Proc. Natl. Acad. Sci. USA 79, 7415–7419.

Means, G. (1971) Holden Day, Inc.

Means, G. & Feeney, R. (1971) Holden Day p. 105 & p. 217.

Mita, E., Hayashi, N., Ueda. K., Kasahara, A., Fusamoto, H., Takamizawa. A., Matsubara, K., Okayama, H. & Kamada T. (1992) Biochem. Biophys. Res. Comm. 183:925–930.

Moore, S. (1963) J. Biol. Chem. 238, 235–237.

Okamoto, H., Okada, S., Sugiyama, Y., Yotsumoto, S., Tanaka, T., Yoshizawa, H., Tsuda, F., Miyakawa, Y. & Mayumi, M. (1990) Jpn. J. Exp. Med. 60:167–177.

Panicali & Paoletti (1982) Proc. Natl. Acad. Sci. USA 79, 4927–4931.

Piccini, A., Perkus, M. & Paoletti, E. (1987) Meth. Enzymol. 153, 545–563.

Rose (1988) Annu. Rev. Cell Biol. 1988, 4: 257–288;

Ruegg, V. and Rudinger, J. (1977) Methods Enzymol. 47, 111–116.

Shan, S. & Wong (1993) CRC-press p. 30–33.

Spaete, R., Alexander, D., Rugroden, M., Choo, C., Berger, K., Crawford, K., Kuo. C., Leng, S., Lee, C., Ralston, R., et al. (1992) Virology 188(2):819–30.

Skehel, J., (1984) Proc. Natl. Acad. Sci. USA 81, 1179–1783.

Stunnenberg, H., Lange, H., Philipson, L., Miltenburg, R. & van der Vliet, R. (1988) Nucl. Acids Res. 16, 2431–2444.

Stuyver, L., Van Arnhem, W., Wyaeur, A., DeLeys, R. & Maertens, G. (1993a) Biochem. Biophys. Res. Commun. 192, 635–641.

Stuyver, L., Rossau, R., Wyseur, A., Duhamel, M., Vanderborght, B., Van Heuverswyn, H., & Maertens, G. (1993b) J. Gen. Virol. 74, 1093–1102.

Stuyver, L., Van Arnhem, W., Wyseur, A., Hernandez, F., Delaporte, E., Maertens, G. (1994), Proc. Natl. Acad. Sci. USA 91:10134–10138.

Weil, L. & Seibler, S. (1961) Arch. Biochem. Biophys. 95, 470.

Yokosuka, O., Ito, Y., Imazek, F., Ohto, M. & Omata, M. (1992) Biochem. Biophys. Res. Commun. 189:565–571.

Miller P, Yano J, Yano E, Carroll C, Jayaram K, Ts'o P (1979) Biochemistry 18:5134–43.

Nielsen P, Egholm M, Berg R, Buchardt O (1991) Science 254:1497–500.

Nielsen P, Egholm M, Berg R, Buchardt O (1993) Nucleic-Acids-Res. 21:197–200.

Asseline U, Delarue M, Lancelot G, Toulme F, Thuong N (1984) Proc. Natl. Acad. Sci. USA 81:3297–301.

Matsukura M, Shinozuka K, Zon G, Mitsuya H, Reitz M, Cohen J, Broder S (1987) Proc. Natl. Acad. Sci. USA 84:7706–10.

---

What is claimed is:

1. An isolated E2 specific monoclonal antibody, said antibody specifically binding to at least one region within a domain spanning amino acids 416–650 or 655–809 of the hepatitis C virus polyprotein.

2. An isolated monoclonal antibody binds to the same epitope as the E2 specific monoclonal antibody according to claim 1.

3. The monoclonal antibody according to claim 1 or 2 which has been produced from a mammal immunized with a composition comprising purified recombinant HCV single or specific oligomeric recombinant E2 envelope proteins.

4. The monoclonal antibody according to claim 3 wherein said recombinant HCV E2 envelope proteins are produced by a recombinant mammalian cell.

5. The monoclonal antibody of claim 4 wherein said mammalian cell is infected with recombinant vaccinia virus carrying DNA for expressing said HCV E2 envelope proteins.

6. The monoclonal antibody according to claim 3 wherein said recombinant HCV E2 envelope proteins are produced by a recombinant yeast cell.

7. The monoclonal antibody according to claim 3 wherein said recombinant HCV E2 envelope proteins are the expression product of at least one of the following recombinant vectors:

a) a recombinant vector comprising a vector sequence, a prokaryotic, eukaryotic or viral promoter sequence followed by a nucleotide sequence encoding said single or specific oligomeric E2 protein;

b) a recombinant vector according to (a), with said nucleotide sequence being characterized further in that in encodes a single HCV E2 protein starting in the region between amino acid positions 290 and 406 and ending in the region between amino acid positions 600 and 820;

c) a recombinant vector according to (b), with said nucleotide sequence being characterized further in that it ends at any of amino acid positions 623, 650, 661, 673, 710, 715, 720, 746 or 809;

d) a recombinant vector according to any one of (b)–(c), said nucleotide sequence further comprising a 5'-terminal ATG codon and a 3'-terminal stop codon; and e) a recombinant vector according to any one of (b)–(d) further comprising a factor Xa cleavage site and/or 3 to 10 histidine codons positioned 3'-terminally to said nucleotide sequence.

8. An isolated antibody of claim 3 which is an E2 specific monoclonal antibody.

9. The isolated protein of claim 3 wherein said E2 protein is at least 90% pure.

10. The isolated protein of claim 3 wherein said E2 protein is at least 95% pure.

11. The isolated protein of claim 3 wherein said E2 protein is at least 97% pure.

12. The isolated antibody of claim 3 wherein said E2 protein is at least 97% pure.

13. The isolated antibody of claim 3 wherein said E2 protein is at least 99% pure.

14. The monoclonal antibody according to claim 1 or 2 which has been produced from a mammal immunized with a composition comprising at least one purified recombinant HCV single or specific oligomeric recombinant E2 envelope protein.

15. Kit for determining the presence of HCV antigens present in a biological sample, comprising:
    at least one E2 specific monoclonal antibody according to claim 1 or 2,
    a buffer or components necessary for producing the buffer enabling binding reaction between these antibodies and the HCV antigens present in said biological sample,
    a means for detecting the immune complexes formed in the preceding binding reaction.

16. The isolated E2 specific monoclonal antibody secreted by the hybridoma cell line deposited Dec. 3, 1998 with the European Collection or Cell Cultures and assigned the accession number 98031215 or a hybridoma cell line selected from deposit accession numbers DSM ACC 2616 or DSM ACC 2615, each of which were deposited Sep. 10, 2003 with DSMZ.

17. An isolated monoclonal antibody which binds to the same epitope as the E2 specific monoclonal antibody of claim 16.

18. An isolated E2 specific monoclonal antibody which specifically binds to a region in the E2 domain spanning an amino acid segment selected from the group consisting of 409–428 (SEQ ID NO:73), 427–446 (SEQ ID NO: 74), 439–458 (SEQ ID NO:75), 451–470 (SEQ ID NO:76), 463–482 (SEQ ID NO:77), 478–494 (SEQ ID NO:78), 487–506 (SEQ ID NO:79), 499–518 (SEQ ID NO:80), 511–530 (SEQ ID NO:81), 523–542 (SEQ ID NO:82), 547–566 (SEQ ID NO:83), 559–578 (SEQ ID NO: 84), 571–590 (SEQ ID NO:85), 583–602 (SEQ ID NO:86), 595–614 (SEQ ID NO:87), 607–626 (SEQ ID NO:88), 619–638 (SEQ ID NO:89), 631–650 (SEQ ID NO:90) and 655–674 (SEQ ID NO:92).

* * * * *

SEQUENCE LISTING (1) GENERAL INFORMATION:

(iii) NUMBER OF SEQUENCES: 111

(2) INFORMATION FOR SEQ ID NO: 1:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1:

GGCATGCAAG CTTAATTAAT T                   21

(2) INFORMATION FOR SEQ ID NO: 2:

(i) SEQUENCE CHARACTERISTICS:
    (A) LENGTH: 68 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 2:

```
CCGGGGAGGC CTGCACGTGA TCGAGGGCAG ACACCATCAC CACCATCACT AATAGTTAAT    60

TAACTGCA                                                            68
```

(2) INFORMATION FOR SEQ ID NO: 3:

(i) SEQUENCE CHARACTERISTICS:
    (A) LENGTH: 642 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (ix) FEATURE:
    (A) NAME/KEY: CDS
    (B) LOCATION: 1..639

(ix) FEATURE:
    (A) NAME/KEY: mat_peptide
    (B) LOCATION: 1..636

(xi) SEQUENCE DESCRIPTION: SEQ ID NO: 3:

```
ATG CCC GGT TGC TCT TTC TCT ATC TTC CTC TTG GCT TTA CTG TCC TGT    48
Met Pro Gly Cys Ser Phe Ser Ile Phe Leu Leu Ala Leu Leu Ser Cys
 1               5                  10                  15

CTG ACC ATT CCA GCT TCC GCT TAT GAG GTG CGC AAC GTG TCC GGG ATG    96
Leu Thr Ile Pro Ala Ser Ala Tyr Glu Val Arg Asn Val Ser Gly Met
             20                  25                  30

TAC CAT GTC ACG AAC GAC TGC TCC AAC TCA AGC ATT GTG TAT GAG GCA   144
Tyr His Val Thr Asn Asp Cys Ser Asn Ser Ser Ile Val Tyr Glu Ala
         35                  40                  45

GCG GAC ATG ATC ATG CAC ACC CCC GGG TGC GTG CCC TGC GTT CGG GAG   192
Ala Asp Met Ile Met His Thr Pro Gly Cys Val Pro Cys Val Arg Glu
     50                  55                  60

AAC AAC TCT TCC CGC TGC TGG GTA GCG CTC ACC CCC ACG CTC GCA GCT   240
Asn Asn Ser Ser Arg Cys Trp Val Ala Leu Thr Pro Thr Leu Ala Ala
 65                  70                  75                  80

AGG AAC GCC AGC GTC CCC ACC ACG ACA ATA CGA CGC CAC GTC GAT TTG   288
Arg Asn Ala Ser Val Pro Thr Thr Thr Ile Arg Arg His Val Asp Leu
                 85                  90                  95

CTC GTT GGG GCG GCT GCT CTC TGT TCC GCT ATG TAC GTG GGG GAT CTC   336
Leu Val Gly Ala Ala Ala Leu Cys Ser Ala Met Tyr Val Gly Asp Leu
            100                 105                 110

TGC GGA TCT GTC TTC CTC GTC TCC CAG CTG TTC ACC ATC TCG CCT CGC   384
Cys Gly Ser Val Phe Leu Val Ser Gln Leu Phe Thr Ile Ser Pro Arg
        115                 120                 125

CGG CAT GAG ACG GTG CAG GAC TGC AAT TGC TCA ATC TAT CCC GGC CAC   432
Arg His Glu Thr Val Gln Asp Cys Asn Cys Ser Ile Tyr Pro Gly His
    130                 135                 140
```

```
ATA ACA GGT CAC CGT ATG GCT TGG GAT ATG ATG ATG AAC TGG TCG CCT        480
Ile Thr Gly His Arg Met Ala Trp Asp Met Met Met Asn Trp Ser Pro
145                 150                 155                 160

ACA ACG GCC CTG GTG GTA TCG CAG CTG CTC CGG ATC CCA CAA GCT GTC        528
Thr Thr Ala Leu Val Val Ser Gln Leu Leu Arg Ile Pro Gln Ala Val
            165                 170                 175

GTG GAC ATG GTG GCG GGG GCC CAT TGG GGA GTC CTG GCG GGC CTC GCC        576
Val Asp Met Val Ala Gly Ala His Trp Gly Val Leu Ala Gly Leu Ala
        180                 185                 190

TAC TAT TCC ATG GTG GGG AAC TGG GCT AAG GTT TTG ATT GTG ATG CTA        624
Tyr Tyr Ser Met Val Gly Asn Trp Ala Lys Val Leu Ile Val Met Leu
        195                 200                 205

CTC TTT GCT CTC TAATAG                                                 642
Leu Phe Ala Leu
    210
```

(2) INFORMATION FOR SEQ ID NO: 4:

(i) SEQUENCE CHARACTERISTICS:
        (A) LENGTH: 212 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Pro Gly Cys Ser Phe Ser Ile Phe Leu Leu Ala Leu Leu Ser Cys
  1               5                  10                  15

Leu Thr Ile Pro Ala Ser Ala Tyr Glu Val Arg Asn Val Ser Gly Met
             20                  25                  30

Tyr His Val Thr Asn Asp Cys Ser Asn Ser Ser Ile Val Tyr Glu Ala
         35                  40                  45

Ala Asp Met Ile Met His Thr Pro Gly Cys Val Pro Cys Val Arg Glu
     50                  55                  60

Asn Asn Ser Ser Arg Cys Trp Val Ala Leu Thr Pro Thr Leu Ala Ala
 65                  70                  75                  80

Arg Asn Ala Ser Val Pro Thr Thr Thr Ile Arg Arg His Val Asp Leu
                 85                  90                  95

Leu Val Gly Ala Ala Ala Leu Cys Ser Ala Met Tyr Val Gly Asp Leu
            100                 105                 110

Cys Gly Ser Val Phe Leu Val Ser Gln Leu Phe Thr Ile Ser Pro Arg
        115                 120                 125

Arg His Glu Thr Val Gln Asp Cys Asn Cys Ser Ile Tyr Pro Gly His
    130                 135                 140

Ile Thr Gly His Arg Met Ala Trp Asp Met Met Met Asn Trp Ser Pro
145                 150                 155                 160

Thr Thr Ala Leu Val Val Ser Gln Leu Leu Arg Ile Pro Gln Ala Val
            165                 170                 175

Val Asp Met Val Ala Gly Ala His Trp Gly Val Leu Ala Gly Leu Ala
        180                 185                 190

Tyr Tyr Ser Met Val Gly Asn Trp Ala Lys Val Leu Ile Val Met Leu
        195                 200                 205

Leu Phe Ala Leu
    210
```

(2) INFORMATION FOR SEQ ID NO: 5:

(i) SEQUENCE CHARACTERISTICS:
        (A) LENGTH: 795 base pairs (B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (ix) FEATURE:
(A) NAME/KEY: CDS
(B) LOCATION: 1..792

(ix) FEATURE:
(A) NAME/KEY: mat_peptide
(B) LOCATION: 1..789

(xi) SEQUENCE DESCRIPTION: SEQ ID NO: 5:

| | |
|---|---|
| ATG TTG GGT AAG GTC ATC GAT ACC CTT ACA TGC GGC TTC GCC GAC CTC<br>Met Leu Gly Lys Val Ile Asp Thr Leu Thr Cys Gly Phe Ala Asp Leu<br>1                5                    10                  15 | 48 |
| GTG GGG TAC ATT CCG CTC GTC GGC GCC CCC CTA GGG GGC GCT GCC AGG<br>Val Gly Tyr Ile Pro Leu Val Gly Ala Pro Leu Gly Gly Ala Ala Arg<br>            20                    25                    30 | 96 |
| GCC CTG GCG CAT GGC GTC CGG GTT CTG GAG GAC GGC GTG AAC TAT GCA<br>Ala Leu Ala His Gly Val Arg Val Leu Glu Asp Gly Val Asn Tyr Ala<br>            35                    40                    45 | 144 |
| ACA GGG AAT TTG CCC GGT TGC TCT TTC TCT ATC TTC CTC TTG GCT TTG<br>Thr Gly Asn Leu Pro Gly Cys Ser Phe Ser Ile Phe Leu Leu Ala Leu<br>                50                    55                    60 | 192 |
| CTG TCC TGT CTG ACC GTT CCA GCT TCC GCT TAT GAA GTG CGC AAC GTG<br>Leu Ser Cys Leu Thr Val Pro Ala Ser Ala Tyr Glu Val Arg Asn Val<br>65                    70                    75                    80 | 240 |
| TCC GGG ATG TAC CAT GTC ACG AAC GAC TGC TCC AAC TCA AGC ATT GTG<br>Ser Gly Met Tyr His Val Thr Asn Asp Cys Ser Asn Ser Ser Ile Val<br>                    85                    90                    95 | 288 |
| TAT GAG GCA GCG GAC ATG ATC ATG CAC ACC CCC GGG TGC GTG CCC TGC<br>Tyr Glu Ala Ala Asp Met Ile Met His Thr Pro Gly Cys Val Pro Cys<br>            100                    105                    110 | 336 |
| GTT CGG GAG AAC AAC TCT TCC CGC TGC TGG GTA GCG CTC ACC CCC ACG<br>Val Arg Glu Asn Asn Ser Ser Arg Cys Trp Val Ala Leu Thr Pro Thr<br>            115                    120                    125 | 384 |
| CTC GCA GCT AGG AAC GCC AGC GTC CCC ACC ACG ACA ATA CGA CGC CAC<br>Leu Ala Ala Arg Asn Ala Ser Val Pro Thr Thr Thr Ile Arg Arg His<br>            130                    135                    140 | 432 |
| GTC GAT TTG CTC GTT GGG GCG GCT GCT TTC TGT TCC GCT ATG TAC GTG<br>Val Asp Leu Leu Val Gly Ala Ala Ala Phe Cys Ser Ala Met Tyr Val<br>145                    150                    155                    160 | 480 |
| GGG GAC CTC TGC GGA TCT GTC TTC CTC GTC TCC CAG CTG TTC ACC ATC<br>Gly Asp Leu Cys Gly Ser Val Phe Leu Val Ser Gln Leu Phe Thr Ile<br>                    165                    170                    175 | 528 |
| TCG CCT CGC CGG CAT GAG ACG GTG CAG GAC TGC AAT TGC TCA ATC TAT<br>Ser Pro Arg Arg His Glu Thr Val Gln Asp Cys Asn Cys Ser Ile Tyr<br>            180                    185                    190 | 576 |
| CCC GGC CAC ATA ACG GGT CAC CGT ATG GCT TGG GAT ATG ATG ATG AAC<br>Pro Gly His Ile Thr Gly His Arg Met Ala Trp Asp Met Met Met Asn<br>            195                    200                    205 | 624 |
| TGG TCG CCT ACA ACG GCC CTG GTG GTA TCG CAG CTG CTC CGG ATC CCA<br>Trp Ser Pro Thr Thr Ala Leu Val Val Ser Gln Leu Leu Arg Ile Pro<br>            210                    215                    220 | 672 |
| CAA GCT GTC GTG GAC ATG GTG GCG GGG GCC CAT TGG GGA GTC CTG GCG<br>Gln Ala Val Val Asp Met Val Ala Gly Ala His Trp Gly Val Leu Ala<br>225                    230                    235                    240 | 720 |

```
GGT CTC GCC TAC TAT TCC ATG GTG GGG AAC TGG GCT AAG GTT TTG ATT     768
Gly Leu Ala Tyr Tyr Ser Met Val Gly Asn Trp Ala Lys Val Leu Ile
            245                 250                 255

GTG ATG CTA CTC TTT GCT CCC TAATAG                                  795
Val Met Leu Leu Phe Ala Pro
            260
```

(2) INFORMATION FOR SEQ ID NO: 6:

(i) SEQUENCE CHARACTERISTICS:
        (A) LENGTH: 263 amino acids
        (B) TYPE: amino acid
        (D) TOPOLOGY: linear (ii) MOLECULE TYPE: protein (xi) SEQUENCE DESCRIPTION: SEQ ID NO: 6:

```
Met Leu Gly Lys Val Ile Asp Thr Leu Thr Cys Gly Phe Ala Asp Leu
 1               5                  10                  15

Val Gly Tyr Ile Pro Leu Val Gly Ala Pro Leu Gly Gly Ala Ala Arg
            20                  25                  30

Ala Leu Ala His Gly Val Arg Val Leu Glu Asp Gly Val Asn Tyr Ala
            35                  40                  45

Thr Gly Asn Leu Pro Gly Cys Ser Phe Ser Ile Phe Leu Leu Ala Leu
        50                  55                  60

Leu Ser Cys Leu Thr Val Pro Ala Ser Ala Tyr Glu Val Arg Asn Val
65                  70                  75                  80

Ser Gly Met Tyr His Val Thr Asn Asp Cys Ser Asn Ser Ser Ile Val
                85                  90                  95

Tyr Glu Ala Ala Asp Met Ile Met His Thr Pro Gly Cys Val Pro Cys
            100                 105                 110

Val Arg Glu Asn Asn Ser Ser Arg Cys Trp Val Ala Leu Thr Pro Thr
            115                 120                 125

Leu Ala Ala Arg Asn Ala Ser Val Pro Thr Thr Thr Ile Arg Arg His
        130                 135                 140

Val Asp Leu Leu Val Gly Ala Ala Ala Phe Cys Ser Ala Met Tyr Val
145                 150                 155                 160

Gly Asp Leu Cys Gly Ser Val Phe Leu Val Ser Gln Leu Phe Thr Ile
                165                 170                 175

Ser Pro Arg Arg His Glu Thr Val Gln Asp Cys Asn Cys Ser Ile Tyr
            180                 185                 190

Pro Gly His Ile Thr Gly His Arg Met Ala Trp Asp Met Met Met Asn
            195                 200                 205

Trp Ser Pro Thr Thr Ala Leu Val Val Ser Gln Leu Leu Arg Ile Pro
        210                 215                 220

Gln Ala Val Val Asp Met Val Ala Gly Ala His Trp Gly Val Leu Ala
225                 230                 235                 240

Gly Leu Ala Tyr Tyr Ser Met Val Gly Asn Trp Ala Lys Val Leu Ile
                245                 250                 255

Val Met Leu Leu Phe Ala Pro
            260
```

(2) INFORMATION FOR SEQ ID NO: 7:

(i) SEQUENCE CHARACTERISTICS:
        (A) LENGTH: 633 base pairs
        (B) TYPE: nucleic acid
        (C) STRANDEDNESS: single -continued (D) TOPOLOGY: linear (ii) MOLECULE TYPE: cDNA (iii) HYPOTHETICAL: NO (iv) ANTI-SENSE: NO (ix) FEATURE:
            (A) NAME/KEY: CDS
            (B) LOCATION: 1..630

(ix) FEATURE:
            (A) NAME/KEY: mat_peptide
            (B) LOCATION: 1..627

(xi) SEQUENCE DESCRIPTION: SEQ ID NO: 7:

```
ATG TTG GGT AAG GTC ATC GAT ACC CTT ACG TGC GGC TTC GCC GAC CTC        48
Met Leu Gly Lys Val Ile Asp Thr Leu Thr Cys Gly Phe Ala Asp Leu
 1               5                  10                  15

ATG GGG TAC ATT CCG CTC GTC GGC GCC CCC CTA GGG GGT GCT GCC AGA        96
Met Gly Tyr Ile Pro Leu Val Gly Ala Pro Leu Gly Gly Ala Ala Arg
             20                  25                  30

GCC CTG GCG CAT GGC GTC CGG GTT CTG GAA GAC GGC GTG AAC TAT GCA       144
Ala Leu Ala His Gly Val Arg Val Leu Glu Asp Gly Val Asn Tyr Ala
         35                  40                  45

ACA GGG AAT TTG CCT GGT TGC TCT TTC TCT ATC TTC CTC TTG GCT TTA       192
Thr Gly Asn Leu Pro Gly Cys Ser Phe Ser Ile Phe Leu Leu Ala Leu
 50                  55                  60

CTG TCC TGT CTG ACC ATT CCA GCT TCC GCT TAT GAG GTG CGC AAC GTG       240
Leu Ser Cys Leu Thr Ile Pro Ala Ser Ala Tyr Glu Val Arg Asn Val
 65                  70                  75                  80

TCC GGG ATG TAC CAT GTC ACG AAC GAC TGC TCC AAC TCA AGC ATT GTG       288
Ser Gly Met Tyr His Val Thr Asn Asp Cys Ser Asn Ser Ser Ile Val
                 85                  90                  95

TAT GAG GCA GCG GAC ATG ATC ATG CAC ACC CCC GGG TGC GTG CCC TGC       336
Tyr Glu Ala Ala Asp Met Ile Met His Thr Pro Gly Cys Val Pro Cys
             100                 105                 110

GTT CGG GAG AAC AAC TCT TCC CGC TGC TGG GTA GCG CTC ACC CCC ACG       384
Val Arg Glu Asn Asn Ser Ser Arg Cys Trp Val Ala Leu Thr Pro Thr
         115                 120                 125

CTC GCA GCT AGG AAC GCC AGC GTC CCC ACT ACG ACA ATA CGA CGC CAC       432
Leu Ala Ala Arg Asn Ala Ser Val Pro Thr Thr Thr Ile Arg Arg His
 130                 135                 140

GTC GAT TTG CTC GTT GGG GCG GCT GCT TTC TGT TCC GCT ATG TAC GTG       480
Val Asp Leu Leu Val Gly Ala Ala Ala Phe Cys Ser Ala Met Tyr Val
145                 150                 155                 160

GGG GAT CTC TGC GGA TCT GTC TTC CTC GTC TCC CAG CTG TTC ACC ATC       528
Gly Asp Leu Cys Gly Ser Val Phe Leu Val Ser Gln Leu Phe Thr Ile
                 165                 170                 175

TCG CCT CGC CGG CAT GAG ACG GTG CAG GAC TGC AAT TGC TCA ATC TAT       576
Ser Pro Arg Arg His Glu Thr Val Gln Asp Cys Asn Cys Ser Ile Tyr
             180                 185                 190

CCC GGC CAC ATA ACA GGT CAC CGT ATG GCT TGG GAT ATG ATG ATG AAC       624
Pro Gly His Ile Thr Gly His Arg Met Ala Trp Asp Met Met Met Asn
         195                 200                 205

TGG TAATAG                                                           633
Trp
 210
```

(2) INFORMATION FOR SEQ ID NO: 8:

(i) SEQUENCE CHARACTERISTICS:

(A) LENGTH: 209 amino acids
(B) TYPE: amino acid
(D) TOPOLOGY: linear (ii) MOLECULE TYPE: protein (xi) SEQUENCE DESCRIPTION: SEQ ID NO: 8:

```
Met Leu Gly Lys Val Ile Asp Thr Leu Thr Cys Gly Phe Ala Asp Leu
 1               5                  10                  15

Met Gly Tyr Ile Pro Leu Val Gly Ala Pro Leu Gly Gly Ala Ala Arg
                20                  25                  30

Ala Leu Ala His Gly Val Arg Val Leu Glu Asp Gly Val Asn Tyr Ala
            35                  40                  45

Thr Gly Asn Leu Pro Gly Cys Ser Phe Ser Ile Phe Leu Leu Ala Leu
        50                  55                  60

Leu Ser Cys Leu Thr Ile Pro Ala Ser Ala Tyr Glu Val Arg Asn Val
65                  70                  75                  80

Ser Gly Met Tyr His Val Thr Asn Asp Cys Ser Asn Ser Ser Ile Val
                85                  90                  95

Tyr Glu Ala Ala Asp Met Ile Met His Thr Pro Gly Cys Val Pro Cys
            100                 105                 110

Val Arg Glu Asn Asn Ser Ser Arg Cys Trp Val Ala Leu Thr Pro Thr
        115                 120                 125

Leu Ala Ala Arg Asn Ala Ser Val Pro Thr Thr Thr Ile Arg Arg His
130                 135                 140

Val Asp Leu Leu Val Gly Ala Ala Ala Phe Cys Ser Ala Met Tyr Val
145                 150                 155                 160

Gly Asp Leu Cys Gly Ser Val Phe Leu Val Ser Gln Leu Phe Thr Ile
                165                 170                 175

Ser Pro Arg Arg His Glu Thr Val Gln Asp Cys Asn Cys Ser Ile Tyr
            180                 185                 190

Pro Gly His Ile Thr Gly His Arg Met Ala Trp Asp Met Met Met Asn
        195                 200                 205

Trp
```

(2) INFORMATION FOR SEQ ID NO: 9:

(i) SEQUENCE CHARACTERISTICS:
(A) LENGTH: 483 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (ix) FEATURE:
(A) NAME/KEY: CDS
(B) LOCATION: 1..480

(ix) FEATURE:
(A) NAME/KEY: mat_peptide
(B) LOCATION: 1..477

(xi) SEQUENCE DESCRIPTION: SEQ ID NO: 9:

```
ATG CCC GGT TGC TCT TTC TCT ATC TTC CTC TTG GCC CTG CTG TCC TGT      48
Met Pro Gly Cys Ser Phe Ser Ile Phe Leu Leu Ala Leu Leu Ser Cys
 1               5                  10                  15

CTG ACC ATA CCA GCT TCC GCT TAT GAA GTG CGC AAC GTG TCC GGG GTG      96
```

-continued

```
Leu Thr Ile Pro Ala Ser Ala Tyr Glu Val Arg Asn Val Ser Gly Val
            20                  25                  30

TAC CAT GTC ACG AAC GAC TGC TCC AAC TCA AGC ATA GTG TAT GAG GCA      144
Tyr His Val Thr Asn Asp Cys Ser Asn Ser Ser Ile Val Tyr Glu Ala
            35                  40                  45

GCG GAC ATG ATC ATG CAC ACC CCC GGG TGC GTG CCC TGC GTT CGG GAG      192
Ala Asp Met Ile Met His Thr Pro Gly Cys Val Pro Cys Val Arg Glu
            50                  55                  60

GGC AAC TCC TCC CGT TGC TGG GTG GCG CTC ACT CCC ACG CTC GCG GCC      240
Gly Asn Ser Ser Arg Cys Trp Val Ala Leu Thr Pro Thr Leu Ala Ala
65                  70                  75                  80

AGG AAC GCC AGC GTC CCC ACA ACG ACA ATA CGA CGC CAC GTC GAT TTG      288
Arg Asn Ala Ser Val Pro Thr Thr Thr Ile Arg Arg His Val Asp Leu
                85                  90                  95

CTC GTT GGG GCT GCT GCT TTC TGT TCC GCT ATG TAC GTG GGG GAT CTC      336
Leu Val Gly Ala Ala Ala Phe Cys Ser Ala Met Tyr Val Gly Asp Leu
            100                 105                 110

TGC GGA TCT GTT TTC CTT GTT TCC CAG CTG TTC ACC TTC TCA CCT CGC      384
Cys Gly Ser Val Phe Leu Val Ser Gln Leu Phe Thr Phe Ser Pro Arg
            115                 120                 125

CGG CAT CAA ACA GTA CAG GAC TGC AAC TGC TCA ATC TAT CCC GGC CAT      432
Arg His Gln Thr Val Gln Asp Cys Asn Cys Ser Ile Tyr Pro Gly His
        130                 135                 140

GTA TCA GGT CAC CGC ATG GCT TGG GAT ATG ATG ATG AAC TGG TCC TAAT     483
Val Ser Gly His Arg Met Ala Trp Asp Met Met Met Asn Trp Ser
145                 150                 155                 160
```

(2) INFORMATION FOR SEQ ID NO: 10:

(i) SEQUENCE CHARACTERISTICS:
        (A) LENGTH: 159 amino acids
        (B) TYPE: amino acid
        (D) TOPOLOGY: linear (ii) MOLECULE TYPE: protein (xi) SEQUENCE DESCRIPTION: SEQ ID NO: 10:

```
Met Pro Gly Cys Ser Phe Ser Ile Phe Leu Leu Ala Leu Leu Ser Cys
1               5                   10                  15

Leu Thr Ile Pro Ala Ser Ala Tyr Glu Val Arg Asn Val Ser Gly Val
            20                  25                  30

Tyr His Val Thr Asn Asp Cys Ser Asn Ser Ser Ile Val Tyr Glu Ala
            35                  40                  45

Ala Asp Met Ile Met His Thr Pro Gly Cys Val Pro Cys Val Arg Glu
        50                  55                  60

Gly Asn Ser Ser Arg Cys Trp Val Ala Leu Thr Pro Thr Leu Ala Ala
65                  70                  75                  80

Arg Asn Ala Ser Val Pro Thr Thr Thr Ile Arg Arg His Val Asp Leu
                85                  90                  95

Leu Val Gly Ala Ala Ala Phe Cys Ser Ala Met Tyr Val Gly Asp Leu
            100                 105                 110

Cys Gly Ser Val Phe Leu Val Ser Gln Leu Phe Thr Phe Ser Pro Arg
        115                 120                 125

Arg His Gln Thr Val Gln Asp Cys Asn Cys Ser Ile Tyr Pro Gly His
    130                 135                 140

Val Ser Gly His Arg Met Ala Trp Asp Met Met Met Asn Trp Ser
145                 150                 155
```

(2) INFORMATION FOR SEQ ID NO: 11:

(i) SEQUENCE CHARACTERISTICS:
    (A) LENGTH: 480 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (ix) FEATURE:
    (A) NAME/KEY: CDS
    (B) LOCATION: 1..477

(ix) FEATURE:
    (A) NAME/KEY: mat_peptide
    (B) LOCATION: 1..474

(xi) SEQUENCE DESCRIPTION: SEQ ID NO: 11:

```
ATG TCC GGT TGC TCT TTC TCT ATC TTC CTC TTG GCC CTG CTG TCC TGT      48
Met Ser Gly Cys Ser Phe Ser Ile Phe Leu Leu Ala Leu Leu Ser Cys
 1               5                  10                  15

CTG ACC ATA CCA GCT TCC GCT TAT GAA GTG CGC AAC GTG TCC GGG GTG      96
Leu Thr Ile Pro Ala Ser Ala Tyr Glu Val Arg Asn Val Ser Gly Val
                 20                  25                  30

TAC CAT GTC ACG AAC GAC TGC TCC AAC TCA AGC ATA GTG TAT GAG GCA     144
Tyr His Val Thr Asn Asp Cys Ser Asn Ser Ser Ile Val Tyr Glu Ala
         35                  40                  45

GCG GAC ATG ATC ATG CAC ACC CCC GGG TGC GTG CCC TGC GTT CGG GAG     192
Ala Asp Met Ile Met His Thr Pro Gly Cys Val Pro Cys Val Arg Glu
 50                  55                  60

GGC AAC TCC TCC CGT TGC TGG GTG GCG CTC ACT CCC ACG CTC GCG GCC     240
Gly Asn Ser Ser Arg Cys Trp Val Ala Leu Thr Pro Thr Leu Ala Ala
 65                  70                  75                  80

AGG AAC GCC AGC GTC CCC ACA ACG ACA ATA CGA CGC CAC GTC GAT TTG     288
Arg Asn Ala Ser Val Pro Thr Thr Thr Ile Arg Arg His Val Asp Leu
                 85                  90                  95

CTC GTT GGG GCT GCT GCT TTC TGT TCC GCT ATG TAC GTG GGG GAT CTC     336
Leu Val Gly Ala Ala Ala Phe Cys Ser Ala Met Tyr Val Gly Asp Leu
            100                 105                 110

TGC GGA TCT GTT TTC CTT GTT TCC CAG CTG TTC ACC TTC TCA CCT CGC     384
Cys Gly Ser Val Phe Leu Val Ser Gln Leu Phe Thr Phe Ser Pro Arg
        115                 120                 125

CGG CAT CAA ACA GTA CAG GAC TGC AAC TGC TCA ATC TAT CCC GGC CAT     432
Arg His Gln Thr Val Gln Asp Cys Asn Cys Ser Ile Tyr Pro Gly His
    130                 135                 140

GTA TCA GGT CAC CGC ATG GCT TGG GAT ATG ATG ATG AAC TGG TAATAG      480
Val Ser Gly His Arg Met Ala Trp Asp Met Met Met Asn Trp
145                 150                 155
```

(2) INFORMATION FOR SEQ ID NO: 12:

(i) SEQUENCE CHARACTERISTICS:
        (A) LENGTH: 158 amino acids
        (B) TYPE: amino acid
        (D) TOPOLOGY: linear (ii) MOLECULE TYPE: protein (xi) SEQUENCE DESCRIPTION: SEQ ID NO: 12:

```
Met Ser Gly Cys Ser Phe Ser Ile Phe Leu Leu Ala Leu Leu Ser Cys
 1               5                  10                  15

Leu Thr Ile Pro Ala Ser Ala Tyr Glu Val Arg Asn Val Ser Gly Val
```

```
                  20                  25                  30
Tyr His Val Thr Asn Asp Cys Ser Asn Ser Ser Ile Val Tyr Glu Ala
        35                  40                  45

Ala Asp Met Ile Met His Thr Pro Gly Cys Val Pro Cys Val Arg Glu
 50                  55                  60

Gly Asn Ser Ser Arg Cys Trp Val Ala Leu Thr Pro Thr Leu Ala Ala
 65                  70                  75                  80

Arg Asn Ala Ser Val Pro Thr Thr Thr Ile Arg Arg His Val Asp Leu
                85                  90                  95

Leu Val Gly Ala Ala Phe Cys Ser Ala Met Tyr Val Gly Asp Leu
            100                 105                 110

Cys Gly Ser Val Phe Leu Val Ser Gln Leu Phe Thr Phe Ser Pro Arg
        115                 120                 125

Arg His Gln Thr Val Gln Asp Cys Asn Cys Ser Ile Tyr Pro Gly His
130                 135                 140

Val Ser Gly His Arg Met Ala Trp Asp Met Met Met Asn Trp
145                 150                 155

(2) INFORMATION FOR SEQ ID NO: 13:

(i) SEQUENCE CHARACTERISTICS:
        (A) LENGTH: 636 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..633

(ix) FEATURE:
        (A) NAME/KEY: mat_peptide
        (B) LOCATION: 1..630

(xi) SEQUENCE DESCRIPTION: SEQ ID NO: 13:

ATG CTG GGT AAG GCC ATC GAT ACC CTT ACG TGC GGC TTC GCC GAC CTC      48
Met Leu Gly Lys Ala Ile Asp Thr Leu Thr Cys Gly Phe Ala Asp Leu
 1               5                  10                  15

GTG GGG TAC ATT CCG CTC GTC GGC GCC CCC CTA GGG GGC GCT GCC AGG      96
Val Gly Tyr Ile Pro Leu Val Gly Ala Pro Leu Gly Gly Ala Ala Arg
                20                  25                  30

GCC CTG GCG CAT GGC GTC CGG GTT CTG GAA GAC GGC GTG AAC TAT GCA     144
Ala Leu Ala His Gly Val Arg Val Leu Glu Asp Gly Val Asn Tyr Ala
            35                  40                  45

ACA GGG AAT TTG CCT GGT TGC TCT TTC TCT ATC TTC CTC TTG GCT TTA     192
Thr Gly Asn Leu Pro Gly Cys Ser Phe Ser Ile Phe Leu Leu Ala Leu
 50                  55                  60

CTG TCC TGT CTA ACC ATT CCA GCT TCC GCT TAC GAG GTG CGC AAC GTG     240
Leu Ser Cys Leu Thr Ile Pro Ala Ser Ala Tyr Glu Val Arg Asn Val
 65                  70                  75                  80

TCC GGG ATG TAC CAT GTC ACG AAC GAC TGC TCC AAC TCA AGC ATT GTG     288
Ser Gly Met Tyr His Val Thr Asn Asp Cys Ser Asn Ser Ser Ile Val
                85                  90                  95

TAT GAG GCA GCG GAC ATG ATC ATG CAC ACC CCC GGG TGC GTG CCC TGC     336
Tyr Glu Ala Ala Asp Met Ile Met His Thr Pro Gly Cys Val Pro Cys
            100                 105                 110
```

```
                                                             -continued

GTT CGG GAG AAC AAC TCT TCC CGC TGC TGG GTA GCG CTC ACC CCC ACG        384
Val Arg Glu Asn Asn Ser Ser Arg Cys Trp Val Ala Leu Thr Pro Thr
            115                 120                 125

CTC GCG GCT AGG AAC GCC AGC ATC CCC ACT ACA ACA ATA CGA CGC CAC        432
Leu Ala Ala Arg Asn Ala Ser Ile Pro Thr Thr Thr Ile Arg Arg His
    130                 135                 140

GTC GAT TTG CTC GTT GGG GCG GCT GCT TTC TGT TCC GCT ATG TAC GTG        480
Val Asp Leu Leu Val Gly Ala Ala Ala Phe Cys Ser Ala Met Tyr Val
145                 150                 155                 160

GGG GAT CTC TGC GGA TCT GTC TTC CTC GTC TCC CAG CTG TTC ACC ATC        528
Gly Asp Leu Cys Gly Ser Val Phe Leu Val Ser Gln Leu Phe Thr Ile
                165                 170                 175

TCG CCT CGC CGG CAT GAG ACG GTG CAG GAC TGC AAT TGC TCA ATC TAT        576
Ser Pro Arg Arg His Glu Thr Val Gln Asp Cys Asn Cys Ser Ile Tyr
            180                 185                 190

CCC GGC CAC ATA ACG GGT CAC CGT ATG GCT TGG GAT ATG ATG ATG AAC        624
Pro Gly His Ile Thr Gly His Arg Met Ala Trp Asp Met Met Met Asn
        195                 200                 205

TGG TAC TAATAG                                                          636
Trp Tyr
    210

(2) INFORMATION FOR SEQ ID NO: 14:

(i) SEQUENCE CHARACTERISTICS:
        (A) LENGTH: 210 amino acids
        (B) TYPE: amino acid
        (D) TOPOLOGY: linear (ii) MOLECULE TYPE: protein (xi) SEQUENCE DESCRIPTION: SEQ ID NO: 14:

Met Leu Gly Lys Ala Ile Asp Thr Leu Thr Cys Gly Phe Ala Asp Leu
 1               5                  10                  15

Val Gly Tyr Ile Pro Leu Val Gly Ala Pro Leu Gly Gly Ala Ala Arg
            20                  25                  30

Ala Leu Ala His Gly Val Arg Val Leu Glu Asp Gly Val Asn Tyr Ala
        35                  40                  45

Thr Gly Asn Leu Pro Gly Cys Ser Phe Ser Ile Phe Leu Leu Ala Leu
    50                  55                  60

Leu Ser Cys Leu Thr Ile Pro Ala Ser Ala Tyr Glu Val Arg Asn Val
65                  70                  75                  80

Ser Gly Met Tyr His Val Thr Asn Asp Cys Ser Asn Ser Ser Ile Val
                85                  90                  95

Tyr Glu Ala Ala Asp Met Ile Met His Thr Pro Gly Cys Val Pro Cys
            100                 105                 110

Val Arg Glu Asn Asn Ser Ser Arg Cys Trp Val Ala Leu Thr Pro Thr
        115                 120                 125

Leu Ala Ala Arg Asn Ala Ser Ile Pro Thr Thr Thr Ile Arg Arg His
    130                 135                 140

Val Asp Leu Leu Val Gly Ala Ala Ala Phe Cys Ser Ala Met Tyr Val
145                 150                 155                 160

Gly Asp Leu Cys Gly Ser Val Phe Leu Val Ser Gln Leu Phe Thr Ile
                165                 170                 175

Ser Pro Arg Arg His Glu Thr Val Gln Asp Cys Asn Cys Ser Ile Tyr
            180                 185                 190

Pro Gly His Ile Thr Gly His Arg Met Ala Trp Asp Met Met Met Asn
        195                 200                 205
```

Trp Tyr
    210

(2) INFORMATION FOR SEQ ID NO: 15:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 15:

ATGCCCGGTT GCTCTTTCTC TATCTT                                              26

(2) INFORMATION FOR SEQ ID NO: 16:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 16:

ATGTTGGGTA AGGTCATCGA TACCCT                                              26

(2) INFORMATION FOR SEQ ID NO: 17:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 17:

CTATTAGGAC CAGTTCATCA TCATATCCCA                                          30

(2) INFORMATION FOR SEQ ID NO: 18:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 18:

CTATTACCAG TTCATCATCA TATCCCA                                             27

(2) INFORMATION FOR SEQ ID NO: 19:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 19:

```
ATACGACGCC ACGTCGATTC CCAGCTGTTC ACCATC                                    36
```

(2) INFORMATION FOR SEQ ID NO: 20:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 20:

```
GATGGTGAAC AGCTGGGAAT CGACGTGGCG TCGTAT                                    36
```

(2) INFORMATION FOR SEQ ID NO: 21:

(i) SEQUENCE CHARACTERISTICS:
        (A) LENGTH: 723 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..720

(ix) FEATURE:
        (A) NAME/KEY: mat_peptide
        (B) LOCATION: 1..717

(xi) SEQUENCE DESCRIPTION: SEQ ID NO: 21:

```
ATG TTG GGT AAG GTC ATC GAT ACC CTT ACA TGC GGC TTC GCC GAC CTC            48
Met Leu Gly Lys Val Ile Asp Thr Leu Thr Cys Gly Phe Ala Asp Leu
 1               5                  10                  15

GTG GGG TAC ATT CCG CTC GTC GGC GCC CCC CTA GGG GGC GCT GCC AGG            96
Val Gly Tyr Ile Pro Leu Val Gly Ala Pro Leu Gly Gly Ala Ala Arg
                20                  25                  30

GCC CTG GCG CAT GGC GTC CGG GTT CTG GAG GAC GGC GTG AAC TAT GCA           144
Ala Leu Ala His Gly Val Arg Val Leu Glu Asp Gly Val Asn Tyr Ala
                35                  40                  45

ACA GGG AAT TTG CCC GGT TGC TCT TTC TCT ATC TTC CTC TTG GCT TTG           192
Thr Gly Asn Leu Pro Gly Cys Ser Phe Ser Ile Phe Leu Leu Ala Leu
        50                  55                  60
```

-continued

```
CTG TCC TGT CTG ACC GTT CCA GCT TCC GCT TAT GAA GTG CGC AAC GTG      240
Leu Ser Cys Leu Thr Val Pro Ala Ser Ala Tyr Glu Val Arg Asn Val
 65                  70                  75                  80

TCC GGG ATG TAC CAT GTC ACG AAC GAC TGC TCC AAC TCA AGC ATT GTG      288
Ser Gly Met Tyr His Val Thr Asn Asp Cys Ser Asn Ser Ser Ile Val
                 85                  90                  95

TAT GAG GCA GCG GAC ATG ATC ATG CAC ACC CCC GGG TGC GTG CCC TGC      336
Tyr Glu Ala Ala Asp Met Ile Met His Thr Pro Gly Cys Val Pro Cys
            100                 105                 110

GTT CGG GAG AAC AAC TCT TCC CGC TGC TGG GTA GCG CTC ACC CCC ACG      384
Val Arg Glu Asn Asn Ser Ser Arg Cys Trp Val Ala Leu Thr Pro Thr
        115                 120                 125

CTC GCA GCT AGG AAC GCC AGC GTC CCC ACC ACG ACA ATA CGA CGC CAC      432
Leu Ala Ala Arg Asn Ala Ser Val Pro Thr Thr Thr Ile Arg Arg His
    130                 135                 140

GTC GAT TCC CAG CTG TTC ACC ATC TCG CCT CGC CGG CAT GAG ACG GTG      480
Val Asp Ser Gln Leu Phe Thr Ile Ser Pro Arg Arg His Glu Thr Val
145                 150                 155                 160

CAG GAC TGC AAT TGC TCA ATC TAT CCC GGC CAC ATA ACG GGT CAC CGT      528
Gln Asp Cys Asn Cys Ser Ile Tyr Pro Gly His Ile Thr Gly His Arg
                165                 170                 175

ATG GCT TGG GAT ATG ATG ATG AAC TGG TCG CCT ACA ACG GCC CTG GTG      576
Met Ala Trp Asp Met Met Met Asn Trp Ser Pro Thr Thr Ala Leu Val
            180                 185                 190

GTA TCG CAG CTG CTC CGG ATC CCA CAA GCT GTC GTG GAC ATG GTG GCG      624
Val Ser Gln Leu Leu Arg Ile Pro Gln Ala Val Val Asp Met Val Ala
        195                 200                 205

GGG GCC CAT TGG GGA GTC CTG GCG GGT CTC GCC TAC TAT TCC ATG GTG      672
Gly Ala His Trp Gly Val Leu Ala Gly Leu Ala Tyr Tyr Ser Met Val
    210                 215                 220

GGG AAC TGG GCT AAG GTT TTG ATT GTG ATG CTA CTC TTT GCT CCC TAAT    723
Gly Asn Trp Ala Lys Val Leu Ile Val Met Leu Leu Phe Ala Pro
225                 230                 235                 240
```

(2) INFORMATION FOR SEQ ID NO: 22:

(i) SEQUENCE CHARACTERISTICS:
        (A) LENGTH: 239 amino acids
        (B) TYPE: amino acid
        (D) TOPOLOGY: linear (ii) MOLECULE TYPE: protein (xi) SEQUENCE DESCRIPTION: SEQ ID NO: 22:

```
Met Leu Gly Lys Val Ile Asp Thr Leu Thr Cys Gly Phe Ala Asp Leu
 1               5                  10                  15

Val Gly Tyr Ile Pro Leu Val Gly Ala Pro Leu Gly Gly Ala Ala Arg
                20                  25                  30

Ala Leu Ala His Gly Val Arg Val Leu Glu Asp Gly Val Asn Tyr Ala
            35                  40                  45

Thr Gly Asn Leu Pro Gly Cys Ser Phe Ser Ile Phe Leu Leu Ala Leu
        50                  55                  60

Leu Ser Cys Leu Thr Val Pro Ala Ser Ala Tyr Glu Val Arg Asn Val
 65                  70                  75                  80

Ser Gly Met Tyr His Val Thr Asn Asp Cys Ser Asn Ser Ser Ile Val
                 85                  90                  95

Tyr Glu Ala Ala Asp Met Ile Met His Thr Pro Gly Cys Val Pro Cys
            100                 105                 110

Val Arg Glu Asn Asn Ser Ser Arg Cys Trp Val Ala Leu Thr Pro Thr
        115                 120                 125
```

```
Leu Ala Ala Arg Asn Ala Ser Val Pro Thr Thr Thr Ile Arg Arg His
    130                 135                 140

Val Asp Ser Gln Leu Phe Thr Ile Ser Pro Arg Arg His Glu Thr Val
145                 150                 155                 160

Gln Asp Cys Asn Cys Ser Ile Tyr Pro Gly His Ile Thr Gly His Arg
                165                 170                 175

Met Ala Trp Asp Met Met Met Asn Trp Ser Pro Thr Thr Ala Leu Val
                180                 185                 190

Val Ser Gln Leu Leu Arg Ile Pro Gln Ala Val Val Asp Met Val Ala
            195                 200                 205

Gly Ala His Trp Gly Val Leu Ala Gly Leu Ala Tyr Tyr Ser Met Val
        210                 215                 220

Gly Asn Trp Ala Lys Val Leu Ile Val Met Leu Leu Phe Ala Pro
225                 230                 235
```

(2) INFORMATION FOR SEQ ID NO: 23:

(i) SEQUENCE CHARACTERISTICS:
        (A) LENGTH: 561 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..558

(ix) FEATURE:
        (A) NAME/KEY: mat_peptide
        (B) LOCATION: 1..555

(xi) SEQUENCE DESCRIPTION: SEQ ID NO: 23:

```
ATG TTG GGT AAG GTC ATC GAT ACC CTT ACA TGC GGC TTC GCC GAC CTC      48
Met Leu Gly Lys Val Ile Asp Thr Leu Thr Cys Gly Phe Ala Asp Leu
 1               5                  10                  15

GTG GGG TAC ATT CCG CTC GTC GGC GCC CCC CTA GGG GGC GCT GCC AGG      96
Val Gly Tyr Ile Pro Leu Val Gly Ala Pro Leu Gly Gly Ala Ala Arg
                20                  25                  30

GCC CTG GCG CAT GGC GTC CGG GTT CTG GAG GAC GGC GTG AAC TAT GCA     144
Ala Leu Ala His Gly Val Arg Val Leu Glu Asp Gly Val Asn Tyr Ala
            35                  40                  45

ACA GGG AAT TTG CCC GGT TGC TCT TTC TCT ATC TTC CTC TTG GCT TTG     192
Thr Gly Asn Leu Pro Gly Cys Ser Phe Ser Ile Phe Leu Leu Ala Leu
         50                  55                  60

CTG TCC TGT CTG ACC GTT CCA GCT TCC GCT TAT GAA GTG CGC AAC GTG     240
Leu Ser Cys Leu Thr Val Pro Ala Ser Ala Tyr Glu Val Arg Asn Val
 65                  70                  75                  80

TCC GGG ATG TAC CAT GTC ACG AAC GAC TGC TCC AAC TCA AGC ATT GTG     288
Ser Gly Met Tyr His Val Thr Asn Asp Cys Ser Asn Ser Ser Ile Val
                 85                  90                  95

TAT GAG GCA GCG GAC ATG ATC ATG CAC ACC CCC GGG TGC GTG CCC TGC     336
Tyr Glu Ala Ala Asp Met Ile Met His Thr Pro Gly Cys Val Pro Cys
            100                 105                 110

GTT CGG GAG AAC AAC TCT TCC CGC TGC TGG GTA GCG CTC ACC CCC ACG     384
Val Arg Glu Asn Asn Ser Ser Arg Cys Trp Val Ala Leu Thr Pro Thr
        115                 120                 125
```

```
CTC GCA GCT AGG AAC GCC AGC GTC CCC ACC ACG ACA ATA CGA CGC CAC      432
Leu Ala Ala Arg Asn Ala Ser Val Pro Thr Thr Thr Ile Arg Arg His
    130                 135                 140

GTC GAT TCC CAG CTG TTC ACC ATC TCG CCT CGC CGG CAT GAG ACG GTG      480
Val Asp Ser Gln Leu Phe Thr Ile Ser Pro Arg Arg His Glu Thr Val
145                 150                 155                 160

CAG GAC TGC AAT TGC TCA ATC TAT CCC GGC CAC ATA ACG GGT CAC CGT      528
Gln Asp Cys Asn Cys Ser Ile Tyr Pro Gly His Ile Thr Gly His Arg
                165                 170                 175

ATG GCT TGG GAT ATG ATG ATG AAC TGG TAATAG                           561
Met Ala Trp Asp Met Met Met Asn Trp
            180             185

(2) INFORMATION FOR SEQ ID NO: 24:

(i) SEQUENCE CHARACTERISTICS:
        (A) LENGTH: 185 amino acids
        (B) TYPE: amino acid
        (D) TOPOLOGY: linear (ii) MOLECULE TYPE: protein (xi) SEQUENCE DESCRIPTION: SEQ ID NO: 24:

Met Leu Gly Lys Val Ile Asp Thr Leu Thr Cys Gly Phe Ala Asp Leu
1               5                   10                  15

Val Gly Tyr Ile Pro Leu Val Gly Ala Pro Leu Gly Gly Ala Ala Arg
            20                  25                  30

Ala Leu Ala His Gly Val Arg Val Leu Glu Asp Gly Val Asn Tyr Ala
        35                  40                  45

Thr Gly Asn Leu Pro Gly Cys Ser Phe Ser Ile Phe Leu Leu Ala Leu
    50                  55                  60

Leu Ser Cys Leu Thr Val Pro Ala Ser Ala Tyr Glu Val Arg Asn Val
65                  70                  75                  80

Ser Gly Met Tyr His Val Thr Asn Asp Cys Ser Asn Ser Ser Ile Val
            85                  90                  95

Tyr Glu Ala Ala Asp Met Ile Met His Thr Pro Gly Cys Val Pro Cys
            100                 105                 110

Val Arg Glu Asn Asn Ser Ser Arg Cys Trp Val Ala Leu Thr Pro Thr
        115                 120                 125

Leu Ala Ala Arg Asn Ala Ser Val Pro Thr Thr Thr Ile Arg Arg His
    130                 135                 140

Val Asp Ser Gln Leu Phe Thr Ile Ser Pro Arg Arg His Glu Thr Val
145                 150                 155                 160

Gln Asp Cys Asn Cys Ser Ile Tyr Pro Gly His Ile Thr Gly His Arg
                165                 170                 175

Met Ala Trp Asp Met Met Met Asn Trp
            180             185

(2) INFORMATION FOR SEQ ID NO: 25:

(i) SEQUENCE CHARACTERISTICS:
        (A) LENGTH: 606 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO
```

(ix) FEATURE:
        (A) NAME/KEY: CDS
        (B) LOCATION: 1..603

(ix) FEATURE:
        (A) NAME/KEY: mat_peptide
        (B) LOCATION: 1..600

(xi) SEQUENCE DESCRIPTION: SEQ ID NO: 25:

```
ATG TTG GGT AAG GTC ATC GAT ACC CTT ACA TGC GGC TTC GCC GAC CTC      48
Met Leu Gly Lys Val Ile Asp Thr Leu Thr Cys Gly Phe Ala Asp Leu
 1               5                  10                  15

GTG GGG TAC ATT CCG CTC GTC GGC GCC CCC CTA GGG GGC GCT GCC AGG      96
Val Gly Tyr Ile Pro Leu Val Gly Ala Pro Leu Gly Gly Ala Ala Arg
                20                  25                  30

GCC CTG GCG CAT GGC GTC CGG GTT CTG GAG GAC GGC GTG AAC TAT GCA     144
Ala Leu Ala His Gly Val Arg Val Leu Glu Asp Gly Val Asn Tyr Ala
            35                  40                  45

ACA GGG AAT TTG CCC GGT TGC TCT TTC TCT ATC TTC CTC TTG GCT TTG     192
Thr Gly Asn Leu Pro Gly Cys Ser Phe Ser Ile Phe Leu Leu Ala Leu
        50                  55                  60

CTG TCC TGT CTG ACC GTT CCA GCT TCC GCT TAT GAA GTG CGC AAC GTG     240
Leu Ser Cys Leu Thr Val Pro Ala Ser Ala Tyr Glu Val Arg Asn Val
65                  70                  75                  80

TCC GGG ATG TAC CAT GTC ACG AAC GAC TGC TCC AAC TCA AGC ATT GTG     288
Ser Gly Met Tyr His Val Thr Asn Asp Cys Ser Asn Ser Ser Ile Val
                85                  90                  95

TAT GAG GCA GCG GAC ATG ATC ATG CAC ACC CCC GGG TGC GTG CCC TGC     336
Tyr Glu Ala Ala Asp Met Ile Met His Thr Pro Gly Cys Val Pro Cys
            100                 105                 110

GTT CGG GAG AAC AAC TCT TCC CGC TGC TGG GTA GCG CTC ACC CCC ACG     384
Val Arg Glu Asn Asn Ser Ser Arg Cys Trp Val Ala Leu Thr Pro Thr
        115                 120                 125

CTC GCA GCT AGG AAC GCC AGC GTC CCC ACC ACG ACA ATA CGA CGC CAC     432
Leu Ala Ala Arg Asn Ala Ser Val Pro Thr Thr Thr Ile Arg Arg His
    130                 135                 140

GTC GAT TCC CAG CTG TTC ACC ATC TCG CCT CGC CGG CAT GAG ACG GTG     480
Val Asp Ser Gln Leu Phe Thr Ile Ser Pro Arg Arg His Glu Thr Val
145                 150                 155                 160

CAG GAC TGC AAT TGC TCA ATC TAT CCC GGC CAC ATA ACG GGT CAC CGT     528
Gln Asp Cys Asn Cys Ser Ile Tyr Pro Gly His Ile Thr Gly His Arg
                165                 170                 175

ATG GCT TGG GAT ATG ATG ATG AAC TGG TCG CCT ACA ACG GCC CTG GTG     576
Met Ala Trp Asp Met Met Met Asn Trp Ser Pro Thr Thr Ala Leu Val
            180                 185                 190

GTA TCG CAG CTG CTC CGG ATC CTC TAATAG                              606
Val Ser Gln Leu Leu Arg Ile Leu
        195                 200
```

(2) INFORMATION FOR SEQ ID NO: 26:

(i) SEQUENCE CHARACTERISTICS:
        (A) LENGTH: 200 amino acids
        (B) TYPE: amino acid
        (D) TOPOLOGY: linear (ii) MOLECULE TYPE: protein (xi) SEQUENCE DESCRIPTION: SEQ ID NO: 26:

```
Met Leu Gly Lys Val Ile Asp Thr Leu Thr Cys Gly Phe Ala Asp Leu
 1               5                  10                  15

Val Gly Tyr Ile Pro Leu Val Gly Ala Pro Leu Gly Gly Ala Ala Arg
                20                  25                  30
```

```
Ala Leu Ala His Gly Val Arg Val Leu Glu Asp Gly Val Asn Tyr Ala
            35                  40                  45

Thr Gly Asn Leu Pro Gly Cys Ser Phe Ser Ile Phe Leu Leu Ala Leu
 50                  55                  60

Leu Ser Cys Leu Thr Val Pro Ala Ser Ala Tyr Glu Val Arg Asn Val
 65                  70                  75                  80

Ser Gly Met Tyr His Val Thr Asn Asp Cys Ser Asn Ser Ser Ile Val
                 85                  90                  95

Tyr Glu Ala Ala Asp Met Ile Met His Thr Pro Gly Cys Val Pro Cys
            100                 105                 110

Val Arg Glu Asn Asn Ser Ser Arg Cys Trp Val Ala Leu Thr Pro Thr
        115                 120                 125

Leu Ala Ala Arg Asn Ala Ser Val Pro Thr Thr Thr Ile Arg Arg His
    130                 135                 140

Val Asp Ser Gln Leu Phe Thr Ile Ser Pro Arg Arg His Glu Thr Val
145                 150                 155                 160

Gln Asp Cys Asn Cys Ser Ile Tyr Pro Gly His Ile Thr Gly His Arg
                165                 170                 175

Met Ala Trp Asp Met Met Met Asn Trp Ser Pro Thr Thr Ala Leu Val
            180                 185                 190

Val Ser Gln Leu Leu Arg Ile Leu
        195                 200

(2) INFORMATION FOR SEQ ID NO: 27:

(i) SEQUENCE CHARACTERISTICS:
        (A) LENGTH: 636 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
         (A) NAME/KEY: CDS
         (B) LOCATION: 1..633

(ix) FEATURE:
         (A) NAME/KEY: mat_peptide
         (B) LOCATION: 1..630

(xi) SEQUENCE DESCRIPTION: SEQ ID NO: 27:

ATG TTG GGT AAG GTC ATC GAT ACC CTT ACA TGC GGC TTC GCC GAC CTC      48
Met Leu Gly Lys Val Ile Asp Thr Leu Thr Cys Gly Phe Ala Asp Leu
 1               5                  10                  15

GTG GGG TAC ATT CCG CTC GTC GGC GCC CCC CTA GGG GGC GCT GCC AGG      96
Val Gly Tyr Ile Pro Leu Val Gly Ala Pro Leu Gly Gly Ala Ala Arg
                20                  25                  30

GCC CTG GCG CAT GGC GTC CGG GTT CTG GAG GAC GGC GTG AAC TAT GCA     144
Ala Leu Ala His Gly Val Arg Val Leu Glu Asp Gly Val Asn Tyr Ala
            35                  40                  45

ACA GGG AAT TTG CCC GGT TGC TCT TTC TCT ATC TTC CTC TTG GCT TTG     192
Thr Gly Asn Leu Pro Gly Cys Ser Phe Ser Ile Phe Leu Leu Ala Leu
 50                  55                  60

CTG TCC TGT CTG ACC GTT CCA GCT TCC GCT TAT GAA GTG CGC AAC GTG     240
Leu Ser Cys Leu Thr Val Pro Ala Ser Ala Tyr Glu Val Arg Asn Val
 65                  70                  75                  80
```

```
TCC GGG ATG TAC CAT GTC ACG AAC GAC TGC TCC AAC TCA AGC ATT GTG     288
Ser Gly Met Tyr His Val Thr Asn Asp Cys Ser Asn Ser Ser Ile Val
            85                  90                  95

TAT GAG GCA GCG GAC ATG ATC ATG CAC ACC CCC GGG TGC GTG CCC TGC     336
Tyr Glu Ala Ala Asp Met Ile Met His Thr Pro Gly Cys Val Pro Cys
            100                 105                 110

GTT CGG GAG AAC AAC TCT TCC CGC TGC TGG GTA GCG CTC ACC CCC ACG     384
Val Arg Glu Asn Asn Ser Ser Arg Cys Trp Val Ala Leu Thr Pro Thr
            115                 120                 125

CTC GCA GCT AGG AAC GCC AGC GTC CCC ACC ACG ACA ATA CGA CGC CAC     432
Leu Ala Ala Arg Asn Ala Ser Val Pro Thr Thr Thr Ile Arg Arg His
            130                 135                 140

GTC GAT TCC CAG CTG TTC ACC ATC TCG CCT CGC CGG CAT GAG ACG GTG     480
Val Asp Ser Gln Leu Phe Thr Ile Ser Pro Arg Arg His Glu Thr Val
145                 150                 155                 160

CAG GAC TGC AAT TGC TCA ATC TAT CCC GGC CAC ATA ACG GGT CAC CGT     528
Gln Asp Cys Asn Cys Ser Ile Tyr Pro Gly His Ile Thr Gly His Arg
            165                 170                 175

ATG GCT TGG GAT ATG ATG ATG AAC TGG TCG CCT ACA ACG GCC CTG GTG     576
Met Ala Trp Asp Met Met Met Asn Trp Ser Pro Thr Thr Ala Leu Val
            180                 185                 190

GTA TCG CAG CTG CTC CGG ATC GTG ATC GAG GGC AGA CAC CAT CAC CAC     624
Val Ser Gln Leu Leu Arg Ile Val Ile Glu Gly Arg His His His His
            195                 200                 205

CAT CAC TAATAG                                                      636
His His
    210

(2) INFORMATION FOR SEQ ID NO: 28:

(i) SEQUENCE CHARACTERISTICS:
        (A) LENGTH: 210 amino acids
        (B) TYPE: amino acid
        (D) TOPOLOGY: linear (ii) MOLECULE TYPE: protein (xi) SEQUENCE DESCRIPTION: SEQ ID NO: 28:

Met Leu Gly Lys Val Ile Asp Thr Leu Thr Cys Gly Phe Ala Asp Leu
 1               5                  10                  15

Val Gly Tyr Ile Pro Leu Val Gly Ala Pro Leu Gly Gly Ala Ala Arg
            20                  25                  30

Ala Leu Ala His Gly Val Arg Val Leu Glu Asp Gly Val Asn Tyr Ala
        35                  40                  45

Thr Gly Asn Leu Pro Gly Cys Ser Phe Ser Ile Phe Leu Leu Ala Leu
    50                  55                  60

Leu Ser Cys Leu Thr Val Pro Ala Ser Ala Tyr Glu Val Arg Asn Val
65                  70                  75                  80

Ser Gly Met Tyr His Val Thr Asn Asp Cys Ser Asn Ser Ser Ile Val
            85                  90                  95

Tyr Glu Ala Ala Asp Met Ile Met His Thr Pro Gly Cys Val Pro Cys
            100                 105                 110

Val Arg Glu Asn Asn Ser Ser Arg Cys Trp Val Ala Leu Thr Pro Thr
            115                 120                 125

Leu Ala Ala Arg Asn Ala Ser Val Pro Thr Thr Thr Ile Arg Arg His
            130                 135                 140

Val Asp Ser Gln Leu Phe Thr Ile Ser Pro Arg Arg His Glu Thr Val
145                 150                 155                 160

Gln Asp Cys Asn Cys Ser Ile Tyr Pro Gly His Ile Thr Gly His Arg
```

```
                165                 170                 175
Met Ala Trp Asp Met Met Met Asn Trp Ser Pro Thr Thr Ala Leu Val
            180                 185                 190

Val Ser Gln Leu Leu Arg Ile Val Ile Glu Gly Arg His His His His
        195                 200                 205

His His
    210

(2) INFORMATION FOR SEQ ID NO: 29:

(i) SEQUENCE CHARACTERISTICS:
        (A) LENGTH: 630 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..627

(ix) FEATURE:
        (A) NAME/KEY: mat_peptide
        (B) LOCATION: 1..624

(xi) SEQUENCE DESCRIPTION: SEQ ID NO: 29:

ATG GGT AAG GTC ATC GAT ACC CTT ACG TGC GGA TTC GCC GAT CTC ATG         48
Met Gly Lys Val Ile Asp Thr Leu Thr Cys Gly Phe Ala Asp Leu Met
  1               5                  10                  15

GGG TAC ATC CCG CTC GTC GGC GCT CCC GTA GGA GGC GTC GCA AGA GCC         96
Gly Tyr Ile Pro Leu Val Gly Ala Pro Val Gly Gly Val Ala Arg Ala
                 20                  25                  30

CTT GCG CAT GGC GTG AGG GCC CTT GAA GAC GGG ATA AAT TTC GCA ACA        144
Leu Ala His Gly Val Arg Ala Leu Glu Asp Gly Ile Asn Phe Ala Thr
             35                  40                  45

GGG AAT TTG CCC GGT TGC TCC TTT TCT ATT TTC CTT CTC GCT CTG TTC        192
Gly Asn Leu Pro Gly Cys Ser Phe Ser Ile Phe Leu Leu Ala Leu Phe
         50                  55                  60

TCT TGC TTA ATT CAT CCA GCA GCT AGT CTA GAG TGG CGG AAT ACG TCT        240
Ser Cys Leu Ile His Pro Ala Ala Ser Leu Glu Trp Arg Asn Thr Ser
 65                  70                  75                  80

GGC CTC TAT GTC CTT ACC AAC GAC TGT TCC AAT AGC AGT ATT GTG TAC        288
Gly Leu Tyr Val Leu Thr Asn Asp Cys Ser Asn Ser Ser Ile Val Tyr
                 85                  90                  95

GAG GCC GAT GAC GTT ATT CTG CAC ACA CCC GGC TGC ATA CCT TGT GTC        336
Glu Ala Asp Asp Val Ile Leu His Thr Pro Gly Cys Ile Pro Cys Val
             100                 105                 110

CAG GAC GGC AAT ACA TCC ACG TGC TGG ACC CCA GTG ACA CCT ACA GTG        384
Gln Asp Gly Asn Thr Ser Thr Cys Trp Thr Pro Val Thr Pro Thr Val
         115                 120                 125

GCA GTC AAG TAC GTC GGA GCA ACC ACC GCT TCG ATA CGC AGT CAT GTG        432
Ala Val Lys Tyr Val Gly Ala Thr Thr Ala Ser Ile Arg Ser His Val
130                 135                 140

GAC CTA TTA GTG GGC GCG GCC ACG ATG TGC TCT GCG CTC TAC GTG GGT        480
Asp Leu Leu Val Gly Ala Ala Thr Met Cys Ser Ala Leu Tyr Val Gly
145                 150                 155                 160

GAC ATG TGT GGG GCT GTC TTC CTC GTG GGA CAA GCC TTC ACG TTC AGA        528
Asp Met Cys Gly Ala Val Phe Leu Val Gly Gln Ala Phe Thr Phe Arg
                 165                 170                 175
```

```
CCT CGT CGC CAT CAA ACG GTC CAG ACC TGT AAC TGC TCG CTG TAC CCA      576
Pro Arg Arg His Gln Thr Val Gln Thr Cys Asn Cys Ser Leu Tyr Pro
            180                 185                 190

GGC CAT CTT TCA GGA CAT CGA ATG GCT TGG GAT ATG ATG ATG AAC TGG      624
Gly His Leu Ser Gly His Arg Met Ala Trp Asp Met Met Met Asn Trp
            195                 200                 205

TAATAG                                                                630

(2) INFORMATION FOR SEQ ID NO: 30:

(i) SEQUENCE CHARACTERISTICS:
        (A) LENGTH: 208 amino acids
        (B) TYPE: amino acid
        (D) TOPOLOGY: linear (ii) MOLECULE TYPE: protein (xi) SEQUENCE DESCRIPTION: SEQ ID NO: 30:

Met Gly Lys Val Ile Asp Thr Leu Thr Cys Gly Phe Ala Asp Leu Met
 1               5                  10                  15

Gly Tyr Ile Pro Leu Val Gly Ala Pro Val Gly Gly Val Ala Arg Ala
                20                  25                  30

Leu Ala His Gly Val Arg Ala Leu Glu Asp Gly Ile Asn Phe Ala Thr
            35                  40                  45

Gly Asn Leu Pro Gly Cys Ser Phe Ser Ile Phe Leu Leu Ala Leu Phe
         50                 55                  60

Ser Cys Leu Ile His Pro Ala Ala Ser Leu Glu Trp Arg Asn Thr Ser
65                  70                  75                  80

Gly Leu Tyr Val Leu Thr Asn Asp Cys Ser Asn Ser Ser Ile Val Tyr
                85                  90                  95

Glu Ala Asp Asp Val Ile Leu His Thr Pro Gly Cys Ile Pro Cys Val
            100                 105                 110

Gln Asp Gly Asn Thr Ser Thr Cys Trp Thr Pro Val Thr Pro Thr Val
            115                 120                 125

Ala Val Lys Tyr Val Gly Ala Thr Thr Ala Ser Ile Arg Ser His Val
130                 135                 140

Asp Leu Leu Val Gly Ala Ala Thr Met Cys Ser Ala Leu Tyr Val Gly
145                 150                 155                 160

Asp Met Cys Gly Ala Val Phe Leu Val Gly Gln Ala Phe Thr Phe Arg
                165                 170                 175

Pro Arg Arg His Gln Thr Val Gln Thr Cys Asn Cys Ser Leu Tyr Pro
            180                 185                 190

Gly His Leu Ser Gly His Arg Met Ala Trp Asp Met Met Met Asn Trp
            195                 200                 205

(2) INFORMATION FOR SEQ ID NO: 31:

(i) SEQUENCE CHARACTERISTICS:
        (A) LENGTH: 630 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
```

(B) LOCATION: 1..627

(ix) FEATURE:
        (A) NAME/KEY: mat_peptide
        (B) LOCATION: 1..624

(xi) SEQUENCE DESCRIPTION: SEQ ID NO: 31:

| | | | | | | | | | | | | | | | | |
|---|---|---|---|---|---|---|---|---|---|---|---|---|---|---|---|---|
| ATG | GGT | AAG | GTC | ATC | GAT | ACC | CTA | ACG | TGC | GGA | TTC | GCC | GAT | CTC | ATG | 48 |
| Met | Gly | Lys | Val | Ile | Asp | Thr | Leu | Thr | Cys | Gly | Phe | Ala | Asp | Leu | Met | |
| 1 | | | | 5 | | | | | 10 | | | | | 15 | | |
| GGG | TAT | ATC | CCG | CTC | GTA | GGC | GGC | CCC | ATT | GGG | GGC | GTC | GCA | AGG | GCT | 96 |
| Gly | Tyr | Ile | Pro | Leu | Val | Gly | Gly | Pro | Ile | Gly | Gly | Val | Ala | Arg | Ala | |
| | | | 20 | | | | | 25 | | | | | 30 | | | |
| CTC | GCA | CAC | GGT | GTG | AGG | GTC | CTT | GAG | GAC | GGG | GTA | AAC | TAT | GCA | ACA | 144 |
| Leu | Ala | His | Gly | Val | Arg | Val | Leu | Glu | Asp | Gly | Val | Asn | Tyr | Ala | Thr | |
| | | 35 | | | | | 40 | | | | | 45 | | | | |
| GGG | AAT | TTA | CCC | GGT | TGC | TCT | TTC | TCT | ATC | TTT | ATT | CTT | GCT | CTT | CTC | 192 |
| Gly | Asn | Leu | Pro | Gly | Cys | Ser | Phe | Ser | Ile | Phe | Ile | Leu | Ala | Leu | Leu | |
| | 50 | | | | | 55 | | | | | 60 | | | | | |
| TCG | TGT | CTG | ACC | GTT | CCG | GCC | TCT | GCA | GTT | CCC | TAC | CGA | AAT | GCC | TCT | 240 |
| Ser | Cys | Leu | Thr | Val | Pro | Ala | Ser | Ala | Val | Pro | Tyr | Arg | Asn | Ala | Ser | |
| 65 | | | | | 70 | | | | | 75 | | | | | 80 | |
| GGG | ATT | TAT | CAT | GTT | ACC | AAT | GAT | TGC | CCA | AAC | TCT | TCC | ATA | GTC | TAT | 288 |
| Gly | Ile | Tyr | His | Val | Thr | Asn | Asp | Cys | Pro | Asn | Ser | Ser | Ile | Val | Tyr | |
| | | | | 85 | | | | | 90 | | | | | 95 | | |
| GAG | GCA | GAT | AAC | CTG | ATC | CTA | CAC | GCA | CCT | GGT | TGC | GTG | CCT | TGT | GTC | 336 |
| Glu | Ala | Asp | Asn | Leu | Ile | Leu | His | Ala | Pro | Gly | Cys | Val | Pro | Cys | Val | |
| | | | 100 | | | | | 105 | | | | | 110 | | | |
| ATG | ACA | GGT | AAT | GTG | AGT | AGA | TGC | TGG | GTC | CAA | ATT | ACC | CCT | ACA | CTG | 384 |
| Met | Thr | Gly | Asn | Val | Ser | Arg | Cys | Trp | Val | Gln | Ile | Thr | Pro | Thr | Leu | |
| | | 115 | | | | | 120 | | | | | 125 | | | | |
| TCA | GCC | CCG | AGC | CTC | GGA | GCA | GTC | ACG | GCT | CCT | CTT | CGG | AGA | GCC | GTT | 432 |
| Ser | Ala | Pro | Ser | Leu | Gly | Ala | Val | Thr | Ala | Pro | Leu | Arg | Arg | Ala | Val | |
| | 130 | | | | | 135 | | | | | 140 | | | | | |
| GAC | TAC | CTA | GCG | GGA | GGG | GCT | GCC | CTC | TGC | TCC | GCG | TTA | TAC | GTA | GGA | 480 |
| Asp | Tyr | Leu | Ala | Gly | Gly | Ala | Ala | Leu | Cys | Ser | Ala | Leu | Tyr | Val | Gly | |
| 145 | | | | | 150 | | | | | 155 | | | | | 160 | |
| GAC | GCG | TGT | GGG | GCA | CTA | TTC | TTG | GTA | GGC | CAA | ATG | TTC | ACC | TAT | AGG | 528 |
| Asp | Ala | Cys | Gly | Ala | Leu | Phe | Leu | Val | Gly | Gln | Met | Phe | Thr | Tyr | Arg | |
| | | | | 165 | | | | | 170 | | | | | 175 | | |
| CCT | CGC | CAG | CAC | GCT | ACG | GTG | CAG | AAC | TGC | AAC | TGT | TCC | ATT | TAC | AGT | 576 |
| Pro | Arg | Gln | His | Ala | Thr | Val | Gln | Asn | Cys | Asn | Cys | Ser | Ile | Tyr | Ser | |
| | | | 180 | | | | | 185 | | | | | 190 | | | |
| GGC | CAT | GTT | ACC | GGC | CAC | CGG | ATG | GCA | TGG | GAT | ATG | ATG | ATG | AAC | TGG | 624 |
| Gly | His | Val | Thr | Gly | His | Arg | Met | Ala | Trp | Asp | Met | Met | Met | Asn | Trp | |
| | | 195 | | | | | 200 | | | | | 205 | | | | |

TAATAG                                                                                    630

(2) INFORMATION FOR SEQ ID NO: 32:

(i) SEQUENCE CHARACTERISTICS:
        (A) LENGTH: 208 amino acids
        (B) TYPE: amino acid
        (D) TOPOLOGY: linear (ii) MOLECULE TYPE: protein (xi) SEQUENCE DESCRIPTION: SEQ ID NO: 32:

| | | | | | | | | | | | | | | | |
|---|---|---|---|---|---|---|---|---|---|---|---|---|---|---|---|
| Met | Gly | Lys | Val | Ile | Asp | Thr | Leu | Thr | Cys | Gly | Phe | Ala | Asp | Leu | Met |
| 1 | | | | 5 | | | | | 10 | | | | | 15 | |
| Gly | Tyr | Ile | Pro | Leu | Val | Gly | Gly | Pro | Ile | Gly | Gly | Val | Ala | Arg | Ala |
| | | | 20 | | | | | 25 | | | | | 30 | | |

```
Leu Ala His Gly Val Arg Val Leu Glu Asp Gly Val Asn Tyr Ala Thr
        35                  40                  45

Gly Asn Leu Pro Gly Cys Ser Phe Ser Ile Phe Ile Leu Ala Leu Leu
 50                  55                  60

Ser Cys Leu Thr Val Pro Ala Ser Ala Val Pro Tyr Arg Asn Ala Ser
 65                  70                  75                  80

Gly Ile Tyr His Val Thr Asn Asp Cys Pro Asn Ser Ser Ile Val Tyr
                 85                  90                  95

Glu Ala Asp Asn Leu Ile Leu His Ala Pro Gly Cys Val Pro Cys Val
                100                 105                 110

Met Thr Gly Asn Val Ser Arg Cys Trp Val Gln Ile Thr Pro Thr Leu
            115                 120                 125

Ser Ala Pro Ser Leu Gly Ala Val Thr Ala Pro Leu Arg Arg Ala Val
        130                 135                 140

Asp Tyr Leu Ala Gly Gly Ala Ala Leu Cys Ser Ala Leu Tyr Val Gly
145                 150                 155                 160

Asp Ala Cys Gly Ala Leu Phe Leu Val Gly Gln Met Phe Thr Tyr Arg
                165                 170                 175

Pro Arg Gln His Ala Thr Val Gln Asn Cys Asn Cys Ser Ile Tyr Ser
            180                 185                 190

Gly His Val Thr Gly His Arg Met Ala Trp Asp Met Met Met Asn Trp
        195                 200                 205
```

(2) INFORMATION FOR SEQ ID NO: 33:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 33:

TGGGATATGA TGATGAACTG GTC        23

(2) INFORMATION FOR SEQ ID NO: 34:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 34:

CTATTATGGT GGTAAGCCAC AGAGCAGGAG        30

(2) INFORMATION FOR SEQ ID NO: 35:

(i) SEQUENCE CHARACTERISTICS:
        (A) LENGTH: 1476 base pairs
        (B) TYPE: nucleic acid
        (C) STRANDEDNESS: single (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..1473

(ix) FEATURE:
        (A) NAME/KEY: mat_peptide
        (B) LOCATION: 1..1470

(xi) SEQUENCE DESCRIPTION: SEQ ID NO: 35:

```
TGG GAT ATG ATG ATG AAC TGG TCG CCT ACA ACG GCC CTG GTG GTA TCG        48
Trp Asp Met Met Met Asn Trp Ser Pro Thr Thr Ala Leu Val Val Ser
 1               5                  10                  15

CAG CTG CTC CGG ATC CCA CAA GCT GTC GTG GAC ATG GTG GCG GGG GCC        96
Gln Leu Leu Arg Ile Pro Gln Ala Val Val Asp Met Val Ala Gly Ala
             20                  25                  30

CAT TGG GGA GTC CTG GCG GGC CTC GCC TAC TAT TCC ATG GTG GGG AAC       144
His Trp Gly Val Leu Ala Gly Leu Ala Tyr Tyr Ser Met Val Gly Asn
         35                  40                  45

TGG GCT AAG GTT TTG GTT GTG ATG CTA CTC TTT GCC GGC GTC GAC GGG       192
Trp Ala Lys Val Leu Val Val Met Leu Leu Phe Ala Gly Val Asp Gly
     50                  55                  60

CAT ACC CGC GTG TCA GGA GGG GCA GCA GCC TCC GAT ACC AGG GGC CTT       240
His Thr Arg Val Ser Gly Gly Ala Ala Ala Ser Asp Thr Arg Gly Leu
 65                  70                  75                  80

GTG TCC CTC TTT AGC CCC GGG TCG GCT CAG AAA ATC CAG CTC GTA AAC       288
Val Ser Leu Phe Ser Pro Gly Ser Ala Gln Lys Ile Gln Leu Val Asn
                 85                  90                  95

ACC AAC GGC AGT TGG CAC ATC AAC AGG ACT GCC CTG AAC TGC AAC GAC       336
Thr Asn Gly Ser Trp His Ile Asn Arg Thr Ala Leu Asn Cys Asn Asp
            100                 105                 110

TCC CTC CAA ACA GGG TTC TTT GCC GCA CTA TTC TAC AAA CAC AAA TTC       384
Ser Leu Gln Thr Gly Phe Phe Ala Ala Leu Phe Tyr Lys His Lys Phe
        115                 120                 125

AAC TCG TCT GGA TGC CCA GAG CGC TTG GCC AGC TGT CGC TCC ATC GAC       432
Asn Ser Ser Gly Cys Pro Glu Arg Leu Ala Ser Cys Arg Ser Ile Asp
    130                 135                 140

AAG TTC GCT CAG GGG TGG GGT CCC CTC ACT TAC ACT GAG CCT AAC AGC       480
Lys Phe Ala Gln Gly Trp Gly Pro Leu Thr Tyr Thr Glu Pro Asn Ser
145                 150                 155                 160

TCG GAC CAG AGG CCC TAC TGC TGG CAC TAC GCG CCT CGA CCG TGT GGT       528
Ser Asp Gln Arg Pro Tyr Cys Trp His Tyr Ala Pro Arg Pro Cys Gly
                165                 170                 175

ATT GTA CCC GCG TCT CAG GTG TGC GGT CCA GTG TAT TGC TTC ACC CCG       576
Ile Val Pro Ala Ser Gln Val Cys Gly Pro Val Tyr Cys Phe Thr Pro
            180                 185                 190

AGC CCT GTT GTG GTG GGG ACG ACC GAT CGG TTT GGT GTC CCC ACG TAT       624
Ser Pro Val Val Val Gly Thr Thr Asp Arg Phe Gly Val Pro Thr Tyr
        195                 200                 205

AAC TGG GGG GCG AAC GAC TCG GAT GTG CTG ATT CTC AAC AAC ACG CGG       672
Asn Trp Gly Ala Asn Asp Ser Asp Val Leu Ile Leu Asn Asn Thr Arg
    210                 215                 220

CCG CCG CGA GGC AAC TGG TTC GGC TGT ACA TGG ATG AAT GGC ACT GGG       720
Pro Pro Arg Gly Asn Trp Phe Gly Cys Thr Trp Met Asn Gly Thr Gly
225                 230                 235                 240

TTC ACC AAG ACG TGT GGG GGC CCC CCG TGC AAC ATC GGG GGG GCC GGC       768
```

```
Phe Thr Lys Thr Cys Gly Gly Pro Pro Cys Asn Ile Gly Gly Ala Gly
            245                 250                 255

AAC AAC ACC TTG ACC TGC CCC ACT GAC TGT TTT CGG AAG CAC CCC GAG       816
Asn Asn Thr Leu Thr Cys Pro Thr Asp Cys Phe Arg Lys His Pro Glu
            260                 265                 270

GCC ACC TAC GCC AGA TGC GGT TCT GGG CCC TGG CTG ACA CCT AGG TGT       864
Ala Thr Tyr Ala Arg Cys Gly Ser Gly Pro Trp Leu Thr Pro Arg Cys
            275                 280                 285

ATG GTT CAT TAC CCA TAT AGG CTC TGG CAC TAC CCC TGC ACT GTC AAC       912
Met Val His Tyr Pro Tyr Arg Leu Trp His Tyr Pro Cys Thr Val Asn
            290                 295                 300

TTC ACC ATC TTC AAG GTT AGG ATG TAC GTG GGG GGC GTG GAG CAC AGG       960
Phe Thr Ile Phe Lys Val Arg Met Tyr Val Gly Gly Val Glu His Arg
305                 310                 315                 320

TTC GAA GCC GCA TGC AAT TGG ACT CGA GGA GAG CGT TGT GAC TTG GAG      1008
Phe Glu Ala Ala Cys Asn Trp Thr Arg Gly Glu Arg Cys Asp Leu Glu
                325                 330                 335

GAC AGG GAT AGA TCA GAG CTT AGC CCG CTG CTG CTG TCT ACA ACA GAG      1056
Asp Arg Asp Arg Ser Glu Leu Ser Pro Leu Leu Leu Ser Thr Thr Glu
            340                 345                 350

TGG CAG ATA CTG CCC TGT TCC TTC ACC ACC CTG CCG GCC CTA TCC ACC      1104
Trp Gln Ile Leu Pro Cys Ser Phe Thr Thr Leu Pro Ala Leu Ser Thr
            355                 360                 365

GGC CTG ATC CAC CTC CAT CAG AAC ATC GTG GAC GTG CAA TAC CTG TAC      1152
Gly Leu Ile His Leu His Gln Asn Ile Val Asp Val Gln Tyr Leu Tyr
            370                 375                 380

GGT GTA GGG TCG GCG GTT GTC TCC CTT GTC ATC AAA TGG GAG TAT GTC      1200
Gly Val Gly Ser Ala Val Val Ser Leu Val Ile Lys Trp Glu Tyr Val
385                 390                 395                 400

CTG TTG CTC TTC CTT CTC CTG GCA GAC GCG CGC ATC TGC GCC TGC TTA      1248
Leu Leu Leu Phe Leu Leu Leu Ala Asp Ala Arg Ile Cys Ala Cys Leu
                405                 410                 415

TGG ATG ATG CTG CTG ATA GCT CAA GCT GAG GCC GCC TTA GAG AAC CTG      1296
Trp Met Met Leu Leu Ile Ala Gln Ala Glu Ala Ala Leu Glu Asn Leu
            420                 425                 430

GTG GTC CTC AAT GCG GCG GCC GTG GCC GGG GCG CAT GGC ACT CTT TCC      1344
Val Val Leu Asn Ala Ala Ala Val Ala Gly Ala His Gly Thr Leu Ser
            435                 440                 445

TTC CTT GTG TTC TTC TGT GCT GCC TGG TAC ATC AAG GGC AGG CTG GTC      1392
Phe Leu Val Phe Phe Cys Ala Ala Trp Tyr Ile Lys Gly Arg Leu Val
            450                 455                 460

CCT GGT GCG GCA TAC GCC TTC TAT GGC GTG TGG CCG CTC CTC CTG CTT      1440
Pro Gly Ala Ala Tyr Ala Phe Tyr Gly Val Trp Pro Leu Leu Leu Leu
465                 470                 475                 480

CTG CTG GCC TTA CCA CCA CGA GCT TAT GCC TAGTAA                       1476
Leu Leu Ala Leu Pro Pro Arg Ala Tyr Ala
            485                 490

(2) INFORMATION FOR SEQ ID NO: 36:

(i) SEQUENCE CHARACTERISTICS:
        (A) LENGTH: 490 amino acids
        (B) TYPE: amino acid
        (D) TOPOLOGY: linear (ii) MOLECULE TYPE: protein (xi) SEQUENCE DESCRIPTION: SEQ ID NO: 36:

Trp Asp Met Met Met Asn Trp Ser Pro Thr Thr Ala Leu Val Val Ser
 1               5                  10                  15

Gln Leu Leu Arg Ile Pro Gln Ala Val Val Asp Met Val Ala Gly Ala
```

-continued

```
                 20                  25                  30
His Trp Gly Val Leu Ala Gly Leu Ala Tyr Tyr Ser Met Val Gly Asn
         35                  40                  45

Trp Ala Lys Val Leu Val Val Met Leu Leu Phe Ala Gly Val Asp Gly
     50                  55                  60

His Thr Arg Val Ser Gly Ala Ala Ala Ser Asp Thr Arg Gly Leu
 65              70                  75                      80

Val Ser Leu Phe Ser Pro Gly Ser Ala Gln Lys Ile Gln Leu Val Asn
                 85                  90                  95

Thr Asn Gly Ser Trp His Ile Asn Arg Thr Ala Leu Asn Cys Asn Asp
            100                 105                 110

Ser Leu Gln Thr Gly Phe Phe Ala Ala Leu Phe Tyr Lys His Lys Phe
            115                 120                 125

Asn Ser Ser Gly Cys Pro Glu Arg Leu Ala Ser Cys Arg Ser Ile Asp
            130                 135                 140

Lys Phe Ala Gln Gly Trp Gly Pro Leu Thr Tyr Thr Glu Pro Asn Ser
145                 150                 155                 160

Ser Asp Gln Arg Pro Tyr Cys Trp His Tyr Ala Pro Arg Pro Cys Gly
                165                 170                 175

Ile Val Pro Ala Ser Gln Val Cys Gly Pro Val Tyr Cys Phe Thr Pro
            180                 185                 190

Ser Pro Val Val Gly Thr Thr Asp Arg Phe Gly Val Pro Thr Tyr
        195                 200                 205

Asn Trp Gly Ala Asn Asp Ser Asp Val Leu Ile Leu Asn Asn Thr Arg
210                 215                 220

Pro Pro Arg Gly Asn Trp Phe Gly Cys Thr Trp Met Asn Gly Thr Gly
225                 230                 235                 240

Phe Thr Lys Thr Cys Gly Gly Pro Pro Cys Asn Ile Gly Gly Ala Gly
                245                 250                 255

Asn Asn Thr Leu Thr Cys Pro Thr Asp Cys Phe Arg Lys His Pro Glu
            260                 265                 270

Ala Thr Tyr Ala Arg Cys Gly Ser Gly Pro Trp Leu Thr Pro Arg Cys
        275                 280                 285

Met Val His Tyr Pro Tyr Arg Leu Trp His Tyr Pro Cys Thr Val Asn
        290                 295                 300

Phe Thr Ile Phe Lys Val Arg Met Tyr Val Gly Gly Val Glu His Arg
305                 310                 315                 320

Phe Glu Ala Ala Cys Asn Trp Thr Arg Gly Glu Arg Cys Asp Leu Glu
                325                 330                 335

Asp Arg Asp Arg Ser Glu Leu Ser Pro Leu Leu Leu Ser Thr Thr Glu
            340                 345                 350

Trp Gln Ile Leu Pro Cys Ser Phe Thr Thr Leu Pro Ala Leu Ser Thr
            355                 360                 365

Gly Leu Ile His Leu His Gln Asn Ile Val Asp Val Gln Tyr Leu Tyr
        370                 375                 380

Gly Val Gly Ser Ala Val Val Ser Leu Val Ile Lys Trp Glu Tyr Val
385                 390                 395                 400

Leu Leu Leu Phe Leu Leu Leu Ala Asp Ala Arg Ile Cys Ala Cys Leu
                405                 410                 415

Trp Met Met Leu Leu Ile Ala Gln Ala Glu Ala Ala Leu Glu Asn Leu
            420                 425                 430

Val Val Leu Asn Ala Ala Ala Val Ala Gly Ala His Gly Thr Leu Ser
            435                 440                 445
```

```
Phe Leu Val Phe Phe Cys Ala Ala Trp Tyr Ile Lys Gly Arg Leu Val
    450                 455                 460

Pro Gly Ala Ala Tyr Ala Phe Tyr Gly Val Trp Pro Leu Leu Leu Leu
465                 470                 475                 480

Leu Leu Ala Leu Pro Pro Arg Ala Tyr Ala
            485                 490

(2) INFORMATION FOR SEQ ID NO: 37:

(i) SEQUENCE CHARACTERISTICS:
        (A) LENGTH: 1021 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 2..1018

(ix) FEATURE:
        (A) NAME/KEY: mat_peptide
        (B) LOCATION: 2..1015

(xi) SEQUENCE DESCRIPTION: SEQ ID NO: 37:

G ATC CCA CAA GCT GTC GTG GAC ATG GTG GCG GGG GCC CAT TGG GGA         46
  Ile Pro Gln Ala Val Val Asp Met Val Ala Gly Ala His Trp Gly
  1               5                  10                  15

GTC CTG GCG GGC CTC GCC TAC TAT TCC ATG GTG GGG AAC TGG GCT AAG       94
Val Leu Ala Gly Leu Ala Tyr Tyr Ser Met Val Gly Asn Trp Ala Lys
                20                  25                  30

GTT TTG GTT GTG ATG CTA CTC TTT GCC GGC GTC GAC GGG CAT ACC CGC      142
Val Leu Val Val Met Leu Leu Phe Ala Gly Val Asp Gly His Thr Arg
            35                  40                  45

GTG TCA GGA GGG GCA GCA GCC TCC GAT ACC AGG GGC CTT GTG TCC CTC      190
Val Ser Gly Gly Ala Ala Ala Ser Asp Thr Arg Gly Leu Val Ser Leu
        50                  55                  60

TTT AGC CCC GGG TCG GCT CAG AAA ATC CAG CTC GTA AAC ACC AAC GGC      238
Phe Ser Pro Gly Ser Ala Gln Lys Ile Gln Leu Val Asn Thr Asn Gly
    65                  70                  75

AGT TGG CAC ATC AAC AGG ACT GCC CTG AAC TGC AAC GAC TCC CTC CAA      286
Ser Trp His Ile Asn Arg Thr Ala Leu Asn Cys Asn Asp Ser Leu Gln
80                  85                  90                  95

ACA GGG TTC TTT GCC GCA CTA TTC TAC AAA CAC AAA TTC AAC TCG TCT      334
Thr Gly Phe Phe Ala Ala Leu Phe Tyr Lys His Lys Phe Asn Ser Ser
                100                 105                 110

GGA TGC CCA GAG CGC TTG GCC AGC TGT CGC TCC ATC GAC AAG TTC GCT      382
Gly Cys Pro Glu Arg Leu Ala Ser Cys Arg Ser Ile Asp Lys Phe Ala
            115                 120                 125

CAG GGG TGG GGT CCC CTC ACT TAC ACT GAG CCT AAC AGC TCG GAC CAG      430
Gln Gly Trp Gly Pro Leu Thr Tyr Thr Glu Pro Asn Ser Ser Asp Gln
        130                 135                 140

AGG CCC TAC TGC TGG CAC TAC GCG CCT CGA CCG TGT GGT ATT GTA CCC      478
Arg Pro Tyr Cys Trp His Tyr Ala Pro Arg Pro Cys Gly Ile Val Pro
    145                 150                 155

GCG TCT CAG GTG TGC GGT CCA GTG TAT TGC TTC ACC CCG AGC CCT GTT      526
Ala Ser Gln Val Cys Gly Pro Val Tyr Cys Phe Thr Pro Ser Pro Val
160                 165                 170                 175
```

```
GTG GTG GGG ACG ACC GAT CGG TTT GGT GTC CCC ACG TAT AAC TGG GGG          574
Val Val Gly Thr Thr Asp Arg Phe Gly Val Pro Thr Tyr Asn Trp Gly
                180                 185                 190

GCG AAC GAC TCG GAT GTG CTG ATT CTC AAC AAC ACG CGG CCG CCG CGA          622
Ala Asn Asp Ser Asp Val Leu Ile Leu Asn Asn Thr Arg Pro Pro Arg
                195                 200                 205

GGC AAC TGG TTC GGC TGT ACA TGG ATG AAT GGC ACT GGG TTC ACC AAG          670
Gly Asn Trp Phe Gly Cys Thr Trp Met Asn Gly Thr Gly Phe Thr Lys
                210                 215                 220

ACG TGT GGG GGC CCC CCG TGC AAC ATC GGG GGG GCC GGC AAC AAC ACC          718
Thr Cys Gly Gly Pro Pro Cys Asn Ile Gly Gly Ala Gly Asn Asn Thr
225                 230                 235

TTG ACC TGC CCC ACT GAC TGT TTT CGG AAG CAC CCC GAG GCC ACC TAC          766
Leu Thr Cys Pro Thr Asp Cys Phe Arg Lys His Pro Glu Ala Thr Tyr
240                 245                 250                 255

GCC AGA TGC GGT TCT GGG CCC TGG CTG ACA CCT AGG TGT ATG GTT CAT          814
Ala Arg Cys Gly Ser Gly Pro Trp Leu Thr Pro Arg Cys Met Val His
                260                 265                 270

TAC CCA TAT AGG CTC TGG CAC TAC CCC TGC ACT GTC AAC TTC ACC ATC          862
Tyr Pro Tyr Arg Leu Trp His Tyr Pro Cys Thr Val Asn Phe Thr Ile
                275                 280                 285

TTC AAG GTT AGG ATG TAC GTG GGG GGC GTG GAG CAC AGG TTC GAA GCC          910
Phe Lys Val Arg Met Tyr Val Gly Gly Val Glu His Arg Phe Glu Ala
                290                 295                 300

GCA TGC AAT TGG ACT CGA GGA GAG CGT TGT GAC TTG GAG GAC AGG GAT          958
Ala Cys Asn Trp Thr Arg Gly Glu Arg Cys Asp Leu Glu Asp Arg Asp
305                 310                 315

AGA TCA GAG CTT AGC CCG CTG CTG CTG TCT ACA ACA GAG TGG CAG AGT         1006
Arg Ser Glu Leu Ser Pro Leu Leu Leu Ser Thr Thr Glu Trp Gln Ser
320                 325                 330                 335

GGC AGA GCT TAATTA                                                      1021
Gly Arg Ala (2) INFORMATION FOR SEQ ID NO: 38:

(i) SEQUENCE CHARACTERISTICS:
        (A) LENGTH: 338 amino acids
        (B) TYPE: amino acid
        (D) TOPOLOGY: linear (ii) MOLECULE TYPE: protein (xi) SEQUENCE DESCRIPTION: SEQ ID NO: 38:

Ile Pro Gln Ala Val Val Asp Met Val Ala Gly Ala His Trp Gly Val
  1               5                  10                  15

Leu Ala Gly Leu Ala Tyr Tyr Ser Met Val Gly Asn Trp Ala Lys Val
                 20                  25                  30

Leu Val Val Met Leu Leu Phe Ala Gly Val Asp Gly His Thr Arg Val
             35                  40                  45

Ser Gly Gly Ala Ala Ala Ser Asp Thr Arg Gly Leu Val Ser Leu Phe
         50                  55                  60

Ser Pro Gly Ser Ala Gln Lys Ile Gln Leu Val Asn Thr Asn Gly Ser
 65                  70                  75                  80

Trp His Ile Asn Arg Thr Ala Leu Asn Cys Asn Asp Ser Leu Gln Thr
                 85                  90                  95

Gly Phe Phe Ala Ala Leu Phe Tyr Lys His Lys Phe Asn Ser Ser Gly
                100                 105                 110

Cys Pro Glu Arg Leu Ala Ser Cys Arg Ser Ile Asp Lys Phe Ala Gln
                115                 120                 125
```

-continued

```
Gly Trp Gly Pro Leu Thr Tyr Thr Glu Pro Asn Ser Ser Asp Gln Arg
    130                 135                 140
Pro Tyr Cys Trp His Tyr Ala Pro Arg Pro Cys Gly Ile Val Pro Ala
145                 150                 155                 160
Ser Gln Val Cys Gly Pro Val Tyr Cys Phe Thr Pro Ser Pro Val Val
                165                 170                 175
Val Gly Thr Thr Asp Arg Phe Gly Val Pro Thr Tyr Asn Trp Gly Ala
            180                 185                 190
Asn Asp Ser Asp Val Leu Ile Leu Asn Asn Thr Arg Pro Pro Arg Gly
        195                 200                 205
Asn Trp Phe Gly Cys Thr Trp Met Asn Gly Thr Gly Phe Thr Lys Thr
    210                 215                 220
Cys Gly Gly Pro Pro Cys Asn Ile Gly Gly Ala Gly Asn Asn Thr Leu
225                 230                 235                 240
Thr Cys Pro Thr Asp Cys Phe Arg Lys His Pro Glu Ala Thr Tyr Ala
                245                 250                 255
Arg Cys Gly Ser Gly Pro Trp Leu Thr Pro Arg Cys Met Val His Tyr
            260                 265                 270
Pro Tyr Arg Leu Trp His Tyr Pro Cys Thr Val Asn Phe Thr Ile Phe
        275                 280                 285
Lys Val Arg Met Tyr Val Gly Gly Val Glu His Arg Phe Glu Ala Ala
    290                 295                 300
Cys Asn Trp Thr Arg Gly Glu Arg Cys Asp Leu Glu Asp Arg Asp Arg
305                 310                 315                 320
Ser Glu Leu Ser Pro Leu Leu Leu Ser Thr Thr Glu Trp Gln Ser Gly
                325                 330                 335
Arg Ala
```

(2) INFORMATION FOR SEQ ID NO: 39:

(i) SEQUENCE CHARACTERISTICS:
        (A) LENGTH: 1034 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 2..1032

(ix) FEATURE:
        (A) NAME/KEY: mat_peptide
        (B) LOCATION: 2..1029

(xi) SEQUENCE DESCRIPTION: SEQ ID NO: 39:

```
G ATC CCA CAA GCT GTC GTG GAC ATG GTG GCG GGG GCC CAT TGG GGA         46
  Ile Pro Gln Ala Val Val Asp Met Val Ala Gly Ala His Trp Gly
   1               5                  10                  15

GTC CTG GCG GGC CTC GCC TAC TAT TCC ATG GTG GGG AAC TGG GCT AAG        94
Val Leu Ala Gly Leu Ala Tyr Tyr Ser Met Val Gly Asn Trp Ala Lys
                20                  25                  30

GTT TTG GTT GTG ATG CTA CTC TTT GCC GGC GTC GAC GGG CAT ACC CGC       142
Val Leu Val Val Met Leu Leu Phe Ala Gly Val Asp Gly His Thr Arg
            35                  40                  45
```

```
GTG TCA GGA GGG GCA GCA GCC TCC GAT ACC AGG GGC CTT GTG TCC CTC      190
Val Ser Gly Gly Ala Ala Ala Ser Asp Thr Arg Gly Leu Val Ser Leu
         50                  55                  60

TTT AGC CCC GGG TCG GCT CAG AAA ATC CAG CTC GTA AAC ACC AAC GGC      238
Phe Ser Pro Gly Ser Ala Gln Lys Ile Gln Leu Val Asn Thr Asn Gly
 65                  70                  75

AGT TGG CAC ATC AAC AGG ACT GCC CTG AAC TGC AAC GAC TCC CTC CAA      286
Ser Trp His Ile Asn Arg Thr Ala Leu Asn Cys Asn Asp Ser Leu Gln
 80                  85                  90                  95

ACA GGG TTC TTT GCC GCA CTA TTC TAC AAA CAC AAA TTC AAC TCG TCT      334
Thr Gly Phe Phe Ala Ala Leu Phe Tyr Lys His Lys Phe Asn Ser Ser
                 100                 105                 110

GGA TGC CCA GAG CGC TTG GCC AGC TGT CGC TCC ATC GAC AAG TTC GCT      382
Gly Cys Pro Glu Arg Leu Ala Ser Cys Arg Ser Ile Asp Lys Phe Ala
             115                 120                 125

CAG GGG TGG GGT CCC CTC ACT TAC ACT GAG CCT AAC AGC TCG GAC CAG      430
Gln Gly Trp Gly Pro Leu Thr Tyr Thr Glu Pro Asn Ser Ser Asp Gln
             130                 135                 140

AGG CCC TAC TGC TGG CAC TAC GCG CCT CGA CCG TGT GGT ATT GTA CCC      478
Arg Pro Tyr Cys Trp His Tyr Ala Pro Arg Pro Cys Gly Ile Val Pro
        145                 150                 155

GCG TCT CAG GTG TGC GGT CCA GTG TAT TGC TTC ACC CCG AGC CCT GTT      526
Ala Ser Gln Val Cys Gly Pro Val Tyr Cys Phe Thr Pro Ser Pro Val
160                 165                 170                 175

GTG GTG GGG ACG ACC GAT CGG TTT GGT GTC CCC ACG TAT AAC TGG GGG      574
Val Val Gly Thr Thr Asp Arg Phe Gly Val Pro Thr Tyr Asn Trp Gly
                 180                 185                 190

GCG AAC GAC TCG GAT GTG CTG ATT CTC AAC AAC ACG CGG CCG CCG CGA      622
Ala Asn Asp Ser Asp Val Leu Ile Leu Asn Asn Thr Arg Pro Pro Arg
             195                 200                 205

GGC AAC TGG TTC GGC TGT ACA TGG ATG AAT GGC ACT GGG TTC ACC AAG      670
Gly Asn Trp Phe Gly Cys Thr Trp Met Asn Gly Thr Gly Phe Thr Lys
             210                 215                 220

ACG TGT GGG GGC CCC CCG TGC AAC ATC GGG GGG GCC GGC AAC AAC ACC      718
Thr Cys Gly Gly Pro Pro Cys Asn Ile Gly Gly Ala Gly Asn Asn Thr
225                 230                 235

TTG ACC TGC CCC ACT GAC TGT TTT CGG AAG CAC CCC GAG GCC ACC TAC      766
Leu Thr Cys Pro Thr Asp Cys Phe Arg Lys His Pro Glu Ala Thr Tyr
240                 245                 250                 255

GCC AGA TGC GGT TCT GGG CCC TGG CTG ACA CCT AGG TGT ATG GTT CAT      814
Ala Arg Cys Gly Ser Gly Pro Trp Leu Thr Pro Arg Cys Met Val His
                 260                 265                 270

TAC CCA TAT AGG CTC TGG CAC TAC CCC TGC ACT GTC AAC TTC ACC ATC      862
Tyr Pro Tyr Arg Leu Trp His Tyr Pro Cys Thr Val Asn Phe Thr Ile
             275                 280                 285

TTC AAG GTT AGG ATG TAC GTG GGG GGC GTG GAG CAC AGG TTC GAA GCC      910
Phe Lys Val Arg Met Tyr Val Gly Gly Val Glu His Arg Phe Glu Ala
             290                 295                 300

GCA TGC AAT TGG ACT CGA GGA GAG CGT TGT GAC TTG GAG GAC AGG GAT      958
Ala Cys Asn Trp Thr Arg Gly Glu Arg Cys Asp Leu Glu Asp Arg Asp
        305                 310                 315

AGA TCA GAG CTT AGC CCG CTG CTG CTG TCT ACA ACA GGT GAT CGA GGG     1006
Arg Ser Glu Leu Ser Pro Leu Leu Leu Ser Thr Thr Gly Asp Arg Gly
320                 325                 330                 335

CAG ACA CCA TCA CCA CCA TCA CTA AT AG                               1034
Gln Thr Pro Ser Pro Pro Ser Leu
                 340
```

(2) INFORMATION FOR SEQ ID NO: 40:

(i) SEQUENCE CHARACTERISTICS:
    (A) LENGTH: 343 amino acids
    (B) TYPE: amino acid
    (D) TOPOLOGY: linear (ii) MOLECULE TYPE: protein (xi) SEQUENCE DESCRIPTION: SEQ ID NO: 40:

```
Ile Pro Gln Ala Val Val Asp Met Val Ala Gly Ala His Trp Gly Val
 1               5                  10                  15

Leu Ala Gly Leu Ala Tyr Tyr Ser Met Val Gly Asn Trp Ala Lys Val
                20                  25                  30

Leu Val Val Met Leu Leu Phe Ala Gly Val Asp Gly His Thr Arg Val
                35                  40                  45

Ser Gly Gly Ala Ala Ala Ser Asp Thr Arg Gly Leu Val Ser Leu Phe
 50                  55                  60

Ser Pro Gly Ser Ala Gln Lys Ile Gln Leu Val Asn Thr Asn Gly Ser
 65                  70                  75                  80

Trp His Ile Asn Arg Thr Ala Leu Asn Cys Asn Asp Ser Leu Gln Thr
                85                  90                  95

Gly Phe Phe Ala Ala Leu Phe Tyr Lys His Lys Phe Asn Ser Ser Gly
                100                 105                 110

Cys Pro Glu Arg Leu Ala Ser Cys Arg Ser Ile Asp Lys Phe Ala Gln
                115                 120                 125

Gly Trp Gly Pro Leu Thr Tyr Thr Glu Pro Asn Ser Ser Asp Gln Arg
                130                 135                 140

Pro Tyr Cys Trp His Tyr Ala Pro Arg Pro Cys Gly Ile Val Pro Ala
145                 150                 155                 160

Ser Gln Val Cys Gly Pro Val Tyr Cys Phe Thr Pro Ser Pro Val Val
                165                 170                 175

Val Gly Thr Thr Asp Arg Phe Gly Val Pro Thr Tyr Asn Trp Gly Ala
                180                 185                 190

Asn Asp Ser Asp Val Leu Ile Leu Asn Asn Thr Arg Pro Pro Arg Gly
                195                 200                 205

Asn Trp Phe Gly Cys Thr Trp Met Asn Gly Thr Gly Phe Thr Lys Thr
                210                 215                 220

Cys Gly Gly Pro Pro Cys Asn Ile Gly Gly Ala Gly Asn Asn Thr Leu
225                 230                 235                 240

Thr Cys Pro Thr Asp Cys Phe Arg Lys His Pro Glu Ala Thr Tyr Ala
                245                 250                 255

Arg Cys Gly Ser Gly Pro Trp Leu Thr Pro Arg Cys Met Val His Tyr
                260                 265                 270

Pro Tyr Arg Leu Trp His Tyr Pro Cys Thr Val Asn Phe Thr Ile Phe
                275                 280                 285

Lys Val Arg Met Tyr Val Gly Gly Val Glu His Arg Phe Glu Ala Ala
                290                 295                 300

Cys Asn Trp Thr Arg Gly Glu Arg Cys Asp Leu Glu Asp Arg Asp Arg
305                 310                 315                 320

Ser Glu Leu Ser Pro Leu Leu Leu Ser Thr Thr Gly Asp Arg Gly Gln
                325                 330                 335

Thr Pro Ser Pro Pro Ser Leu
                340
```

(2) INFORMATION FOR SEQ ID NO: 41:

(i) SEQUENCE CHARACTERISTICS:

(A) LENGTH: 945 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..942

(ix) FEATURE:
        (A) NAME/KEY: mat_peptide
        (B) LOCATION: 1..939

(xi) SEQUENCE DESCRIPTION: SEQ ID NO: 41:

```
ATG GTG GGG AAC TGG GCT AAG GTT TTG GTT GTG ATG CTA CTC TTT GCC        48
Met Val Gly Asn Trp Ala Lys Val Leu Val Val Met Leu Leu Phe Ala
 1               5                  10                  15

GGC GTC GAC GGG CAT ACC CGC GTG TCA GGA GGG GCA GCA GCC TCC GAT        96
Gly Val Asp Gly His Thr Arg Val Ser Gly Gly Ala Ala Ala Ser Asp
                 20                  25                  30

ACC AGG GGC CTT GTG TCC CTC TTT AGC CCC GGG TCG GCT CAG AAA ATC       144
Thr Arg Gly Leu Val Ser Leu Phe Ser Pro Gly Ser Ala Gln Lys Ile
         35                  40                  45

CAG CTC GTA AAC ACC AAC GGC AGT TGG CAC ATC AAC AGG ACT GCC CTG       192
Gln Leu Val Asn Thr Asn Gly Ser Trp His Ile Asn Arg Thr Ala Leu
 50                  55                  60

AAC TGC AAC GAC TCC CTC CAA ACA GGG TTC TTT GCC GCA CTA TTC TAC       240
Asn Cys Asn Asp Ser Leu Gln Thr Gly Phe Phe Ala Ala Leu Phe Tyr
 65                  70                  75                  80

AAA CAC AAA TTC AAC TCG TCT GGA TGC CCA GAG CGC TTG GCC AGC TGT       288
Lys His Lys Phe Asn Ser Ser Gly Cys Pro Glu Arg Leu Ala Ser Cys
                 85                  90                  95

CGC TCC ATC GAC AAG TTC GCT CAG GGG TGG GGT CCC CTC ACT TAC ACT       336
Arg Ser Ile Asp Lys Phe Ala Gln Gly Trp Gly Pro Leu Thr Tyr Thr
                100                 105                 110

GAG CCT AAC AGC TCG GAC CAG AGG CCC TAC TGC TGG CAC TAC GCG CCT       384
Glu Pro Asn Ser Ser Asp Gln Arg Pro Tyr Cys Trp His Tyr Ala Pro
         115                 120                 125

CGA CCG TGT GGT ATT GTA CCC GCG TCT CAG GTG TGC GGT CCA GTG TAT       432
Arg Pro Cys Gly Ile Val Pro Ala Ser Gln Val Cys Gly Pro Val Tyr
 130                 135                 140

TGC TTC ACC CCG AGC CCT GTT GTG GTG GGG ACG ACC GAT CGG TTT GGT       480
Cys Phe Thr Pro Ser Pro Val Val Val Gly Thr Thr Asp Arg Phe Gly
145                 150                 155                 160

GTC CCC ACG TAT AAC TGG GGG GCG AAC GAC TCG GAT GTG CTG ATT CTC       528
Val Pro Thr Tyr Asn Trp Gly Ala Asn Asp Ser Asp Val Leu Ile Leu
                165                 170                 175

AAC AAC ACG CGG CCG CCG CGA GGC AAC TGG TTC GGC TGT ACA TGG ATG       576
Asn Asn Thr Arg Pro Pro Arg Gly Asn Trp Phe Gly Cys Thr Trp Met
                180                 185                 190

AAT GGC ACT GGG TTC ACC AAG ACG TGT GGG GGC CCC CCG TGC AAC ATC       624
Asn Gly Thr Gly Phe Thr Lys Thr Cys Gly Gly Pro Pro Cys Asn Ile
         195                 200                 205

GGG GGG GCC GGC AAC AAC ACC TTG ACC TGC CCC ACT GAC TGT TTT CGG       672
Gly Gly Ala Gly Asn Asn Thr Leu Thr Cys Pro Thr Asp Cys Phe Arg
 210                 215                 220

AAG CAC CCC GAG GCC ACC TAC GCC AGA TGC GGT TCT GGG CCC TGG CTG       720
Lys His Pro Glu Ala Thr Tyr Ala Arg Cys Gly Ser Gly Pro Trp Leu
```

```
                225                 230                 235                 240
ACA CCT AGG TGT ATG GTT CAT TAC CCA TAT AGG CTC TGG CAC TAC CCC                 768
Thr Pro Arg Cys Met Val His Tyr Pro Tyr Arg Leu Trp His Tyr Pro
                    245                 250                 255

TGC ACT GTC AAC TTC ACC ATC TTC AAG GTT AGG ATG TAC GTG GGG GGC                 816
Cys Thr Val Asn Phe Thr Ile Phe Lys Val Arg Met Tyr Val Gly Gly
                260                 265                 270

GTG GAG CAC AGG TTC GAA GCC GCA TGC AAT TGG ACT CGA GGA GAG CGT                 864
Val Glu His Arg Phe Glu Ala Ala Cys Asn Trp Thr Arg Gly Glu Arg
            275                 280                 285

TGT GAC TTG GAG GAC AGG GAT AGA TCA GAG CTT AGC CCG CTG CTG CTG                 912
Cys Asp Leu Glu Asp Arg Asp Arg Ser Glu Leu Ser Pro Leu Leu Leu
        290                 295                 300

TCT ACA ACA GAG TGG CAG AGC TTA ATT AAT TAG                                     945
Ser Thr Thr Glu Trp Gln Ser Leu Ile Asn
305                 310

(2) INFORMATION FOR SEQ ID NO: 42:

(i) SEQUENCE CHARACTERISTICS:
        (A) LENGTH: 314 amino acids
        (B) TYPE: amino acid
        (D) TOPOLOGY: linear (ii) MOLECULE TYPE: protein (xi) SEQUENCE DESCRIPTION: SEQ ID NO: 42:

Met Val Gly Asn Trp Ala Lys Val Leu Val Met Leu Leu Phe Ala
1               5                   10                  15

Gly Val Asp Gly His Thr Arg Val Ser Gly Ala Ala Ala Ser Asp
                20                  25                  30

Thr Arg Gly Leu Val Ser Leu Phe Ser Pro Gly Ser Ala Gln Lys Ile
            35                  40                  45

Gln Leu Val Asn Thr Asn Gly Ser Trp His Ile Asn Arg Thr Ala Leu
        50                  55                  60

Asn Cys Asn Asp Ser Leu Gln Thr Gly Phe Phe Ala Ala Leu Phe Tyr
65                  70                  75                  80

Lys His Lys Phe Asn Ser Ser Gly Cys Pro Glu Arg Leu Ala Ser Cys
                85                  90                  95

Arg Ser Ile Asp Lys Phe Ala Gln Gly Trp Gly Pro Leu Thr Tyr Thr
            100                 105                 110

Glu Pro Asn Ser Ser Asp Gln Arg Pro Tyr Cys Trp His Tyr Ala Pro
        115                 120                 125

Arg Pro Cys Gly Ile Val Pro Ala Ser Gln Val Cys Gly Pro Val Tyr
    130                 135                 140

Cys Phe Thr Pro Ser Pro Val Val Val Gly Thr Thr Asp Arg Phe Gly
145                 150                 155                 160

Val Pro Thr Tyr Asn Trp Gly Ala Asn Asp Ser Asp Val Leu Ile Leu
                165                 170                 175

Asn Asn Thr Arg Pro Pro Arg Gly Asn Trp Phe Gly Cys Thr Trp Met
            180                 185                 190

Asn Gly Thr Gly Phe Thr Lys Thr Cys Gly Gly Pro Pro Cys Asn Ile
        195                 200                 205

Gly Gly Ala Gly Asn Asn Thr Leu Thr Cys Pro Thr Asp Cys Phe Arg
    210                 215                 220

Lys His Pro Glu Ala Thr Tyr Ala Arg Cys Gly Ser Gly Pro Trp Leu
225                 230                 235                 240
```

-continued

```
Thr Pro Arg Cys Met Val His Tyr Pro Tyr Arg Leu Trp His Tyr Pro
            245                 250                 255

Cys Thr Val Asn Phe Thr Ile Phe Lys Val Arg Met Tyr Val Gly Gly
            260                 265                 270

Val Glu His Arg Phe Glu Ala Ala Cys Asn Trp Thr Arg Gly Glu Arg
        275                 280                 285

Cys Asp Leu Glu Asp Arg Asp Arg Ser Glu Leu Ser Pro Leu Leu Leu
    290                 295                 300

Ser Thr Thr Glu Trp Gln Ser Leu Ile Asn
305                 310
```

(2) INFORMATION FOR SEQ ID NO: 43:

(i) SEQUENCE CHARACTERISTICS:
        (A) LENGTH: 961 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..958

(ix) FEATURE:
        (A) NAME/KEY: mat_peptide
        (B) LOCATION: 1..955

(xi) SEQUENCE DESCRIPTION: SEQ ID NO: 43:

```
ATG GTG GGG AAC TGG GCT AAG GTT TTG GTT GTG ATG CTA CTC TTT GCC      48
Met Val Gly Asn Trp Ala Lys Val Leu Val Val Met Leu Leu Phe Ala
  1               5                  10                  15

GGC GTC GAC GGG CAT ACC CGC GTG TCA GGA GGG GCA GCA GCC TCC GAT      96
Gly Val Asp Gly His Thr Arg Val Ser Gly Gly Ala Ala Ala Ser Asp
                 20                  25                  30

ACC AGG GGC CTT GTG TCC CTC TTT AGC CCC GGG TCG GCT CAG AAA ATC     144
Thr Arg Gly Leu Val Ser Leu Phe Ser Pro Gly Ser Ala Gln Lys Ile
         35                  40                  45

CAG CTC GTA AAC ACC AAC GGC AGT TGG CAC ATC AAC AGG ACT GCC CTG     192
Gln Leu Val Asn Thr Asn Gly Ser Trp His Ile Asn Arg Thr Ala Leu
 50                  55                  60

AAC TGC AAC GAC TCC CTC CAA ACA GGG TTC TTT GCC GCA CTA TTC TAC     240
Asn Cys Asn Asp Ser Leu Gln Thr Gly Phe Phe Ala Ala Leu Phe Tyr
 65                  70                  75                  80

AAA CAC AAA TTC AAC TCG TCT GGA TGC CCA GAG CGC TTG GCC AGC TGT     288
Lys His Lys Phe Asn Ser Ser Gly Cys Pro Glu Arg Leu Ala Ser Cys
                 85                  90                  95

CGC TCC ATC GAC AAG TTC GCT CAG GGG TGG GGT CCC CTC ACT TAC ACT     336
Arg Ser Ile Asp Lys Phe Ala Gln Gly Trp Gly Pro Leu Thr Tyr Thr
                100                 105                 110

GAG CCT AAC AGC TCG GAC CAG AGG CCC TAC TGC TGG CAC TAC GCG CCT     384
Glu Pro Asn Ser Ser Asp Gln Arg Pro Tyr Cys Trp His Tyr Ala Pro
         115                 120                 125

CGA CCG TGT GGT ATT GTA CCC GCG TCT CAG GTG TGC GGT CCA GTG TAT     432
Arg Pro Cys Gly Ile Val Pro Ala Ser Gln Val Cys Gly Pro Val Tyr
    130                 135                 140

TGC TTC ACC CCG AGC CCT GTT GTG GTG GGG ACG ACC GAT CGG TTT GGT     480
Cys Phe Thr Pro Ser Pro Val Val Val Gly Thr Thr Asp Arg Phe Gly
145                 150                 155                 160
```

```
GTC CCC ACG TAT AAC TGG GGG GCG AAC GAC TCG GAT GTG CTG ATT CTC       528
Val Pro Thr Tyr Asn Trp Gly Ala Asn Asp Ser Asp Val Leu Ile Leu
            165                 170                 175

AAC AAC ACG CGG CCG CCG CGA GGC AAC TGG TTC GGC TGT ACA TGG ATG       576
Asn Asn Thr Arg Pro Pro Arg Gly Asn Trp Phe Gly Cys Thr Trp Met
            180                 185                 190

AAT GGC ACT GGG TTC ACC AAG ACG TGT GGG GGC CCC CCG TGC AAC ATC       624
Asn Gly Thr Gly Phe Thr Lys Thr Cys Gly Gly Pro Pro Cys Asn Ile
            195                 200                 205

GGG GGG GCC GGC AAC AAC ACC TTG ACC TGC CCC ACT GAC TGT TTT CGG       672
Gly Gly Ala Gly Asn Asn Thr Leu Thr Cys Pro Thr Asp Cys Phe Arg
    210                 215                 220

AAG CAC CCC GAG GCC ACC TAC GCC AGA TGC GGT TCT GGG CCC TGG CTG       720
Lys His Pro Glu Ala Thr Tyr Ala Arg Cys Gly Ser Gly Pro Trp Leu
225                 230                 235                 240

ACA CCT AGG TGT ATG GTT CAT TAC CCA TAT AGG CTC TGG CAC TAC CCC       768
Thr Pro Arg Cys Met Val His Tyr Pro Tyr Arg Leu Trp His Tyr Pro
                245                 250                 255

TGC ACT GTC AAC TTC ACC ATC TTC AAG GTT AGG ATG TAC GTG GGG GGC       816
Cys Thr Val Asn Phe Thr Ile Phe Lys Val Arg Met Tyr Val Gly Gly
            260                 265                 270

GTG GAG CAC AGG TTC GAA GCC GCA TGC AAT TGG ACT CGA GGA GAG CGT       864
Val Glu His Arg Phe Glu Ala Ala Cys Asn Trp Thr Arg Gly Glu Arg
            275                 280                 285

TGT GAC TTG GAG GAC AGG GAT AGA TCA GAG CTT AGC CCG CTG CTG CTG       912
Cys Asp Leu Glu Asp Arg Asp Arg Ser Glu Leu Ser Pro Leu Leu Leu
            290                 295                 300

TCT ACA ACA GGT GAT CGA GGG CAG ACA CCA TCA CCA CCA TCA CTA A        958
Ser Thr Thr Gly Asp Arg Gly Gln Thr Pro Ser Pro Pro Ser Leu
305                 310                 315

TAG                                                                    961

(2) INFORMATION FOR SEQ ID NO: 44:

(i) SEQUENCE CHARACTERISTICS:
        (A) LENGTH: 319 amino acids
        (B) TYPE: amino acid
        (D) TOPOLOGY: linear (ii) MOLECULE TYPE: protein (xi) SEQUENCE DESCRIPTION: SEQ ID NO: 44:

Met Val Gly Asn Trp Ala Lys Val Leu Val Met Leu Leu Phe Ala
 1               5                  10                  15

Gly Val Asp Gly His Thr Arg Val Ser Gly Ala Ala Ala Ser Asp
                20                  25                  30

Thr Arg Gly Leu Val Ser Leu Phe Ser Pro Gly Ser Ala Gln Lys Ile
            35                  40                  45

Gln Leu Val Asn Thr Asn Gly Ser Trp His Ile Asn Arg Thr Ala Leu
    50                  55                  60

Asn Cys Asn Asp Ser Leu Gln Thr Gly Phe Phe Ala Ala Leu Phe Tyr
65                  70                  75                  80

Lys His Lys Phe Asn Ser Ser Gly Cys Pro Glu Arg Leu Ala Ser Cys
                85                  90                  95

Arg Ser Ile Asp Lys Phe Ala Gln Gly Trp Gly Pro Leu Thr Tyr Thr
                100                 105                 110

Glu Pro Asn Ser Ser Asp Gln Arg Pro Tyr Cys Trp His Tyr Ala Pro
            115                 120                 125
```

```
Arg Pro Cys Gly Ile Val Pro Ala Ser Gln Val Cys Gly Pro Val Tyr
130                 135                 140

Cys Phe Thr Pro Ser Pro Val Val Gly Thr Thr Asp Arg Phe Gly
145                 150                 155                 160

Val Pro Thr Tyr Asn Trp Gly Ala Asn Asp Ser Asp Val Leu Ile Leu
                165                 170                 175

Asn Asn Thr Arg Pro Pro Arg Gly Asn Trp Phe Gly Cys Thr Trp Met
            180                 185                 190

Asn Gly Thr Gly Phe Thr Lys Thr Cys Gly Pro Pro Cys Asn Ile
        195                 200                 205

Gly Gly Ala Gly Asn Asn Thr Leu Thr Cys Pro Thr Asp Cys Phe Arg
    210                 215                 220

Lys His Pro Glu Ala Thr Tyr Ala Arg Cys Gly Ser Gly Pro Trp Leu
225                 230                 235                 240

Thr Pro Arg Cys Met Val His Tyr Pro Tyr Arg Leu Trp His Tyr Pro
                245                 250                 255

Cys Thr Val Asn Phe Thr Ile Phe Lys Val Arg Met Tyr Val Gly Gly
                260                 265                 270

Val Glu His Arg Phe Glu Ala Ala Cys Asn Trp Thr Arg Gly Glu Arg
            275                 280                 285

Cys Asp Leu Glu Asp Arg Asp Arg Ser Glu Leu Ser Pro Leu Leu Leu
290                 295                 300

Ser Thr Thr Gly Asp Arg Gly Gln Thr Pro Ser Pro Pro Ser Leu
305                 310                 315

(2) INFORMATION FOR SEQ ID NO: 45:

(i) SEQUENCE CHARACTERISTICS:
        (A) LENGTH: 1395 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..1392

(ix) FEATURE:
        (A) NAME/KEY: mat_peptide
        (B) LOCATION: 1..1389

(xi) SEQUENCE DESCRIPTION: SEQ ID NO: 45:

ATG GTG GCG GGG GCC CAT TGG GGA GTC CTG GCG GGC CTC GCC TAC TAT      48
Met Val Ala Gly Ala His Trp Gly Val Leu Ala Gly Leu Ala Tyr Tyr
1               5                   10                  15

TCC ATG GTG GGG AAC TGG GCT AAG GTT TTG GTT GTG ATG CTA CTC TTT      96
Ser Met Val Gly Asn Trp Ala Lys Val Leu Val Val Met Leu Leu Phe
                20                  25                  30

GCC GGC GTC GAC GGG CAT ACC CGC GTG TCA GGA GGG GCA GCA GCC TCC     144
Ala Gly Val Asp Gly His Thr Arg Val Ser Gly Gly Ala Ala Ala Ser
            35                  40                  45

GAT ACC AGG GGC CTT GTG TCC CTC TTT AGC CCC GGG TCG GCT CAG AAA     192
Asp Thr Arg Gly Leu Val Ser Leu Phe Ser Pro Gly Ser Ala Gln Lys
        50                  55                  60

ATC CAG CTC GTA AAC ACC AAC GGC AGT TGG CAC ATC AAC AGG ACT GCC     240
Ile Gln Leu Val Asn Thr Asn Gly Ser Trp His Ile Asn Arg Thr Ala
```

-continued

```
             65                  70                  75                  80
CTG AAC TGC AAC GAC TCC CTC CAA ACA GGG TTC TTT GCC GCA CTA TTC          288
Leu Asn Cys Asn Asp Ser Leu Gln Thr Gly Phe Phe Ala Ala Leu Phe
                     85                  90                  95

TAC AAA CAC AAA TTC AAC TCG TCT GGA TGC CCA GAG CGC TTG GCC AGC          336
Tyr Lys His Lys Phe Asn Ser Ser Gly Cys Pro Glu Arg Leu Ala Ser
                100                 105                 110

TGT CGC TCC ATC GAC AAG TTC GCT CAG GGG TGG GGT CCC CTC ACT TAC          384
Cys Arg Ser Ile Asp Lys Phe Ala Gln Gly Trp Gly Pro Leu Thr Tyr
            115                 120                 125

ACT GAG CCT AAC AGC TCG GAC CAG AGG CCC TAC TGC TGG CAC TAC GCG          432
Thr Glu Pro Asn Ser Ser Asp Gln Arg Pro Tyr Cys Trp His Tyr Ala
    130                 135                 140

CCT CGA CCG TGT GGT ATT GTA CCC GCG TCT CAG GTG TGC GGT CCA GTG          480
Pro Arg Pro Cys Gly Ile Val Pro Ala Ser Gln Val Cys Gly Pro Val
145                 150                 155                 160

TAT TGC TTC ACC CCG AGC CCT GTT GTG GTG GGG ACG ACC GAT CGG TTT          528
Tyr Cys Phe Thr Pro Ser Pro Val Val Val Gly Thr Thr Asp Arg Phe
                165                 170                 175

GGT GTC CCC ACG TAT AAC TGG GGG GCG AAC GAC TCG GAT GTG CTG ATT          576
Gly Val Pro Thr Tyr Asn Trp Gly Ala Asn Asp Ser Asp Val Leu Ile
            180                 185                 190

CTC AAC AAC ACG CGG CCG CCG CGA GGC AAC TGG TTC GGC TGT ACA TGG          624
Leu Asn Asn Thr Arg Pro Pro Arg Gly Asn Trp Phe Gly Cys Thr Trp
        195                 200                 205

ATG AAT GGC ACT GGG TTC ACC AAG ACG TGT GGG GGC CCC CCG TGC AAC          672
Met Asn Gly Thr Gly Phe Thr Lys Thr Cys Gly Gly Pro Pro Cys Asn
    210                 215                 220

ATC GGG GGG GCC GGC AAC AAC ACC TTG ACC TGC CCC ACT GAC TGT TTT          720
Ile Gly Gly Ala Gly Asn Asn Thr Leu Thr Cys Pro Thr Asp Cys Phe
225                 230                 235                 240

CGG AAG CAC CCC GAG GCC ACC TAC GCC AGA TGC GGT TCT GGG CCC TGG          768
Arg Lys His Pro Glu Ala Thr Tyr Ala Arg Cys Gly Ser Gly Pro Trp
                245                 250                 255

CTG ACA CCT AGG TGT ATG GTT CAT TAC CCA TAT AGG CTC TGG CAC TAC          816
Leu Thr Pro Arg Cys Met Val His Tyr Pro Tyr Arg Leu Trp His Tyr
            260                 265                 270

CCC TGC ACT GTC AAC TTC ACC ATC TTC AAG GTT AGG ATG TAC GTG GGG          864
Pro Cys Thr Val Asn Phe Thr Ile Phe Lys Val Arg Met Tyr Val Gly
        275                 280                 285

GGC GTG GAG CAC AGG TTC GAA GCC GCA TGC AAT TGG ACT CGA GGA GAG          912
Gly Val Glu His Arg Phe Glu Ala Ala Cys Asn Trp Thr Arg Gly Glu
    290                 295                 300

CGT TGT GAC TTG GAG GAC AGG GAT AGA TCA GAG CTT AGC CCG CTG CTG          960
Arg Cys Asp Leu Glu Asp Arg Asp Arg Ser Glu Leu Ser Pro Leu Leu
305                 310                 315                 320

CTG TCT ACA ACA GAG TGG CAG ATA CTG CCC TGT TCC TTC ACC ACC CTG         1008
Leu Ser Thr Thr Glu Trp Gln Ile Leu Pro Cys Ser Phe Thr Thr Leu
                325                 330                 335

CCG GCC CTA TCC ACC GGC CTG ATC CAC CTC CAT CAG AAC ATC GTG GAC         1056
Pro Ala Leu Ser Thr Gly Leu Ile His Leu His Gln Asn Ile Val Asp
            340                 345                 350

GTG CAA TAC CTG TAC GGT GTA GGG TCG GCG GTT GTC TCC CTT GTC ATC         1104
Val Gln Tyr Leu Tyr Gly Val Gly Ser Ala Val Val Ser Leu Val Ile
        355                 360                 365

AAA TGG GAG TAT GTC CTG TTG CTC TTC CTT CTC CTG GCA GAC GCG CGC         1152
Lys Trp Glu Tyr Val Leu Leu Leu Phe Leu Leu Leu Ala Asp Ala Arg
    370                 375                 380

ATC TGC GCC TGC TTA TGG ATG ATG CTG CTG ATA GCT CAA GCT GAG GCC         1200
```

```
Ile Cys Ala Cys Leu Trp Met Met Leu Leu Ile Ala Gln Ala Glu Ala
385                 390                 395                 400

GCC TTA GAG AAC CTG GTG GTC CTC AAT GCG GCG GCC GTG GCC GGG GCG      1248
Ala Leu Glu Asn Leu Val Val Leu Asn Ala Ala Ala Val Ala Gly Ala
                405                 410                 415

CAT GGC ACT CTT TCC TTC CTT GTG TTC TTC TGT GCT GCC TGG TAC ATC      1296
His Gly Thr Leu Ser Phe Leu Val Phe Phe Cys Ala Ala Trp Tyr Ile
                420                 425                 430

AAG GGC AGG CTG GTC CCT GGT GCG GCA TAC GCC TTC TAT GGC GTG TGG      1344
Lys Gly Arg Leu Val Pro Gly Ala Ala Tyr Ala Phe Tyr Gly Val Trp
                435                 440                 445

CCG CTG CTC CTG CTT CTG CTG GCC TTA CCA CCA CGA GCT TAT GCC TAG      1395
Pro Leu Leu Leu Leu Leu Leu Ala Leu Pro Pro Arg Ala Tyr Ala
450                 455                 460
```

(2) INFORMATION FOR SEQ ID NO: 46:

(i) SEQUENCE CHARACTERISTICS:
        (A) LENGTH: 463 amino acids
        (B) TYPE: amino acid
        (D) TOPOLOGY: linear (ii) MOLECULE TYPE: protein (xi) SEQUENCE DESCRIPTION: SEQ ID NO: 46:

```
Met Val Ala Gly Ala His Trp Gly Val Leu Ala Gly Leu Ala Tyr Tyr
1               5                   10                  15

Ser Met Val Gly Asn Trp Ala Lys Val Leu Val Val Met Leu Leu Phe
                20                  25                  30

Ala Gly Val Asp Gly His Thr Arg Val Ser Gly Gly Ala Ala Ala Ser
                35                  40                  45

Asp Thr Arg Gly Leu Val Ser Leu Phe Ser Pro Gly Ser Ala Gln Lys
        50                  55                  60

Ile Gln Leu Val Asn Thr Asn Gly Ser Trp His Ile Asn Arg Thr Ala
65                  70                  75                  80

Leu Asn Cys Asn Asp Ser Leu Gln Thr Gly Phe Phe Ala Ala Leu Phe
                85                  90                  95

Tyr Lys His Lys Phe Asn Ser Ser Gly Cys Pro Glu Arg Leu Ala Ser
                100                 105                 110

Cys Arg Ser Ile Asp Lys Phe Ala Gln Gly Trp Gly Pro Leu Thr Tyr
        115                 120                 125

Thr Glu Pro Asn Ser Ser Asp Gln Arg Pro Tyr Cys Trp His Tyr Ala
        130                 135                 140

Pro Arg Pro Cys Gly Ile Val Pro Ala Ser Gln Val Cys Gly Pro Val
145                 150                 155                 160

Tyr Cys Phe Thr Pro Ser Pro Val Val Val Gly Thr Thr Asp Arg Phe
                165                 170                 175

Gly Val Pro Thr Tyr Asn Trp Gly Ala Asn Asp Ser Asp Val Leu Ile
                180                 185                 190

Leu Asn Asn Thr Arg Pro Pro Arg Gly Asn Trp Phe Gly Cys Thr Trp
                195                 200                 205

Met Asn Gly Thr Gly Phe Thr Lys Thr Cys Gly Gly Pro Pro Cys Asn
        210                 215                 220

Ile Gly Gly Ala Gly Asn Asn Thr Leu Thr Cys Pro Thr Asp Cys Phe
225                 230                 235                 240

Arg Lys His Pro Glu Ala Thr Tyr Ala Arg Cys Gly Ser Gly Pro Trp
                245                 250                 255
```

```
Leu Thr Pro Arg Cys Met Val His Tyr Pro Tyr Arg Leu Trp His Tyr
            260                 265                 270

Pro Cys Thr Val Asn Phe Thr Ile Phe Lys Val Arg Met Tyr Val Gly
        275                 280                 285

Gly Val Glu His Arg Phe Glu Ala Ala Cys Asn Trp Thr Arg Gly Glu
    290                 295                 300

Arg Cys Asp Leu Glu Asp Arg Asp Arg Ser Glu Leu Ser Pro Leu Leu
305                 310                 315                 320

Leu Ser Thr Thr Glu Trp Gln Ile Leu Pro Cys Ser Phe Thr Thr Leu
                325                 330                 335

Pro Ala Leu Ser Thr Gly Leu Ile His Leu His Gln Asn Ile Val Asp
            340                 345                 350

Val Gln Tyr Leu Tyr Gly Val Gly Ser Ala Val Val Ser Leu Val Ile
        355                 360                 365

Lys Trp Glu Tyr Val Leu Leu Leu Phe Leu Leu Leu Ala Asp Ala Arg
    370                 375                 380

Ile Cys Ala Cys Leu Trp Met Met Leu Leu Ile Ala Gln Ala Glu Ala
385                 390                 395                 400

Ala Leu Glu Asn Leu Val Val Leu Asn Ala Ala Val Ala Gly Ala
                405                 410                 415

His Gly Thr Leu Ser Phe Leu Val Phe Phe Cys Ala Ala Trp Tyr Ile
            420                 425                 430

Lys Gly Arg Leu Val Pro Gly Ala Ala Tyr Ala Phe Tyr Gly Val Trp
            435                 440                 445

Pro Leu Leu Leu Leu Leu Ala Leu Pro Pro Arg Ala Tyr Ala
    450                 455                 460
```

(2) INFORMATION FOR SEQ ID NO: 47:

(i) SEQUENCE CHARACTERISTICS:
        (A) LENGTH: 2082 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..2079

(ix) FEATURE:
        (A) NAME/KEY: mat_peptide
        (B) LOCATION: 1..2076

(xi) SEQUENCE DESCRIPTION: SEQ ID NO: 47:

```
AAT TTG GGT AAG GTC ATC GAT ACC CTT ACA TGC GGC TTC GCC GAC CTC      48
Asn Leu Gly Lys Val Ile Asp Thr Leu Thr Cys Gly Phe Ala Asp Leu
  1               5                  10                  15

GTG GGG TAC ATT CCG CTC GTC GGC GCC CCC CTA GGG GGC GCT GCC AGG      96
Val Gly Tyr Ile Pro Leu Val Gly Ala Pro Leu Gly Gly Ala Ala Arg
                 20                  25                  30

GCC CTG GCG CAT GGC GTC CGG GTT CTG GAG GAC GGC GTG AAC TAT GCA     144
Ala Leu Ala His Gly Val Arg Val Leu Glu Asp Gly Val Asn Tyr Ala
             35                  40                  45

ACA GGG AAT TTG CCC GGT TGC TCT TTC TCT ATC TTC CTC TTG GCT TTG     192
Thr Gly Asn Leu Pro Gly Cys Ser Phe Ser Ile Phe Leu Leu Ala Leu
         50                  55                  60
```

-continued

| | |
|---|---|
| CTG TCC TGT CTG ACC GTT CCA GCT TCC GCT TAT GAA GTG CGC AAC GTG<br>Leu Ser Cys Leu Thr Val Pro Ala Ser Ala Tyr Glu Val Arg Asn Val<br>65                        70                     75                    80 | 240 |
| TCC GGG ATG TAC CAT GTC ACG AAC GAC TGC TCC AAC TCA AGC ATT GTG<br>Ser Gly Met Tyr His Val Thr Asn Asp Cys Ser Asn Ser Ser Ile Val<br>                    85                     90                    95 | 288 |
| TAT GAG GCA GCG GAC ATG ATC ATG CAC ACC CCC GGG TGC GTG CCC TGC<br>Tyr Glu Ala Ala Asp Met Ile Met His Thr Pro Gly Cys Val Pro Cys<br>          100                    105                   110 | 336 |
| GTT CGG GAG AAC AAC TCT TCC CGC TGC TGG GTA GCG CTC ACC CCC ACG<br>Val Arg Glu Asn Asn Ser Ser Arg Cys Trp Val Ala Leu Thr Pro Thr<br>          115                    120                   125 | 384 |
| CTC GCA GCT AGG AAC GCC AGC GTC CCC ACC ACG ACA ATA CGA CGC CAC<br>Leu Ala Ala Arg Asn Ala Ser Val Pro Thr Thr Thr Ile Arg Arg His<br>130                        135                    140 | 432 |
| GTC GAT TTG CTC GTT GGG GCG GCT GCT TTC TGT TCC GCT ATG TAC GTG<br>Val Asp Leu Leu Val Gly Ala Ala Ala Phe Cys Ser Ala Met Tyr Val<br>145                        150                    155                   160 | 480 |
| GGG GAC CTC TGC GGA TCT GTC TTC CTC GTC TCC CAG CTG TTC ACC ATC<br>Gly Asp Leu Cys Gly Ser Val Phe Leu Val Ser Gln Leu Phe Thr Ile<br>                    165                    170                    175 | 528 |
| TCG CCT CGC CGG CAT GAG ACG GTG CAG GAC TGC AAT TGC TCA ATC TAT<br>Ser Pro Arg Arg His Glu Thr Val Gln Asp Cys Asn Cys Ser Ile Tyr<br>          180                    185                   190 | 576 |
| CCC GGC CAC ATA ACG GGT CAC CGT ATG GCT TGG GAT ATG ATG ATG AAC<br>Pro Gly His Ile Thr Gly His Arg Met Ala Trp Asp Met Met Met Asn<br>          195                    200                   205 | 624 |
| TGG TCG CCT ACA ACG GCC CTG GTG GTA TCG CAG CTG CTC CGG ATC CCA<br>Trp Ser Pro Thr Thr Ala Leu Val Val Ser Gln Leu Leu Arg Ile Pro<br>210                        215                    220 | 672 |
| CAA GCT GTC GTG GAC ATG GTG GCG GGG GCC CAT TGG GGA GTC CTG GCG<br>Gln Ala Val Val Asp Met Val Ala Gly Ala His Trp Gly Val Leu Ala<br>225                        230                    235                   240 | 720 |
| GGC CTC GCC TAC TAT TCC ATG GTG GGG AAC TGG GCT AAG GTT TTG GTT<br>Gly Leu Ala Tyr Tyr Ser Met Val Gly Asn Trp Ala Lys Val Leu Val<br>                    245                    250                    255 | 768 |
| GTG ATG CTA CTC TTT GCC GGC GTC GAC GGG CAT ACC CGC GTG TCA GGA<br>Val Met Leu Leu Phe Ala Gly Val Asp Gly His Thr Arg Val Ser Gly<br>          260                    265                   270 | 816 |
| GGG GCA GCA GCC TCC GAT ACC AGG GGC CTT GTG TCC CTC TTT AGC CCC<br>Gly Ala Ala Ala Ser Asp Thr Arg Gly Leu Val Ser Leu Phe Ser Pro<br>          275                    280                   285 | 864 |
| GGG TCG GCT CAG AAA ATC CAG CTC GTA AAC ACC AAC GGC AGT TGG CAC<br>Gly Ser Ala Gln Lys Ile Gln Leu Val Asn Thr Asn Gly Ser Trp His<br>          290                    295                   300 | 912 |
| ATC AAC AGG ACT GCC CTG AAC TGC AAC GAC TCC CTC CAA ACA GGG TTC<br>Ile Asn Arg Thr Ala Leu Asn Cys Asn Asp Ser Leu Gln Thr Gly Phe<br>305                        310                    315                   320 | 960 |
| TTT GCC GCA CTA TTC TAC AAA CAC AAA TTC AAC TCG TCT GGA TGC CCA<br>Phe Ala Ala Leu Phe Tyr Lys His Lys Phe Asn Ser Ser Gly Cys Pro<br>                    325                    330                   335 | 1008 |
| GAG CGC TTG GCC AGC TGT CGC TCC ATC GAC AAG TTC GCT CAG GGG TGG<br>Glu Arg Leu Ala Ser Cys Arg Ser Ile Asp Lys Phe Ala Gln Gly Trp<br>          340                    345                   350 | 1056 |
| GGT CCC CTC ACT TAC ACT GAG CCT AAC AGC TCG GAC CAG AGG CCC TAC<br>Gly Pro Leu Thr Tyr Thr Glu Pro Asn Ser Ser Asp Gln Arg Pro Tyr<br>          355                    360                   365 | 1104 |
| TGC TGG CAC TAC GCG CCT CGA CCG TGT GGT ATT GTA CCC GCG TCT CAG<br>Cys Trp His Tyr Ala Pro Arg Pro Cys Gly Ile Val Pro Ala Ser Gln | 1152 |

-continued

```
            370                 375                 380
GTG TGC GGT CCA GTG TAT TGC TTC ACC CCG AGC CCT GTT GTG GTG GGG    1200
Val Cys Gly Pro Val Tyr Cys Phe Thr Pro Ser Pro Val Val Val Gly
385                 390                 395                 400

ACG ACC GAT CGG TTT GGT GTC CCC ACG TAT AAC TGG GGG GCG AAC GAC    1248
Thr Thr Asp Arg Phe Gly Val Pro Thr Tyr Asn Trp Gly Ala Asn Asp
            405                 410                 415

TCG GAT GTG CTG ATT CTC AAC AAC ACG CGG CCG CCG CGA GGC AAC TGG    1296
Ser Asp Val Leu Ile Leu Asn Asn Thr Arg Pro Pro Arg Gly Asn Trp
                420                 425                 430

TTC GGC TGT ACA TGG ATG AAT GGC ACT GGG TTC ACC AAG ACG TGT GGG    1344
Phe Gly Cys Thr Trp Met Asn Gly Thr Gly Phe Thr Lys Thr Cys Gly
            435                 440                 445

GGC CCC CCG TGC AAC ATC GGG GGG GCC GGC AAC AAC ACC TTG ACC TGC    1392
Gly Pro Pro Cys Asn Ile Gly Gly Ala Gly Asn Asn Thr Leu Thr Cys
450                 455                 460

CCC ACT GAC TGT TTT CGG AAG CAC CCC GAG GCC ACC TAC GCC AGA TGC    1440
Pro Thr Asp Cys Phe Arg Lys His Pro Glu Ala Thr Tyr Ala Arg Cys
465                 470                 475                 480

GGT TCT GGG CCC TGG CTG ACA CCT AGG TGT ATG GTT CAT TAC CCA TAT    1488
Gly Ser Gly Pro Trp Leu Thr Pro Arg Cys Met Val His Tyr Pro Tyr
            485                 490                 495

AGG CTC TGG CAC TAC CCC TGC ACT GTC AAC TTC ACC ATC TTC AAG GTT    1536
Arg Leu Trp His Tyr Pro Cys Thr Val Asn Phe Thr Ile Phe Lys Val
            500                 505                 510

AGG ATG TAC GTG GGG GGC GTG GAG CAC AGG TTC GAA GCC GCA TGC AAT    1584
Arg Met Tyr Val Gly Gly Val Glu His Arg Phe Glu Ala Ala Cys Asn
            515                 520                 525

TGG ACT CGA GGA GAG CGT TGT GAC TTG GAG GAC AGG GAT AGA TCA GAG    1632
Trp Thr Arg Gly Glu Arg Cys Asp Leu Glu Asp Arg Asp Arg Ser Glu
530                 535                 540

CTT AGC CCG CTG CTG CTG TCT ACA ACA GAG TGG CAG ATA CTG CCC TGT    1680
Leu Ser Pro Leu Leu Leu Ser Thr Thr Glu Trp Gln Ile Leu Pro Cys
545                 550                 555                 560

TCC TTC ACC ACC CTG CCG GCC CTA TCC ACC GGC CTG ATC CAC CTC CAT    1728
Ser Phe Thr Thr Leu Pro Ala Leu Ser Thr Gly Leu Ile His Leu His
            565                 570                 575

CAG AAC ATC GTG GAC GTG CAA TAC CTG TAC GGT GTA GGG TCG GCG GTT    1776
Gln Asn Ile Val Asp Val Gln Tyr Leu Tyr Gly Val Gly Ser Ala Val
            580                 585                 590

GTC TCC CTT GTC ATC AAA TGG GAG TAT GTC CTG TTG CTC TTC CTT CTC    1824
Val Ser Leu Val Ile Lys Trp Glu Tyr Val Leu Leu Leu Phe Leu Leu
            595                 600                 605

CTG GCA GAC GCG CGC ATC TGC GCC TGC TTA TGG ATG ATG CTG CTG ATA    1872
Leu Ala Asp Ala Arg Ile Cys Ala Cys Leu Trp Met Met Leu Leu Ile
610                 615                 620

GCT CAA GCT GAG GCC GCC TTA GAG AAC CTG GTG GTC CTC AAT GCG GCG    1920
Ala Gln Ala Glu Ala Ala Leu Glu Asn Leu Val Val Leu Asn Ala Ala
625                 630                 635                 640

GCC GTG GCC GGG GCG CAT GGC ACT CTT TCC TTC CTT GTG TTC TTC TGT    1968
Ala Val Ala Gly Ala His Gly Thr Leu Ser Phe Leu Val Phe Phe Cys
            645                 650                 655

GCT GCC TGG TAC ATC AAG GGC AGG CTG GTC CCT GGT GCG GCA TAC GCC    2016
Ala Ala Trp Tyr Ile Lys Gly Arg Leu Val Pro Gly Ala Ala Tyr Ala
            660                 665                 670

TTC TAT GGC GTG TGG CCG CTG CTC CTG CTT CTG CTG GCC TTA CCA CCA    2064
Phe Tyr Gly Val Trp Pro Leu Leu Leu Leu Leu Leu Ala Leu Pro Pro
            675                 680                 685

CGA GCT TAT GCC TAGTAA                                             2082
```

Arg Ala Tyr Ala
690

(2) INFORMATION FOR SEQ ID NO: 48:

(i) SEQUENCE CHARACTERISTICS:
        (A) LENGTH: 692 amino acids
        (B) TYPE: amino acid
        (D) TOPOLOGY: linear (ii) MOLECULE TYPE: protein (xi) SEQUENCE DESCRIPTION: SEQ ID NO: 48:

```
Asn Leu Gly Lys Val Ile Asp Thr Leu Thr Cys Gly Phe Ala Asp Leu
 1               5                  10                  15

Val Gly Tyr Ile Pro Leu Val Gly Ala Pro Leu Gly Gly Ala Ala Arg
            20                  25                  30

Ala Leu Ala His Gly Val Arg Val Leu Glu Asp Gly Val Asn Tyr Ala
        35                  40                  45

Thr Gly Asn Leu Pro Gly Cys Ser Phe Ser Ile Phe Leu Leu Ala Leu
    50                  55                  60

Leu Ser Cys Leu Thr Val Pro Ala Ser Ala Tyr Glu Val Arg Asn Val
65                  70                  75                  80

Ser Gly Met Tyr His Val Thr Asn Asp Cys Ser Asn Ser Ser Ile Val
                85                  90                  95

Tyr Glu Ala Ala Asp Met Ile Met His Thr Pro Gly Cys Val Pro Cys
            100                 105                 110

Val Arg Glu Asn Asn Ser Ser Arg Cys Trp Val Ala Leu Thr Pro Thr
        115                 120                 125

Leu Ala Ala Arg Asn Ala Ser Val Pro Thr Thr Thr Ile Arg Arg His
    130                 135                 140

Val Asp Leu Leu Val Gly Ala Ala Ala Phe Cys Ser Ala Met Tyr Val
145                 150                 155                 160

Gly Asp Leu Cys Gly Ser Val Phe Leu Val Ser Gln Leu Phe Thr Ile
                165                 170                 175

Ser Pro Arg Arg His Glu Thr Val Gln Asp Cys Asn Cys Ser Ile Tyr
            180                 185                 190

Pro Gly His Ile Thr Gly His Arg Met Ala Trp Asp Met Met Met Asn
        195                 200                 205

Trp Ser Pro Thr Thr Ala Leu Val Val Ser Gln Leu Leu Arg Ile Pro
    210                 215                 220

Gln Ala Val Val Asp Met Val Ala Gly Ala His Trp Gly Val Leu Ala
225                 230                 235                 240

Gly Leu Ala Tyr Tyr Ser Met Val Gly Asn Trp Ala Lys Val Leu Val
                245                 250                 255

Val Met Leu Leu Phe Ala Gly Val Asp Gly His Thr Arg Val Ser Gly
            260                 265                 270

Gly Ala Ala Ala Ser Asp Thr Arg Gly Leu Val Ser Leu Phe Ser Pro
        275                 280                 285

Gly Ser Ala Gln Lys Ile Gln Leu Val Asn Thr Asn Gly Ser Trp His
    290                 295                 300

Ile Asn Arg Thr Ala Leu Asn Cys Asn Asp Ser Leu Gln Thr Gly Phe
305                 310                 315                 320

Phe Ala Ala Leu Phe Tyr Lys His Lys Phe Asn Ser Ser Gly Cys Pro
                325                 330                 335

Glu Arg Leu Ala Ser Cys Arg Ser Ile Asp Lys Phe Ala Gln Gly Trp
```

```
                340             345             350
Gly Pro Leu Thr Tyr Thr Glu Pro Asn Ser Ser Asp Gln Arg Pro Tyr
            355                 360                 365
Cys Trp His Tyr Ala Pro Arg Pro Cys Gly Ile Val Pro Ala Ser Gln
    370                 375                 380
Val Cys Gly Pro Val Tyr Cys Phe Thr Pro Ser Pro Val Val Val Gly
385                 390                 395                 400
Thr Thr Asp Arg Phe Gly Val Pro Thr Tyr Asn Trp Gly Ala Asn Asp
                405                 410                 415
Ser Asp Val Leu Ile Leu Asn Asn Thr Arg Pro Pro Arg Gly Asn Trp
            420                 425                 430
Phe Gly Cys Thr Trp Met Asn Gly Thr Gly Phe Thr Lys Thr Cys Gly
        435                 440                 445
Gly Pro Pro Cys Asn Ile Gly Gly Ala Gly Asn Asn Thr Leu Thr Cys
    450                 455                 460
Pro Thr Asp Cys Phe Arg Lys His Pro Glu Ala Thr Tyr Ala Arg Cys
465                 470                 475                 480
Gly Ser Gly Pro Trp Leu Thr Pro Arg Cys Met Val His Tyr Pro Tyr
                485                 490                 495
Arg Leu Trp His Tyr Pro Cys Thr Val Asn Phe Thr Ile Phe Lys Val
            500                 505                 510
Arg Met Tyr Val Gly Gly Val Glu His Arg Phe Glu Ala Ala Cys Asn
        515                 520                 525
Trp Thr Arg Gly Glu Arg Cys Asp Leu Glu Asp Arg Asp Arg Ser Glu
    530                 535                 540
Leu Ser Pro Leu Leu Leu Ser Thr Thr Glu Trp Gln Ile Leu Pro Cys
545                 550                 555                 560
Ser Phe Thr Thr Leu Pro Ala Leu Ser Thr Gly Leu Ile His Leu His
                565                 570                 575
Gln Asn Ile Val Asp Val Gln Tyr Leu Tyr Gly Val Gly Ser Ala Val
            580                 585                 590
Val Ser Leu Val Ile Lys Trp Glu Tyr Val Leu Leu Leu Phe Leu Leu
        595                 600                 605
Leu Ala Asp Ala Arg Ile Cys Ala Cys Leu Trp Met Met Leu Leu Ile
    610                 615                 620
Ala Gln Ala Glu Ala Ala Leu Glu Asn Leu Val Val Leu Asn Ala Ala
625                 630                 635                 640
Ala Val Ala Gly Ala His Gly Thr Leu Ser Phe Leu Val Phe Phe Cys
                645                 650                 655
Ala Ala Trp Tyr Ile Lys Gly Arg Leu Val Pro Gly Ala Ala Tyr Ala
            660                 665                 670
Phe Tyr Gly Val Trp Pro Leu Leu Leu Leu Leu Ala Leu Pro Pro
        675                 680                 685
Arg Ala Tyr Ala
    690

(2) INFORMATION FOR SEQ ID NO: 49:

(i) SEQUENCE CHARACTERISTICS:
        (A) LENGTH: 2433 base pairs
        (B) TYPE: nucleic acid
        (C) STRANDEDNESS: single
        (D) TOPOLOGY: linear (ii) MOLECULE TYPE: cDNA
```

(iii) HYPOTHETICAL: NO (iv) ANTI-SENSE: NO (ix) FEATURE:
    (A) NAME/KEY: CDS
    (B) LOCATION: 1..2430

(ix) FEATURE:
    (A) NAME/KEY: mat_peptide
    (B) LOCATION: 1..2427

(xi) SEQUENCE DESCRIPTION: SEQ ID NO: 49:

```
ATG AGC ACG AAT CCT AAA CCT CAA AGA AAA ACC AAA CGT AAC ACC AAC        48
Met Ser Thr Asn Pro Lys Pro Gln Arg Lys Thr Lys Arg Asn Thr Asn
 1               5                  10                  15

CGC CGC CCA CAG GAC GTC AAG TTC CCG GGC GGT GGT CAG ATC GTT GGT        96
Arg Arg Pro Gln Asp Val Lys Phe Pro Gly Gly Gly Gln Ile Val Gly
             20                  25                  30

GGA GTT TAC CTG TTG CCG CGC AGG GGC CCC AGG TTG GGT GTG CGC GCG       144
Gly Val Tyr Leu Leu Pro Arg Arg Gly Pro Arg Leu Gly Val Arg Ala
         35                  40                  45

ACT AGG AAG ACT TCC GAG CGG TCG CAA CCT CGT GGG AGG CGA CAA CCT       192
Thr Arg Lys Thr Ser Glu Arg Ser Gln Pro Arg Gly Arg Arg Gln Pro
     50                  55                  60

ATC CCC AAG GCT CGC CGA CCC GAG GGT AGG GCC TGG GCT CAG CCC GGG       240
Ile Pro Lys Ala Arg Arg Pro Glu Gly Arg Ala Trp Ala Gln Pro Gly
 65                  70                  75                  80

TAC CCT TGG CCC CTC TAT GGC AAT GAG GGC ATG GGG TGG GCA GGA TGG       288
Tyr Pro Trp Pro Leu Tyr Gly Asn Glu Gly Met Gly Trp Ala Gly Trp
                 85                  90                  95

CTC CTG TCA CCC CGC GGC TCT CGG CCT AGT TGG GGC CCT ACA GAC CCC       336
Leu Leu Ser Pro Arg Gly Ser Arg Pro Ser Trp Gly Pro Thr Asp Pro
            100                 105                 110

CGG CGT AGG TCG CGT AAT TTG GGT AAG GTC ATC GAT ACC CTT ACA TGC       384
Arg Arg Arg Ser Arg Asn Leu Gly Lys Val Ile Asp Thr Leu Thr Cys
        115                 120                 125

GGC TTC GCC GAC CTC GTG GGG TAC ATT CCG CTC GTC GGC GCC CCC CTA       432
Gly Phe Ala Asp Leu Val Gly Tyr Ile Pro Leu Val Gly Ala Pro Leu
    130                 135                 140

GGG GGC GCT GCC AGG GCC CTG GCG CAT GGC GTC CGG GTT CTG GAG GAC       480
Gly Gly Ala Ala Arg Ala Leu Ala His Gly Val Arg Val Leu Glu Asp
145                 150                 155                 160

GGC GTG AAC TAT GCA ACA GGG AAT TTG CCC GGT TGC TCT TTC TCT ATC       528
Gly Val Asn Tyr Ala Thr Gly Asn Leu Pro Gly Cys Ser Phe Ser Ile
                165                 170                 175

TTC CTC TTG GCT TTG CTG TCC TGT CTG ACC GTT CCA GCT TCC GCT TAT       576
Phe Leu Leu Ala Leu Leu Ser Cys Leu Thr Val Pro Ala Ser Ala Tyr
            180                 185                 190

GAA GTG CGC AAC GTG TCC GGG ATG TAC CAT GTC ACG AAC GAC TGC TCC       624
Glu Val Arg Asn Val Ser Gly Met Tyr His Val Thr Asn Asp Cys Ser
        195                 200                 205

AAC TCA AGC ATT GTG TAT GAG GCA GCG GAC ATG ATC ATG CAC ACC CCC       672
Asn Ser Ser Ile Val Tyr Glu Ala Ala Asp Met Ile Met His Thr Pro
    210                 215                 220

GGG TGC GTG CCC TGC GTT CGG GAG AAC AAC TCT TCC CGC TGC TGG GTA       720
Gly Cys Val Pro Cys Val Arg Glu Asn Asn Ser Ser Arg Cys Trp Val
225                 230                 235                 240

GCG CTC ACC CCC ACG CTC GCA GCT AGG AAC GCC AGC GTC CCC ACC ACG       768
Ala Leu Thr Pro Thr Leu Ala Ala Arg Asn Ala Ser Val Pro Thr Thr
                245                 250                 255

ACA ATA CGA CGC CAC GTC GAT TTG CTC GTT GGG GCG GCT GCT TTC TGT       816
```

```
Thr Ile Arg Arg His Val Asp Leu Leu Val Gly Ala Ala Phe Cys
            260                 265                 270

TCC GCT ATG TAC GTG GGG GAC CTC TGC GGA TCT GTC TTC CTC GTC TCC        864
Ser Ala Met Tyr Val Gly Asp Leu Cys Gly Ser Val Phe Leu Val Ser
        275                 280                 285

CAG CTG TTC ACC ATC TCG CCT CGC CGG CAT GAG ACG GTG CAG GAC TGC        912
Gln Leu Phe Thr Ile Ser Pro Arg Arg His Glu Thr Val Gln Asp Cys
    290                 295                 300

AAT TGC TCA ATC TAT CCC GGC CAC ATA ACG GGT CAC CGT ATG GCT TGG        960
Asn Cys Ser Ile Tyr Pro Gly His Ile Thr Gly His Arg Met Ala Trp
305                 310                 315                 320

GAT ATG ATG ATG AAC TGG TCG CCT ACA ACG GCC CTG GTG GTA TCG CAG       1008
Asp Met Met Met Asn Trp Ser Pro Thr Thr Ala Leu Val Val Ser Gln
                325                 330                 335

CTG CTC CGG ATC CCA CAA GCT GTC GTG GAC ATG GTG GCG GGG GCC CAT       1056
Leu Leu Arg Ile Pro Gln Ala Val Val Asp Met Val Ala Gly Ala His
            340                 345                 350

TGG GGA GTC CTG GCG GGC CTC GCC TAC TAT TCC ATG GTG GGG AAC TGG       1104
Trp Gly Val Leu Ala Gly Leu Ala Tyr Tyr Ser Met Val Gly Asn Trp
        355                 360                 365

GCT AAG GTT TTG GTT GTG ATG CTA CTC TTT GCC GGC GTC GAC GGG CAT       1152
Ala Lys Val Leu Val Val Met Leu Leu Phe Ala Gly Val Asp Gly His
    370                 375                 380

ACC CGC GTG TCA GGA GGG GCA GCA GCC TCC GAT ACC AGG GGC CTT GTG       1200
Thr Arg Val Ser Gly Gly Ala Ala Ala Ser Asp Thr Arg Gly Leu Val
385                 390                 395                 400

TCC CTC TTT AGC CCC GGG TCG GCT CAG AAA ATC CAG CTC GTA AAC ACC       1248
Ser Leu Phe Ser Pro Gly Ser Ala Gln Lys Ile Gln Leu Val Asn Thr
                405                 410                 415

AAC GGC AGT TGG CAC ATC AAC AGG ACT GCC CTG AAC TGC AAC GAC TCC       1296
Asn Gly Ser Trp His Ile Asn Arg Thr Ala Leu Asn Cys Asn Asp Ser
            420                 425                 430

CTC CAA ACA GGG TTC TTT GCC GCA CTA TTC TAC AAA CAC AAA TTC AAC       1344
Leu Gln Thr Gly Phe Phe Ala Ala Leu Phe Tyr Lys His Lys Phe Asn
        435                 440                 445

TCG TCT GGA TGC CCA GAG CGC TTG GCC AGC TGT CGC TCC ATC GAC AAG       1392
Ser Ser Gly Cys Pro Glu Arg Leu Ala Ser Cys Arg Ser Ile Asp Lys
    450                 455                 460

TTC GCT CAG GGG TGG GGT CCC CTC ACT TAC ACT GAG CCT AAC AGC TCG       1440
Phe Ala Gln Gly Trp Gly Pro Leu Thr Tyr Thr Glu Pro Asn Ser Ser
465                 470                 475                 480

GAC CAG AGG CCC TAC TGC TGG CAC TAC GCG CCT CGA CCG TGT GGT ATT       1488
Asp Gln Arg Pro Tyr Cys Trp His Tyr Ala Pro Arg Pro Cys Gly Ile
                485                 490                 495

GTA CCC GCG TCT CAG GTG TGC GGT CCA GTG TAT TGC TTC ACC CCG AGC       1536
Val Pro Ala Ser Gln Val Cys Gly Pro Val Tyr Cys Phe Thr Pro Ser
            500                 505                 510

CCT GTT GTG GTG GGG ACG ACC GAT CGG TTT GGT GTC CCC ACG TAT AAC       1584
Pro Val Val Val Gly Thr Thr Asp Arg Phe Gly Val Pro Thr Tyr Asn
        515                 520                 525

TGG GGG GCG AAC GAC TCG GAT GTG CTG ATT CTC AAC AAC ACG CGG CCG       1632
Trp Gly Ala Asn Asp Ser Asp Val Leu Ile Leu Asn Asn Thr Arg Pro
    530                 535                 540

CCG CGA GGC AAC TGG TTC GGC TGT ACA TGG ATG AAT GGC ACT GGG TTC       1680
Pro Arg Gly Asn Trp Phe Gly Cys Thr Trp Met Asn Gly Thr Gly Phe
545                 550                 555                 560

ACC AAG ACG TGT GGG GGC CCC CCG TGC AAC ATC GGG GGG GCC GGC AAC       1728
Thr Lys Thr Cys Gly Gly Pro Pro Cys Asn Ile Gly Gly Ala Gly Asn
                565                 570                 575
```

```
AAC ACC TTG ACC TGC CCC ACT GAC TGT TTT CGG AAG CAC CCC GAG GCC      1776
Asn Thr Leu Thr Cys Pro Thr Asp Cys Phe Arg Lys His Pro Glu Ala
            580                 585                 590

ACC TAC GCC AGA TGC GGT TCT GGG CCC TGG CTG ACA CCT AGG TGT ATG      1824
Thr Tyr Ala Arg Cys Gly Ser Gly Pro Trp Leu Thr Pro Arg Cys Met
            595                 600                 605

GTT CAT TAC CCA TAT AGG CTC TGG CAC TAC CCC TGC ACT GTC AAC TTC      1872
Val His Tyr Pro Tyr Arg Leu Trp His Tyr Pro Cys Thr Val Asn Phe
            610                 615                 620

ACC ATC TTC AAG GTT AGG ATG TAC GTG GGG GGC GTG GAG CAC AGG TTC      1920
Thr Ile Phe Lys Val Arg Met Tyr Val Gly Gly Val Glu His Arg Phe
625                 630                 635                 640

GAA GCC GCA TGC AAT TGG ACT CGA GGA GAG CGT TGT GAC TTG GAG GAC      1968
Glu Ala Ala Cys Asn Trp Thr Arg Gly Glu Arg Cys Asp Leu Glu Asp
            645                 650                 655

AGG GAT AGA TCA GAG CTT AGC CCG CTG CTG CTG TCT ACA ACA GAG TGG      2016
Arg Asp Arg Ser Glu Leu Ser Pro Leu Leu Leu Ser Thr Thr Glu Trp
            660                 665                 670

CAG ATA CTG CCC TGT TCC TTC ACC ACC CTG CCG GCC CTA TCC ACC GGC      2064
Gln Ile Leu Pro Cys Ser Phe Thr Thr Leu Pro Ala Leu Ser Thr Gly
            675                 680                 685

CTG ATC CAC CTC CAT CAG AAC ATC GTG GAC GTG CAA TAC CTG TAC GGT      2112
Leu Ile His Leu His Gln Asn Ile Val Asp Val Gln Tyr Leu Tyr Gly
            690                 695                 700

GTA GGG TCG GCG GTT GTC TCC CTT GTC ATC AAA TGG GAG TAT GTC CTG      2160
Val Gly Ser Ala Val Val Ser Leu Val Ile Lys Trp Glu Tyr Val Leu
705                 710                 715                 720

TTG CTC TTC CTT CTC CTG GCA GAC GCG CGC ATC TGC GCC TGC TTA TGG      2208
Leu Leu Phe Leu Leu Leu Ala Asp Ala Arg Ile Cys Ala Cys Leu Trp
            725                 730                 735

ATG ATG CTG CTG ATA GCT CAA GCT GAG GCC GCC TTA GAG AAC CTG GTG      2256
Met Met Leu Leu Ile Ala Gln Ala Glu Ala Ala Leu Glu Asn Leu Val
            740                 745                 750

GTC CTC AAT GCG GCG GCC GTG GCC GGG GCG CAT GGC ACT CTT TCC TTC      2304
Val Leu Asn Ala Ala Ala Val Ala Gly Ala His Gly Thr Leu Ser Phe
            755                 760                 765

CTT GTG TTC TTC TGT GCT GCC TGG TAC ATC AAG GGC AGG CTG GTC CCT      2352
Leu Val Phe Phe Cys Ala Ala Trp Tyr Ile Lys Gly Arg Leu Val Pro
            770                 775                 780

GGT GCG GCA TAC GCC TTC TAT GGC GTG TGG CCG CTG CTC CTG CTT CTG      2400
Gly Ala Ala Tyr Ala Phe Tyr Gly Val Trp Pro Leu Leu Leu Leu Leu
785                 790                 795                 800

CTG GCC TTA CCA CCA CGA GCT TAT GCC TAGTAA                            2433
Leu Ala Leu Pro Pro Arg Ala Tyr Ala
            805                 810

(2) INFORMATION FOR SEQ ID NO: 50:

(i) SEQUENCE CHARACTERISTICS:
        (A) LENGTH: 809 amino acids
        (B) TYPE: amino acid
        (D) TOPOLOGY: linear (ii) MOLECULE TYPE: protein (xi) SEQUENCE DESCRIPTION: SEQ ID NO: 50:

Met Ser Thr Asn Pro Lys Pro Gln Arg Lys Thr Lys Arg Asn Thr Asn
  1               5                  10                  15

Arg Arg Pro Gln Asp Val Lys Phe Pro Gly Gly Gly Gln Ile Val Gly
                 20                  25                  30

Gly Val Tyr Leu Leu Pro Arg Arg Gly Pro Arg Leu Gly Val Arg Ala
```

-continued

```
            35                  40                  45
Thr Arg Lys Thr Ser Glu Arg Ser Gln Pro Arg Gly Arg Gln Pro
        50                  55                  60

Ile Pro Lys Ala Arg Arg Pro Glu Gly Arg Ala Trp Ala Gln Pro Gly
65                  70                  75                  80

Tyr Pro Trp Pro Leu Tyr Gly Asn Glu Gly Met Gly Trp Ala Gly Trp
                85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
            115                 120                 125

Gly Phe Ala Asp Leu Val Gly Tyr Ile Pro Leu Val Gly Ala Pro Leu
        130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
                180                 185                 190

Glu Val Arg Asn Val Ser Gly Met Tyr His Val Thr Asn Asp Cys Ser
            195                 200                 205

Asn Ser Ser Ile Val Tyr Glu Ala Asp Met Ile Met His Thr Pro
210                 215                 220

Gly Cys Val Pro Cys Val Arg Glu Asn Asn Ser Ser Arg Cys Trp Val
225                 230                 235                 240

Ala Leu Thr Pro Thr Leu Ala Ala Arg Asn Ala Ser Val Pro Thr Thr
                245                 250                 255

Thr Ile Arg Arg His Val Asp Leu Leu Val Gly Ala Ala Phe Cys
            260                 265                 270

Ser Ala Met Tyr Val Gly Asp Leu Cys Gly Ser Val Phe Leu Val Ser
            275                 280                 285

Gln Leu Phe Thr Ile Ser Pro Arg Arg His Glu Thr Val Gln Asp Cys
        290                 295                 300

Asn Cys Ser Ile Tyr Pro Gly His Ile Thr Gly His Arg Met Ala Trp
305                 310                 315                 320

Asp Met Met Met Asn Trp Ser Pro Thr Thr Ala Leu Val Val Ser Gln
                325                 330                 335

Leu Leu Arg Ile Pro Gln Ala Val Val Asp Met Val Ala Gly Ala His
            340                 345                 350

Trp Gly Val Leu Ala Gly Leu Ala Tyr Tyr Ser Met Val Gly Asn Trp
        355                 360                 365

Ala Lys Val Leu Val Val Met Leu Leu Phe Ala Gly Val Asp Gly His
    370                 375                 380

Thr Arg Val Ser Gly Gly Ala Ala Ala Ser Asp Thr Arg Gly Leu Val
385                 390                 395                 400

Ser Leu Phe Ser Pro Gly Ser Ala Gln Lys Ile Gln Leu Val Asn Thr
                405                 410                 415

Asn Gly Ser Trp His Ile Asn Arg Thr Ala Leu Asn Cys Asn Asp Ser
            420                 425                 430

Leu Gln Thr Gly Phe Phe Ala Ala Leu Phe Tyr Lys His Lys Phe Asn
        435                 440                 445

Ser Ser Gly Cys Pro Glu Arg Leu Ala Ser Cys Arg Ser Ile Asp Lys
    450                 455                 460
```

```
Phe Ala Gln Gly Trp Gly Pro Leu Thr Tyr Thr Glu Pro Asn Ser Ser
465                 470                 475                 480

Asp Gln Arg Pro Tyr Cys Trp His Tyr Ala Pro Arg Pro Cys Gly Ile
                485                 490                 495

Val Pro Ala Ser Gln Val Cys Gly Pro Val Tyr Cys Phe Thr Pro Ser
                500                 505                 510

Pro Val Val Gly Thr Thr Asp Arg Phe Gly Val Pro Thr Tyr Asn
            515                 520                 525

Trp Gly Ala Asn Asp Ser Asp Val Leu Ile Leu Asn Asn Thr Arg Pro
530                 535                 540

Pro Arg Gly Asn Trp Phe Gly Cys Thr Trp Met Asn Gly Thr Gly Phe
545                 550                 555                 560

Thr Lys Thr Cys Gly Gly Pro Pro Cys Asn Ile Gly Gly Ala Gly Asn
                565                 570                 575

Asn Thr Leu Thr Cys Pro Thr Asp Cys Phe Arg Lys His Pro Glu Ala
                580                 585                 590

Thr Tyr Ala Arg Cys Gly Ser Gly Pro Trp Leu Thr Pro Arg Cys Met
                595                 600                 605

Val His Tyr Pro Tyr Arg Leu Trp His Tyr Pro Cys Thr Val Asn Phe
            610                 615                 620

Thr Ile Phe Lys Val Arg Met Tyr Val Gly Gly Val Glu His Arg Phe
625                 630                 635                 640

Glu Ala Ala Cys Asn Trp Thr Arg Gly Glu Arg Cys Asp Leu Glu Asp
                645                 650                 655

Arg Asp Arg Ser Glu Leu Ser Pro Leu Leu Leu Ser Thr Thr Glu Trp
                660                 665                 670

Gln Ile Leu Pro Cys Ser Phe Thr Thr Leu Pro Ala Leu Ser Thr Gly
                675                 680                 685

Leu Ile His Leu His Gln Asn Ile Val Asp Val Gln Tyr Leu Tyr Gly
            690                 695                 700

Val Gly Ser Ala Val Val Ser Leu Val Ile Lys Trp Glu Tyr Val Leu
705                 710                 715                 720

Leu Leu Phe Leu Leu Leu Ala Asp Ala Arg Ile Cys Ala Cys Leu Trp
                725                 730                 735

Met Met Leu Leu Ile Ala Gln Ala Glu Ala Ala Leu Glu Asn Leu Val
                740                 745                 750

Val Leu Asn Ala Ala Ala Val Ala Gly Ala His Gly Thr Leu Ser Phe
                755                 760                 765

Leu Val Phe Phe Cys Ala Ala Trp Tyr Ile Lys Gly Arg Leu Val Pro
                770                 775                 780

Gly Ala Ala Tyr Ala Phe Tyr Gly Val Trp Pro Leu Leu Leu Leu Leu
785                 790                 795                 800

Leu Ala Leu Pro Pro Arg Ala Tyr Ala
                805

(2) INFORMATION FOR SEQ ID NO: 51:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (ix) FEATURE:
```

```
            (A) NAME/KEY: Modified-site
            (B) LOCATION: 1..17

(xi) SEQUENCE DESCRIPTION: SEQ ID NO: 51:

Ser Asn Ser Ser Glu Ala Ala Asp Met Ile Met His Thr Pro Gly Cys
1               5                  10                  15

Val (2) INFORMATION FOR SEQ ID NO: 52:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 1..22

(xi) SEQUENCE DESCRIPTION: SEQ ID NO: 52:

Gly Gly Ile Thr Gly His Arg Met Ala Trp Asp Met Met Met Asn Trp
1               5                  10                  15

Ser Pro Thr Thr Ala Leu
            20

(2) INFORMATION FOR SEQ ID NO: 53:

(i) SEQUENCE CHARACTERISTICS:
            (A) LENGTH: 37 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 1..37

(xi) SEQUENCE DESCRIPTION: SEQ ID NO: 53:

Tyr Glu Val Arg Asn Val Ser Gly Ile Tyr His Val Thr Asn Asp Cys
1               5                  10                  15

Ser Asn Ser Ser Ile Val Tyr Glu Ala Ala Asp Met Ile Met His Thr
            20                  25                  30

Pro Gly Cys Gly Lys
            35

(2) INFORMATION FOR SEQ ID NO: 54:

(i) SEQUENCE CHARACTERISTICS:
            (A) LENGTH: 25 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 1..25

(xi) SEQUENCE DESCRIPTION: SEQ ID NO: 54:

Gly Gly Thr Pro Thr Val Ala Thr Arg Asp Gly Lys Leu Pro Ala Thr
1               5                  10                  15
```

```
Gln Leu Arg Arg His Ile Asp Leu Leu
        20                  25

(2) INFORMATION FOR SEQ ID NO: 55:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1..25

(xi) SEQUENCE DESCRIPTION: SEQ ID NO: 55:

Gly Gly Thr Pro Thr Leu Ala Ala Arg Asp Ala Ser Val Pro Thr Thr
1               5                  10                  15

Thr Ile Arg Arg His Val Asp Leu Leu
        20                  25

(2) INFORMATION FOR SEQ ID NO: 56:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 56:

Leu Leu Ser Cys Leu Thr Val Pro Ala Ser Ala Tyr Gln Val Arg Asn
1               5                  10                  15

Ser Thr Gly Leu
        20

(2) INFORMATION FOR SEQ ID NO: 57:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 57:

Gln Val Arg Asn Ser Thr Gly Leu Tyr His Val Thr Asn Asp Cys Pro
1               5                  10                  15

Asn Ser Ser Ile
        20

(2) INFORMATION FOR SEQ ID NO: 58:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 58:

Asn Asp Cys Pro Asn Ser Ser Ile Val Tyr Glu Ala His Asp Ala Ile
1               5                  10                  15
```

```
Leu His Thr Pro
        20

(2) INFORMATION FOR SEQ ID NO: 59:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 59:

Ser Asn Ser Ser Ile Val Tyr Glu Ala Ala Asp Met Ile Met His Thr
1               5                   10                  15

Pro Gly Cys Val
        20

(2) INFORMATION FOR SEQ ID NO: 60:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 60:

His Asp Ala Ile Leu His Thr Pro Gly Val Pro Cys Val Arg Glu Gly
1               5                   10                  15

Asn Val Ser (2) INFORMATION FOR SEQ ID NO: 61:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 61:

Cys Val Arg Glu Gly Asn Val Ser Arg Cys Trp Val Ala Met Thr Pro
1               5                   10                  15

Thr Val Ala Thr
        20

(2) INFORMATION FOR SEQ ID NO: 62:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 62:

Ala Met Thr Pro Thr Val Ala Thr Arg Asp Gly Lys Leu Pro Ala Thr
1               5                   10                  15

Gln Leu Arg Arg
        20
```

(2) INFORMATION FOR SEQ ID NO: 63:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 63:

```
Leu Pro Ala Thr Gln Leu Arg Arg His Ile Asp Leu Leu Val Gly Ser
1               5                   10                  15

Ala Thr Leu Cys
        20
```

(2) INFORMATION FOR SEQ ID NO: 64:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 64:

```
Leu Val Gly Ser Ala Thr Leu Cys Ser Ala Leu Tyr Val Gly Asp Leu
1               5                   10                  15

Cys Gly Ser Val
        20
```

(2) INFORMATION FOR SEQ ID NO: 65:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 65:

```
Gln Leu Phe Thr Phe Ser Pro Arg Arg His Trp Thr Thr Gln Gly Cys
1               5                   10                  15

Asn Cys Ser Ile
        20
```

(2) INFORMATION FOR SEQ ID NO: 66:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 66:

```
Thr Gln Gly Cys Asn Cys Ser Ile Tyr Pro Gly His Ile Thr Gly His
1               5                   10                  15

Arg Met Ala Trp
        20
```

(2) INFORMATION FOR SEQ ID NO: 67:

```
        (i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 67:

Ile Thr Gly His Arg Met Ala Trp Asp Met Met Met Asn Trp Ser Pro
1               5                   10                  15

Thr Ala Ala Leu
            20

(2) INFORMATION FOR SEQ ID NO: 68:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 68:

Asn Trp Ser Pro Thr Ala Ala Leu Val Met Ala Gln Leu Leu Arg Ile
1               5                   10                  15

Pro Gln Ala Ile
            20

(2) INFORMATION FOR SEQ ID NO: 69:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 69:

Leu Leu Arg Ile Pro Gln Ala Ile Leu Asp Met Ile Ala Gly Ala His
1               5                   10                  15

Trp Gly Val Leu
            20

(2) INFORMATION FOR SEQ ID NO: 70:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 70:

Ala Gly Ala His Trp Gly Val Leu Ala Gly Ile Ala Tyr Phe Ser Met
1               5                   10                  15

Val Gly Asn Met
            20

(2) INFORMATION FOR SEQ ID NO: 71:

(i) SEQUENCE CHARACTERISTICS:
            (A) LENGTH: 20 amino acids
            (B) TYPE: amino acid
```

(C) STRANDEDNESS: single
        (D) TOPOLOGY: linear (ii) MOLECULE TYPE: peptide (xi) SEQUENCE DESCRIPTION: SEQ ID NO: 71:

Val Val Leu Leu Leu Phe Ala Gly Val Asp Ala Glu Thr Ile Val Ser
1               5                   10                  15

Gly Gly Gln Ala
            20

(2) INFORMATION FOR SEQ ID NO: 72:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 72:

Ser Gly Leu Val Ser Leu Phe Thr Pro Gly Ala Lys Gln Asn Ile Gln
1               5                   10                  15

Leu Ile Asn Thr
            20

(2) INFORMATION FOR SEQ ID NO: 73:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 73:

Gln Asn Ile Gln Leu Ile Asn Thr Asn Gly Gln Trp His Ile Asn Ser
1               5                   10                  15

Thr Ala Leu Asn
            20

(2) INFORMATION FOR SEQ ID NO: 74:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 74:

Leu Asn Cys Asn Glu Ser Leu Asn Thr Gly Trp Trp Leu Ala Gly Leu
1               5                   10                  15

Ile Tyr Gln His Lys
            20

(2) INFORMATION FOR SEQ ID NO: 75:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 75:

Ala Gly Leu Ile Tyr Gln His Lys Phe Asn Ser Ser Gly Cys Pro Glu
1               5                   10                  15

Arg Leu Ala Ser
            20

(2) INFORMATION FOR SEQ ID NO: 76:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 76:

Gly Cys Pro Glu Arg Leu Ala Ser Cys Arg Pro Leu Thr Asp Phe Asp
1               5                   10                  15

Gln Gly Trp Gly
            20

(2) INFORMATION FOR SEQ ID NO: 77:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 77:

Thr Asp Phe Asp Gln Gly Trp Gly Pro Ile Ser Tyr Ala Asn Gly Ser
1               5                   10                  15

Gly Pro Asp Gln
            20

(2) INFORMATION FOR SEQ ID NO: 78:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 78:

Ala Asn Gly Ser Gly Pro Asp Gln Arg Pro Tyr Cys Trp His Tyr Pro
1               5                   10                  15

Pro Lys Pro Cys
            20

(2) INFORMATION FOR SEQ ID NO: 79:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 79:

Trp His Tyr Pro Pro Lys Pro Cys Gly Ile Val Pro Ala Lys Ser Val
1               5                   10                  15

Cys Gly Pro Val
            20

(2) INFORMATION FOR SEQ ID NO: 80:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 80:

Ala Lys Ser Val Cys Gly Pro Val Tyr Cys Phe Thr Pro Ser Pro Val
1               5                   10                  15

Val Val Gly Thr
            20

(2) INFORMATION FOR SEQ ID NO: 81:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 81:

Pro Ser Pro Val Val Val Gly Thr Thr Asp Arg Ser Gly Ala Pro Thr
1               5                   10                  15

Tyr Ser Trp Gly
            20

(2) INFORMATION FOR SEQ ID NO: 82:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 82:

Gly Ala Pro Thr Tyr Ser Trp Gly Glu Asn Asp Thr Asp Val Phe Val
1               5                   10                  15

Leu Asn Asn Thr
            20

(2) INFORMATION FOR SEQ ID NO: 83:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 83:

Gly Asn Trp Phe Gly Cys Thr Trp Met Asn Ser Thr Gly Phe Thr Lys
1               5                   10                  15

```
Val Cys Gly Ala
            20

(2) INFORMATION FOR SEQ ID NO: 84:

(i) SEQUENCE CHARACTERISTICS:
         (A) LENGTH: 20 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 84:

Gly Phe Thr Lys Val Cys Gly Ala Pro Pro Val Cys Ile Gly Gly Ala
1               5                   10                  15

Gly Asn Asn Thr
            20

(2) INFORMATION FOR SEQ ID NO: 85:

(i) SEQUENCE CHARACTERISTICS:
         (A) LENGTH: 19 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 85:

Ile Gly Gly Ala Gly Asn Asn Thr Leu His Cys Pro Thr Asp Cys Arg
1               5                   10                  15

Lys His Pro (2) INFORMATION FOR SEQ ID NO: 86:

(i) SEQUENCE CHARACTERISTICS:
         (A) LENGTH: 20 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 86:

Thr Asp Cys Phe Arg Lys His Pro Asp Ala Thr Tyr Ser Arg Cys Gly
1               5                   10                  15

Ser Gly Pro Trp
            20

(2) INFORMATION FOR SEQ ID NO: 87:

(i) SEQUENCE CHARACTERISTICS:
         (A) LENGTH: 20 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 87:

Ser Arg Cys Gly Ser Gly Pro Trp Ile Thr Pro Arg Cys Leu Val Asp
1               5                   10                  15

Tyr Pro Tyr Arg
            20
```

(2) INFORMATION FOR SEQ ID NO: 88:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 88:

```
Cys Leu Val Asp Tyr Pro Tyr Arg Leu Trp His Tyr Pro Cys Thr Ile
1               5                  10                  15

Asn Tyr Thr Ile
            20
```

(2) INFORMATION FOR SEQ ID NO: 89:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 89:

```
Pro Cys Thr Ile Asn Tyr Thr Ile Phe Lys Ile Arg Met Tyr Val Gly
1               5                  10                  15

Gly Val Glu His
            20
```

(2) INFORMATION FOR SEQ ID NO: 90:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 90:

```
Met Tyr Val Gly Gly Val Glu His Arg Leu Glu Ala Ala Cys Asn Trp
1               5                  10                  15

Thr Pro Gly Glu
            20
```

(2) INFORMATION FOR SEQ ID NO: 91:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 91:

```
Ala Cys Asn Trp Thr Pro Gly Glu Arg Cys Asp Leu Glu Asp Arg Asp
1               5                  10                  15

Arg Ser Glu Leu
            20
```

(2) INFORMATION FOR SEQ ID NO: 92:

```
        (i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 92:

Glu Asp Arg Asp Arg Ser Glu Leu Ser Pro Leu Leu Leu Thr Thr Thr
  1               5                  10                  15

Gln Trp Gln Val
            20

(2) INFORMATION FOR SEQ ID NO: 93:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 93:

Tyr Gln Val Arg Asn Ser Thr Gly Leu
  1               5

(2) INFORMATION FOR SEQ ID NO: 94:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 94:

ACGTCCGTAC GTTCGAATTA ATTAATCGA                                            29

(2) INFORMATION FOR SEQ ID NO: 95:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 95:

CCTCCGGACG TGCACTAGCT CCCGTCTGTG GTAGTGGTGG TAGTGATTAT CAATTAATTG           60

(2) INFORMATION FOR SEQ ID NO: 96:

(i) SEQUENCE CHARACTERISTICS:
            (A) LENGTH: 19 base pairs
            (B) TYPE: nucleic acid
            (C) STRANDEDNESS: single
            (D) TOPOLOGY: linear
```

(ii) MOLECULE TYPE: DNA (genomic)

(iii) HYPOTHETICAL: NO (iv) ANTI-SENSE: NO (xi) SEQUENCE DESCRIPTION: SEQ ID NO: 96:

GTTTAACCAC TGCATGATG                                                                            19

(2) INFORMATION FOR SEQ ID NO: 97:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 97:

GTCCCATCGA GTGCGGCTAC                                                                           20

(2) INFORMATION FOR SEQ ID NO: 98:

(i) SEQUENCE CHARACTERISTICS:
              (A) LENGTH: 45 base pairs
              (B) TYPE: nucleic acid
              (C) STRANDEDNESS: single
              (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 98:

CGTGACATGG TACATTCCGG ACACTTGGCG CACTTCATAA GCGGA                                                45

(2) INFORMATION FOR SEQ ID NO: 99:

(i) SEQUENCE CHARACTERISTICS:
              (A) LENGTH: 42 base pairs
              (B) TYPE: nucleic acid
              (C) STRANDEDNESS: single
              (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 99:

TGCCTCATAC ACAATGGAGC TCTGGGACGA GTCGTTCGTG AC                                                   42

(2) INFORMATION FOR SEQ ID NO: 100:

(i) SEQUENCE CHARACTERISTICS:
              (A) LENGTH: 42 base pairs
              (B) TYPE: nucleic acid
              (C) STRANDEDNESS: single
              (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 100:

TACCCAGCAG CGGGAGCTCT GTTGCTCCCG AACGCAGGGC AC　　　　　　　　　　42

(2) INFORMATION FOR SEQ ID NO: 101:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 101:

TGTCGTGGTG GGGACGGAGG CCTGCCTAGC TGCGAGCGTG GG　　　　　　　　　　42

(2) INFORMATION FOR SEQ ID NO: 102:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 102:

CGTTATGTGG CCCGGGTAGA TTGAGCACTG GCAGTCCTGC ACCGTCTC　　　　　　48

(2) INFORMATION FOR SEQ ID NO: 103:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 103:

CAGGGCCGTT CTAGGCCTCC ACTGCATCAT CATATCCCAA GC　　　　　　　　　　42

(2) INFORMATION FOR SEQ ID NO: 104:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 104:

CCGGAATGTA CCATGTCACG AACGAC                                                26

(2) INFORMATION FOR SEQ ID NO: 105:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 105:

GCTCCATTGT GTATGAGGCA GCGG                                                  24

(2) INFORMATION FOR SEQ ID NO: 106:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 106:

GAGCTCCCGC TGCTGGGTAG CGC                                                   23

(2) INFORMATION FOR SEQ ID NO: 107:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 107:

CCTCCGTCCC CACCACGACA ATACG                                                 25

(2) INFORMATION FOR SEQ ID NO: 108:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 108:

CTACCCGGGC CACATAACGG GTCACCG                                               27

(2) INFORMATION FOR SEQ ID NO: 109:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 109:

GGAGGCCTAC AACGGCCCTG GTGG    24

(2) INFORMATION FOR SEQ ID NO: 110:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 110:

TTCTATCGAT TAAATAGAAT TC    22

(2) INFORMATION FOR SEQ ID NO: 111:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 111:

GCCATACGCT CACAGCCGAT CCC    23